US012365689B2

(12) United States Patent
Mohamed et al.

(10) Patent No.: US 12,365,689 B2
(45) Date of Patent: *Jul. 22, 2025

(54) PROCESSES FOR THE PREPARATION OF (3S,4R)-3-ETHYL-4-(3H-IMIDAZO[1,2-A]PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

(71) Applicant: AbbVie Inc., North Chicago, IL (US)

(72) Inventors: Mohamed-Eslam F. Mohamed, Gurnee, IL (US); Ahmed A. Othman, Libertyville, IL (US); Aileen L. Pangan, La Grange, IL (US); Ben Klünder, Ludwigshafen (DE); Heidi S. Camp, Winnetka, IL (US); Robert J. Padley, Highland Park, IL (US); Jeffrey W. Voss, Hudson, MA (US); Cheng Thiam Tan, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/913,645

(22) Filed: Oct. 11, 2024

(65) Prior Publication Data

US 2025/0034157 A1 Jan. 30, 2025

Related U.S. Application Data

(63) Continuation-in-part of application No. 18/812,217, filed on Aug. 22, 2024, which is a continuation of application No. 18/533,564, filed on Dec. 8, 2023, now abandoned, which is a continuation of application No. 18/137,804, filed on Apr. 21, 2023, now abandoned, which is a continuation of application No. 17/902,690, filed on Sep. 2, 2022, now abandoned, which is a continuation of application No. 17/184,194, filed on Feb. 24, 2021, now abandoned, which is a continuation of application No. 16/656,237, filed on Oct. 17, 2019, now abandoned, which is a continuation of application No. 15/891,012, filed on Feb. 7, 2018, now abandoned, which is a continuation of application No. 15/295,561, filed on Oct. 17, 2016, now abandoned, application No. 18/913,645, filed on Oct. 11, 2024 is a continuation-in-part of application No. 18/612,955, filed on Mar. 21, 2024, now abandoned.

(60) Provisional application No. 62/352,380, filed on Jun. 20, 2016, provisional application No. 62/301,537, filed on Feb. 29, 2016, provisional application No. 62/267,672, filed on Dec. 15, 2015, provisional application No. 62/242,797, filed on Oct. 16, 2015, provisional application No. 63/623,994, filed on Jan. 23, 2024, provisional application No. 63/491,665, filed on Mar. 22, 2023.

(51) Int. Cl.
| | |
|---|---|
| *A61K 31/4985* | (2006.01) |
| *A61K 9/00* | (2006.01) |
| *A61K 47/02* | (2006.01) |
| *A61K 47/12* | (2006.01) |
| *A61K 47/38* | (2006.01) |
| *C07D 487/04* | (2006.01) |
| *C07D 487/14* | (2006.01) |

(52) U.S. Cl.
CPC ......... *C07D 487/14* (2013.01); *A61K 9/0053* (2013.01); *A61K 31/4985* (2013.01); *A61K 47/02* (2013.01); *A61K 47/12* (2013.01); *A61K 47/38* (2013.01); *C07D 487/04* (2013.01); *C07B 2200/13* (2013.01)

(58) Field of Classification Search
CPC .. C07D 487/14; C07D 487/04; A61K 9/0053; A61K 31/4985; A61K 47/02; A61K 47/38; C07B 2200/13
USPC ......................................................... 514/250
See application file for complete search history.

(56) References Cited

U.S. PATENT DOCUMENTS

| | | | |
|---|---|---|---|
| 3,119,742 A | 1/1964 | MacDonnell et al. |
| 3,492,397 A | 1/1970 | Lieberman et al. |
| 3,538,214 A | 11/1970 | Shoop et al. |
| 3,663,559 A | 5/1972 | Antoon et al. |
| 3,929,992 A | 12/1975 | Sehgal et al. |
| 4,053,474 A | 10/1977 | Treuner et al. |

(Continued)

FOREIGN PATENT DOCUMENTS

| | | |
|---|---|---|
| CA | 2675288 A1 | 7/2008 |
| CN | 1762333 A | 4/2006 |

(Continued)

OTHER PUBLICATIONS

Adamczyk, M., et al., "Synthesis of 3,7-dihydroimidazo[1,2a]pyrazine-3-ones and their Chemiluminescent Properties," Tetrahedron 59(41):8129-8142, Elsevier, England (2003).

(Continued)

*Primary Examiner* — Kristin A Vajda
(74) *Attorney, Agent, or Firm* — WOMBLE BOND DICKINSON (US) LLP; Danielle L. Herritt; Scott R. Breining

(57) ABSTRACT

The present disclosure relates to solid-state forms and corresponding pharmaceutical compositions of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide, and methods of treatment, including treatment of rheumatoid arthritis and juvenile idiopathic arthritis using the same. The treatment methods generally comprise administering to a patient (e.g., a pediatric patient) a therapeutically effective amount of upadacitinib as a stable liquid pharmaceutical composition or a solid dosage form, at a dose based on patient body weight.

30 Claims, 36 Drawing Sheets

(56) References Cited

U.S. PATENT DOCUMENTS

| | | |
|---|---|---|
| 4,060,598 A | 11/1977 | Groppenbacher et al. |
| 4,173,626 A | 11/1979 | Dempski et al. |
| 5,212,310 A | 5/1993 | Thurkauf et al. |
| 5,266,698 A | 11/1993 | Shaw et al. |
| 5,521,173 A | 5/1996 | Venkatesan et al. |
| 5,605,690 A | 2/1997 | Jacobs et al. |
| 5,693,801 A | 12/1997 | Shaw et al. |
| 5,703,244 A | 12/1997 | Li et al. |
| 5,733,905 A | 3/1998 | Albright et al. |
| 5,736,540 A | 4/1998 | Albright et al. |
| 5,753,648 A | 5/1998 | Albright et al. |
| 5,763,137 A | 6/1998 | Deprez et al. |
| 5,840,888 A | 11/1998 | Shaw et al. |
| 5,990,109 A | 11/1999 | Chen et al. |
| 6,090,382 A | 7/2000 | Salfeld et al. |
| 6,120,778 A | 9/2000 | Simonnet |
| 6,245,801 B1 | 6/2001 | Bryans et al. |
| 6,262,241 B1 | 7/2001 | Cook et al. |
| 6,653,471 B2 | 11/2003 | Yohannes et al. |
| 6,949,562 B2 | 9/2005 | Yohannes et al. |
| 7,169,926 B1 | 1/2007 | Burgess et al. |
| 7,452,981 B2 | 11/2008 | Wijdenes et al. |
| 7,593,820 B2 | 9/2009 | Wilks et al. |
| 7,772,231 B2 | 8/2010 | Sheppard et al. |
| 7,834,024 B2 | 11/2010 | Li et al. |
| 7,902,197 B2 | 3/2011 | Elworthy et al. |
| 8,039,009 B2 | 10/2011 | Rastogi et al. |
| 8,168,624 B2 | 5/2012 | Agarwal et al. |
| 8,361,962 B2 | 1/2013 | Billedeau et al. |
| 8,367,689 B2 | 2/2013 | Bauer et al. |
| 8,426,411 B2 | 4/2013 | Wishart et al. |
| 8,637,529 B2 | 1/2014 | Woller et al. |
| 8,785,639 B2 | 7/2014 | Wishart et al. |
| 8,962,629 B2 | 2/2015 | Wishart et al. |
| 9,011,912 B2 | 4/2015 | Zu et al. |
| 9,365,579 B2 | 6/2016 | Wishart et al. |
| 9,879,018 B2 | 1/2018 | Mulhern et al. |
| 9,879,019 B2 | 1/2018 | Nordstroem et al. |
| 9,951,080 B2 | 4/2018 | Allian et al. |
| 9,963,459 B1 | 5/2018 | Jayanth et al. |
| 10,017,517 B2 | 7/2018 | Borchardt et al. |
| RE47,221 E | 2/2019 | Wishart et al. |
| 10,202,393 B2 | 2/2019 | Jayanth et al. |
| 10,202,394 B2 | 2/2019 | Jayanth et al. |
| 10,344,036 B2 | 7/2019 | Jayanth et al. |
| 10,519,164 B2 | 12/2019 | Jayanth et al. |
| 10,550,126 B2 | 2/2020 | Pangan et al. |
| 10,597,400 B2 | 3/2020 | Othman et al. |
| 10,730,883 B2 | 8/2020 | Allian et al. |
| 10,981,923 B2 | 4/2021 | Allian et al. |
| 10,981,924 B2 | 4/2021 | Jayanth et al. |
| 10,995,095 B2 | 5/2021 | Pangan et al. |
| 11,186,584 B2 | 11/2021 | Allian et al. |
| 11,198,697 B1 | 12/2021 | Allian et al. |
| 11,365,198 B2 | 6/2022 | Mohamed et al. |
| 11,512,092 B2 | 11/2022 | Allian et al. |
| 11,524,964 B2 | 12/2022 | Mohamed et al. |
| 11,535,624 B2 | 12/2022 | Othman et al. |
| 11,535,625 B2 | 12/2022 | Pangan et al. |
| 11,535,626 B2 | 12/2022 | Pangan et al. |
| 11,564,922 B2 | 1/2023 | Pangan et al. |
| 11,607,411 B2 | 3/2023 | Machado De Lacerda et al. |
| 11,661,425 B2 | 5/2023 | Allian et al. |
| 11,680,069 B2 | 6/2023 | Allian et al. |
| 11,718,627 B2 | 8/2023 | Allian |
| 11,767,326 B2 | 9/2023 | Pangan et al. |
| 11,773,105 B2 | 10/2023 | Allian |
| 11,773,106 B2 | 10/2023 | Mohamed et al. |
| 11,780,847 B1 | 10/2023 | Jayanth et al. |
| 11,780,848 B2 | 10/2023 | Mohamed et al. |
| 11,787,815 B1 | 10/2023 | Jayanth et al. |
| 11,795,175 B2 | 10/2023 | Mohamed et al. |
| 11,976,077 B2 | 5/2024 | Pangan et al. |
| 11,993,605 B2 | 5/2024 | Mohamed et al. |
| 11,993,606 B2 | 5/2024 | Mohamed et al. |
| 12,091,415 B2 | 9/2024 | Jayanth et al. |
| 12,103,933 B2 | 10/2024 | Jayanth et al. |
| 12,110,297 B2 | 10/2024 | Jayanth et al. |
| 12,110,298 B2 | 10/2024 | Mulhern et al. |
| 2003/0078277 A1 | 4/2003 | Hibi et al. |
| 2004/0023992 A1 | 2/2004 | Das et al. |
| 2005/0176796 A1 | 8/2005 | D'Alessio et al. |
| 2006/0160806 A1 | 7/2006 | Haviv et al. |
| 2006/0183758 A1 | 8/2006 | Beard et al. |
| 2006/0183779 A1 | 8/2006 | Brauns et al. |
| 2007/0232653 A1 | 10/2007 | Bachmann et al. |
| 2008/0038347 A1 | 2/2008 | Eisenreich et al. |
| 2008/0070914 A1 | 3/2008 | Freyne et al. |
| 2009/0169618 A1 | 7/2009 | Ari-Pardo et al. |
| 2009/0215724 A1 | 8/2009 | Dubois et al. |
| 2009/0215750 A1 | 8/2009 | Bamberg et al. |
| 2009/0215788 A1 | 8/2009 | Elworthy et al. |
| 2009/0264399 A1 | 10/2009 | Inoue et al. |
| 2009/0312338 A1 | 12/2009 | Wishart et al. |
| 2011/0021425 A1 | 1/2011 | Billedeau et al. |
| 2011/0190489 A1 | 8/2011 | Wishart et al. |
| 2011/0224190 A1 | 9/2011 | Huang et al. |
| 2011/0311474 A1 | 12/2011 | Wishart et al. |
| 2012/0015963 A1 | 1/2012 | Woller et al. |
| 2012/0034250 A1 | 2/2012 | Shirakami et al. |
| 2012/0231083 A1 | 9/2012 | Carley et al. |
| 2012/0330012 A1 | 12/2012 | Frank et al. |
| 2013/0072470 A1 | 3/2013 | Wishart et al. |
| 2013/0216497 A1 | 8/2013 | Wishart et al. |
| 2013/0295189 A1 | 11/2013 | Maier et al. |
| 2014/0140944 A1 | 5/2014 | Duccini et al. |
| 2014/0243312 A1 | 8/2014 | Brown et al. |
| 2014/0271842 A1 | 9/2014 | Herbig et al. |
| 2015/0118229 A1 | 4/2015 | Voss et al. |
| 2015/0210708 A1 | 7/2015 | Wishart et al. |
| 2016/0222020 A1 | 8/2016 | Wishart et al. |
| 2016/0326181 A1 | 11/2016 | Wishart et al. |
| 2017/0129902 A1 | 5/2017 | Allian et al. |
| 2017/0266289 A1 | 9/2017 | Lipari et al. |
| 2018/0057502 A1 | 3/2018 | Allian |
| 2018/0162865 A1 | 6/2018 | Borchardt et al. |
| 2018/0186805 A1 | 7/2018 | Jayanth et al. |
| 2018/0291029 A1 | 10/2018 | Wishart et al. |
| 2018/0298016 A1 | 10/2018 | Pangan et al. |
| 2019/0023714 A1 | 1/2019 | Ayman et al. |
| 2019/0046527 A1 | 2/2019 | Thakkar et al. |
| 2020/0291040 A1 | 9/2020 | Allian et al. |
| 2021/0061813 A1 | 3/2021 | Wishart et al. |
| 2021/0361647 A1 | 11/2021 | Thakkar et al. |
| 2021/0363149 A1 | 11/2021 | Allian et al. |
| 2022/0281882 A1 | 9/2022 | Allian et al. |
| 2023/0233555 A1 | 7/2023 | Mohamed |
| 2023/0312594 A1 | 10/2023 | Mohamed et al. |
| 2023/0312595 A1 | 10/2023 | Allian et al. |
| 2023/0374027 A1 | 11/2023 | Allian et al. |
| 2024/0034740 A1 | 2/2024 | Allian et al. |
| 2024/0166657 A1 | 5/2024 | Allian et al. |

FOREIGN PATENT DOCUMENTS

| | | |
|---|---|---|
| EA | 007415 B1 | 10/2006 |
| EP | 0423805 A2 | 4/1991 |
| EP | 0423805 B1 | 8/2000 |
| EP | 1097709 A2 | 5/2001 |
| EP | 1112253 B1 | 10/2004 |
| EP | 2123651 A1 | 11/2009 |
| EP | 2438909 A1 | 4/2012 |
| GB | 716327 A | 10/1954 |
| RU | 2158127 C2 | 10/2000 |
| RU | 2250904 C2 | 4/2005 |
| WO | 1991/010671 A1 | 7/1991 |
| WO | 199216553 A1 | 10/1992 |
| WO | 1992/022552 A1 | 12/1992 |
| WO | 1993/022314 A1 | 11/1993 |
| WO | 1994/005665 A1 | 3/1994 |
| WO | 1994/011026 A2 | 5/1994 |
| WO | 1994/019351 A1 | 9/1994 |
| WO | 199519970 A1 | 7/1995 |
| WO | 1996/009304 A1 | 3/1996 |

(56) References Cited

FOREIGN PATENT DOCUMENTS

| | | |
|---|---|---|
| WO | 9822437 A1 | 5/1998 |
| WO | 9833782 A1 | 8/1998 |
| WO | 1999/045009 A1 | 9/1999 |
| WO | 0015611 A1 | 3/2000 |
| WO | 200015231 A1 | 3/2000 |
| WO | 0031606 A2 | 6/2000 |
| WO | 2003000695 A1 | 1/2003 |
| WO | 2003/031606 A2 | 4/2003 |
| WO | 2004032874 A2 | 4/2004 |
| WO | 2004/065378 A1 | 8/2004 |
| WO | 2004092126 A2 | 10/2004 |
| WO | 2004106293 A2 | 12/2004 |
| WO | 2005035524 A1 | 4/2005 |
| WO | 2005/110410 A2 | 11/2005 |
| WO | 2006002051 A1 | 1/2006 |
| WO | 2006010567 A1 | 2/2006 |
| WO | 2006015124 A2 | 2/2006 |
| WO | 2006058120 A1 | 6/2006 |
| WO | 2006069363 A2 | 6/2006 |
| WO | 2006/074984 A1 | 7/2006 |
| WO | 2006/074985 A1 | 7/2006 |
| WO | 2006107771 A2 | 10/2006 |
| WO | 2006122137 A1 | 11/2006 |
| WO | 2007007919 A2 | 1/2007 |
| WO | 2007/022268 A2 | 2/2007 |
| WO | 2007/035935 A1 | 3/2007 |
| WO | 2007061764 A2 | 5/2007 |
| WO | 2007/077949 A1 | 7/2007 |
| WO | 2007/079164 A2 | 7/2007 |
| WO | 2007143434 A2 | 12/2007 |
| WO | 2008019996 A2 | 2/2008 |
| WO | 2008021369 A2 | 2/2008 |
| WO | 2008/063287 A2 | 5/2008 |
| WO | 2008/078091 A1 | 7/2008 |
| WO | 2008/084861 A1 | 7/2008 |
| WO | 2008/094602 A2 | 8/2008 |
| WO | 2008/112695 A2 | 9/2008 |
| WO | 2008/119792 A1 | 10/2008 |
| WO | 2008121748 A2 | 10/2008 |
| WO | 2008124850 A1 | 10/2008 |
| WO | 2008135090 A1 | 11/2008 |
| WO | 2008139293 A1 | 11/2008 |
| WO | 2009/005675 A1 | 1/2009 |
| WO | 2009011705 A1 | 1/2009 |
| WO | 2009/047506 A1 | 4/2009 |
| WO | 2009106443 A1 | 9/2009 |
| WO | 2009108827 A1 | 9/2009 |
| WO | 2009/150240 A1 | 12/2009 |
| WO | 2009/152133 A1 | 12/2009 |
| WO | 2010003133 A2 | 1/2010 |
| WO | 2010099039 A1 | 9/2010 |
| WO | 2010/119284 A1 | 10/2010 |
| WO | 2010/119285 A1 | 10/2010 |
| WO | 2010117796 A2 | 10/2010 |
| WO | 201113082 A1 | 2/2011 |
| WO | 2011012540 A1 | 2/2011 |
| WO | 2011068881 A1 | 6/2011 |
| WO | 2011068899 A1 | 6/2011 |
| WO | 2011141791 A2 | 11/2011 |
| WO | 2011156543 A2 | 12/2011 |
| WO | 2012041814 A1 | 4/2012 |
| WO | 2013043826 A1 | 3/2013 |
| WO | 2013178752 A1 | 12/2013 |
| WO | 2014/015107 A1 | 1/2014 |
| WO | 2014004863 A2 | 1/2014 |
| WO | 2014/128588 A1 | 8/2014 |
| WO | 2014/147526 A1 | 9/2014 |
| WO | 2014150289 A1 | 9/2014 |
| WO | 2014/174073 A1 | 10/2014 |
| WO | 2015061665 A1 | 4/2015 |
| WO | 2016033308 A1 | 3/2016 |
| WO | 2016198983 A1 | 12/2016 |
| WO | 2017025849 A1 | 2/2017 |
| WO | 2017033093 A1 | 3/2017 |
| WO | 2017066775 A1 | 4/2017 |
| WO | 2017093857 A1 | 6/2017 |
| WO | 2017126488 A1 | 7/2017 |
| WO | 2017143014 A1 | 8/2017 |
| WO | 2018009566 A1 | 1/2018 |

OTHER PUBLICATIONS

Aletaha, D., et al., "2010 Rheumatoid Arthritis Classification Criteria: an American College of Rheumatology/ european League Against Rheumatism Collaborative Initiative," Arthritis & Rheumatism 62(9):2569-2581, Wiley-Blackwell, United States (2010).

ALLEN., et al., Editors, "Ansel's Pharmaceutical Dosage Forms and Drug Delivery Systems," 9th Edition, Lippincott Williams & Wilkins, 2005 (8 pages, Table of Contents).

Anderson, J., et al., "Rheumatoid Arthritis Disease Activity Measures: American College of Rheumatology Recommendations for Use in Clinical Practice," Arthritis Care & Research 64(5):640-647, American College of Rheumatology, United States (2012).

Arnett, F.C., et al., "The American Rheumatism Association 1987 Revised Criteria for the Classification of Rheumatoid Arthritis," Arthritis and Rheumatism 31(3):315-324, Wiley-Blackwell, United States (1988).

Banerjee, S., et al., "JAK-STAT Signaling as a Target for Inflammatory and Autoimmune Diseases: Current and Future Prospects," Drugs 77(5):521-546, Springer International, Switzerland (Mar. 2017).

Banker, G.S. and Rhodes, C.T., "Prodrugs," in Modern Pharmaceutics, Third edition, p. 596, Marcel Dekker, Inc., United States (1996).

Baslund, B., et al., "Targeting Interleukin-15 in Patients With Rheumatoid Arthritis, A Proof-of-Concept Study," Arthritis & Rheumatism 52(9):2686-2692, American College of Rheumatology, United States (2005).

Bathon, J.M., et al., "A Comparison of Etanercept and Methotrexate in Patients with Early Rheumatoid Arthritis," The New England Journal of Medicine 343(22):1586-1593, Massachusetts Medical Society, United States (2000).

Bunnage, M.E., et al., "Asymmetric Synthesis of the cis- and trans-stereoisomers of 4-arninopyrrolidine-3-Carboxylic Acid and 4-arninotetrahydrofuran-3-carboxylic Acid," Organic & Biomolecular Chemistry 2(19):2763-2776, Royal Society of Chemistry, England (2004).

Burmester, G.R., et al., "Tofacitinib (CP-690,550) in Combination with Methotrexate in Patients with Active Rheumatoid Arthritis with an Inadequate Response to Tumour Necrosis Factor Inhibitors: A Randomised Phase 3 Trial.," Lancet 381(9865):451-460, Elsevier, England (2013).

Chaudhari, K., et al., "Rheumatoid Arthritis: Current and Future Trends," Nature Reviews. Drug Discovery 15(5):305-306, Macmillan Publishers Limited, England (May 2016).

Croasdell, G., "American College of Rheumatology/Association of Rheumatology Health Professionals—2015 Annual Meeting," Drugs of the Future 40(12):857-862, Prous Science S.A.U., United States (2015).

Dupre, et al., "An Improved Synthesis of Ethyl N-(methoxycarbonyl)-2,5-dihydro-IH-pyrrole-3-carboxylate," Journal of Organic Chemistry 56(9):3197-3198, (1991).

Dutta, S. and Reed, R.C., "Functional Half-Life is a Meaningful Descriptor of Steady-State Pharmacokinetics of an Extended-Release Formulation of a Rapidly Cleared Drug," Clinical Drug Investigation 26(12):681-690, Springer International, New Zealand (2006).

El-Nabi, H.A.A., et al., "1-Aryl-2-chloro-5-methoxy-1H-3-pyrrolecarbaldehyde as synthons for fused heterocycles: synthesis of pyrazolo[3,4-d]pyrrolo[2,3-b]pyridine derivatives," Journal of Chemical Research 5:325-327, Science Reviews Ltd., England (2004).

Farnia, et al., "Stille Reaction," Organic Reactions, L. Paquette et al., Editors, John Wiley & Sons, vol. 50, 1997 5 pages, 1997 (Table of Contents).

FDA, "Clinical Pharmacology and Biopharmaceutics Review(s)—Tofacitinib," Application No. 203214Origls000, Center for Drug Evaluation and Research, 181 pages (2011).

(56) References Cited

OTHER PUBLICATIONS

FDA, "Guidance for Industry Toxicity Grading Scale for Healthy Adult and Adolescent Volunteers Emolled in Preventive Vaccine Clinical Trials," Department of Health and Human Services, FDA, Center for Biologics Evaluation and Research, 10 pages (2007).
FDA, "Medical Review; Addendum to Primary Clinical Review—Tofacitinib," Application No. 203214Origls000, Center for Drug Evaluation and Research, 303 pages (2012).
Fleischmann, R.M., et al., "A Randomized, Double-blind, Placebo-controlled, Twelve-week, Dose-ranging Study of Decemotinib, an Oral Selective JAK-3 Inhibitor, as Monotherapy in Patients With Active Rheumatoid Arthritis," Arthritis and Rheumatology 67(2):334-343, Wiley, United States (2015).
Gennaro, A., Editor "Remington's Pharmaceutical Sciences", 18th Edition, Mack Publishing Co., 5 pages, 1990 (Table of Contents).
Genovese, M.C., et al., "Safety and Efficacy of ABT-494, a Novel Selective JAK1 Inhibitor, in Patients with Active Rheumatoid Arthritis with an Inadequate Response to Methotrexate," Annals of the Rheumatic Diseases 75(2):141-142, Abstract OP0223, BMJ Publishing Group, England (Jun. 2016).
Genovese, M.C., et al., "Efficacy and Safety of ABT-494, a Selective JAK-1 Inhibitor, in a Phase IIb Study in Patients With Rheumatoid Arthritis and an Inadequate Response to Methotrexate," Arthritis & Rheumatology 68(12):2857-2866, Wiley, United States (Dec. 2016).
Genovese, M.C., et al., "OP0029 Baricitinib, An Oral Janus Kinase (Jak) 1/JAK2 Inhibitor, in Patients with Active Rheumatoid Arthritis (RA) and an Inadequate Response to TNF Inhibitors: Results of the Phase 3 RA-Beacon Study:," Annals of the Rheumatic Diseases 74(2):75.3-76, H.K. Lewis, England (2015).
Genovese, M.C., et al., "VX-509 (Decernotinib), an Oral Selective JAK-3 Inhibitor, in Combination with Methotrexate in Patients with Rheumatoid Arthritis," Arthritis & Rheumatology 68(1):46-55, Wiley, United States (2016).
Gilworth, G., et al., "Development of a Work Instability Scale for Rheumatoid Arthritis," Arthritis and Rheumatism 49(3):349-354, Wiley-Blackwell, United States (2003).
Graff, C., et al., "Characterization of ABT-494, a Second Generation JAK1 Selective Inhibitor," 2014 ACR/ARHP Annual Meeting, Abstract No. 1499, 3 pages.
Graul, A.I., et al., "The Year's New Drugs and Biologics 2015—Part II: Trends and highlights that Marked a Complicated Year," Drugs of Today 52(2):131-163, Prous Science S.A.U., United States (Feb. 2016).
Greene, et al., Editors, "Protective Groups in Organic Synthesis," 3rd Ed., John Wiley & Sons, NY, 52 pages, 1999 (Table of Contents, Abbreviations).
Hauser, M., et al., "Pyrazolono(3,4-d)pyrimidines. II. 6-Methylpyrazolono(3,4-d)pyrimidines and some reactions of pyrazolono(3,4-d)pyrimidines," The Journal of Organic Chemistry 26(2):451-455, American Chemical Society, United States (1960).
Hirahara, K., et al., "Targeting Cytokine Signaling in Autoimmunity: Back to the Future and Beyond," Current Opinion in Immunology 43:89-97, Elsevier Ltd., England (Dec. 2016).
Iwata, S. and Tanaka, Y., "Progress in Understanding the Safety and Efficacy of Janus Kinase Inhibitors for Treatment of Rheumatoid Arthritis," Expert Review of Clinical Immunology 12(10):1047-1057, Informa UK Limited, England (Jun. 2016).
Jacobson, K.A., "Comprehensive Organic Transformations: A Guide to Functional Group Preparations," 2nd ed. Richard C. Larock. Wiley New York, 1999, pp. 2583.
Jain, S., et al., "A Novel Synthesis of DI(1-Methlazacycloalkeno)[2,3-b:2',3'-d]Pyridines Through Annulation on Lactam Acetals," Tetrahedron Letters 31(1):131-134, Pergamon Press PLC, Great Britain (1990).
Jenkins, et al., Editors, "Introduction to X-Ray Powder Diffractometry," John Wiley & Sons, 13 pages, 1996 (Table of Contents).

Jordan, V.C., "Tamoxifen: a most unlikely pioneering medicine," Nat Rev Drug Discov. 2(3):205-213, Nature Publishing Group, England (2003).
Kempson, J., et al., "Synthesis, initial SAR and biological evaluation of 1,6-dihydroimidazo[4,5-d]pyrrolo[2,3-b] pyridin-4-amine derived inhibitors of I?B kinase," Bioorg Med Chem Lett. < https://www.ncbi.nlm.nih.gov/pubmed?term=%22Bioorganic+%26+medicinal+chemistry+letters%22%5BJour%5D+AND+19%5Bvolume%5D+AND+2646%5Bpage%5D&cmd=detailssearch> 19(10):2646-2649, Elsevier Ltd., England (2009).
Kettle, J.G., et al., "Inhibitors of JAK-family Kinases: An Update on the Patent Literature 2013-2015, part 1," Expert Opinion on Therapeutic Patents 27(2):127-143, Informa UK Limited, England (Feb. 2017).
Keystone, E.C., et al., "Safety and Efficacy of Baricitinib at 24 Weeks in Patients with Rheumatoid Arthritis Who Have Had an Inadequate Response to Methotrexate," Annals of the Rheumatic Diseases 74(2):333-340, H.K. Lewis, England (2015).
Keystone, E.C., et al., "Certolizumab Pegol Plus Methotrexate Is Significantly More Effective Than Placebo Plus Methotrexate in Active Rheumatoid Arthritis: Findings of a Fifty-two-week, Phase III, Multicenter, Randomized, Double-blind, Placebo-controlled, Parallel-group Study," Arthritis & Rheumatology 58(11):3319-3329, Wiley, United States (2008).
Keystone, E.C., et al., "Radiographic, Clinical, and Functional Outcomes of Treatment With Adalimumab (a Human Anti-tumor Necrosis Factor Monoclonal Antibody) in Patients With Active Rheumatoid Arthritis Receiving Concomitant Methotrexate Therapy: a Randomized, Placebo-controlled, 52-week Trial," Arthritis and Rheumatism 50(5):1400-1411, Wiley-Blackwell, United States (2004).
Ko, et al., "N-Protecting Group Dependent Aromatization of 3-Pyrroline Systems to Pyrroles," Bulletin of the Korean Chemical Society 11(1):83-84, (1990).
Kremer, J.M., et al., "A Phase IIb Study of ABT-494, a Selective JAK-1 Inhibitor, in Patients with Rheumatoid Arthritis and an Inadequate Response to Anti-Tumor Necrosis Factor Therapy," Arthritis & Rheumatology 68(12):2867-2877, Wiley, United States (Nov. 2016).
Kremer, J.M., et al., "Safety and Efficacy of ABT-494, a Novel Selective JAK1 Inhibitor, in Patients with Active Rheumatoid Arthritis and Inadequate Response or Intolerance to Anti-TNF Biologic Therapy," 2015 ACR/ARHP Annual Meeting, Abstract 14L, 4 pages.
Lam, S., "Jak Inhibitors: A Broadening Approach in Rheumatoid Arthritis," Drugs of Today 52(8):467-469, Prous Science S.A.U., United States (Aug. 2016).
Larock, R.C., Editor, "Comprehensive Organic Transformations, A Guide to Functional Group Preparations," 2nd edition, Wiley-VCH, 22 pages, 1999 (Table of Contents).
Larson, G.L., et al., "Ionic and Organometallic-Catalyzed Organosilane Reductions," Organic Reactions 71:1-737, (2008).
Ma, M.H., et al., "A Systematic Comparison of Combination DMARD Therapy and Tumour Necrosis Inhibitor Therapy With Methotrexate in Patients With Early Rheumatoid Arthritis," Rheumatology 49(1):91-98, Mercury International, England (2010).
Mangoni, A.A. and Jackson, S.H., "Age-related Changes in Pharmacokinetics and Pharmacodynamics: Basic Principles and Practical Applications," British Journal of Clinical Pharmacology 57(1):42900, Wiley-Blackwell, England (2004).
Third Pivotal Phase 3 Study Shows RINVOQ™ (upadacitinib) Plus Topical Corticosteroids Improves Skin and Itch Symptoms in Atopic Dermatitis Patients, Retrieved on Jul. 28, 2020. Retrieved from the Internet: [URL: https://news.abbvie.com/news/press-releases/third-pivotal-phase-3-study-shows-rinvoq-upadacitinib-plus-topical-corticosteroids-improves-skin-and-itch-symptoms-in-atopic-dermatitis-patients.html], 5 pages.
Mease et al. "Ixekizumab, an interleukin-17A specific monoclonal antibody, for the treatment of biologic-naive patients with active psoriatic arthritis: results from the 24-week randomised, double-blind, placebo-controlled and active (adalimumab)-controlled period of the phase III trial SPIRIT-PI," Annals of Rheumatic Diseases, 76(1):79-87 (2017).

(56) References Cited

OTHER PUBLICATIONS

AbbVie News Release, "AbbVie's ABT-494 Meets Primary Endpoint in Two Phase 2 Studies in Rheumatoid Arthritis" (2015).
Abbvie, Morgan Stanley Health Care Conference, Sep. 10, 2014 (JAK 1 Inhibitors is use for the treatment of the rheumatoid arthritis).
Anderson et al., "Surgery in Ulcerative Colitis: Indication and Timing" Dig Dis (2009), 27(3), p. 335-340.
Badawy et al. "Microenvironmental pH Modulation in Solid Dosage Forms", Journal of Pharmaceutical Sciences, vol. 96, No. 5, May 2007.
Bao et al., The Involvement of the JAK-STAT Signaling Pathway in Chronic Inflammatory Skin Disease Atopic Dermatitis, 2:3, e24137, p. 1-8, Jul./Aug./Sep. 2013.
Bechman et al., "The new entries in the therapeutic armamentarium: The small molecule JAK ; Inhibitors", Pharmacological Research, Aug. 2019, 147, 1-10.
Bolourchian, "pH-independent release of propranolol hydrochloride from HPMC-based matrices using organic acids", DARU Journal of Pharmaceutical Sciences 16(3):136-142, Dec. 2008.
Danese et al., "JAK inhibition using tofacitinib for inflammatory bowel disease treatment: a hub for multiple inflammatory cytokines", Am J Physiol Gastrointest Liver Physiol, Published online Nov. 25, 2015.
Dvorackova, "The Effect of Acid pH Modifiers on the Release Characteristics of Weakly Basic Drug from Hydrophilic-Lipophilic Matrices", AAPS PharmSciTech, vol. 14, No. 4, Dec. 2013.
Eichenfield et al. "Guidelines of care for the management of atopic dermatitis", Journal of the American Academy of Dermatology, vol. 70, No. 2, Feb. 2014.
EMA, "Guideline on the pharmacokinetic and clinical evaluation of modified release dosage forms", published Nov. 2014.
FDA, "Guidance for Industry; Extended-Release Oral Dosage Forms: Development, Evaluation, and Application of In Vitro/In Vivo Correlations"; published Sep. 1997.
FDA, "Guidance for Industry; Rheumatoid Arthritis: Developing Drug Products for Treatment", published May 2013.
Fragoulis et al., "JAK-inhibitors. New players in the field of immune-mediated diseases, beyond rheumatoid arthritis", Rheumatology, Feb. 2019, 58, i43-i54.
Gupta et al., "Evaluation of the Effect of Fluconazole and Ketoconazole on the Pharmacokinetics of Tofacitinib in Healthy Adult Subjects", Clinical Pharmacology in Drug Development, 2013, 3(1), 72-77.
Hanifin et al. "The eczema area and severity index (EASI): assessment of reliability in atopic dermatitis", Experimental Dermatology, 2001: 10: 11-18.
Hsu et al., "JAK Inhibitors: Treatment Efficacy and Safety Profile in Patients with Psoriasis", Journal of Immunology Research, 2014, 1-7.
Lamba et al., "Pharmacokinetics, Bioavailability and Safety of a Modified-Release Once-Daily Formulation of Tofacitinib in Healthy Volunteers", Poster 1478, ACR/ARHP Annual Meeting, Nov. 17, 2014.
Lamba et al., "Evaluating Pharmacokinetic Predictors of Tofacitinib Clinical Response in Rheumatoid Arthritis", Poster Abstract THU0192, Jun. 9, 2016, http://dx.doi.org/10.1136/annrheumdis-2016-eular.1696.
Lamba et al., "Pharmacokinetics, Bioavailability and Safety of a Modified Release Once Daily Formulation of Tofacitinib in Healthy Volunteers", Poster Abstract THU0143, Eular Jun. 12, 2014, 2014; Annals of the Rheumatic Diseases, 2014, 73(2), 228.
Lawendy et al. "The Effect of Mild and Moderate Hepatic Impairment on the Pharmacokinetics of Tofacitinib, an Orally Active Janus Kinase Inhibitor", Clinical Pharmacology in Drug Development, 2014, 3(6), 421-427.
NCT02281552: "A Multicenter, Randomized, Double-Blind, Parallel-Group, Phase 3 Study to Demonstrate Non-Inferiority for the Efficacy of a Once Daily Dose of Tofacitinib Modified Release Tablet to a Twice Daily Dose of the Immediate Release Tablet in Adult Patients with Rheumatoid Arthritis on Background Methotrexate", Final Protocol Amendment, Aug. 13, 2015.
Nokhodchi et al., "The role of oral controlled release matrix tablets in drug delivery systems", BioImpacts, 2012, 2(4), 175-187.
Novosad et al., "Beyond TNF inhibition: the expanding pipeline of biologic therapies for inflammatory disease and their associated infectious sequelae", Clinical infectious disease advance access, Feb. 27, 2014, 1-38.
O'Shea et al., "Janus kinase inhibitors in autoimmune disease", Annual Rheumatoid disease, 2013, 72, iiIII-ii115.
Remington: The Science and Practice of Pharmacy. 22nd Ed. Linda A. Felton. Pharmaceutical Press, 2012.
Rudwaleit et al., "Atopic disorders in ankylosing spondylitis and rheumatoid arthritis", Ann Rheum Dis., Nov. 2002; 61(11): 968-974.
Saini et al. "Effect of Medication Dosing Frequency on Adherence in Chronic Diseases", Am J Manag Care, Jun. 1;15(6):e22-33.2009.
Schmitt et al., Assessment of clinical signs of atopic dermatitis: a systematic review and recommendation, J Allergy Clin Immunol 2013; 132(6):1337-1347.
Siepe et al., "Strategies for the design of hydrophilic matrix tablets with controlled microenvironmental pH", Int J Pharm Jun. 19, 2006;316(1-2):14-20.
Siepe et al., "Microenvironmental pH and microviscosity inside pH-controlled matrix tablets: An EPR imaging study", J Control Release May 1, 2006;112(1):72-8.
Siepe et al., "Assessment of Tailor-Made HPMC-Based Matrix Minitablets Comprising a Weakly Basic Drug Compound", Drug Dev Ind Pharm Jan. 2008;34(1):46-52.
Singh et al., "Use of Clinical Disease Activity Index Score for Assessment of Disease Activity in Rheumatoid Arthritis Patients: An Indian Experience", Arthritis (2011).
Streubel et al., "pH-independent release of a weakly basic drug from water-insoluble and -soluble matrix tablets", J Control Release Jun. 1, 20005;67(1):101-10.
Timmins et al., Ed., "Hydrophilic Matrix Tablets for Oral Controlled Release", In: AAPS vol. 16, 2014, Springer.
Van der Heijde et al., "Efficacy and safety of upadacitinib in patients with active ankylosing spondylitis (SELECT-AXIS 1): a multicentre, randomised, double-blind, placebo-controlled, phase 2/3 trial", The Lancet, Elsevier, Amsterdam, NL, Nov. 2019, 394 (10214), 2108-2117.
Varma et al., "Influence of micro-environmental pH on the gel layer behavior and release of a basic drug from various hydrophilic matrices", J Control Release Mar. 21, 2005;103(2):499-510.
Vippagunta et al., "Crystalline Solids", Advanced Drug Delivery Reviews 48 (2001) 3-26.
Walpole et al., "The weight of nations: an estimation of adult human biomass", BMC Public Health 2012, 12:439, pp. 1-6.
Zalte et al., "Review on Sustained Release Matrix Tablet", International Journal of Pharmacy and Biological Sciences, Dec. 2013, 3(4), 17-29.
Zhang et al., "A Randomized, Placebo-Controlled Study of the Pharmacokinetics, Pharmacodynamics, and Tolerability of the Oral JAK2 Inhibitor Fedratinib (SAR302503) in Healthy Volunteers", The Journal of Clinical Pharmacology, 2013, 54(4) 415-421.
Center for Drug Evaluation and Research, "Clinical Pharmacology and Biopharmaceutics Review(s)", Application No. 211675Orig1s000, 138 pages (Sep. 12, 2019).
Abbvie, Press Release on Jan. 8, 2018, "AbbVie's Upadacitinib Granted Breatkthrough Therapy Designation from the U.S. Food and Drug Administration for Atopic Dermatitis", accessed at http://news.abbvie.com/2018-01-08-AbbVies-Upadacitinib-Granted-Breakthrough-Therapy-Designation-from-the-U-S-Food-and-Drug-Administration-for-Atopic-Dermatitis, 2 pages.
Product Label: "SEPINEO P 600", XP002744402, accessed at http://gyermedhu/pdf/3664_Leaftet_Sepineo_P600_gb.pdf, accessed on Apr. 2008, pp. 1-2.
Bannister, M.J. and Freeman, S., "Adult-onset Atopic Dermatitis," Australasian Journal of Dermatology 41(4):225-228 (Nov. 2000).
Burmester, G.R., et al., "A Phase 3 Randomized, Placebo-Controlled, Double-Blind Study of Upadacitinib (ABT-494), a Selective JAK-1 Inhibitor, in Patients with Active Rheumatoid

(56) References Cited

OTHER PUBLICATIONS

Arthritis with Inadequate Response to Conventional Synthetic Dmards," 2017 ACR/ARHP Annual Meeting, Abstract No. 1904, United States, 5 pages (2017).

Chamlin, S.L., et al., "The Price of Pruritus: Sleep Disturbance and Cosleeping in Atopic Dermatitis," Archives of Pediatrics & Adolescent Medicine 159(8):745-750, American Medical Association, United States (Aug. 2005).

Cotter, D.G., et al., "Emerging Therapies for Atopic Dermatitis: JAK Inhibitors," Journal of the American Academy of Dermatology 78(3S1):S53-S62, Mosby, United States (Mar. 2018).

Ellis, C.N., et al., "Understanding and Managing Atopic Dermatitis in Adult Patients," Seminars in Cutaneous Medicine and Surgery 31(3 Suppl):S18-S22, Frontline Medical Communications, United States (Sep. 2012).

Fraser, K.A., American Academy of Dermatology Annual Meeting: San Diego, CA, USA, Feb. 16-20, 2018, American Journal of Clinical Dermatology, vol. 19 (2), pp. 287-290 (Apr. 2018).

Genovese, M.C., "Long-Term Safety and Efficacy of Upadacitinib (ABT-494), an Oral JAK-1 Inhibitor in Patients with Rheumatoid Arthritis in an Open Label Extension Study," 2017 ACR/ARHP Annual Meeting, Abstract No. 509, 4 pages.

Goedken, E.R, et al., "Minimum Significant Ratio of Selectivity Ratios (MSRSR) and Confidence in Ratio of Selectivity Ratios (CRSR): Quantitative Measures for Selectivity Ratios Obtained by Screening Assays," Journal of Biomolecular Screening 17(7):857-867, Sage Publications, United States (Apr. 2012).

Grebien, F., et al., "Stat5 Activation Enables Erythropoiesis in the Absence of EpoR and Jak2," Blood 111(9):4511-4522, American Society of Hematology, United States (May 2008).

Guschin, D., et al., "A Major Role for the Protein Tyrosine Kinase JAL1 in the JAK/STAT Signal Transduction Pathway in Response to Interleukin-6," The EMBO Journal 14(7):1421-1429, Wiley Blackwell, England (Apr. 1995).

Hanifin, J.M. and Rajka, G., "Diagnostic Features of Atopic Dermatitis," Acta Dermatovener 60(92):44-47 (1980).

Hanifin, J.M., et al., "A Population-based Survey of Eczema Prevalence in the United States," Dermatitis 18(2):82-91, Lippincott Williams & Wilkins, United States (Jun. 2007).

Klunder, B., et al., "Exposure-Response Analyses of the Effect of Upadacitinib on ACR Responses in th Phase 2b Rheumatoid Arthritis Trials in Patients with Inadequate Response to Methotrxate or to Anti-Tumor Necrosis Factor Therapy," 2017 ACR/ ARHP Annual Meeting, Abstract No. 505, 4 pages (2017).

Merriam-Webster: Metabolite, accessed at https://www.merriam-webster.com/dictionary/metabolite, accessed on Dec. 2013.

Mohamed, M.E.F., et al., "ABT-494 Pharmacokinetics Following Administration of the Once-Daily Extended-Release Tablet Formulation Being Utilized in the Ongoing Rheumatoid Arthritis Phase 3 Trials," Annals of the Rheumatic Diseases, Abstract No. THU0177, 2 pages (Jun. 2017).

Mohamed, M.F., et al., "Assessment of Effect of CYP3A Inhibition, CYP Induction, OATP1B Inhibition, and High-fat Meal on Pharmacokinetics of the JAK1 Inhibitor Upadacitinib," British Journal of Clinical Pharmacology 83(10):2242-2248, Wiley-Blackwell, England (Oct. 2017).

Mohamed, M.E.F., et al., "ABT-494 Has no Effect on the QT Interval at the Doses Being Evaluated in Rheumatoid Arthritis Phase 3 Trials," Annals of the Rheumatic Diseases, Abstract No. AB0432, 1 page (Jun. 2017).

Mohamed, M.E.F., "Exposure-Response Analysis to Assess the Effect of ABT-494 on QT Interval and Utilization of a Non-Pharmacological Approach to Demonstrate ECG Assay Sensitivity," Clinical Pharmacology & Therapeutics 101 (S1): S39, Abstract PI-076, John Wiley & Sons, Inc., United States (Feb. 2017).

Mohamed, M.E.F., et al., "Use of Early Clinical Trial Data to Support Thorough QT Study Waiver for Upadacitinib and Utility of Food Effect to Demonstrate ECG Assay Sensitivity," Clinical Pharmacology & Therapeutics, 7 pages, John Wiley & Sons, Inc., United States (Jul. 2017).

Mohamed, M.E.F., et al., "The Selective JAK1 Inhibitor Upadacitinib has no Effect on Pharmacokinetics of the Hormonal Contraceptives Levonorgesrel and Ethinylestradiol," 2017 ACR/ARHP Annual Meeting, Abstract No. 506, 4 pages (Sep. 2017).

Neubauer, H., et al., "JAK2 Deficiency Defines an Essential Developmental Checkpoint in Definitive Hematopoiesis," Cell 93(3):397-409, Cell Press, United States (May 1998).

Notice of Opposition for European Patent Application No. EP2506716, mailed on Feb. 16, 2018, 5 pages.

Nygaard, U., et al., "Emerging Treatment Options in Atopic Dermatitis: Systemic Therapies," Dermatology 233(5):344-357, Karger, Switzerland (2017).

Opposition Brief for European Patent Application No. EP2506716, mailed on Feb. 16, 2018, 16 pages.

Ortmann, R.A., et al., "Janus Kinases and Signal Transducers and Activators of Transcription: Their Roles in Cytokine Signaling, Development and Immunoregulation," Arthritis Research 2(1):16-32, BioMed Central Ltd, England (Dec. 1999).

AbbVie's Upadacitinib Meets All Primary and Ranked Secondary Endpoint including Superiority versus Adalimumab in Phase 3 Study in Rheumatoid Arthritis (Apr. 9, 2018), accessed at https://news.abbvie.com/article_print.cfm?article_id=11629, accessed on Aug. 1, 2018, 5 pages.

Response to Communication pursuant to Art. 94(3) EPC dated Jul. 12, 2016, submitted in European Application No. EP10835061.2-1462, cited as Document TM4 in Opposition to European Patent EP2506716, mailed on Feb. 16, 2018, 3 pages.

"Rituximab," in The Merck Index. 14th Ed., John Wiley & Sons, 2006; p. 1422.

Schwartz, D.M., et al., "JAK Inhibition as a Therapeutic Strategy for Immune and Inflammatory Diseases," Nature Reviews. Drug discovery 16(12):843-862, Nature Pub. Group, England (Dec. 2017).

SEPPIC: "How to use Sepineo P600 in a formulation", XP054976186, accessed at https://www.youtube.com/watch?v=SHiwvwnx1tA, access on Aug. 30, 2012, 1 page.

Silverberg, J.I. and Simpson, E.L., "Association Between Severe Eczema in Children and Multiple Comorbid Conditions and Increased Healthcare Utilization," Pediatric Allergy and Immunology 24(5):476-486, Blackwell Publishing, England (Aug. 2013).

Statement of Case in Opposition for Israel Patent Application 248466, mailed on Nov. 23, 2017, 4 pages.

Strand, V., et al., "Changes in Hemoglobin levels upon Treatment with ABT-494, a Selective JAK-1 Inhibitor and relation to baseline levels of C-Reactive Protein," THU0210, p. 283 (Jun. 2017).

Strand, V., et al., "Early Patient-Reported Outcomes and Clinical Outcomes with ABT-494 in Patients with Active Rheumatoid Arthritis who are Inadequate Responses to Methotrexate or Tumor Necrosis Factor Inhibitors: Post-Hoc Analysis of Phase 2 Randomized Controlled Trials," Annals of the Rheumatic Diseases, Abstract No. SAT0217, Jun. 2017, 1 page.

Strand, V., et al., "Economic Burden of Non-Responders to Biologic DMARD Treatments in Rheumatoid Arthritis," 2016 ACR/ARHP Annual Meeting, Abstract No. 2617, 2 pages (2016).

Strand, V., et al., "Patient-Reported Outcomes of Long-Term Upadacitinib Use in Patients with Rheumatoid Arthritis: Interim Analysis Results of a Phase 2, Open-Label Extension Study," 2017 ACR/ARHP Annual Meeting, Abstract No. 501, 3 pages (2017).

Torres, T., "Atopic Dermatitis: The New Therapeutic Revolution in Dermatology," Acta medica portuguesa 30(10):669-670, Lisboa, Portugal (Oct. 2017).

Voss, J., et al., "THU0127 Pharmacodynamics of a Novel JAK1 Selective Inhibitor in Rat Arthritis and Anemia Models and in Healthy Human Subjects," 2013 ACR/ARHP Annual Meeting, Abstract No. 2374, 4 pages.

Weiss, G. and Goodnough, L.T., "Anemia of Chronic Disease," The New England Journal of Medicine 352:1011-1023, Massachusetts Medical Society, United States (Mar. 2005).

Wermuth, C., et al., "Molecular Variations D Based on Isoteric Replacements," in the Practice of Medicinal Chemistry, Chapter 13, pp. 203-237, Academic Press, London (1996).

Williams, H.C. and Wuthrich, B., The Natural History of Atopic Dermatitis, Supplied by the British Library, pp. 41-59 (Apr. 2018).

(56) References Cited

OTHER PUBLICATIONS

Williams, H.C., "Atopic Dermatitis," The New England Journal of Medicine 352(22):2314-2324, Massachusetts Medical Society, United States (Jun. 2005).

Inami, M., "Small molecule drug development beyond biologics: Kinase inhibitors as an approach to autoimmune disease treatment," Folia Pharmacologica Japonica (2013) 142:63-67. With English certified language translation dated Jun. 17, 2019, 13 pages.

Kranz, H. et al., "Development of a single unit extended release formulation for ZK 811 752, a weakly basic drug," European Journal of Pharmaceutical Sciences 26 (2005) 47-53.

Search results of Upadacitinib in File Registry Database of STN® Search from Chemical Abstracts Service (CAS) conducted on May 4, 2020.

Caira, M.R., "Crystalline Polymorhism of Organic Compounds", Topics in Current Chemistry, v. 198, Chapter 3.1, p. 188, paragraph 2 (1998).

AbbVie's Upadacitinib (ABT-494) meets Primary Endpoint in Phase 2b Study in Atopic Dermatitis (Sep. 7, 2017), accessed at https://news.abbvie.com/news/abbvies-upadacitinib-abt-494-meets-primary-endpoint-in-phase-2b-study-in-atopic-dermatitis.htm, accessed on Dec. 18, 2017, 3 pages.

Declaration of Michael Friedman, dated Sep. 7, 2018, submitted in Response to Notice of Opposition in European Patent EP2506716, 15 pages.

Dorwald, F.Z., "Side Reactions in Organic Synthesis: A Guide to Successful Synthesis Design," Weinheim: Wiley-VCH Verlag Gmbh & Co_ KGaA, 2005.

U.S. Appl. No. 12/481,028, filed Jun. 9, 2009, Granted, U.S. Pat. No. 8,962,629-B2.

U.S. Appl. No. 12/958,115, filed Dec. 1, 2010, Granted, U.S. Pat. No. 8,426,411-B2.

U.S. Appl. No. 13/761,501, filed Feb. 7, 2013, Abandoned, US-20130216497-A1.

U.S. Appl. No. 14/523,052, filed Oct. 24, 2014, Abandoned, US-20150118229-A1.

U.S. Appl. No. 14/610,119, filed Jan. 30, 2015, Granted, U.S. Pat. No. 9,365,579-B2.

U.S. Appl. No. 15/017,802, filed Feb. 8, 2016, Abandoned, US-20160222020-A1.

U.S. Appl. No. 15/152,823, filed May 12, 2016, Abandoned, US-20160326181-A1.

U.S. Appl. No. 15/295,561, filed Oct. 17, 2016, Abandoned, US-20170129902-A1.

U.S. Appl. No. 15/446,102, filed Mar. 1, 2017, Granted, U.S. Pat. No. Re. 47,221-E1.

U.S. Appl. No. 15/682,451, filed Aug. 21, 2017, Granted, U.S. Pat. No. 9,879,018-B2.

U.S. Appl. No. 15/682,457, filed Aug. 21, 2017, Granted, U.S. Pat. No. 9,879,019-B2.

U.S. Appl. No. 15/803,538, filed Nov. 3, 2017, Granted, U.S. Pat. No. 9,951,080-B2.

U.S. Appl. No. 15/806,104, filed Nov. 7, 2017, Abandoned, US-20180291029-A1.

U.S. Appl. No. 15/857,892, filed Dec. 29, 2017, Granted, U.S. Pat. No. 9,963,459-B1.

U.S. Appl. No. 15/891,012, filed Feb. 7, 2018, Abandoned, US-20190023714-A1.

U.S. Appl. No. 15/891,306, filed Feb. 7, 2017, Granted, U.S. Pat. No. 10,017,517-B2.

U.S. Appl. No. 15/908,347, filed Feb. 28, 2018, Granted, U.S. Pat. No. 10,344,036-B2.

U.S. Appl. No. 15/917,013, filed Mar. 9, 2018, Abandoned, US-20190046527-A1.

U.S. Appl. No. 15/945,225, filed Apr. 4, 2018, Granted, U.S. Pat. No. 10,202,393-B2.

U.S. Appl. No. 15/945,231, filed Apr. 4, 2018, Granted, U.S. Pat. No. 10,020,394-B2.

U.S. Appl. No. 15/954,039, filed Apr. 16, 2018, Granted, U.S. Pat. No. 10,550,126-B2.

U.S. Appl. No. 16/440,442, filed Jun. 13, 2019, Abandoned, US-2021-0061813-A1.

U.S. Appl. No. 16/453,684, filed Jun. 26, 2019, Granted, U.S. Pat. No. 10,519,164-B2.

U.S. Appl. No. 16/458,622, filed Jul. 1, 2019, Granted, U.S. Pat. No. 10,597,400-B2.

U.S. Appl. No. 16/656,237, filed Oct. 17, 2019, Abandoned, US-2020-0291040-A1.

U.S. Appl. No. 16/721,076, filed Dec. 19, 2019, Granted, U.S. Pat. No. 10,995,095.

U.S. Appl. No. 16/787,251, filed Feb. 11, 2020, Granted, U.S. Pat. No. 10,730,883-B2.

U.S. Appl. No. 16/905,667, filed Jun. 18, 2020, Granted, U.S. Pat. No. 10,981,923-B2.

U.S. Appl. No. 16/983,703, filed Aug. 3, 2020, Granted, U.S. Pat. No. 10,981,924-B2.

U.S. Appl. No. 17/039,470, filed Sep. 30, 2020, Abandoned, Not yet published.

U.S. Appl. No. 17/115,833, filed Dec. 9, 2020, Abandoned, US-2021-0361647-A1.

U.S. Appl. No. 17/184,194, filed Feb. 24, 2021, Abandoned, US-2021-0363149-A1.

U.S. Appl. No. 17/205,066, filed Mar. 18, 2021, Abandoned, Not yet published.

U.S. Appl. No. 17/230,288, filed Apr. 14, 2021, Granted, U.S. Pat. No. 11,186,584-B2.

U.S. Appl. No. 17/230,418, filed Apr. 14, 2021, Granted, U.S. Pat. No. 11,198,697-B1.

U.S. Appl. No. 17/338,322, filed Jun. 3, 2021, Abandoned, Not yet published..

U.S. Appl. No. 17/507,885, filed Oct. 22, 2021, Abandoned, Not yet published.

U.S. Appl. No. 17/508,451, filed Oct. 22, 2021, Abandoned, Not yet published.

U.S. Appl. No. 17/508,576, filed Oct. 22, 2021, Abandoned, Not yet published.

U.S. Appl. No. 17/527,717, filed Nov. 16, 2021, Granted, U.S. Pat. No. 11,365,198-A1.

U.S. Appl. No. 17/566,748, filed Dec. 31, 2021, Abandoned, Not yet published.

U.S. Appl. No. 17/575,731, filed Jan. 14, 2022, Abandoned, Not yet published.

U.S. Appl. No. 17/667,748, filed Feb. 9, 2022, Abandoned, Not yet published.

U.S. Appl. No. 17/668,249, filed Feb. 9, 2022, Abandoned, Not yet published.

U.S. Appl. No. 17/672,854, filed Feb. 16, 2022, Abandoned, Not yet published.

U.S. Appl. No. 17/712,008, filed Apr. 1, 2022, Granted, U.S. Pat. No. 11,607,411.

U.S. Appl. No. 17/717,486, filed Apr. 11, 2022, Granted, U.S. Pat. No. 11,524,964.

U.S. Appl. No. 17/732,070, filed Apr. 28, 2022, Granted, U.S. Pat. No. 11,564,922.

U.S. Appl. No. 17/735,061, filed May 2, 2022, Granted, U.S. Pat. No. 11,512,092.

U.S. Appl. No. 17/827,054, filed May 27, 2022, Granted, U.S. Pat. No. 11,535,624.

U.S. Appl. No. 17/827,064, filed May 27, 2022, Granted, U.S. Pat. No. 11,535,625.

U.S. Appl. No. 17/827,083, filed May 27, 2022, Granted, U.S. Pat. No. 11,535,626.

U.S. Appl. No. 17/831,226, filed Jun. 2, 2022, Abandoned, Not yet published.

U.S. Appl. No. 17/890,346, filed Aug. 18, 2022, Abandoned, Not yet published.

U.S. Appl. No. 17/890,365, filed Aug. 18, 2022, Abandoned, Not yet published.

U.S. Appl. No. 17/902,690, filed Sep. 2, 2022, Abandoned, Not yet published.

U.S. Appl. No. 17/943,253, filed Sep. 13, 2022, Abandoned, Not yet published.

(56) References Cited

OTHER PUBLICATIONS

U.S. Appl. No. 17/950,406, filed Sep. 22, 2022, Abandoned, Not yet published.
U.S. Appl. No. 17/951,332, filed Sep. 23, 2022, Granted, U.S. Pat. No. 11,680,069.
U.S. Appl. No. 17/951,334, filed Sep. 23, 2022, Granted, U.S. Pat. No. 11,661,425.
U.S. Appl. No. 17/979,703, filed Nov. 2, 2022, Abandoned, Not yet published.
U.S. Appl. No. 18/086,744, filed Dec. 22, 2022, Abandoned, Not yet published.
U.S. Appl. No. 18/093,222, filed Jan. 4, 2023, Abandoned, Not yet published.
U.S. Appl. No. 18/094,263, filed Jan. 6, 2023, Granted, U.S. Pat. No. 11,773,105.
U.S. Appl. No. 18/094,266, filed Jan. 6, 2023, Granted, U.S. Pat. No. 11,718,627.
U.S. Appl. No. 18/094,691, filed Jan. 9, 2023, Abandoned, Not yet published.
U.S. Appl. No. 18/127,211, filed Mar. 28, 2023, Allowed, US-20230233555-A1.
U.S. Appl. No. 18/137,804, filed Apr. 21, 2023, Abandoned, Not yet published.
U.S. Appl. No. 18/140,653, filed Apr. 28, 2023, Granted, U.S. Pat. No. 11,767,326.
U.S. Appl. No. 18/174,736, filed Feb. 27, 2023, Granted, U.S. Pat. No. 11,787,815.
U.S. Appl. No. 18/174,738, filed Feb. 27, 2023, Granted, U.S. Pat. No. 11,780,847.
U.S. Appl. No. 18/176,647, filed Mar. 1, 2023, Granted, U.S. Pat. No. 11,795,175.
U.S. Appl. No. 18/176,651, filed Mar. 1, 2023, Granted, U.S. Pat. No. 11,976,077.
U.S. Appl. No. 18/176,653, filed Mar. 1, 2023, Granted, U.S. Pat. No. 11,767,326.
U.S. Appl. No. 18/176,664, filed Mar. 1, 2023, Granted, U.S. Pat. No. 11,993,605.
U.S. Appl. No. 18/176,848, filed Mar. 1, 2023, Granted, U.S. Pat. No. 11,780,848.
U.S. Appl. No. 18/176,850, filed Mar. 1, 2023, Granted, U.S. Pat. No. 11,773,106.
U.S. Appl. No. 18/210,278, filed Jun. 15, 2023, Abandoned, Not yet published.
U.S. Appl. No. 18/328,325, filed Jun. 2, 2023, Allowed, US-20240034740-A1.
U.S. Appl. No. 18/328,350, filed Jun. 2, 2023, Allowed, US-20230312595-A1.
U.S. Appl. No. 18/329,980, filed Jun. 6, 2023, Granted, U.S. Pat. No. 12,091,415.
U.S. Appl. No. 18/329,986, filed Jun. 6, 2023, Granted, U.S. Pat. No. 12,110,297.
U.S. Appl. No. 18/329,988, filed Jun. 6, 2023, Granted, U.S. Pat. No. 12,103,933.
U.S. Appl. No. 18/360,434, filed Jul. 27, 2023, Abandoned, Not yet published.
U.S. Appl. No. 18/360,548, filed Jul. 27, 2023, Abandoned, Not yet published.
U.S. Appl. No. 18/361,582, filed Jul. 28, 2023, Abandoned, US-20230374027-A1.
U.S. Appl. No. 18/369,272, filed Sep. 18, 2023, Granted, U.S. Pat. No. 12,110,298.
U.S. Appl. No. 18/451,501, filed Aug. 17, 2023, Abandoned, Not yet published.
U.S. Appl. No. 18/453,085, filed Aug. 21, 2023, Granted, U.S. Pat. No. 11,993,606.
U.S. Appl. No. 18/460,541, filed Sep. 2, 2023, Abandoned, Not yet published.
U.S. Appl. No. 18/468,696, filed Sep. 16, 2023, Abandoned, Not yet published.
U.S. Appl. No. 18/486,378, filed Oct. 13, 2023, Abandoned, Not yet published.
U.S. Appl. No. 18/501,540, filed Nov. 3, 2023, Abandoned, Not yet published.
U.S. Appl. No. 18/530,071, filed Dec. 5, 2023, Published, US-20240166657-A1.
U.S. Appl. No. 18/530,077, filed Dec. 5, 2023, Allowed, US-20240174682-A1.
U.S. Appl. No. 18/533,564, filed Dec. 8, 2023, Pending, Not yet published.
U.S. Appl. No. 18/536,842, filed Dec. 12, 2023, Abandoned, Not yet published.
U.S. Appl. No. 18/433,308, filed Feb. 5, 2024, Pending, Not yet published.
U.S. Appl. No. 18/614,437, filed Mar. 22, 2024, Pending, Not yet published.
U.S. Appl. No. 18/622,259, filed Mar. 29, 2024, Pending, Not yet published.
U.S. Appl. No. 18/634,915, filed Apr. 13, 2024, Pending, Not yet published.
U.S. Appl. No. 18/648,404, filed Apr. 28, 2024, Pending, Not yet published.
U.S. Appl. No. 18/654,974, filed May 3, 2024, Pending, Not yet published.
U.S. Appl. No. 18/674,477, filed May 24, 2024, Pending, Not yet published.
U.S. Appl. No. 18/734,105, filed Jun. 5, 2024, Published, US-20240317770A1.
U.S. Appl. No. 18/774,783, filed Jul. 16, 2024, Pending, Not yet published.
U.S. Appl. No. 18/776,040, filed Jul. 16, 2024, Pending, Not yet published.
U.S. Appl. No. 18/807,549, filed Aug. 16, 2024, Pending, Not yet published.
U.S. Appl. No. 18/812,217, filed Aug. 22, 2024, Pending, Not yet published.
Malemud, C.J, "Suppression of Autoimmune Arthritis by Small Molecule Inhibitors of the JAK/STAT Pathway," Pharmaceuticals (Basel) 3(5):1446-1455, MDPI, Switzerland (May 2010).
Milici, A.J., et al., "Cartilage Preservation by Inhibition of Janus Kinase 3 in Two Rodent Models of Rheumatoid Arthritis," Arthritis Research & Therapy 10(1):R14, BioMed Central, England (2008).
Response to Notice of Opposition, dated Sep. 10, 2018, submitted in European Patent EP2506716, 31 pages.
Roskoski, R Jr, "Janus Kinase (Jak) Inhibitors in the Treatment of Inflammatory and Neoplastic Diseases," Pharmacological Research 111:784-803, Elsevier, Netherlands (Sep. 2016).
Verstovsek, S, "Therapeutic Potential of JAK2 Inhibitors," Hematology American Society of Hematology Education Program 636-642, American Society of Hematology, United States (2009).
Mohamed, M.F., et al., "Pharmacokinetics, Safety and Tolerability of ABT-494, a Novel Selective JAK 1 Inhibitor, in Healthy Volunteers and Subjects with Rheumatoid Arthritis," Clinical Pharmacokinetics 55(12):1547-1558, ADIS Press, Switzerland (2016).
Abbvie, Press Release on Feb. 17, 2018, "AbbVie Presents New Late-Breaking Phase 2b Data on Upadacitinib in Atopic Dermatitis at the 2018 American Academy of Dermatology Annual Meeting", accessed at https://news.abbvie.com/article_print.cfm?article_id=11608, 3 pages.
AbbVie's Upadacitinib Shows Positive Results as Monotherapy in Phase 3 Rheumatoid Arthritis Study, Meeting All Primary and Key Secondary Endpoints, Dec. 2017, 5 pages.
Alabdulaai, M.K., et al., "The Role of JAK2 Abnormalities in Hematologic Neoplasms", Hematology Reviews 1(1): e10, PagePress, Italy (Mar. 2009).
Clinical Trials,"A Phase 3, Randomized, Double-Blind Study Comparing Upadacitinib (ABT-494) to Placebo and to Adalimumab in Subjects With Moderately to Severely Active Rheumatoid Arthritis Who Are on a Stable Background of Methotrexate {MTX) and Who Have an Inadequate Response to MTX (MTX-IR)," Identifier NCT02629159 accessed at https://clinicaltrials_gov/ct2/show/NCT02629159 accessed on Oct. 23, 2018, 10 pages.

(56) References Cited

OTHER PUBLICATIONS

Lin, TH, et aL, "Selective Functional Inhibition of JAK-3 Is Sufficient for Efficacy in Collagen-induced Arthritis in Mice," Arthritis and Rheumatism 62(8):2283-2293, Wiley-Blackwell, United States (Aug. 2010).

Clinical Trials, "A Phase 3, Randomized, Double-Blind Study Comparing Upadacitinib (ABT-494) Monotherapy to Methotrexate (MTX) in Subjects With Moderately to Severely Active Rheumatoid Arthritis With Inadequate Response to MTX," Identifier NCT02706951 accessed at https://clinicaltrials.gov/ct2/show/ NCT02706951 accessed on Oct. 23, 2018, 8 pages.

Parmentier, J.M., et al., "In Vitro and in Vivo Characterization of the JAKI Selectivity of upadacitinib (ABT-494)," BMC Rheumatology 2(23):16, BioMed Central, United Kingdom (2018).

Third Declaration of Michael Friedman, dated Oct. 23, 2018, submitted in U.S. Appl. No. 15/446,102, 41 pages.

Upadacitinib Meets All Primary and Ranked Secondary Endpoints Including Superiority Versus Adalimumab in Phase 3 Study in Rheumatoid Arthritis, [retrieved on Apr. 9, 2018]. Retrieved from the Internet: [URL http://www.prnewswire.com/news-releases/upadacitinib-meets-all-primary-and-ranked-secondary-endpoints-including-superiority-versus-adalimumab-in-phase-3-study-in-rheumatoid-arthritis-300626157.html], accessed on Apr. 10, 2018, 5 pages.

Clinical Trials, "A Phase 2 Study, Multicenter, Open-Label Extension (OLE) Study in Rheumatoid Arthritis Subjects Who Have Completed a Preceding Phase 2 Randomized Controlled Trial (RCT) With Upadacitinib (ABT-494)," Identifier NCT02049138, accessed at https://clinicaltrials.gov/ct2/show/NCT02049138, accessed on Oct. 3, 2018, 10 pages.

Clinical Trials, "A Randomized, Double-Blind, Placebo-Controlled, Phase 2 Study to Investigate the Safety and Efficacy of ABT-494 With Background Methotrexate (MTX) in Subjects With Active Rheumatoid Arthritis (RA) Who Have Had an Inadequate Response to MTX Alone," Identifier NCT02066389, accessed at https://clinicaltrials.gov/ct2/show/NCT02066389, accessed on Oct. 11, 2018, 11 pages.

Clinical Trials, "A Study in Healthy Adult Volunteers and Adult Subjects With Rheumatoid Arthritis to Evaluate the Safety, Tolerability, and Pharmacokinetics After Multiple Dosing of ABT-494," Identifier NCT01741493, accessed at https://clinicaltrials.gov/ct2/show/NCT01741493, accessed on Sep. 27, 2018, 7 pages.

Clinical Trials, "A Randomized, Double-Blind, Placebo-Controlled, Phase 2 Study to Investigate the Safety and Efficacy of ABT-494 Given With Methotrexate (MTX) in Subjects With Moderately to Severely Active Rheumatoid Arthritis (RA) Who Have Had an Inadequate Response or Intolerance to Anti-TNF Biologic Therapy," Identifier NCT01960855, accessed at https://clinicaltrials.gov/ct2/show/NCT01960855, accessed on Sep. 13, 2018, 8 pages.

Clinical Trials, "A Multicenter, Randomized, Double-Blind, Placebo-Controlled Study of ABT-494 for the Induction of Symptomatic and Endoscopic Remission in Subjects With Moderately to Severely Active Crohn's Disease Who Have Inadequately Responded to or Are Intolerant to Immunomodulators or Anti-TNF Therapy," Identifier NCT02365649, accessed at https://clinicaltrials.gov/ct2/show/NCT02365649, accessed on Aug. 24, 2018, 7 pages.

Clinical Trials, "A Phase 3, Randomized, Double-Blind Study Comparing Upadacitinib (ABT-494) to Placebo in Subjects With Moderately to Severely Active Rheumatoid Arthritis Who Are on a Stable Dose of Conventional Synthetic Disease-Modifying Anti-Rheumatic Drugs (csDMARDs) and Have an Inadequate Response to csDMARDs" Identifier NCT02675426, accessed at https://clinicaltrials.gov/ct2/show/NCT02675426, accessed on Oct. 22, 2018, 9 pages.

Clinical Trials, "A Phase 3, Randomized, Double-Blind Study Comparing Upadacitinib (ABT-494) Once Daily Monotherapy to Methotrexate (MTX) Monotherapy in MTX-Naive Subjects With Moderately to Severely Active Rheumatoid Arthritis", accessed at https://clinicaltrials.gov/ct2/show/NCT02706873, accessed on Oct. 17, 2018, 9 pages.

Clinical Trials, "A Phase 3, Randomized, Double-Blind Study Comparing Upadacitinib (ABT-494) to Placebo on Stable Conventional Synthetic Disease-Modifying Anti-Rheumatic Drugs (csDMARDs) in Subjects With Moderately to Severely Active Rheumatoid Arthritis With Inadequate Response or Intolerance to Biologic DMARDs (bDMARDs)," Identifier NCT02706847, accessed at https://clinicaltrials.gov/ct2/show/NCT02706847, accessed on Oct. 23, 2018, 8 pages.

Klunder, B ., et al., "Population Pharmacokinetics of Upadacitinib in Healthy Subjects and Subjects with Rheumatoid Arthritis: Analyses of Phase I and II Clinical Trials," Clinical Pharmacokinetics, 57(8):977-988, Adis, part of Springer Science+Business Media, Switzerland (Aug. 2018).

Mohamed, M.F., et al., "Pharmacokinetics of Upadacitinib With the Clinical Regimens of the Extended-Release Formulation Utilized in Rheumatoid Arthritis Phase 3 Trials," Clinical Pharmacology in Drug Development, 0(0):1-9, Wiley Periodicals, Inc., United States (Apr. 2018).

Clinical Trials, "A Phase 3 Randomized, Multicenter, Double-Blind Study to Evaluate the Safety of Upadacitinib in Combination With Topical Corticosteroids in Adolescent and Adult Subjects in Japan With Moderate to Severe Atopic Dermatitis," Identifier NCT03661138, accessed at https://clinicaltrials.gov/ct2/show/NCT03661138, accessed on Oct. 23, 2018, 10 pages.

Clinical Trials, "A Phase 2b/3, Randomized, Double-Blind Study Comparing Upadacitinib (ABT-494) to Placebo in Japanese Subjects With Moderately to Severely Active Rheumatoid Arthritis Who Are on a Stable Dose of Conventional Synthetic Disease-Modifying Anti-Rheumatic Drugs (csDMARDs) and Have an Inadequate Response to csDMARDs," Identifier NCT02720523, accessed at https://clinicaltrials.gov/ct2/show/NCT02720523, accessed on Oct. 23, 2018, 9 pages.

Clinical Trials, "A Phase 2, Multicenter, Open-Label Extension (OLE) Study to Observe the Long-Term Efficacy, Safety, and Tolerability of Repeated Administration of Upadacitinib (ABT-494) in Subjects With Crohn's Disease," Identifier NCT02782663, accessed at https://clinicaltrials.gov/ct2/show/NCT02782663 accessed on Oct. 23, 2018, 7 pages.

Clinical Trials,"A Multicenter, Randomized, Double-Blind, Placebo-Controlled Study to Evaluate the Safety and Efficacy of Upadacitinib (ABT-494) for Induction and Maintenance Therapy in Subjects With Moderately to Severely Active Ulcerative Colitis," Identifier NCT02819635, accessed at https://clinicaltrials.gov/ct2/show/ NCT02819635, accessed on Oct. 23, 2018, 8 pages.

Clinical Trials, "A Phase 2b Multicenter, Randomized, Placebo-Controlled, Double-Blind Dose-Ranging Study to Evaluate ABT-494 (Upadacitinib) in Adult Subjects With Moderate to Severe Atopic Dermatitis," Identifier NCT02925117, accessed at https://clinicaltrials.gov/ct2/show/NCT02925117 accessed on Oct. 23, 2018, 9 pages.

Clinical Trials, "A Phase 3, Randomized, Double-Blind, Placebo-Controlled Study With Upadacitinib (ABT-494) in Subjects From China and Selected Countries With Moderately to Severely Active Rheumatoid Arthritis Who Have Had an Inadequate Response to Conventional Synthetic Disease-Modifying Anti-Rheumatic Drugs (csDMARDs)," Identifier NCT02955212, accessed at https://clinicaltrials.gov/ct2/show/NCT02955212 accessed on Oct. 23, 2018, 9 pages.

Clinical Trials, "A Phase 3 Multicenter, Long-Term Extension Study to Evaluate the Safety and Efficacy of Upadacitinib (ABT-494) in Subjects With Ulcerative Colitis," Identifier NCT03006068, accessed at https://clinicaltrials.gov/ct2/show/NCT03006068, accessed on Oct. 23, 2018, 8 pages.

Clinical Trials, "A Phase 3, Randomized, Active-Controlled, Double Blind Study Comparing Upadacitinib (ABT-494) to Abatacept in Subjects With Moderately to Severely Active Rheumatoid Arthritis With Inadequate Response or Intolerance to Biologic DMARDs (bDMARDs) on Stable Conventional Synthetic Disease Modifying Anti-Rheumatic Drugs (csDMARDs)," Identifier NCT03086343, accessed at https://clinicaltrials.gov/ct2/show/NCT03086343, accessed on Oct. 23, 2018, 8 pages.

Clinical Trials, "A Phase 3, Randomized, Double-Blind, Study Comparing Upadacitinib (ABT-494) to Placebo in Subjects With

(56) References Cited

OTHER PUBLICATIONS

Active Psoriatic Arthritis Who Have a History of Inadequate Response to at Least One Biologic Disease Modifying Anti-Rheumatic Drug (bDMARD)," Identifier NCT03104374, accessed at https://clinicaltrials.gov/ct2/show/NCT03104374, accessed on Oct. 23, 2018, 10 pages.
Clinical Trials, "A Phase 3, Randomized, Double-Blind, Study Comparing Upadacitinib (ABT-494) to Placebo and to Adalimumab in Subjects With Active Psoriatic Arthritis Who Have a History of Inadequate Response to at Least One Non-Biologic Disease Modifying Anti-Rheumatic Drug (DMARD)—SELECT—PsA 1," Identifier NCT03104400, accessed at https://clinicaltrials.gov/ct2/show/NCT03104400, accessed on Oct. 23, 2018, 12 pages.
Clinical Trials, "A Multicenter, Randomized, Double-Blind, Placebo-Controlled Study Evaluating the Safety and Efficacy of Upadacitinib in Subjects With Active Ankylosing Spondylitis," Identifier NCT03178487, accessed at https://clinicaltrials.gov/ct2/show/NCT03178487, accessed on Oct. 23, 2018, 10 pages.
Clinical Trials, "A Multicenter, Randomized, Double-Blind, Placebo-Controlled Maintenance and Long-Term Extension Study of the Efficacy and Safety of Upadacitinib (ABT-494) in Subjects With Crohn's Disease Who Completed the Studies M14-431 or M14-433," Identifier NCT03345823, accessed at https://clinicaltrials.gov/ct2/show/NCT03345823, accessed on Oct. 23, 2018, 9 pages.
Clinical Trials,"A Multicenter, Randomized, Double-Blind, Placebo-Controlled Induction Study of the Efficacy and Safety of Upadacitinib (ABT-494) in Subjects With Moderately to Severely Active Crohn's Disease Who Have Inadequately Responded to or Are Intolerant to Biologic Therapy," Identifier NCT03345836, accessed at https://clinicaltrials.gov/ct2/show/NCT03345836, accessed on Oct. 23, 2018, 8 pages.
Clinical Trials, "A Phase 3 Randomized, Placebo-Controlled, Double-Blind Study to Evaluate Upadacitinib in Combination With Topical Corticosteroids in Adolescent and Adult Subjects With Moderate to Severe Atopic Dermatitis," Identifier NCT03568318, accessed at https://clinicaltrials.gov/ct2/show/NCT03568318, accessed on Oct. 23, 2018, 8 pages.
Clinical Trials, "A Phase 3 Randomized, Placebo-Controlled, Double-Blind Study to Evaluate Upadacitinib in Adolescent and Adult Subjects With Moderate to Severe Atopic Dermatitis," Identifier NCT03569293, accessed at https://clinicaltrials.gov/ct2/show/NCT03569293, accessed on Oct. 23, 2018, 9 pages.
Clinical Trials, "An Open-label Multiple Dose Study to Evaluate the Pharmacokinetics, Safety and Tolerability of Upadacitinib in Pediatric Subjects With Severe Atopic Dermatitis," Identifier NCT03646604, accessed at https://clinicaltrials.gov/ct2/show/NCT03646604, accessed on Oct. 23, 2018, 6 pages.
Clinical Trials, "A Multicenter, Randomized, Double-Blind, Placebo-Controlled Induction Study to Evaluate the Efficacy and Safety of Upadacitinib (ABT-494) in Subjects With Moderately to Severely Active Ulcerative Colitis," Identifier NCT03653026, accessed at https://clinicaltrials.gov/ct2/show/NCT03653026, accessed on Oct. 23, 2018, 8 pages.
Clinical Trials, "A Phase 2 Study to Investigate the Safety and Efficacy of ABBV-105 Given Alone or in Combination With Upadacitinib (ABBV-599 Combination) With a Background of Conventional Synthetic DMARDs in Subjects With Active Rheumatoid Arthritis With Inadequate Response or Intolerance to Biologic DMARDs," Identifier NCT03682705, accessed at https://clinicaltrials.gov/ct2/show/NCT03682705, accessed on Oct. 23, 2018, 10 pages.
Bissonnette, R., et al., "Topical tofacitinib for atopic dermatitis: a phase II a randomized trial," British Journal of Dermatology (2016) 175:902-911.
Guttman-Yassky, E., et al., "Baricitinib in adult patients with moderate-to-severe atopic dermatitis: A phase 2 parallel, double-blinded, randomized placebo-controlled multiple-dose study," J Am Acad Dermatol (2018) 80(4):913-921.
Levy, L.L., et al., "Treatment of recalcitrant atopic dermatitis with the oral Janus kinase inhibitor tofacitinib citrate," J Am Acad Dematol (2015) 73(3):395-398.

Vu, M., et al., "Oral tofacitinib: a promising treatment in atopic dermatitis, alopecia areata and vitiligo," Clinical and Experimental Dermatology (2017) 42:942-944.
Guttman-Yassky et al., "Upadacitinib in adults with moderate to severe atopic dermatitis: 16-week results from a randomized, placebo-controlled trial" J Allergy Clin Immunol, 2020, pp. 877-884.
RINVOQ™ (upadacitinib) Monotherapy Shows Improvement in Skin Clearance and Itch in First Phase 3 Study for Atopic Dermatitis Retrieved on Jun. 18, 2020. Retrieved from the Internet: [URL: https://news.abbvie.com/news/press-releases/rinvoq-upadacitinib-monotherapy-shows-improvement-in-skin-clearance-and-itch-in-first-phase-3-study-for-atopic-dermatitis.htm], 5 pages.
RINVOQ™ (upadacitinib) Monotherapy Meets All Primary and Secondary Endpoints in Second Phase 3 Study for Atopic Dermatitis. Retrieved on Jul. 21, 2020. Retrieved from the Internet: [URL: https://news.abbvie.com/news/press-releases/rinvoq-upadacitinib-monotherapy-meets-all-primary-and-secondary-endpoints-in-second-phase-3-study-for-atopic-dermatitis.htm], 5 pages.
MedDRA, Medical Dictionary for Regulatory Activities (MedDRA, version 17.1), http://www.meddra.ond (2014).
Menet, C.J., et al., "Progress Toward JAK1-selective Inhibitors," Future Medicinal Chemistry 7(2):203-235, Future Science Ltd., England (2015).
Mikhaleva, M.A. and Mamaev, V.P., "XXXV. 6-Hydroxypyrazolo[3,4-d]Pyrimidines," Khimiya Geterotsiklicheskikh Soedinenii, No. 12, pp. 1696-1699, Latvian Institute of Organic Synthesis, Latvia (1972).
Mohamed, M-E., et al., "Assessment of the Effect of CYP3A Inhibition, CYP Induction, OATP1B Inhibition and Administration of High-Fat Meal on the Pharmacokinetics of the Potent and Selective JAK1 Inhibitor ABT-494," 2015 ACR/ARHP Annual Meeting, Abstract 2751, 2 pages.
Mohamed, M-E., et al., "Pharmacokinetics of ABT-494 with the Once-Daily Extended-Release Tablet Formulation Being Utilized in the Ongoing Rheumatoid Arthritis Phase 3 Trials," 2016 ACR/ARHP Annual Meeting, Abstract No. 1629, 2 pages.
Mohamed, M-E., et al., "Pharmacokinetics, Safety and Tolerability of the Selective JAK1 Inhibitor, ABT-494, in Healthy Volunteers and Subjects with Rheumatoid Arthritis," Annals of the Rheumatic Diseases 74(2):258, Abstract THU0176, BMJ Publishing Group Ltd., (2015).
Mohamed, M-E., et al., "Preferential Inhibition of IL-6 Relative to IL-7 Signaling Pathways by ABT-494: Exposure-Response Analysis of Ex-Vivo Data from Two Phase 1 Clinical Trials and Comparison to Tofacitinib," Annals of the Rheumatic Diseases 75(2):256, Abstract THU0195, BMJ Publishing Group Ltd., England (Jun. 2016).
Mohamed, M-E.F., et al., "Population Pharmacokinetics of ABT-494 in Healthy Subjects and in Subjects With Rheumatoid Arthritis: Combined Analysis of Phase I and II Trials," Clinical Pharmacology & Therapeutics 101(1):S79, Abstract PII-098, John Wiley & Sons, Inc., United States (Feb. 2017).
Mohamed-Eslam, F., et al., "Pharmacokinetics, Safety and Tolerability of ABT-494, a Novel Selective JAK 1 Inhibitor, in Healthy Volunteers and Subjects with Rheumatoid Arthritis," Clinical Pharmacokinetics 55(12):1547-1558, Springer International, Switzerland (Jun. 2016).
Nakayamada, S., et al., "Chemical JAK Inhibitors for the Treatment of Rheumatoid Arthritis," Expert Opinion on Pharmacotherapy 17(16):2215-2225, Informa UK Limited, England (Oct. 2016).
Nakayamada, S., et al., "Recent Progress in JAK Inhibitors for the Treatment of Rheumatoid Arthritis," BioDrugs 30 (5):407-419, Springer International, Switzerland (Aug. 2016).
Namour, F., "Pharmacokinetics and Pharmacokinetic/Pharmacodynamic Modeling of Filgotinib (GLPG0634), a Selective JAK1 Inhibitor, in Support of Phase IIB Dose Selection," Clinical pharmacokinetics 54(8):859-874, Springer Science+Business Media, Switzerland (2015).
Nayana, M.R.S., et al., "CoMFA and Docking Studies on Triazolopyridine Oxazole Derivatives as p38 MAP Kinase Inhibitors," European Journal of Medicinal Chemistry 43(6):1261-1269, Elsevier Masson SAS, France (2008).
Noble, M.E.M., et al., "Protein Kinase Inhibitors: Insights Into Drug Design From Structure," Science 303(5665):1800-1805, American Association for the Advancement of Science, United States (2004).

(56) References Cited

OTHER PUBLICATIONS

Norman, P., "Selective JAK Inhibitors in Development for Rheumatoid Arthritis," Expert Opinion on Investigational Drugs 23(8):1067-1077, Informa UK, Ltd., England (2014).
Olivera, P., et al., "Next Generation of Small Molecules in Inflammatory Bowel Disease," Gut 66(2):199-209, British Medical Assn, England (Feb. 2017).
Paulus, E.F. and Rivo, E., "1-Phenyl-3-carbethoxy-4-hydroxypyrroline," Acta Crystallographica C44:1242-1244, (1988).
Rochais, C., et al., "Synthesis of new dipyrrolo- and furopyrrolopyrazinones related to tripentones and their biological evaluation as potential kinases (CDKs1-5, GSK-3) inhibitors," Eur J Med Chem. 44(2):708-716, Elsevier Masson SAS, France (2009).
Rowe, et al., Editors, "Handbook of Phamlaceutical Excipients," 7th Ed., Pharmaceutical Press, 7 pages, 2012 (Table of Contents).
Rowe, R.C., et al., "Handbook of Pharmaceutical Excipients—7th Edition," Pharmaceutical Development and Technology, 18(2):544, Informa Healthcare USA, Inc., United States (2013).
Sahin, S. and Benet, L.Z., "The Operational Multiple Dosing Half-life: A Key to Defining Drug Accumulation in Patients and to Designing Extended Release Dosage Forms," Pharmaceutical Research 25(12):2869-2877, Kluwer Academic/Plenum Publishers, United States (2008).
Sandborn, W.J., "The Present and Future of Inflammatory Bowel Disease Treatment," Gastroenterology & Hepatology 12(7):438-441, Gastro-Hep Communications, United States (Jul. 2016).
Schram, K.H., et al., "Tricyclic nucleosides I. Synthesis of the new tricyclic ring system tetrazolo[1,5-c]pyrrolo[2,3-d] pyrimidine and certain tetrazolo[],5-c] pyrrolo[2,3-d] pyrimidine ribonucleosides," Journal of Heterocyclic Chemistry 12:1021-1023, Journal of Heterocyclic Chemistry, United States (1975).
Schwartz, D.M., et al., "Type I/II Cytokines, JAKs, and New Strategies for Treating Autoimmune Diseases," Nature Reviews. Rheumatology 12(1):25-36, Macmillan Publishers Limited, United States (Jan. 2016).
Scott, I.C and Scott, D., "Joint Counts in Inflammatory Arthritis," Clinical and Experimental Rheumatology 32(85):S7-S12, (2014).
Semerano, L., et al., "Developments with Investigational Janus Kinase Inhibitors for Rheumatoid Arthritis," Expert Opinion on Investigational Drugs 25(12):1355-1359, Informa UK Limited, England (Oct. 2016).
Semerano, L., et al., "Novel Immunotherapeutic Avenues for Rheumatoid Arthritis," Trends in Molecular Medicine 22(3):214-229, Elsevier Science Ltd., England (Mar. 2016).
Singh, J.A., et al., "2012 Update of the 2008 American College of Rheumatology Recommendations for the Use of Disease-Modifying Antirheumatic Drugs and Biologic Agents in the Treatment of Rheumatoid Arthritis," Arthritis Care & Research 64(5):625-639, John Wiley & Sons, United States (2012).
Sivaraman, P. and Cohen, S.B., "Malignancy and Janus Kinase Inhibition," Rheumatic Diseases Clinics of North America 43(1):79-93, Elsevier Inc., United States (Feb. 2017).
Smolen, J., et al., "EULAR recommendation for the management of rheumatoid arthritis with synthetic and biological disease-modifying antirheumatic drugs," Annals of the Rheumatic Diseases 69(6):964-975, BMJ, England (2010).
Smolen, J.S., et al., "Eular Reconnnendations for the Management of Rheumatoid Arthritis With Synthetic and Biological Disease-modifying Antirheumatic Drugs: 2013 Update," Annals of the Rheumatic Diseases 73(3):492-509, H.K. Lewis, England (2014).
Solomon, D.H. and Bucala, R.J., "The Enduring Value of Reporting Randomized Controlled Clinical Trials in Arthritis & Rheumatology: 2016 and Beyond," Arthritis & Rheumatology 68(12):2831-2833, American College of Rheumatology, United States (Aug. 2016).
Stahl, et al., Editors "IUPAC Handbook of Pharmaceutical Salts: Properties, Selection, and Use," Wiley-VCH, Weinheim, Geffilany, 5 pages (2002) (Table of Contents).
Stella, V.J., et al., "A Case for Prodrugs," in Prodrugs: Challenges and Rewards Part 1, p. 24, American Association of Pharmaceutical Sciences, United States (2007).
Strand, V., et al., "Sustained Benefit in Rheumatoid Arthritis Following One Course of Rituximab: Improvements in Physical Function Over 2 Years," Rheumatology 45(12):1505-1513, Mercury International, England (2006).
Trost, B.M., et al., "Palladium-catalyzed DYKAT of Vinyl Epoxides: Enantioselective Total Synthesis and Assignment of the Configuration of (+)-Broussonetine G," Angewandte Chemie 42(48):5987-5990, Wiley-VCH, Germany (2003).
Van Epps, S., et al., "Design and synthesis of tricyclic cores for kinase inhibition," Bioorg Med Chem Lett. 23(3):693-698, Elsevier Ltd., England (2013).
Van Vollenhoven, R.F., et al., "THU0178 Relationship Between NK Cell Count and Important Safety Events in Rheumatoid Arthritis Patients Treated with Tofacitinib," Annals of the Rheumatic Diseases 74(2):258-259, H.K. Lewis, England (2015).
Wang, G.T., et al., "Design, Synthesis, and Structural Analysis of Influenza Neuraminidase Inhibitors Containing Pyrrolidine Cores," Journal of Medicinal Chemistry 44(8):1192-1201, American Chemical Society, United States (2001).
Winthrop, K.L., "The Emerging Safety Profile of JAK Inhibitors in Rheumatic Disease," Nature Reviews. Rheumatology 13(4):234-243, Macmillan Publishers Limited, United States (Apr. 2017).
Wolff, M.E., "Some Considerations for Prodrug Design," in Burger's Medicinal Chemistry and Drug Discovery, Fifth Edition, vol. 1: Principles and Practices, pp. 975-977, John Wiley and Sons, United States (1995).
Woodworth, T., et al., "Standardizing Assessment and Reporting of Adverse Effects in Rheumatology Clinical Trials II: the Rheumatology Common Toxicity Criteria V.2.0.," The Journal of Rheumatology 34(6): 1401-1414, Journal of Rheumatology Publishing Co, Canada (2007).
Wormser, H. C., "Synthesis of Azabiotin Analogs as Potential Cofactors for Biotin-dependent Enzymes," Journal of Pharmaceutical Sciences 59(12):1732-1737, Elsevier, United States (1970).
Stahl, P.H., et al., Chapters 7, 8, and 10 in Handbook of Pharmaceutical Salts, Stahl, P.H., et al., eds., pp. 161-189, 191-220, 237-247, 330-350, Verlag Helvetica Chimica Acta, Switzerland (2002).
AbbVie Announces Positive Phase 2 Study Results for Upadacitinib (ABT-494), an Investigational JAK1-Selective Inhibitor, in Crohn's Disease (May 9, 2017), accessed at https://news.abbvie.com/news/press-releases/abbvie-announces-positive-phase-2-study-results-for-upadacitinib-abt-494-an-investigational-jak1-selective-inhibitor-in-crohns-disease.htm, accessed on Dec. 18, 2017, 3 pages.
AbbVie's Upadacitinib (ABT-494) Meets All Primary and Ranked Secondary Endpoint in Phase 3 Study in Rheumatoid Arthritis (Jun. 7, 2017), accessed at https://news.abbvie.com/news/abbvies-upadacitinib-abt-494-meets-all-primary-and-ranked-secondary-endpoints-in-phase-3-study-in-rheumatoid-arthritis.htm, accessed on Dec. 18, 2017, 4 pages.
AbbVie's Upadacitinib (ABT-494) Meets All Primary and Ranked Secondary Endpoint in Second Phase 3 Study in Rheumatoid Arthritis (Sep. 11, 2017), accessed at https://news.abbvie.com/alert-topics/immunology/abbvies-upadacitinib-abt-494-meets-all-primary-and-ranked-secondary-endpoints-in-second-phase-3-study-in-rheumatoid-arthritis.htm, accessed on Dec. 18, 2017, 4 pages.
AbbVie's Upadacitinib Granted Breakthrough Therapy Designation from the U.S. Food and Drug Administration for Atopic Dermatitis (Jan. 8, 2018), accessed at https://news.abbvie.com/news/abbvies-upadacitinib-granted-breakthrough-therapy-designation-from-food-and-drug-administration-for-atopic-dermatitis.htm, accessed on Aug. 1, 2018, 2 pages.
Amended Pleadings on Behalf of the Opponent in Opposition to Israel Patent Application 248466, mailed on Mar. 26, 2018, 12 pages.
Annex A—Relative IC50 Values for Compounds of Formula I(c), submitted in European Application No. EP10835061.2-1462, dated Nov. 7, 2014, cited as Document TM3 in Opposition to European Patent EP2506 716, mailed on Feb. 16, 2018, 10 pages.

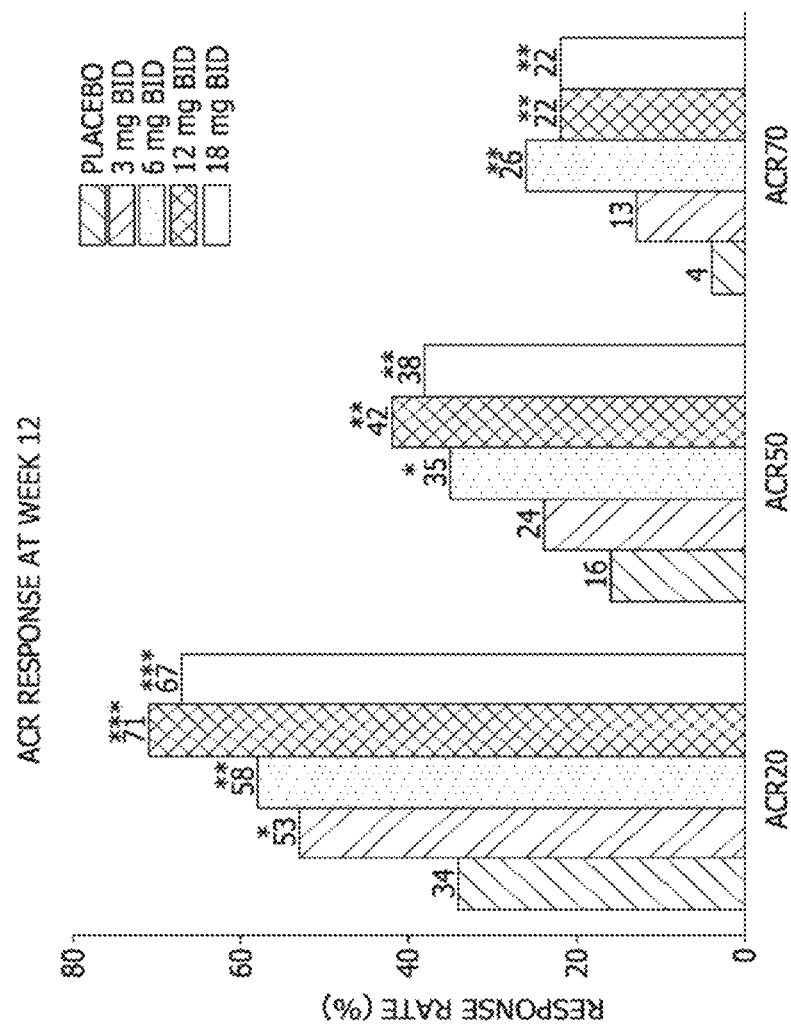

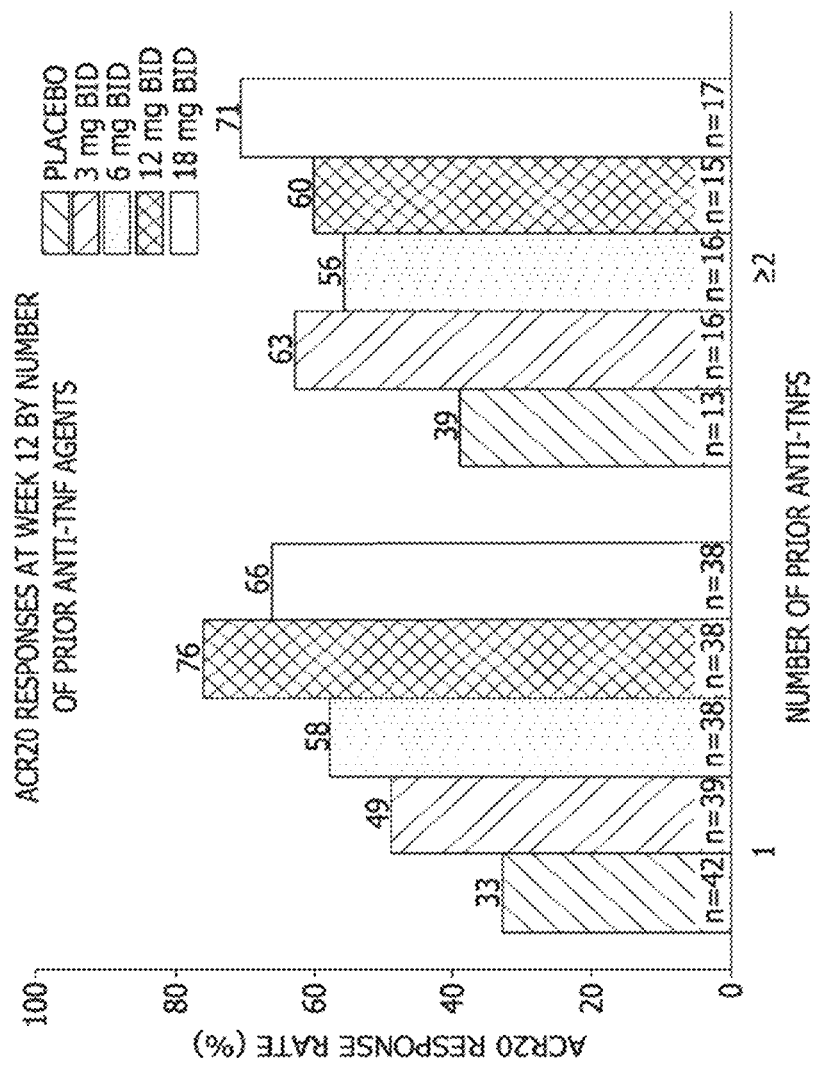

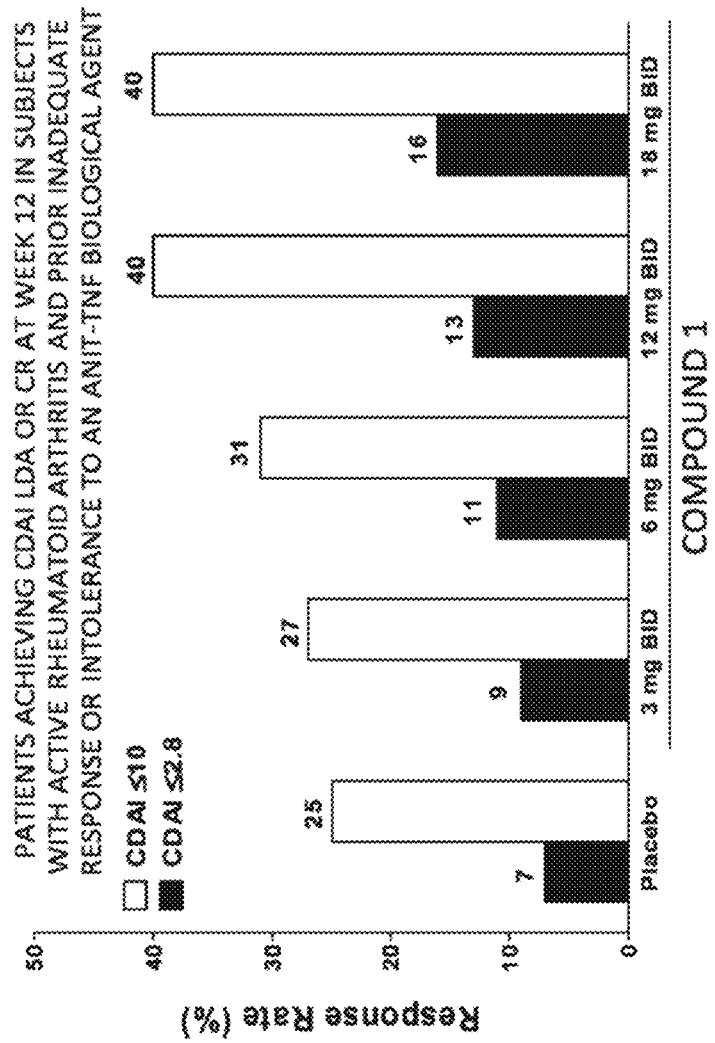

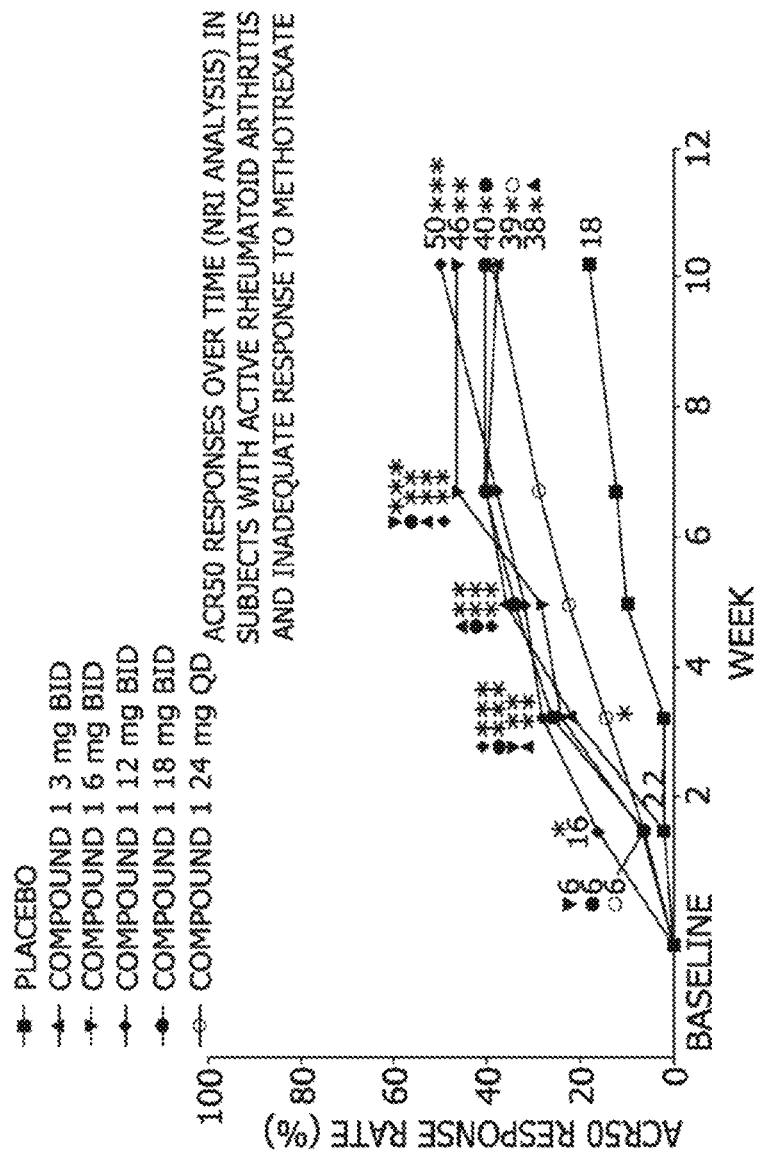

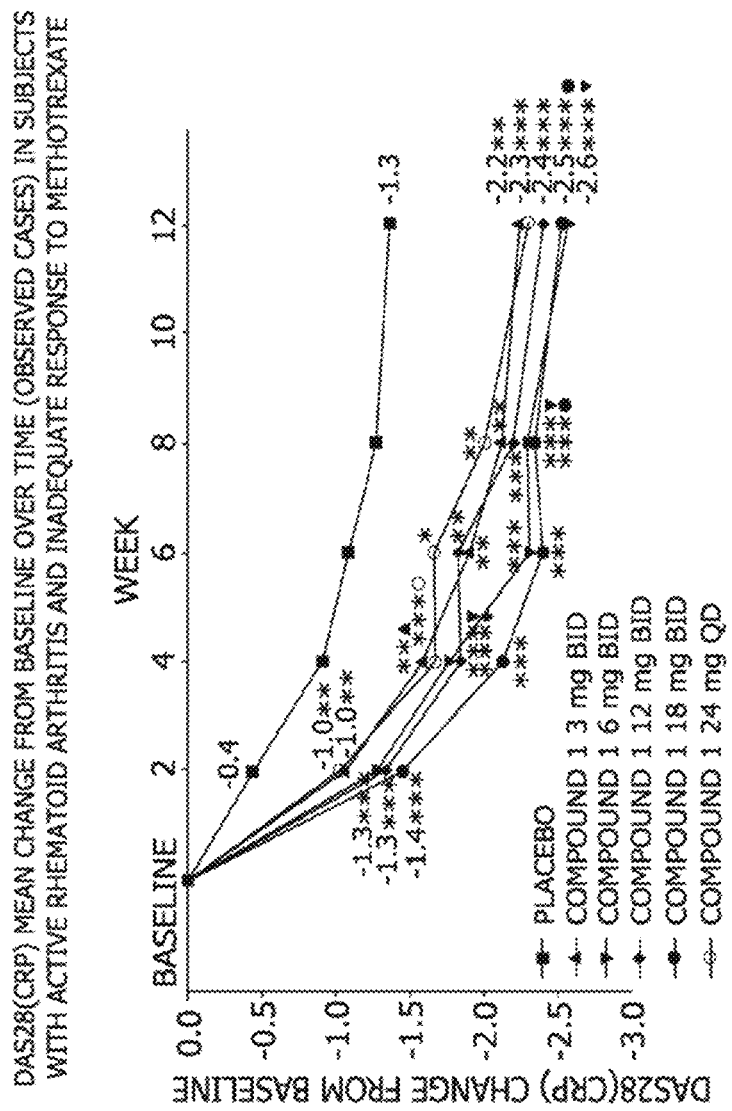

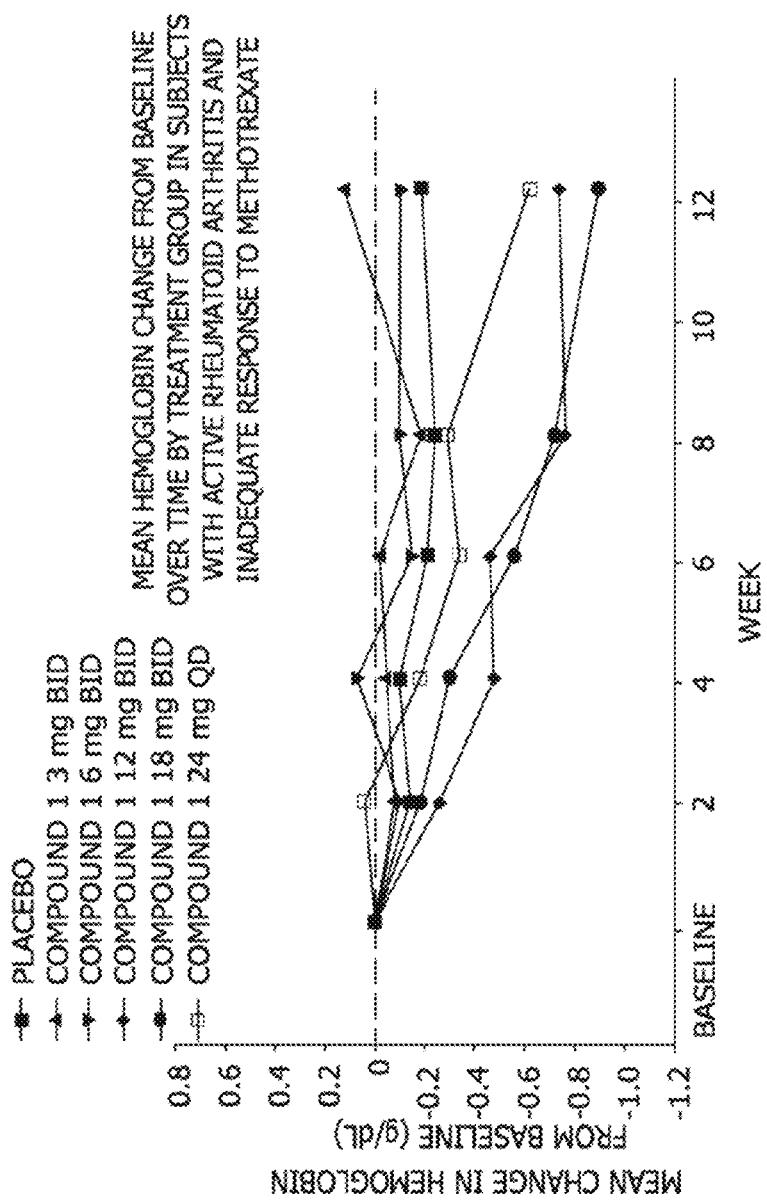

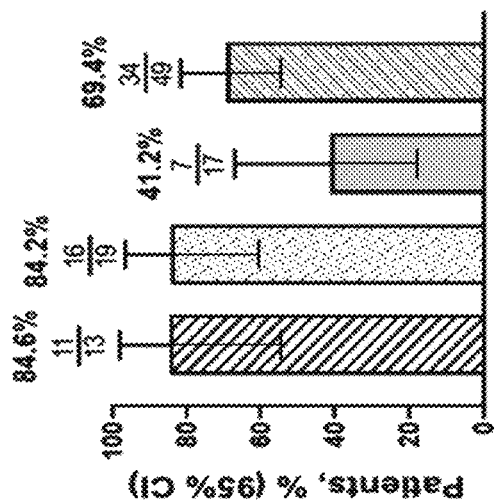
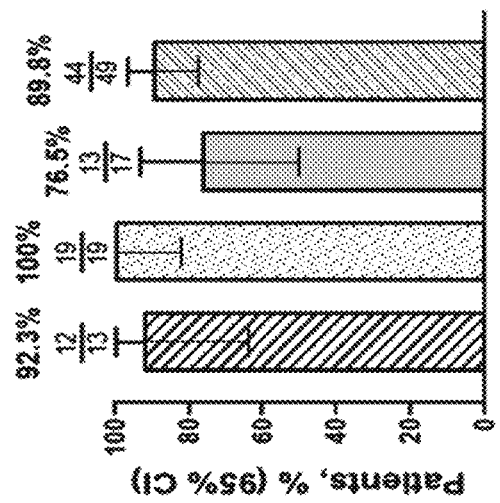
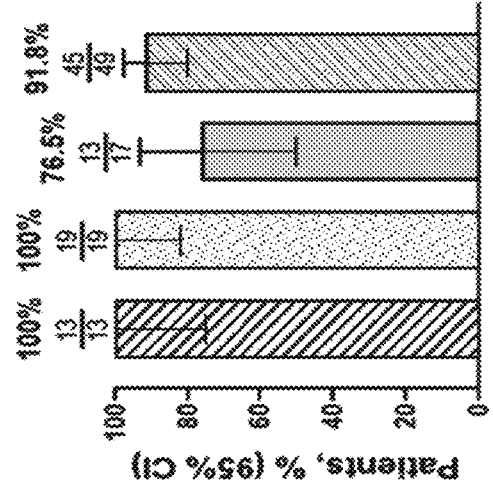

[a] Negative change from baseline indicates improvement in health or disease activity.

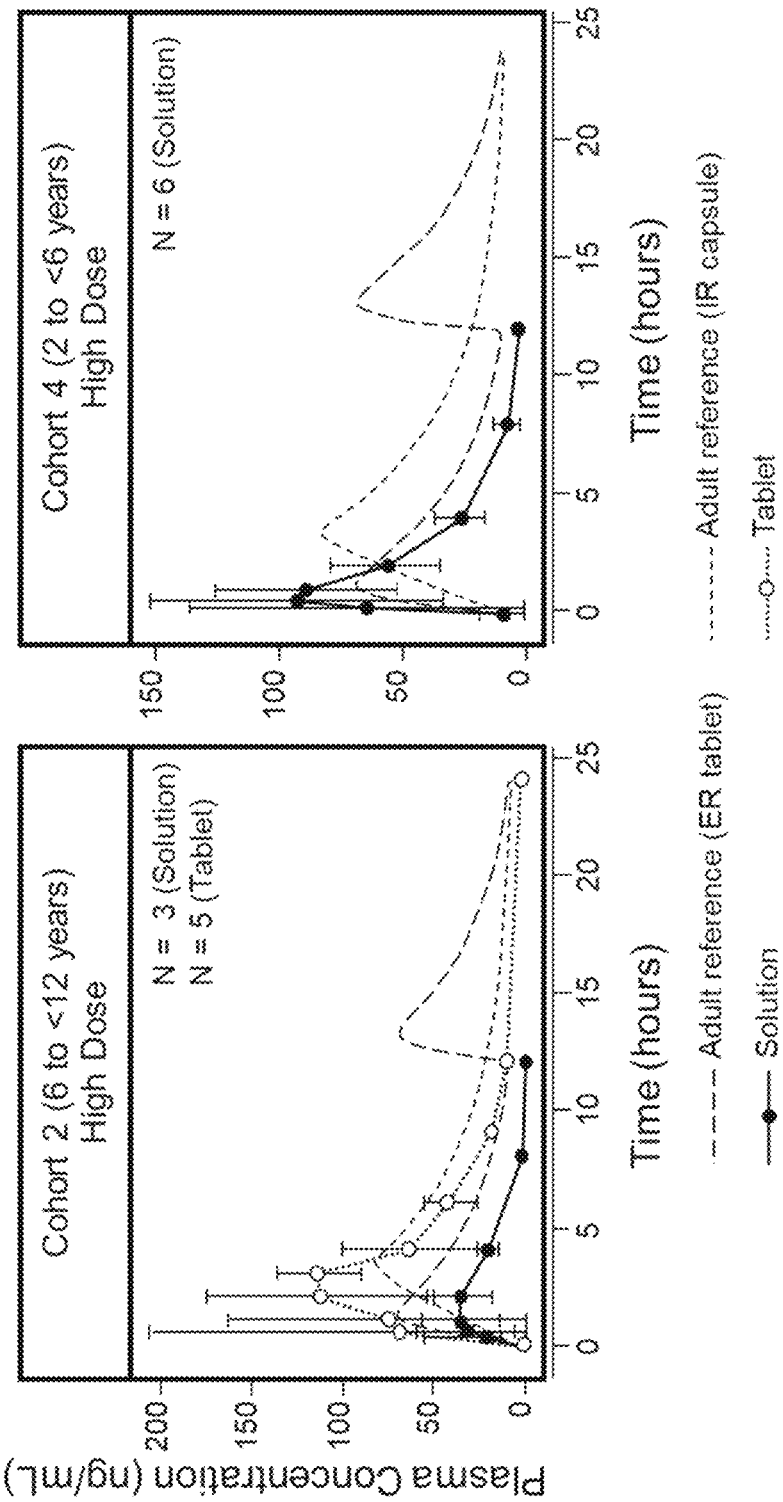

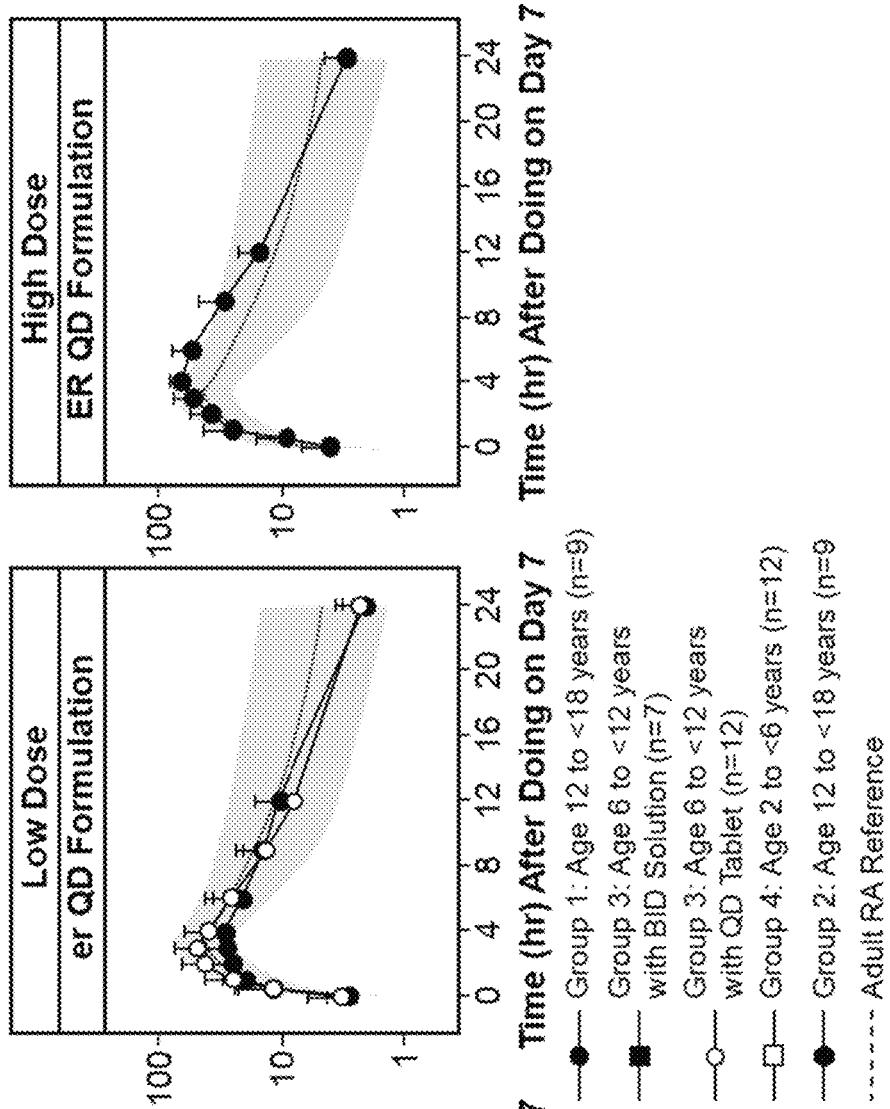

[b]Negative change from baseline indicates improvement in health or disease activity.

PROCESSES FOR THE PREPARATION OF (3S,4R)-3-ETHYL-4-(3H-IMIDAZO[1,2-A]PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

CROSS-REFERENCE TO RELATED APPLICATIONS

This application is a continuation-in-part of U.S. patent application Ser. No. 18/812,217, filed Aug. 22, 2024; which is a continuation of U.S. patent application Ser. No. 18/533,564, filed Dec. 8, 2023; which is a continuation of U.S. patent application Ser. No. 18/137,804, filed Apr. 21, 2023; which is a continuation of U.S. patent application Ser. No. 17/902,690, filed Sep. 2, 2022; which is a continuation of U.S. patent application Ser. No. 17/184,194, filed Feb. 24, 2021; which is a continuation of U.S. patent application Ser. No. 16/656,237, filed Oct. 17, 2019; which is a continuation of U.S. patent application Ser. No. 15/891,012, filed Feb. 7, 2018; which is a continuation of U.S. patent application Ser. No. 15/295,561, filed Oct. 17, 2017; and which claims the benefit of U.S. Provisional Application No. 62/242,797, filed Oct. 16, 2015; and claims the benefit of U.S. Provisional Application No. 62/267,672, filed Dec. 15, 2015; and claims the benefit of U.S. Provisional Application No. 62/301,537, filed Feb. 29, 2016; and claims the benefit of U.S. Provisional Application No. 62/352,380, filed Jun. 20, 2016; all of which are herein incorporated by reference in their entirety. This application is also a continuation-in-part of U.S. patent application Ser. No. 18/612,955, filed Mar. 21, 2024, and which claims the benefit of U.S. Provisional Application No. 63/623,994, filed Jan. 23, 2024; and claims the benefit of U.S. Provisional Application No. 63/491,665, filed Mar. 22, 2023, all of which are herein incorporated by reference in their entirety and for all purposes.

FIELD OF THE INVENTION

The present disclosure relates to: (a) processes for the preparation of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (referred to herein as "Compound 1"), (b) intermediates used in the preparation of Compound 1 and processes for preparing the intermediates; (c) solid-state forms of Compound 1, (d) pharmaceutical compositions comprising one or more solid-state forms of Compound 1, and, optionally, one or more additional therapeutic agents; (e) methods of treating Janus kinase-associated conditions (including rheumatoid arthritis) by administering one or more solid-state forms of Compound 1 to a subject in need thereof; (f) kits comprising a first pharmaceutical composition comprising a solid-state form of Compound 1, and, optionally, a second pharmaceutical composition comprising one or more additional therapeutic agents; (g) methods for the preparation of solid-state forms of Compound 1; and (h) solid-state forms of Compound 1 prepared in accordance with such methods.

The present disclosure further relates to methods for treating disease in pediatric patients with the JAK1 selective inhibitor upadacitinib.

BACKGROUND OF THE INVENTION (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide ("Compound 1"; "upadacitinib") was first disclosed in International Application WO2011/068881A1, which is herein incorporated by reference in its entirety. The compound has activity as a Janus kinase ("JAK") inhibitor, particularly as a JAK-1 inhibitor.

Upadacitinib is a JAK1 selective inhibitor approved for the treatment of rheumatoid arthritis, psoriatic arthritis, ankylosing spondylitis, non-radiographic spondyloarthritis, and ulcerative colitis in adults, and the treatment of atopic dermatitis in adults and adolescents 12 years of age and older and weighing 40 kg or more. Upadacitinib is also under investigation for use in treating adults having Crohn's disease, hidradenitis suppurativa and systemic lupus erythematosus. Upadacitinib has not been evaluated for the treatment of pediatric patients under 12 years of age or under 18 years of age and weighing less than 40 kg.

While the pharmacokinetics, safety, and tolerability of upadacitinib in adults is known, the pharmacokinetics, safety, and tolerability of upadacitinib in pediatric patients under 12 years of age or under 18 year of age and weighing less than 40 kg has not been studied. Because the above identified diseases also occur in pediatric patients, it is desirable in the art to provide safe and efficacious doses of upadacitinib in pediatric patients. In particular, it is desirable to establish weight-based dosing regimens which provide comparable plasma exposure in pediatric patients to doses determined as efficacious in adults (i.e., 15 mg and 30 mg QD). In addition, tablet formulations may be difficult for younger pediatric patients to swallow, which may result in poor patient compliance and reduced therapeutic efficacy.

SUMMARY OF THE INVENTION

In one aspect, the present disclosure relates to pharmaceutical compositions comprising one or more solid-state forms of Compound 1, and, optionally, one or more additional therapeutic agents.

In another aspect, the present disclosure relates to methods of treating a JAK-associated condition (such as rheumatoid arthritis) in a human subject suffering from or susceptible to such a condition comprising administering to the subject a therapeutically effective amount of a solid-state form of Compound 1. In another aspect, the disclosure relates to a pharmaceutical composition comprising a therapeutically effective amount of a solid-state form of Compound 1 as described in the present disclosure, for use in treatment of a JAK-associated condition (such as rheumatoid arthritis) in a subject, particularly in a human subject suffering from or susceptible to the condition.

In another aspect, the present disclosure relates to methods of treating rheumatoid arthritis, wherein the term "rheumatoid arthritis" includes juvenile rheumatoid arthritis, juvenile idiopathic arthritis, ankylosing spondylitis disease, Sjogren's syndrome, psoriatic arthritis.

In another aspect, the present disclosure relates to methods of treating inflammatory bowel disease, wherein the term "inflammatory bowel disease" includes Crohn's disease, pediatric Crohn's disease and ulcerative colitis.

In another aspect, the present disclosure relates to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis and systemic lupus erythematosus in a human subject suffering from or susceptible to such a condition, the method comprising administering to the subject a therapeutically effective amount a solid-state form of Compound 1. In another aspect, the disclosure relates to a pharmaceutical composition comprising a therapeutically effective amount of a solid-state form of Compound 1 as described in the present disclosure, for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition.

In another aspect, the present disclosure relates to methods of treating a JAK-associated condition (such as rheumatoid arthritis) in a human subject suffering from or susceptible to such a condition comprising administering to the subject a solid-state form of Compound 1, in combination with one or more additional therapeutic agents (e.g., a therapeutic agent for treating rheumatoid arthritis that is not a JAK inhibitor). In another aspect, the disclosure relates to a pharmaceutical composition comprising a solid-state form of Compound 1, as described in the present disclosure, in combination with one or more additional therapeutic agents (e.g., a therapeutic agent for treating rheumatoid arthritis that is not a JAK inhibitor), for use in treatment of a JAK-associated condition (such as rheumatoid arthritis) in a subject, particularly in a human subject suffering from or susceptible to the condition.

In another aspect, the present disclosure relates to a method of treating moderate to severely active rheumatoid arthritis, the method comprising administering a therapeutically effective amount of Compound 1 in one or more forms as disclosed herein to a subject suffering from or susceptible to the condition. In a particular aspect, such a method may comprise administering 7.5 mg once daily or 15 mg once daily, or 30 mg once daily, or 45 mg once daily of the Compound 1, in one or more forms as disclosed herein, to the subject. In this or another particular aspect, the subject may be administered the Compound 1 in Freebase Form C. In this or yet another particular aspect, the subject may have an inadequate response to methotrexate. In this or yet another particular aspect, the subject may have an inadequate response to biologics medicines approved for rheumatoid arthritis. In this or yet another particular aspect, the subject may have not previously been administered biologics medicines approved for rheumatoid arthritis.

In another aspect, the present disclosure relates to a method of treating an adult subject having moderate to severely active rheumatoid arthritis, the method comprising administering to the subject: a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent. In one embodiment, the present disclosure is directed to a pharmaceutical composition for use in treating an adult subject having moderate to severely active rheumatoid arthritis, the use comprising administering the pharmaceutical composition to the subject, wherein the pharmaceutical composition comprises a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent.

In another embodiment, the present disclosure relates to a method of treating structural damage associated with rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened. In one embodiment, the disclosure relates to a pharmaceutical composition for use in treating structural damage associated with rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened.

In another aspect, the disclosure is directed to a method of treating moderate to severely active rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating. In one embodiment, the disclosure is directed to a pharmaceutical composition for use in treating moderate to severely active rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating.

In another aspect, the disclosure is directed to a method of reducing signs and symptoms of rheumatoid arthritis in an adult subject with moderately to severely active rheumatoid arthritis, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent. In one embodiment, the disclosure is directed to a pharmaceutical composition for use in reducing signs and symptoms of rheumatoid arthritis in an adult subject with moderately to severely active rheumatoid arthritis, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of Compound 1 freebase, or a crystalline hydrate of Compound 1 in an amount sufficient to deliver to the subject about 7.5 mg, or about 15 mg, or about 30 mg, or about 45 mg of Compound 1 freebase equivalent. In this or another particular aspect, the hydrate may be a hemihydrate. In this or another aspect, the hemihydrate may be Freebase Hydrate Form C. In this or yet another particular aspect, the subject may have an inadequate response or tolerance to one or more disease-modifying antirheumatic drugs (DMARDS), such as methotrexate. In this or yet another particular aspect, the subject may have not previously been administered DMARDS. In this or yet another particular aspect, the subject may further be administered one or more DMARD.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg per day of Compound 1 freebase or a crystalline hydrate of Compound 1 in an amount sufficient to deliver to the subject about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 15 mg per day of Compound 1 freebase or a crystalline hydrate of Compound 1 in an amount sufficient to deliver to the subject about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 30 mg per day of Compound 1 freebase or a crystalline hydrate of Compound 1 in an amount sufficient to deliver to the subject about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 45 mg per day of Compound 1 freebase or a crystalline hydrate of Compound 1 in an amount sufficient to deliver to the subject about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of a crystalline hydrate of Compound 1. In this or another particular aspect, the hydrate may be a hemihydrate. In this or another aspect, the hemihydrate may be Freebase Hydrate Form C.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of a crystalline hydrate of Compound 1, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of a crystalline hydrate of Compound 1, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg, or about 15 mg, or about 30 mg, or about 45 mg per day of a crystalline hydrate of Compound 1. In this or another particular aspect, the hydrate may be a hemihydrate. In this or another aspect, the hemihydrate may be Freebase Hydrate Form C.

In another aspect, the present disclosure is directed to an extended-release formulation for oral administration comprising Compound 1 or a pharmaceutically acceptable salt thereof, a hydrophilic polymer, and a pH modifier, wherein the hydrophilic polymer, in contact with water, forms a gel layer that provides an environment suitable for Compound 1 and the pH modifier to dissolve.

The present disclosure further provides methods for treating a disease or disorder in a pediatric patient in need thereof with upadacitinib. The diseases and disorders include idiopathic arthritis (pcJIA), systemic juvenile idiopathic arthritis (SJIA), juvenile psoriatic arthritis (JPsA), atopic dermatitis (AD), juvenile ankylosing spondylitis (JAS), juvenile non-radiographic spondyloarthritis (nr-axSpA), hidradenitis suppurativa (HS), systemic lupus erythematosus (SLE), ulcerative colitis (UC), and Crohn's disease (CD). The treatment methods generally comprise administering to a pediatric patient a therapeutically effective amount of upadacitinib as a stable liquid pharmaceutical composition or solid dosage form, at a dose based on patient body weight. Specifically, provided herein are methods of treating pediatric patients in need thereof with a therapeutically effective amount of upadacitinib, in an amount based on body weight category, as either a twice-daily stable liquid pharmaceutical composition or as a once-daily extended-release tablet.

In one aspect is provided a method for treating polyarticular course juvenile idiopathic arthritis (pcJIA) in a pediatric patient, the method comprising administering a therapeutically effective amount of upadacitinib to the pediatric patient. In some embodiments, the therapeutically effective amount of upadacitinib is administered to the pediatric patient as a stable liquid pharmaceutical composition. In some embodiments, the therapeutically effective amount of upadacitinib is administered to the pediatric patient as a solid dosage form.

In some embodiments, the pediatric patient has a body weight in a range from about 10 kg to less than about 20 kg, the method comprising administering a therapeutically effective amount of upadacitinib, wherein:
  (i) the upadacitinib is administered twice daily at a dose of 3 mg each (3 mg BID); or
  (ii) the upadacitinib is administered twice daily at a dose of 6 mg each (6 mg BID).

In some embodiments, the pediatric patient has a body weight in a range from about 20 kg to less than about 30 kg, the method comprising administering a therapeutically effective amount of upadacitinib to the pediatric patient, wherein:
  (i) the upadacitinib is administered twice daily at a dose of 4 mg each (4 mg BID); or
  (ii) the upadacitinib is administered twice daily at a dose of 8 mg each (8 mg BID).

In some embodiments, the pediatric patient has a body weight of about 30 kg or greater, the method comprising administering a therapeutically effective amount of upadacitinib to the pediatric patient, wherein:
  (i) the upadacitinib is administered twice daily at a dose of 6 mg each (6 mg BID); or
  (ii) the upadacitinib is administered twice daily at a dose of 8 mg each (8 mg BID).

In some embodiments, the pediatric patient has a body weight of about 30 kg or greater, the method comprising administering a therapeutically effective amount of upadacitinib to the pediatric patient, wherein:
  (i) the upadacitinib is administered twice daily at a dose of 6 mg each (6 mg BID); or
  (ii) the upadacitinib is administered twice daily at a dose of 12 mg each (12 mg BID).

In some embodiments, if the pediatric patient has a body weight in a range from about 10 kg to less than about 20 kg, the method comprises administering upadacitinib twice daily at a dose of 3 mg each (3 mg BID); if the pediatric patient has a body weight in a range from about 20 kg to less than about 30 kg, the method comprises administering upadacitinib twice daily at a dose of 4 mg each (4 mg BID); and if the pediatric patient has a body weight of about 30 kg or greater, the method comprises administering upadacitinib twice daily at a dose of 6 mg each (6 mg BID) or once daily at a dose of 15 mg (15 mg QD).

In some embodiments, if the pediatric patient has a body weight in a range from about 10 kg to less than about 20 kg, the method comprises administering upadacitinib twice daily at a dose of 6 mg each (6 mg BID); if the pediatric patient has a body weight in a range from about 20 kg to less than about 30 kg, the method comprises administering upadacitinib twice daily at a dose of 8 mg each (8 mg BID); and if the pediatric patient has a body weight of about 30 kg or greater, the method comprises administering upadacitinib twice daily at a dose of 8 mg each (8 mg BID) or once daily at a dose of 30 mg (30 mg QD).

In some embodiments, if the pediatric patient has a body weight in a range from about 10 kg to less than about 20 kg, the method comprising administering upadacitinib twice daily at a dose of 6 mg each (6 mg BID); if the pediatric patient has a body weight in a range from about 20 kg to less than about 30 kg, the method comprises administering upadacitinib twice daily at a dose of 8 mg each (8 mg BID); and if the pediatric patient has a body weight of about 30 kg or greater, the method comprises administering upadacitinib twice daily at a dose of 12 mg each (12 mg BID) or once daily at a dose of 30 mg (30 mg QD).

In some embodiments, the therapeutically effective amount of upadacitinib is administered to the pediatric patient as a stable oral pharmaceutical solution.

In some embodiments, the twice daily at a dose of 3 mg of upadacitinib, the twice daily at a dose of 4 mg of upadacitinib, the twice daily at a dose of 6 mg of upadacitinib, the twice daily at a dose of 8 mg of upadacitinib, or the twice daily at a dose of 12 mg of upadacitinib is administered to the pediatric patient as a stable oral pharmaceutical solution.

In some embodiments, the oral solution comprises upadacitinib, a buffer and/or pH adjusting agent, a preservative, a sweetener, and water.

In some embodiments, the oral solution comprises upadacitinib at a concentration of about 0.5 mg/mL.

In some embodiments, the oral solution comprises upadacitinib at a concentration of about 1 mg/mL.

In some embodiments, the pediatric patient has a body weight of about 30 kg or greater, the method comprising administering a therapeutically effective amount of upadacitinib to the pediatric patient, wherein:
  (i) the upadacitinib is administered once daily at a dose of 15 mg (15 mg QD); or
  (ii) the upadacitinib is administered once daily at a dose of 30 mg (30 mg QD).

In some embodiments, the therapeutically effective amount of upadacitinib is administered to the pediatric patient as an extended-release tablet.

In some embodiments, the pcJIA is rheumatoid factor-positive or rheumatoid factor-negative polyarticular JIA.

In some embodiments, the pediatric patient has a history of arthritis affecting at least 5 joints within the first 6 months of disease.

In some embodiments, the pediatric patient does not have a diagnosis of enthesitis-related arthritis (ERA) or juvenile psoriatic arthritis (JPSA).

In some embodiments, the pediatric patient has:
  a) 5 or more active joints as defined by the presence of swollen joints not due to deformity; or b) in the absence of swelling, joints with limitation of movement (LOM) plus pain on motion and/or tenderness with palpation, with LOM present in at least three of the active joints.

In some embodiments, the pediatric patient is receiving a stable dose of ≤20 mg/m$^2$ of methotrexate for at least 8 weeks before the start of administration.

In some embodiments, the pediatric patient is receiving a stable dose of oral glucocorticoids no greater than 10 mg/day or 0.2 mg/kg/day, whatever is lower, for at least 1 week before the start of administration.

In some embodiments, the pediatric patient achieves one or more of: a JIA ACR pediatric 30/50/70/90/100 response, a change from baseline in JADAS10/27/71 responses, low disease activity according to JADAS-based criteria, or remission according to JADAS-based criteria. In some embodiments, the pediatric patient achieves one or more of: a JIA ACR pediatric 30/50/70/90/100 response, a change from baseline in JADAS10/27/71 responses, low disease activity according to JADAS-based criteria, or remission according to JADAS-based criteria is achieved at 8 weeks, 10 weeks, 12 weeks, 14 weeks, 16 weeks, 18 weeks, 20 weeks, 22 weeks, 24 weeks, 48 weeks, or 52 weeks after the first daily administration. In some embodiments, the pediatric patient achieves a JIA ACR pediatric 30 response at 12 weeks after the first daily administration. In some embodiments, the pediatric patient achieves a JIA ACR pediatric 50 response at 12 weeks after the first daily administration. In some embodiments, the pediatric patient achieves a JIA ACR pediatric 70 response at 12 weeks after the first daily administration. In some embodiments, the pediatric patient achieves a JIA ACR pediatric 90 response at 12 weeks after the first daily administration. In some embodiments, the pediatric patient achieves a JIA ACR pediatric 100 response at 12 weeks after the first daily administration.

In some embodiments, the pediatric patient achieves a JIA ACR pediatric 30 response at 24 weeks after the first daily administration. In some embodiments, the pediatric patient achieves a JIA ACR pediatric 50 response at 24 weeks after the first daily administration. In some embodiments, the pediatric patient achieves a JIA ACR pediatric 70 response at 24 weeks after the first daily administration. In some embodiments, the pediatric patient achieves a JIA ACR pediatric 90 response at 24 weeks after the first daily administration. In some embodiments, the pediatric patient achieves a JIA ACR pediatric 100 response at 24 weeks after the first daily administration.

In some embodiments, the pediatric patient achieves a JIA ACR pediatric 30 response at 48 weeks after the first daily administration. In some embodiments, the pediatric patient achieves a JIA ACR pediatric 50 response at 48 weeks after the first daily administration. In some embodiments, the pediatric patient achieves a JIA ACR pediatric 70 response at 48 weeks after the first daily administration. In some embodiments, the pediatric patient achieves a JIA ACR pediatric 90 response at 48 weeks after the first daily administration. In some embodiments, the pediatric patient achieves a JIA ACR pediatric 100 response at 48 weeks after the first daily administration.

In yet another aspect is provided a stable oral pharmaceutical formulation comprising upadacitinib or a pharmaceutically acceptable salt or solid-state form thereof, a buffer and/or pH adjusting agent, a preservative, a sweetener, and water.

In some embodiments, the stable oral pharmaceutical formulation comprises the anhydrous free base upadacitinib at a concentration of about 0.5 mg/mL.

In some embodiments, the stable oral pharmaceutical formulation comprises the anhydrous free base upadacitinib at a concentration of about 1 mg/mL.

In some embodiments, the buffer is selected from the group consisting of citrate, phosphate, tartrate, succinate, formate, acetate, and combinations thereof.

In some embodiments, the pH adjusting agent is selected from the group consisting of citric acid, phosphoric acid, tartaric acid, succinic acid, formic acid, acetic acid, and combinations thereof.

In some embodiments, the preservative is selected from the group consisting of sodium benzoate, benzoic acid, propyl paraben, sodium metabisulfite, potassium sorbate, para-hydroxybenzoic acid, para-hydroxybenzoate, and combinations thereof.

In some embodiments, the sweetener selected from the group consisting of sucralose, acesulfame potassium, sodium saccharin, neotame, sucrose, maltitol, xylitol, and combinations thereof.

In some embodiments, the stable oral pharmaceutical formulation comprises anhydrous free base upadacitinib, citric acid, sodium citrate, sodium benzoate, sucralose, and water.

In some embodiments, the stable oral pharmaceutical solution has a pH in a range from about 2 to about 5. In some embodiments, the stable oral pharmaceutical solution has a pH in a range from about 3 to about 4. In some embodiments, the stable oral pharmaceutical solution has a pH in a range from about 2.5 to about 3.5.

BRIEF DESCRIPTION OF THE DRAWINGS

FIG. 1A shows the ACR20, ACR50, and ACR70 response rate at week 12 following administration of placebo or various doses of Compound 1 to subjects with active rheumatoid arthritis and prior inadequate response or intolerance to an anti-TNF biologic agent (*P<0.05; P<0.01; *P<0.001 relative to placebo; modified intent-to-treat population (NRI)). FIG. 1B shows the ACR20 response rate at week 12 in the same population, broken down by number of prior anti-TNF biologic agents.

FIG. 2F shows the subjects achieving low disease activity (LDA) or clinical remission (CR) based on clinical disease activity index (CDAI) criteria (LDA is CDAI≤10; CR is CDAI≤2.8) at week 12 in the same population.

FIGS. 7A-7D show the ACR20 (FIG. 7A, NRI analysis), ACR50 (FIG. 7B, NRI analysis), and ACR70 (FIG. 7C, NRI analysis) responses or DAS28(CRP) mean change from baseline (FIG. 7D, observed cases) over time following administration of placebo or various doses of Compound 1 to subjects with active rheumatoid arthritis and inadequate response to methotrexate (*P<0.05; P<0.01; *P<0.001 relative to placebo; modified intent-to-treat population).

FIGS. 9A-9C show the mean change in hemoglobin from baseline over time by treatment group in all subjects (FIG. 9A), subjects with hsCRP≤5 mg/mL at baseline (FIG. 9B), and subjects with hsCRP>5 mg/mL at baseline (FIG. 9C) following administration of placebo or various doses of Compound 1 to subjects with active rheumatoid arthritis and inadequate response to methotrexate (safety population with observed data (no imputation of missing values)).

FIGS. 12A-12E are graphical depictions of efficacy of upadacitinib at week 12 according to various measures and stratified by age group in pediatric polyarticular course juvenile idiopathic arthritis patients according to non-limiting embodiments of the disclosure.

FIGS. 14A to 14D are graphical depictions of mean upadacitinib plasma concentration-time profiles in pediatric atopic dermatitis patients according to non-limiting embodiments of the disclosure.

FIGS. 17A to 17C are graphical depictions of mean upadacitinib plasma concentration-time profiles in pediatric polyarticular course juvenile idiopathic arthritis patients for various formulations according to non-limiting embodiments of the disclosure.

DETAILED DESCRIPTION OF THE INVENTION

Figure 2B:
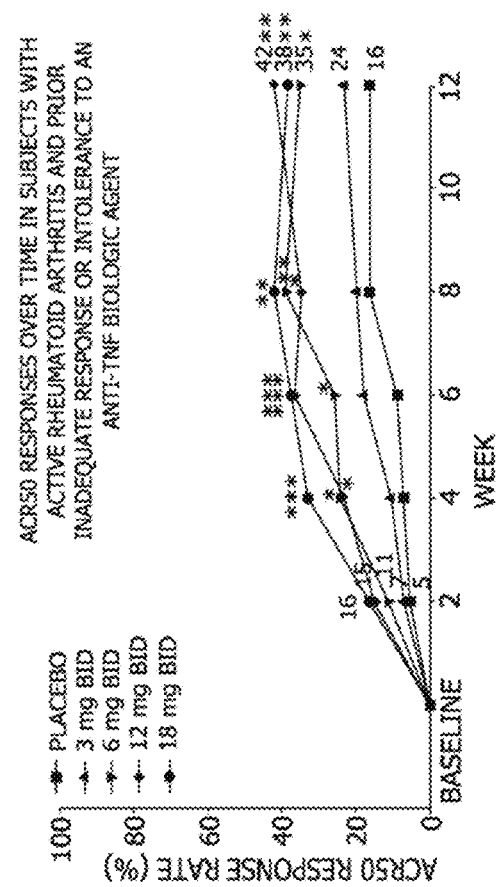
FIGS. 2A-2D show the ACR20 (FIG. 2A), ACR50 (FIG. 2B), and ACR70 (FIG. 2C) responses or DAS28(CRP) mean change from baseline (FIG. 2D) over time following administration of placebo or various doses of Compound 1 to subjects with active rheumatoid arthritis and prior inadequate response or intolerance to an anti-TNF biologic agent (*P<0.05; P<0.01; *P<0.001 relative to placebo; modified intent-to-treat population (NRI)).

This written description uses examples to disclose the invention and also to enable any person skilled in the art to practice the invention, including making and using any of the disclosed solid-state forms or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. Definitions

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "AUC" refers to the area under the curve. AUC is the definite integral of a curve that describes the variation of a drug concentration in blood plasma as a function of time.

The term "$C_{max}$" refers to the plasma concentration of the referent drug at $T_{max}$, expressed herein as ng/mL, produced by the oral ingestion of a single dose, or indicated number of doses, of the dosage form or pharmaceutical composition, such as the dosage forms and compositions of the present disclosure. Unless specifically indicated, $C_{max}$ refers to the overall maximum observed concentration.

The term "pharmaceutically acceptable" (such as in the recitation of a "pharmaceutically acceptable salt" or a "pharmaceutically acceptable diluent") refers to a material that is compatible with administration to a human subject, e.g., the material does not cause an undesirable biological effect. Examples of pharmaceutically acceptable salts are described in "Handbook of Pharmaceutical Salts: Properties, Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7th Ed., 2012). "Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, mono-malic acid, mono oxalic acid, tartaric acid such as mono tartaric acid (e.g., (+) or (−)-tartaric acid or mixtures thereof), amino acids (e.g., (+) or (−)-amino acids or mixtures thereof), and the like. These salts can be prepared by methods known to those skilled in the art. Examples of pharmaceutically acceptable salts of upadacitinib may be found in WO 2017/066775, which is hereby incorporated by reference in its entirety.

The term "subject" refers to a human subject.

A "population of subjects" refers to the group of subjects participating in a clinical trial, with all subjects suffering from the same disease or symptom to be treated, wherein the clinical trial comprises a treatment arm (a subgroup of the subjects treated with the JAK1 inhibitor), and a placebo arm (a subgroup of the subjects not treated with the JAK1 inhibitor). When used in connection with the treatment of a population of subjects, the phrase "at least X % of the subjects in the treated population achieve" a particular response refers to the placebo corrected X % response (subjects treated—subjects not treated).

As used herein, the term "pediatric patient" refers to a human patient of less than 18 years old. The terms "patient" and "subject" are used interchangeably herein.

The terms "treating" and "treatment" refer to ameliorating, suppressing, eradicating, reducing the severity of, decreasing the frequency of incidence of, preventing, reducing the risk of, slowing the progression of damage caused by or delaying the onset of the condition or improving the quality of life of a patient suffering from the condition.

The abbreviation "% CV" refers to the coefficient of variation, expressed as a percent. % CV is calculated according to the following equation: % CV=(SD/x)*100, wherein x is the mean value and SD is the standard deviation.

As used herein, the term "entry into a use environment" means contact of a formulation of the disclosure with the gastric fluids of the subject to whom it is administered, or with a fluid intended to simulate gastric fluid.

The abbreviation "MTX" refers to methotrexate.

The term "upadacitinib freebase" refers to freebase (non-salt, neutral) forms of upadacitinib. Examples of upadacitinib freebase solid-state forms include amorphous upadacitinib freebase and crystalline freebases of upadacitinib, such as crystalline freebase solvates, crystalline freebase hydrates, crystalline freebase hemihydrates, and crystalline freebase anhydrates of upadacitinib. Specific examples of upadacitinib freebase solid-state forms include but are not limited to Amorphous Upadacitinib Freebase, Upadacitinib Freebase Solvate Form A, Upadacitinib Freebase Hydrate Form B, Upadacitinib Freebase Hydrate Form C (which is a hemihydrate), and Upadacitinib Freebase Anhydrate Form D, each as described in WO 2017/066775 and WO 2018/165581.

The term "upadacitinib freebase equivalent" amount of the neutral upadacitinib freebase (active ingredient) administered, and not including any coformer (e.g., solvent or water molecule(s)) of a solvate or hydrate (including hemihydrate), and not including any pharmaceutically acceptable salt counteranions of a pharmaceutically acceptable salt. For example, 15.4 mg of crystalline upadacitinib freebase hemihydrate (which includes ½ of a water conformer molecule per upadacitinib freebase molecule) delivers 15 mg of upadacitinib freebase equivalent, while 30.7 mg of crystalline upadacitinib freebase hemihydrate (which includes ½ of a water conformer molecule per upadacitinib freebase molecule) delivers 30 mg of upadacitinib freebase equivalent.

II. Methods of Treatment

The present disclosure relates to methods of treating a JAK-associated condition in a subject, particularly a human subject suffering from or susceptible to the condition, comprising administering to the subject a therapeutically effective amount of Compound 1 freebase or a pharmaceutically acceptable salt thereof or one or more solid-state forms of Compound 1 as described in the present disclosure. Another aspect of the disclosure relates to Compound 1 freebase or a pharmaceutically acceptable salt thereof or one or more solid-state forms of Compound 1 as described in the present disclosure for use in treatment of a JAK-associated condition in a subject, particularly in a human subject suffering from or susceptible to the condition, the use comprising administering to the subject a therapeutically effective amount of Compound 1 freebase or a pharmaceutically acceptable salt thereof or one or more solid-state forms of Compound 1. In one aspect, the condition is a JAK-1-associated condition. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of immunomodulation, inflammation, and proliferative disorders (such as cancer) in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of immunomodulation, inflammation, and proliferative disorders (such as cancer) in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Anhydrate Form D. In another aspect, the solid-state form is the Freebase Hydrate Form B. In another aspect, the solid-state form is the Freebase Hydrate Form C. In another aspect, the solid-state form is the Tartrate Hydrate.

In one embodiment, the present disclosure relates to methods of treating a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune haemolytic anaemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopaenia in a subject, wherein the method comprises administering to the subject, particularly a human subject suffering from or susceptible to the condition, a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune haemolytic anaemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopaenia in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition, the use comprising administering to the subject a therapeutically effective amount of Compound 1 freebase or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid-state form of Compound 1. In one aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D.

In one embodiment, the present disclosure relates to methods of treating arthritis in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of arthritis in a subject, particularly in a human subject suffering from or susceptible to arthritis, the use comprising administering to the subject a therapeutically effective amount of Compound 1 freebase or a pharmaceutically acceptable salt thereof or a solid-state form of Compound 1. In one aspect, the arthritis is selected from the group consisting of rheumatoid arthritis, juvenile idiopathic arthritis, and psoriatic arthritis. In another aspect, the arthritis is rheumatoid arthritis. In another aspect, the arthritis is juvenile idiopathic arthritis. In another aspect, the arthritis is psoriatic arthritis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

In one embodiment, the present disclosure relates to methods of treating a spondyloarthropathy in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of spondyloarthropathy, particularly in a human subject suffering from or susceptible to spondyloarthropathy, the use comprising administering to the subject a therapeutically effective amount of Compound 1 freebase or a pharmaceutically acceptable salt thereof or a solid-state form of Compound 1. In one aspect, the spondyloarthropathy is ankylosing spondylitis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

In one embodiment, the present disclosure relates to methods of treating a gastrointestinal condition in a subject, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a gastrointestinal condition, particularly in a human subject suffering from or susceptible to a gastrointestinal condition, the use comprising administering to the subject a therapeutically effective amount of Compound 1 freebase or a pharmaceutically acceptable salt thereof or a solid-state form of Compound 1. In one aspect, the gastrointestinal condition is selected from the group consisting of Crohn's disease and ulcerative colitis. In another aspect, the gastrointestinal condition is Crohn's disease. In another aspect, the gastrointestinal condition is ulcerative colitis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

In one embodiment, the present disclosure relates to methods of treating a skin condition, wherein the method comprises administering to the subject a therapeutically effective amount of Compound 1 freebase or a pharmaceutically acceptable salt thereof or a solid-state form of Compound 1. In another aspect, the present disclosure relates to Compound 1 freebase or a pharmaceutically acceptable salt thereof or a solid-state form of Compound 1 for use in treatment of a skin condition, particularly in a human subject suffering from or susceptible to a skin condition, the use comprising administering to the subject a therapeutically effective amount of Compound 1 freebase or a pharmaceutically acceptable salt thereof or a solid-state form of Compound 1. In one aspect, the skin condition is selected from the group consisting of psoriasis, plaque psoriasis, nail psoriasis, and hidradenitis suppurativa. In another aspect, the skin condition is psoriasis. In another aspect, the skin condition is plaque psoriasis. In another aspect, the skin condition is nail psoriasis. In another aspect, the skin condition is hidradenitis suppurativa. In another aspect, the skin condition is atopic dermatitis. In another aspect, the solid-state form is the Amorphous Freebase. In another aspect, the solid-state form is the Freebase Hydrate Form B. In another aspect, the solid-state form is the Freebase Hydrate Form C. In another aspect, the solid-state form is the Tartrate Hydrate. In another aspect, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB.

The therapeutically effective dose level for any particular subject will depend upon the specific situation and can depend upon a variety of factors including the type, age, weight, sex, diet, and condition of the subject being treated; the severity of the pathological condition; activity of the specific compound employed; the specific composition employed; the age, body weight, general health, sex and diet of the subject; the route of administration; the duration of the treatment; pharmacological considerations, such as the activity, efficacy, pharmacokinetic, and toxicology profiles of the particular compound or salt used; whether a drug delivery system is utilized; drugs used in combination or coincidental with the specific compound employed; and like factors well-known in the medical arts. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. It is well within the skill of the art to start doses of the compound at levels lower than required to achieve the desired therapeutic effect and to gradually increase the dosage until the desired effect is achieved. Thus, the dosage regimen actually employed can vary widely, and therefore, can derive from the preferred dosage regimen set forth below.

The total daily dose of the solid-state form (administered in single or divided doses) typically is from about 0.001 to about 100 mg/kg, or from about 0.001 to about 30 mg/kg, or from about 0.001 to about 15 mg/kg. In another embodiment, the total daily dose is from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

In one embodiment, the daily dose of the solid-state form administered to the subject is from about 0.01 mg to about 3000 mg. In one aspect, the daily dose is from about 0.1 mg to about 1000 mg. In another aspect, the daily dose is from is from about 1 mg to about 500 mg. In another aspect, the daily dose is from about 1 mg to about 250 mg. In another aspect, the daily dose is from about 1 mg to about 100 mg. In another aspect, the daily dose is from about 1 mg to about 50 mg. In another aspect, the daily dose is from about 1 mg to about 45 mg. In another aspect, the daily dose is from about 1 mg to about 30 mg. In another aspect, the daily dose is from about 1 mg to about 25 mg. In another aspect, the daily dose is from about 1 mg to about 24 mg. In another aspect, the daily dose is from about 1 mg to about 15 mg. In another aspect, the daily dose is from about 1 mg to about 7.5 mg. In another aspect, the daily dose is from about 25 mg to about 50 mg. In another aspect, the daily dose is from about 1 mg to about 10 mg. In another aspect, the daily dose is from about 10 mg to about 20 mg. In another aspect, the daily dose is from about 20 mg to about 30 mg. In another aspect, the daily dose is from about 30 mg to about 40 mg. In another aspect, the daily dose is from about 7.5 mg to about 45 mg. In another aspect, the daily dose is from about 15 mg to about 30 mg. In another aspect, the daily dose is about 3 mg. In another aspect, the daily dose is about 6 mg. In another aspect, the daily dose is about 7.5 mg. In another aspect, the daily dose is about 12 mg. In another aspect, the daily dose is about 15 mg. In another aspect, the daily dose is about 18 mg. In another aspect, the daily dose is about 24 mg. In another aspect, the daily dose is about 30 mg. In another aspect, the daily dose is about 36 mg. In another aspect, the daily dose is about 45 mg.

In one embodiment, a dose of about 3 mg, about 6 mg, about 12 mg, or about 24 mg per unit dosage form (e.g., per tablet or capsule) of a solid-state form of Compound 1 is administered orally BID (twice daily) in equal amounts (e.g., twice a day, about 3 mg each time) to a human subject.

In one embodiment, the disclosure relates to a method of treating a subject having rheumatoid arthritis, the method comprising administering to the subject about 3 mg, per unit dosage form (e.g., per tablet or capsule) of a solid-state form of Compound 1 orally BID (twice daily) in equal amounts (e.g., twice a day, about 3 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 3 mg, per unit dosage form (e.g., per tablet or capsule) of a solid-state form of Compound 1 orally BID (twice daily) in equal amounts (e.g., twice a day, about 3 mg each time).

In one embodiment, the disclosure relates to a method of treating a subject having rheumatoid arthritis, the method comprising administering to the subject about 6 mg, per unit dosage form (e.g., per tablet or capsule) of a solid-state form of Compound 1 orally BID (twice daily) in equal amounts (e.g., twice a day, about 6 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 6 mg, per unit dosage form (e.g., per tablet or capsule) of a solid-state form of Compound 1 orally BID (twice daily) in equal amounts (e.g., twice a day, about 6 mg each time).

In one embodiment, the disclosure relates to a method of treating a subject having rheumatoid arthritis, the method comprising administering to the subject about 12 mg, per unit dosage form (e.g., per tablet or capsule) of a solid-state form of Compound 1 orally BID (twice daily) in equal amounts (e.g., twice a day, about 12 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 12 mg, per unit dosage form (e.g., per tablet or capsule) of a solid-state form of Compound 1 orally BID (twice daily) in equal amounts (e.g., twice a day, about 12 mg each time).

In one embodiment, the disclosure relates to a method of treating a subject having rheumatoid arthritis, the method comprising administering to the subject about 24 mg, per unit dosage form (e.g., per tablet or capsule) of a solid-state form of Compound 1 orally BID (twice daily) in equal amounts (e.g., twice a day, about 24 mg each time). In another aspect, the present disclosure relates a solid-state form of Compound 1 for use in treating rheumatoid arthritis in a subject, particularly in a human subject suffering from or susceptible to rheumatoid arthritis, the use comprising administering to the subject about 24 mg, per unit dosage form (e.g., per tablet or capsule) of a solid-state form of Compound 1 orally BID (twice daily) in equal amounts (e.g., twice a day, about 24 mg each time).

In another embodiment, the methods or uses comprise administering orally QD (once daily) to a human subject a dose of about 7.5 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 7.5 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 7.5 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C.

In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 15 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 15 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 15 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 24 mg of Compound 1 freebase or a pharmaceutically acceptable salt thereof. The 24 mg QD dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously.

In another embodiment, the methods or uses comprise administering orally QD (once daily) to a human subject a dose of about 24 mg of a solid-state form of Compound 1. In one embodiment, the methods or uses comprise administering orally QD (once daily) to a human subject a solid-state form of Compound 1 in an amount sufficient to deliver 24 mg of Compound 1 freebase equivalent to the subject. The 24 mg QD dose of the solid-state form of Compound 1 may be administered as either a single dosage form comprising about 24 mg per unit dosage form (e.g., per tablet or capsule) of the solid-state form of Compound 1, or two dosage forms comprising about 12 mg per unit dosage form (e.g., per tablet or capsule) of the solid-state form of Compound 1 administered simultaneously. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 30 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 30 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 30 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 36 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 36 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 36 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In another embodiment, the methods or uses comprise administering orally QD (once daily) to a human subject a dose of about 45 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 45 mg per unit dosage form (e.g., per tablet or capsule) of a solid-state form of Compound 1. In one embodiment, the methods or uses comprise administering orally QD (once daily) to a human subject a solid-state form of Compound 1 in an amount sufficient to deliver 45 mg per unit dosage form (e.g., per tablet or capsule) of Compound 1 freebase equivalent to the subject. In one embodiment, the solid-state form is the Amorphous Freebase. In one embodiment, the solid-state form is the Freebase Hydrate Form B. In one embodiment, the solid-state form is the Freebase Hydrate Form C. In one embodiment, the solid-state form is the Tartrate Hydrate. In another aspect, the solid-state form is the Freebase Anhydrate Form D.

In certain embodiments, Compound 1 freebase or a pharmaceutically acceptable salt thereof and/or solid-state forms thereof can be used to treat rheumatoid arthritis (RA), including reducing signs and symptoms of RA, inducing a major clinical response, inhibiting the progression of or treating structural damage associated with RA, and improving physical function in adult subjects, such as adult subjects with moderately to severely active RA. In one embodiment, Compound 1 freebase or a pharmaceutically acceptable salt thereof and/or solid-state forms thereof are used to treat RA in adult subjects. In one embodiment, Compound 1 freebase or a pharmaceutically acceptable salt thereof and/or solid-state forms thereof are used to reduce signs and symptoms of RA in adult subjects. In one embodiment, Compound 1 freebase or a pharmaceutically acceptable salt thereof and/or solid-state forms thereof induce a major clinical response in adult subjects with RA. In one embodiment, Compound 1 freebase or a pharmaceutically acceptable salt thereof and/or solid-state forms thereof are used to inhibit the progression of structural damage associated with RA in adult subjects. In one embodiment, Compound 1 freebase and/or solid-state forms thereof are used to treat structural damage associated with RA in adult subjects. In one embodiment, Compound 1 freebase or a pharmaceutically acceptable salt thereof and/or solid-state forms thereof are used to improve physical function in adult subjects. In one embodiment, the adult subjects have RA. In another embodiment, the adult subjects have moderately to severely active RA.

Compound 1 freebase or a pharmaceutically acceptable salt thereof or solid-state forms thereof may be used alone, or in combination with methotrexate or other non-biologic disease-modifying anti-rheumatic drugs (DMARDs), and/or in combination with anti-TNFα biological agents, such as TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™ CDP 571, and soluble p55 or p75 TNF receptors, derivatives, thereof, etanercept such as p75TNFR1gG (ENBREL™ brand etanercept) or p55TNFR1gG (lenercept).

Patients having active rheumatoid arthritis (RA) may be diagnosed according to 1987-revised American College of Rheumatology (ACR) classification criteria or the 2010 ACR/EULAR criteria. In certain embodiments, RA may be diagnosed based on patients having at least 6 swollen and 6 tender joints. In certain embodiments, patients treatable with Compound 1 or solid-state forms thereof may include those who have failed therapy with at least one (e.g., at least one but no more than four) DMARDs and/or have inadequate response to methotrexate, adalimumab, infliximab, etanercept, or other anti-TNFα biological agents, or non-anti-TNF biologics.

In certain embodiments, Compound 1 freebase or a pharmaceutically acceptable salt thereof or solid-state forms thereof halt disease progression, and/or relieves at least a symptom of the disease, which may be detected or monitored by X-ray results, including radiographic progression of joint damage.

In certain embodiments, therapeutic efficacy can be measured by improvements in ACR20, ACR50, and/or ACR70, either in individual patients or a population of patients in need of treatment. In certain embodiments, statistically significant improvement (as compared placebo or untreated control) over a treatment period (e.g., 1 week, 2 weeks, 4 weeks, 6 weeks, 8 weeks, 12 weeks, 2 months, 3 months, 6 months, 1 year, 2 years, 5 years, 10 years or more) in one or more of the ACR criteria is achieved. Statistical significance is manifested by a p value of less than 0.05, or less than 0.01.

Components of the ACR responses are well known in the art, and may include the median number of tender joints, the median number of swollen joints, physician global assessment such as one measured by visual analog scale (VAS), patient global assessment such as one measured by visual analog scale, pain such as one measured by visual analog scale, disability index of the Health Assessment Questionnaire (HAQ-DI score), and C-reactive protein (CRP) (mg/dL).

In certain embodiments, an ACR20 response is determined based on a 20% or greater improvement in tender joint count (TJC) and swollen joint count (SJC) and greater than or equal to 3 of the 5 measures of Patient's Assessment of Pain (VAS), Patient's Global Assessment of Disease Activity (VAS), Physician's Global Assessment of Disease Activity (VAS), HAQ-DI, or high sensitivity C-reactive protein (hsCRP). In some embodiments, an ACR50 response is determined based on a 50% or greater improvement in TJC and SJC and greater than or equal to 3 of the 5 measures of Patient's Assessment of Pain (VAS), Patient's Global Assessment of Disease Activity (VAS), Physician's Global Assessment of Disease Activity (VAS), HAQ-DI, or hsCRP. An ACR70 response is determined based on a 70% or greater improvement in TJC and SJC and greater than or equal to 3 of the 5 measures of Patient's Assessment of Pain (VAS), Patient's Global Assessment of Disease Activity (VAS), Physician's Global Assessment of Disease Activity (VAS), HAQ-DI, or hsCRP. In certain embodiments, the ACR20, ACR50, or ACR70 response occurs by week 12 of treatment.

In certain embodiments, a DAS28 (disease activity score based on the 28 joints examined) score is determined as a composite score derived from four of the following measures: examination of joints for swelling and tenderness, global scores of pain and overall status, blood markers of inflammation (e.g. ESR (erythrocyte sedimentation rate) and CRP (C reactive protein), referred to herein as DAS28 (CRP)), questionnaires (e.g. the HAQ (health assessment questionnaire) which assess function) and X-rays and other imaging techniques such as ultrasound and MRI.

In certain embodiments, structural joint damage can be assessed radiographically and expressed as change in Total Sharp Score (TSS) and its components, the erosion score and Joint Space Narrowing (JSN) score, for example, at week 12 compared to baseline, or at week 24 as compared to baseline.

In certain embodiments, improvement in signs and symptoms of the disease can be measured by patient physical function response, such as disability index of Health Assessment Questionnaire (HAQ-DI), and/or the health-outcomes as assessed by The Short Form Health Survey (SF 36). In one embodiment, improvement in signs and symptoms of the disease is measured by HAQ-DI, including the minimal clinically important difference (MCID) of −0.22. Improvement can also be measured by one or both of Physical Component Summary (PCS) and the Mental Component Summary (MCS). Improvements can further be measured by Work Instability Scale for RA (RA-WIS) (see Gilworth et al., Arthritis & Rheumatism (Arthritis Care & Research) 49(3): 349-354, 2003, incorporated by reference).

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 7.5 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of a solid-state form of Compound 1 orally QD (once daily). In one embodiment, the solid-state form delivers about 7.5 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 15 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of a solid-state form of Compound 1 orally QD (once daily). In one embodiment, the solid-state form delivers about 15 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 24 mg of Compound 1 freebase or a pharmaceutically acceptable salt thereof orally QD (once daily). The 24 mg dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of a solid-state form of Compound 1 orally QD (once daily). In one embodiment, the method comprising administering to the subject a solid-state form of Compound 1 orally QD (once daily) in an amount sufficient to deliver 24 mg of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 24 mg of a solid-state form of Compound 1 orally QD (once daily). In one embodiment, the solid-state form delivers about 24 mg of Compound 1 freebase equivalent to the subject. The 24 mg dose of the solid-state form of Compound 1 may be administered as either a single dosage form comprising about 24 mg per unit dosage form (e.g., per tablet or capsule) of the solid-state form of Compound 1, or two dosage forms comprising about 12 mg per unit dosage form (e.g., per tablet or capsule) of the solid-state form of Compound 1 administered simultaneously. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhydrate Form D. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 30 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of a solid-state form of Compound 1 orally QD (once daily). In one embodiment, the solid-state form delivers about 30 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 36 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of a solid-state form of Compound 1 orally QD (once daily). In one embodiment, the solid-state form delivers about 36 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhydrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of a solid-state form of Compound 1 orally QD (once daily). In one embodiment, the method comprising administering to the subject a solid-state form of Compound 1 orally QD (once daily) in an amount sufficient to deliver 45 mg, per unit dosage form (e.g., per tablet or capsule) of Compound 1 freebase equivalent to the subject. In another aspect, the present disclosure relates to a solid-state form of Compound 1 for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of a solid-state form of Compound 1 orally QD (once daily). In one embodiment, the solid-state form delivers about 45 mg, per unit dosage form (e.g., per tablet or capsule) of Compound 1 freebase equivalent to the subject. In one embodiment, the solid-state form is the Freebase Hydrate Form B. In one embodiment, the solid-state form is the Freebase Hydrate Form C. In one embodiment, the solid-state form is the Tartrate Hydrate. In one embodiment, the solid-state form is the Freebase Anhdyrate Form D. In one embodiment, the subject has moderately to severely active rheumatoid arthritis. In another aspect, the solid-state form is the Freebase Solvate Form A. In another aspect, the solid-state form is the Hydrochloride Solvate form AA. In another aspect, the solid-state form is the Hydrochloride Solvate Form BB. In another aspect, the solid-state form is the Hydrochloride Solvate Form CC. In another aspect, the solid-state form is the L-Maleate Form AAA. In another aspect, the solid-state form is the L-Maleate Form BBB. In one embodiment, the subject is an adult.

In one embodiment, the disclosure relates to a method of treating moderate to severely active rheumatoid arthritis in an adult subject, particularly in a human subject suffering from or susceptible to moderate to severely active rheumatoid arthritis, the method comprising administering to the subject a therapeutically effective amount of Compound 1 (freebase), or a pharmaceutically acceptable salt thereof or a solid-state form of Compound 1. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule) of Compound 1 freebase equivalent. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid-state form of Compound 1. In one embodiment, the Compound 1 (freebase) or a pharmaceutically acceptable salt thereof or the solid-state form of Compound 1 is administered to the subject orally QD (once daily). In another aspect, the disclosure relates to Compound 1 freebase or a pharmaceutically acceptable salt thereof or a solid-state form of Compound 1 (e.g., a crystalline hydrate or crystalline anhydrate), as described in the present disclosure, for use in treatment of moderate to severely active rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is a hemihydrate. In one embodiment, the hemihydrate is Freebase Hydrate Form C. In one embodiment, the solid-state form is a crystalline anhydrate. In one embodiment, the crystalline anhydrate is Freebase Anhydrate Form D. In one embodiment, the solid-state form is the Freebase Solvate Form A. In another aspect, the solid-state form is the Hydrochloride Solvate form AA. In one embodiment, the solid-state form is the Hydrochloride Solvate Form BB. In one embodiment, the solid-state form is the Hydrochloride Solvate Form CC. In one embodiment, the solid-state form is the L-Maleate Form AAA. In one embodiment, the solid-state form is the L-Maleate Form BBB. In one embodiment, the Compound 1 (freebase) or a pharmaceutically acceptable salt thereof or the solid-state form of Compound 1 is in a once daily extended-release formulation. In one embodiment, the formulation delivers about 7.5 mg or about 15 mg or about 30 mg or about 45 mg per unit dosage form (e.g., per tablet or capsule) of Compound 1 (freebase equivalent) or a solid-state form of Compound 1 orally QD (once daily).

In one embodiment, the subject having moderate to severely active rheumatoid arthritis has, prior to treatment, at least one of the following identifying characteristics: at least 6 swollen joints (based on 66 joint counts), at least 6 tender joints (based on 68 joint counts), high-sensitivity C-reactive protein (hsCRP) greater than the upper limit of normal (ULN), or positive test results for both rheumatoid factor (RF) and anti-cyclic citrullinated peptide (CCP). In one embodiment, the subject having moderate to severely active rheumatoid arthritis has, prior to treatment, at least 6 swollen joints (based on 66 joint counts) and at least 6 tender joints (based on 68 joint counts). Methods for assessing tender and swollen joints are known, and described in, for example, Scott, et al., Clinical and Experimental Rheumatology, 2014, Vol. 32 (Supp. 85), S7-S12.

Thus, in another embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject a therapeutically effective amount of Compound 1 (freebase), or a pharmaceutically acceptable salt thereof or a solid-state form of Compound 1 (e.g., a crystalline hydrate or a crystalline anhydrate) as described herein, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid-state form of Compound 1 in an amount sufficient to deliver to the subject about 7.5 or about 15 mg or about 30 mg or about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule) of a solid-state form of Compound 1. In another aspect, the disclosure relates to Compound 1 freebase or a pharmaceutically acceptable salt thereof or a solid-state form of Compound 1 (e.g., a crystalline hydrate or crystalline anhydrate), as described in the present disclosure, for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject a therapeutically effective amount of Compound 1 freebase or a pharmaceutically acceptable salt thereof or a solid-state form of Compound 1. In one embodiment, the therapeutically effective amount of the solid-state form of Compound 1 delivers to the subject about 7.5 mg or about 15 mg or about 30 mg or about 45 mg per unit dosage form (e.g., per tablet or capsule) of Compound 1 (freebase equivalent) or a solid-state form of Compound 1 orally QD (once daily). In one embodiment, the Compound 1 (freebase) or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is administered to the subject orally QD (once daily). In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is Tartrate Hydrate. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 7.5 mg, per unit dosage form (e.g., per tablet or capsule), per day of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 7.5 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 15 mg, per unit dosage form (e.g., per tablet or capsule), per day of Compound 1 (freebase), or a pharmaceutically acceptable salt thereof or a solid-state form of Compound 1 in an amount sufficient to deliver to the subject about 15 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 15 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 15 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 30 mg, per unit dosage form (e.g., per tablet or capsule), per day of Compound 1 (freebase), or a pharmaceutically acceptable salt thereof or a solid-state form of Compound 1 in an amount sufficient to deliver to the subject about 30 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 30 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 30 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid-state form of Compound 1 in an amount sufficient to deliver to the subject about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 45 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 45 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the symptoms result from the progression of structural damage assessed by radiograph.

In one embodiment, the adult subject receiving the treatment achieves an ACR20 response after treatment. In one embodiment, the adult subject achieves an ACR20 response after treatment for at least twelve weeks (e.g., at week 12 of treating). In another embodiment, the adult subject receiving the treatment achieves an ACR50 response after treatment. In one embodiment, the adult subject achieves an ACR50 response after treatment for at least twelve weeks (e.g., at week 12 of treating), or after at least twenty-four weeks (e.g., at week 24). In another embodiment, the adult subject receiving the treatment achieves an ACR70 response after treatment. In one embodiment, the adult subject achieves an ACR70 response after treatment for at least twelve weeks (e.g., at week 12 of treating). In certain embodiments, the adult subject achieves an ACR20 response, an ACR50 response, and/or an ACR70 response following treatment for at least twelve weeks (e.g., at week 12 of treating).

In one embodiment, the adult subject receiving the treatment achieves an ACR20 response after treatment for at least 8 weeks (e.g., at week 8 of treating). In another embodiment, the adult subject receiving the treatment achieves an ACR20 response after treatment for at least 6 weeks (e.g., at week 6 of treating). In another embodiment, the adult subject receiving the treatment achieves an ACR20 response after treatment for at least 4 weeks (e.g., at week 4 of treating). In another embodiment, the adult subject receiving the treatment achieves an ACR20 response after treatment for at least 2 weeks (e.g., at week 2 of treating).

In one embodiment, the adult subject receiving the treatment achieves an ACR50 response after treatment for at least 8 weeks (e.g., at week 8 of treating). In another embodiment, the adult subject receiving the treatment achieves an ACR50 response after treatment for at least 6 weeks (e.g., at week 6 of treating). In another embodiment, the adult subject receiving the treatment achieves an ACR50 response after treatment for at least 4 weeks (e.g., at week 4 of treating). In another embodiment, the adult subject receiving the treatment achieves an ACR50 response after treatment for at least 2 weeks (e.g., at week 2 of treating).

In one embodiment, the adult subject receiving the treatment achieves an ACR70 response after treatment for at least 8 weeks (e.g., at week 8 of treating). In another embodiment, the adult subject receiving the treatment achieves an ACR70 response after treatment for at least 6 weeks (e.g., at week 6 of treating). In another embodiment, the adult subject receiving the treatment achieves an ACR70 response after treatment for at least 4 weeks (e.g., at week 4 of treating).

In one embodiment, the adult subject receiving the treatment achieves a change in DAS28 score after treatment. In one embodiment, the change in DAS score is a decrease in DAS28(CRP) after treatment, as compared to baseline (i.e., DAS28(CRP) prior to treatment). In one embodiment, the adult subject achieves a decrease in DAS28 score as compared to baseline after treatment for at least twelve weeks (e.g., at week 12 of treating). In one embodiment, the adult subject achieves a decrease in DAS28(CRP) as compared to baseline after treatment for at least 12 weeks (e.g., at week 12 of treating).

In another embodiment, the adult subject achieves a decrease in DAS28(CRP) as compared to baseline after treatment for at least 8 weeks (e.g., at week 8 of treating). In another embodiment, the adult subject achieves a decrease in DAS28(CRP) as compared to baseline after treatment for at least 6 weeks (e.g., at week 6 of treating). In another embodiment, the adult subject achieves a decrease in DAS28(CRP) as compared to baseline after treatment for at least 4 weeks (e.g., at week 4 of treating). In another embodiment, the adult subject achieves a decrease in DAS28(CRP) as compared to baseline after treatment for at least 2 weeks (e.g., at week 2 of treating).

In another embodiment, the adult subject receiving the treatment achieves a low disease activity (LDA) score or clinical remission after treatment. In one embodiment, the LDA score or clinical remission is measured as a DAS28 score (in particular, DAS28(CRP)) of 3.2 or less. In another embodiment, the LDA score or clinical remission is measured as a DAS28(CRP) of less than 2.6. In another embodiment, the LDA score or clinical remission is assessed using Clinical Disease Activity Index (CDAI) criteria. In one embodiment, the adult subject achieves a CDAI score of 10 or less after treatment. In another embodiment, the adult subject achieves a CDAI score of 2.8 or less after treatment. In one embodiment, the adult subject achieves the LDA score or clinical remission after treatment for at least 12 weeks (e.g., at week 12 of treating). In one embodiment, the adult subject achieves the LDA score or clinical remission after treatment for at least 8 weeks (e.g., at week 8 of treating). In one embodiment, the adult subject achieves the LDA score or clinical remission after treatment for at least 6 weeks (e.g., at week 6 of treating). In one embodiment, the adult subject achieves the LDA score or clinical remission after treatment for at least 4 weeks (e.g., at week 4 of treating). In one embodiment, the adult subject achieves the LDA score or clinical remission after treatment for at least 2 weeks (e.g., at week 2 of treating).

In one embodiment, the adult subject receiving the treatment achieves a change in mean modified Total Sharp Score (mTSS). In one embodiment, the adult subject receiving the treatment achieves a change in mTSS after treatment for at least twelve weeks (e.g., at week 12 of treating), or after treatment for at least twenty-four weeks (e.g., at week 24 of treating). In one embodiment, mTSS may be determined by scoring x-rays of the hand/wrist and feet joints for erosions and joint space narrowing. The erosion score and narrowing score are added to determine the total score.

In one embodiment, the adult subject receiving the treatment achieves a change in HAQ-DI score. In one embodiment, the adult subject receiving the treatment achieves a change in HAQ-DI score after treatment for at least twelve weeks (e.g., at week 12 of treating).

In one embodiment, the adult subject receiving the treatment achieves a change in Short Form 36 (SF-36) physical component score (PCS). In one embodiment, the adult subject receiving the treatment achieves a change in SF-36 PCS after treatment for at least twelve weeks (e.g., at week 12 of treating). SF-36 is a 36 item participant questionnaire with questions relating to participant health and daily activities.

In one embodiment, the adult subject receiving the treatment achieves a clinical remission (CR).

In one embodiment, the adult subject receiving the treatment achieves a CR after treatment for at least twelve weeks (e.g., at week 12 of treating). In one embodiment, CR is determined based on DAS28 C-Reactive Protein (DAS28 (CRP)) response rate. In one embodiment, CR is a DAS28 (CRP) score of less than 2.6.

In one embodiment, the adult subject receiving the treatment achieves a change in functional assessment of chronic illness therapy (FACIT-F). In one embodiment, the adult subject receiving the treatment achieves a change in FACIT-F after treatment for at least twelve weeks (e.g., at week 12 of treating). FACIT-F is a participant questionnaire with 13 indexes rated on a 5 point scale. The indexes relate to the participant's level of fatigue during the past seven days.

In one embodiment, the adult subject receiving the treatment achieves a change in work instability score for rheumatoid arthritis (RA-WIS). In one embodiment, the adult subject receiving the treatment achieves a change in RA-WIS after treatment for at least twelve weeks (e.g., at week 12 of treating). RA-WIS is a participant questionnaire containing 23 questions relating to the participant's functioning in their work environment.

In one embodiment, the adult subject receiving the treatment achieves a change in morning stiffness severity. In one embodiment, the adult subject receiving the treatment achieves a change in morning stiffness severity after treatment for at least twelve weeks (e.g., at week 12 of treating). Morning stiffness severity is determined by the Patient's Assessment of Severity and Duration of Morning Stiffness questionnaire.

In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent to the subject, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject achieves an ACR70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 7.5 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 15 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 45 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In another embodiment, the adult subject is a subject who has had an inadequate response or intolerance to one or more disease-modifying antirheumatic drugs (DMARDs). In one embodiment, the DMARD is a conventional synthetic DMARD (csDMARD). In another embodiment, the DMARD is a biologic DMARD (bDMARD). Examples of csDMARDs include, but are not limited to, methotrexate (MTX), sulfasalazine, hydroxychloroquine, chloroquine, leflunomide, and azathioprine. Examples of bDMARDs include, but are not limited to, tocilizumab such as ACTEMRA™, etanercept such as p75TNFR1gG (ENBREL™ brand etanercept), adalimumab (such as HUMIRA™ brand adalimumab), and golimumab such as SIMPONI™ (golimumab). In one embodiment, the csDMARD is MTX. In one embodiment, the bDMARD is an anti-TNF biologic. An inadequate response or intolerance to one or more DMARDs can be measured using any of the indices described herein (e.g., failure to achieve an ACR20 response). In one embodiment, a subject having an inadequate response to a DMARD is a subject who does not achieve reduced disease activity, does not achieve an improvement in physical function, exhibits no evidence of stopping disease progression, or who experiences disease relapse after treatment with the DMARD. In one embodiment, a subject having an inadequate response to a DMARD is a subject who does not achieve an ACR20 response after treatment with the DMARD. In one embodiment, a subject having an inadequate tolerance (intolerance) to a DMARD is a subject who experiences toxicity or complicating co-morbidities after treatment with the DMARD.

In one embodiment, the adult subject is a subject who has had an inadequate response to stable methotrexate therapy. In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject received a supplement of folic acid for at least four weeks prior to treatment. In another embodiment, the adult subject is administered a supplement of folic acid during treatment.

In one embodiment, the adult subject is a subject who has had an inadequate response or intolerance to at least one anti-TNF therapy. Anti-TNF biologic agents are described elsewhere herein, and include TNF antagonists such as chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept). In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject has been treated with at least one anti-TNF biologic agent for at least three months prior to treatment with Compound 1. In another embodiment, the adult subject received a supplement of folic acid for at least four weeks prior to treatment. In another embodiment, the adult subject is administered a supplement of folic acid during treatment In certain embodiments, the adult subject, who has had an inadequate response or tolerance to one or more DMARDS (including methotrexate and/or an anti-TNF biologic agent), achieves an ACR20 response, an ACR50 response, an ACR70 response, and/or a decrease in DAS28(CRP) as compared to baseline following treatment for at least twelve weeks (e.g., at week 12 of treating), and/or following treatment for at least 8 weeks (e.g., at week 8 of treating), and/or following treatment for at least 6 weeks (e.g., at week 6 of treating), and/or following treatment for at least 4 weeks (e.g., at week 4 of treating), and/or following treatment for at least 2 weeks (e.g., at week 2 of treating).

For instance, in one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 7.5 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 15 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 24 mg, per unit dosage form (e.g., per tablet or capsule), of Compound 1 (freebase), or a pharmaceutically acceptable salt thereof or a solid-state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 24 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 30 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 45 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In another embodiment, the adult subject is also administered a csDMARD or a bDMARD in a combination therapy, as described hereinafter. In certain embodiments, the DMARD is MTX. In certain embodiments, the adult subject receiving the combination therapy achieves an ACR20 response, an ACR50 response, an ACR70 response, and/or a decrease in DAS28(CRP) as compared to baseline following treatment. In particular embodiments, the adult subject receiving the combination therapy achieves an ACR20 response, an ACR50 response, an ACR70 response, and/or a decrease in DAS28(CRP) as compared to baseline at week 12 of treating, and/or at week 8 of treating, and/or at week 6 of treating, and/or at week 4 of treating, and/or at week 2 of treating. In one embodiment, the adult subject receiving the combination therapy is administered about 7.5 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), of Compound 1 freebase equivalent. In one embodiment, the adult subject receiving the combination therapy is administered about 15 mg, per unit dosage form (e.g., per tablet or capsule), of Compound 1 (freebase), or a pharmaceutically acceptable salt thereof or a solid-state form of Compound 1 in an amount sufficient to deliver to the subject about 15 mg, per unit dosage form (e.g., per tablet or capsule), of Compound 1 freebase equivalent. In one embodiment, the adult subject receiving the combination therapy is administered about 30 mg, per unit dosage form (e.g., per tablet or capsule), of Compound 1 (freebase), or a pharmaceutically acceptable salt thereof or a solid-state form of Compound 1 in an amount sufficient to deliver to the subject about 30 mg, per unit dosage form (e.g., per tablet or capsule), of Compound 1 freebase equivalent. In one embodiment, the adult subject receiving the combination therapy is administered about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 45 mg, per unit dosage form (e.g., per tablet or capsule), of Compound 1 freebase equivalent. In one embodiment, the method comprises administering about 7.5 mg or about 15 mg or about 30 mg or about 45 mg, per unit dosage form (e.g., per tablet or capsule), of the solid-state form to the subject. In one embodiment, the Compound 1 (freebase) or a pharmaceutically acceptable salt thereof or the solid-state form is in a once daily extended-release formulation. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In another embodiment, any of the methods of treating an adult subject having moderate to severely active rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the present disclosure relates to a method of treating structural damage associated with rheumatoid arthritis in an adult subject, particularly in a human subject suffering from or susceptible to structural damage associated with rheumatoid arthritis. The method comprises administering to the subject a therapeutically effective amount of Compound 1 (freebase), or a pharmaceutically acceptable salt thereof or a solid-state form of Compound 1 (e.g., a crystalline hydrate or a crystalline anhydrate) as described herein, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule) of a solid-state form of Compound 1, such that the structural damage in the adult subject is inhibited or lessened. In one embodiment, the Compound 1 (freebase) or a pharmaceutically acceptable salt thereof or the solid-state form of Compound 1 is administered to the subject orally QD (once daily). In one embodiment, the structural damage is selected from the group consisting of loss of bone and/or cartilage, bone erosion, joint space narrowing as measured by radiography, and combinations thereof. In one embodiment, the structural damaged is inhibited or lessened when the structural damage is reduced by at least 20%, or at least 25%, or at least 30%, or at least 50%. In other embodiments, structural damage is inhibited or lessened when there is no further radiographic progression of the structural damage. In certain embodiments, structural joint damage can be assessed radiographically and expressed as change in Total Sharp Score (TSS) and its components, the erosion score and Joint Space Narrowing (JSN) score, for example, at week 12 compared to baseline. In another aspect, the disclosure relates to a solid-state form (and in particular a crystalline hydrate) of Compound 1, as described in the present disclosure, for use in treatment of structural damage associated with rheumatoid arthritis in an adult subject, particularly in a human subject suffering from or susceptible to rheumatoid arthritis. In one embodiment, the solid-state form is a crystalline hydrate. In one embodiment, the crystalline hydrate is the Freebase Hydrate Form B. In one embodiment, the crystalline hydrate is a hemihydrate. In one embodiment, the hemihydrate is Freebase Hydrate Form C. In one embodiment, the solid-state form is a crystalline anhydrate. In one embodiment, the crystalline anhydrate is Freebase Anhydrate Form D. In one embodiment, the stolid state form is Tartrate Hydrate. In one embodiment, the Compound 1 (freebase) or a pharmaceutically acceptable salt thereof or the crystalline hydrate is in a once daily extended-release formulation. In one embodiment, the Compound 1 (freebase) or a pharmaceutically acceptable salt thereof or the crystalline hydrate is in a once daily extended-release formulation, and the formulation delivers about 7.5 mg or about 15 mg or about 30 mg or about 45 mg per unit dosage form (e.g., per tablet or capsule) of Compound 1 (freebase equivalent) orally QD (once daily).

In another aspect, the disclosure relates to Compound 1 freebase or a pharmaceutically acceptable salt thereof or a solid-state form of Compound 1 (e.g., a crystalline hydrate or crystalline anhydrate), as described in the present disclosure for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject a therapeutically effective amount of Compound 1 freebase or a pharmaceutically acceptable salt thereof or a solid-state form of Compound 1. In one embodiment, the solid-state form is a crystalline hydrate. In one embodiment, the crystalline hydrate is Freebase Hydrate Form B. In one embodiment, the crystalline hydrate is a hemihydrate. In one embodiment, the hemihydrate is Freebase Hydrate Form C. In one embodiment, the solid-state form is a crystalline anhydrate. In one embodiment, the crystalline anhydrate is Freebase Anhydrate Form D. In one embodiment, the Compound 1 (freebase) or a pharmaceutically acceptable salt thereof or the solid-state form of Compound 1 is in a once daily extended-release formulation. In one embodiment, the formulation delivers about 7.5 mg or about 15 mg or about 30 mg or about 45 mg per unit dosage form (e.g., per tablet or capsule) of Compound 1 (freebase equivalent) or a solid-state form of Compound 1 orally QD (once daily).

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 7.5 mg, per unit dosage form (e.g., per tablet or capsule), per day of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 7.5 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 15 mg, per unit dosage form (e.g., per tablet or capsule), per day of Compound 1 (freebase), or a pharmaceutically acceptable salt thereof or a solid-state form of Compound 1 in an amount sufficient to deliver to the subject about 15 mg, per unit dosage form (e.g., per tablet or capsule), per day of Compound 1 freebase equivalent, such that the structural damage in the adult subject is inhibited or lessened. In one embodiment, the method comprises administering to the subject about 15 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 15 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 30 mg, per unit dosage form (e.g., per tablet or capsule), per day of Compound 1 (freebase), or a pharmaceutically acceptable salt thereof or a solid-state form of Compound 1 in an amount sufficient to deliver to the subject about 30 mg, per unit dosage form (e.g., per tablet or capsule), per day of Compound 1 freebase equivalent, such that the structural damage in the adult subject is inhibited or lessened. In one embodiment, the method comprises administering to the subject about 30 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 30 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 45 mg, per unit dosage form (e.g., per tablet or capsule), per day of Compound 1 (freebase), or a pharmaceutically acceptable salt thereof or a solid-state form of Compound 1 in an amount sufficient to deliver to the subject about 45 mg, per unit dosage form (e.g., per tablet or capsule), per day of Compound 1 freebase equivalent, such that the structural damage in the adult subject is inhibited or lessened. In one embodiment, the method comprises administering to the subject about 45 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject 45 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the structural damage is selected from the group consisting of loss of bone and/or cartilage, bone erosion, joint space narrowing as measured by radiography, and combinations thereof.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises administering to the subject a therapeutically effective amount of Compound 1 (freebase), or a pharmaceutically acceptable salt thereof or a solid-state form of Compound 1 (e.g., a crystalline hydrate or a crystalline anhydrate) as described herein. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the method comprises administering to the subject about 7.5 mg or about 15 mg or about 30 mg or about 45 mg, per unit dosage form (e.g., per tablet or capsule) of a solid-state form of Compound 1. In one embodiment, the Compound 1 (freebase) or a pharmaceutically acceptable salt thereof or the solid-state form of Compound 1 is administered to the subject orally QD (once daily). In another aspect, the disclosure relates to Compound 1 freebase or a pharmaceutically acceptable salt thereof or a solid-state form (and in particular a crystalline hydrate) of Compound 1, as described in the present disclosure, for use in reducing signs and symptoms of rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceutically acceptable salt thereof or a solid-state form (and in particular a crystalline hydrate) of Compound 1. In one embodiment, the Compound 1 freebase or a pharmaceutically acceptable salt thereof or the solid-state form of Compound 1 is in a once daily extended-release formulation. In one embodiment, the formulation delivers about 7.5 mg or about 15 mg or about 30 mg or about 45 mg per unit dosage form (e.g., per tablet or capsule) of Compound 1 (freebase equivalent) or the solid-state form of Compound 1 to the subject orally QD (once daily). In one embodiment, the solid-state form is a crystalline hydrate. In one embodiment, the crystalline hydrate is the Freebase Hydrate Form B. In one embodiment, the crystalline hydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 7.5 mg, per unit dosage form (e.g., per tablet or capsule), per day of Compound 1 (freebase), or a pharmaceutically acceptable salt thereof or a solid-state form of Compound 1 in an amount sufficient to deliver to the subject about 7.5 mg, per unit dosage form (e.g., per tablet or capsule), per day of Compound 1 freebase equivalent. In one embodiment, the method comprises administering to the subject about 7.5 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject about 7.5 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is a hemihydrate. In one embodiment, the hemihydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is in a once daily extended-release formulation, and the formulation delivers about 7.5 mg per unit dosage form (e.g., per tablet or capsule) of Compound 1 (freebase equivalent) or the solid-state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 15 mg, per unit dosage form (e.g., per tablet or capsule), per day of Compound 1 (freebase) or a pharmaceutically acceptable salt thereof or a solid-state form of Compound 1 in an amount sufficient to deliver to the subject about 15 mg, per unit dosage form (e.g., per tablet or capsule), per day of Compound 1 freebase equivalent. In one embodiment, the method comprises administering to the subject about 15 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject, about 15 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or the solid-state form of Compound 1 is administered orally QD (once daily). In one embodiment, the Compound 1 (freebase) or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is in a once daily extended-release formulation, and the formulation delivers about 15 mg per unit dosage form (e.g., per tablet or capsule) of Compound 1 (freebase equivalent) or the solid-state form of Compound 1 orally QD (once daily) to the subject.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises administering to the subject about 30 mg, per unit dosage form (e.g., per tablet or capsule), per day of Compound 1 (freebase) or a pharmaceutically acceptable salt thereof or a solid-state form of Compound 1 in an amount sufficient to deliver to the subject about 30 mg, per unit dosage form (e.g., per tablet or capsule), per day of Compound 1 freebase equivalent. In one embodiment, the method comprises administering to the subject about 30 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject about 30 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 (freebase) or the crystalline hydrate is in a once daily extended-release formulation. In one embodiment, the Compound 1 (freebase) or a pharmaceutically acceptable salt thereof or the solid-state form of Compound 1 is in a once daily extended-release formulation, and the formulation delivers about 30 mg per unit dosage form (e.g., per tablet or capsule) of Compound 1 (freebase equivalent) or the solid-state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid-state form of Compound 1 in an amount sufficient to deliver to the subject about 45 mg, per unit dosage form (e.g., per tablet or capsule), per day of Compound 1 freebase equivalent. In one embodiment, the method comprises administering to the subject about 45 mg, per unit dosage form (e.g., per tablet or capsule), per day of a solid-state form of Compound 1. In another aspect, the disclosure relates to Compound 1 freebase or a pharmaceutically acceptable salt thereof or a solid-state form of Compound 1 for use in reducing signs and symptoms of rheumatoid arthritis in an adult subject, particularly in a human subject suffering from or susceptible to moderate to severely active rheumatoid arthritis, the use comprising administering to the subject about 45 mg, per unit dosage form (e.g., per tablet or capsule) of Compound 1 freebase or a pharmaceutically acceptable salt thereof or a solid-state form of Compound 1. In one embodiment, the solid-state form is a crystalline hydrate. In one embodiment, the crystalline hydrate is the Freebase Hydrate Form B. In one embodiment, the crystalline hydrate is a hemihydrate. In one embodiment, the hemihydrate is the Freebase Hydrate Form C. In one embodiment, the solid-state form is a crystalline anhydrate. In one embodiment, the crystalline anhydrate is the Freebase Anhydrate Form D. In one embodiment, the solid-state form is the Tartrate Hydrate. In one embodiment, the Compound 1 freebase or a pharmaceutically acceptable salt thereof or the solid-state form of Compound 1 is administered orally QD (once daily). In one embodiment, the Compound 1 freebase or a pharmaceutically acceptable salt thereof or the solid-state form of Compound 1 is in a once daily extended-release formulation. In one embodiment, the Compound 1 (freebase) or a pharmaceutically acceptable salt thereof or the solid-state form of Compound 1 is in a once daily extended-release formulation, and the formulation delivers about 45 mg per unit dosage form (e.g., per tablet or capsule) of Compound 1 (freebase equivalent) or the solid-state form of Compound 1 orally QD (once daily) to the subject.

In another aspect, the disclosure relates to a solid-state form (and in particular a crystalline hydrate) of Compound 1, as described in the present disclosure, for use in reducing signs and symptoms of rheumatoid arthritis in an adult subject, particularly in a human subject suffering from or susceptible to rheumatoid arthritis.

In another embodiment, any of the methods of reducing signs and symptoms of rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the Compound 1 freebase or a pharmaceutically acceptable salt thereof and/or solid-state forms of Compound 1 used in any of the methods set forth herein may be administered to the subject in a once daily extended-release solid oral dosage form. In particular, in one embodiment, the methods comprise once daily administration to the subject of an extended-release (e.g., modified release) solid oral dosage form comprising the Compound 1 freebase or a pharmaceutically acceptable salt thereof or the solid-state form of Compound 1, and a pharmaceutically acceptable polymeric carrier substantially contributing to the modification of the release of the Compound 1 freebase or a pharmaceutically acceptable salt thereof or the solid-state form of Compound 1. In one aspect, the dosage form sustains release of the Compound 1 freebase or a pharmaceutically acceptable salt thereof or the solid-state form of Compound 1 for from about 4 hours to about 24 hours following entry of the dosage form into a use environment. In one embodiment, the dosage form has a release rate of not more than about 60% after passage of about 4 hours following entry of the dosage form into a use environment. The term "entry into a use environment" refers to contact of the dosage form with gastric fluids of the subject to whom it is administered. As used herein, the term "release rate" refers to the percentage of the active ingredient (e.g., Compound 1 or a solid-state form of Compound 1) in the dosage form that is released in the given time period, and under the specified conditions. In one embodiment, the dosage form comprises about 7.5 mg or about 15 mg or about 30 mg or about 45 mg, per unit dosage form (e.g., per tablet or capsule), of Compound 1 (freebase), or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the dosage form comprises about 7.5 mg or about 15 mg or about 30 mg or about 45 mg, per unit dosage form (e.g., per tablet or capsule), per day of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the pharmaceutically acceptable polymeric carrier is a release control polymer, as set forth herein.

Thus, in one aspect, the dosage form sustains release of the Compound 1 freebase or a pharmaceutically acceptable salt thereof or the solid-state form of Compound 1 for from about 4 hours to about 24 hours. In one embodiment, the dosage form releases the active ingredient (i.e., Compound 1 or a solid-state form of Compound 1), at a release rate of not more than about 25%, or from about 10% to about 25%, or from about 15% to about 20%, or about 20% after passage of about 1 hour following entry into the use environment. In one embodiment, the dosage form releases the active ingredient at a release rate of not more than about 40%, or from about 20% to about 40%, or from about 25% to about 35% after passage of about 2 hours following entry into the use environment. In one embodiment, the dosage form releases the active ingredient at a release rate of not more than about 60%, or from about 30% to about 60%, or from about 40% to about 60%, or from about 45% to about 55% after passage of about 4 hours following entry into the use environment. In one embodiment, the dosage form releases the active ingredient at a release rate of not more than about 70% or from about 40% to about 70%, or from about 55% to about 70% after passage of about 6 hours following entry into the use environment. In one embodiment, the dosage form releases the active ingredient at a release rate of not more than about 80% or from about 55% to about 80%, or from about 60% to about 80% after passage of about 6 hours following entry into the use environment. In one embodiment, the dosage form releases the active ingredient at a release rate of not more than about 80%, or not less than about 50%, or not less than about 60%, or not less than about 70%, or not less than about 75%, or from about 50% to about 80%, or from about 60% to about 80%, or from about 65% to about 80% after passage of about 8 hours following entry into the use environment. In one embodiment, the dosage form releases the active ingredient at a release rate of not less than about 55%, or not less than about 60% or not less than about 70%, or not less than about 80%, or not less than about 85%, or from about 55% to about 90%, or from about 70% to about 90% after passage of about 10 hours following entry into the use environment. In one embodiment, the dosage form releases the active ingredient at a release rate of not less than about 65%, or not less than about 70%, or not less than about 80%, or not less than about 90%, or from about 65% to about 99%, or from about 80% to about 99%, or from about 90% to about 99% after passage of about 16 hours following entry into the use environment. In one embodiment, the dosage form releases the active ingredient at a release rate of not less than about 70%, or not less than about 80%, or not less than about 90%, or from about 70% to 100%, or from about 80% to 100% after passage of about 20 hours following entry into the use environment. In one aspect, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the method comprising once daily administration to a subject suffering from or susceptible to the condition, of an extended-release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended-release solid oral dosage form comprising Compound 1 freebase or a pharmaceutically acceptable salt thereof or a solid-state form of Compound 1 for use in treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the use comprising once daily administration to a subject suffering from or susceptible to the condition, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another embodiment, the disclosure is directed to a method of treating an adult subject having moderate to severely active rheumatoid arthritis, the method comprising once daily administration to the subject, particularly a human subject suffering from or susceptible to rheumatoid arthritis, of an extended-release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In another aspect, the disclosure is directed to an extended-release solid oral dosage form comprising Compound 1 freebase or a pharmaceutically acceptable salt thereof or a solid-state form of Compound 1 for use in treating an adult subject having moderate to severely active rheumatoid arthritis, the use comprising once daily administration to the subject, particularly a subject suffering from or susceptible to moderately to severely active rheumatoid arthritis, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase or a pharmaceutically acceptable salt thereof, or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In one embodiment, the disclosure is directed to a method of treating structural damage associated with rheumatoid arthritis in an adult subject, the method comprising once daily administration to the subject, particularly a human subject suffering from or susceptible to rheumatoid arthritis, of an extended-release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase or a pharmaceutically acceptable salt thereof equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended-release solid oral dosage form comprising Compound 1 freebase or a pharmaceutically acceptable salt thereof or a solid-state form of Compound 1 for use in treating structural damage associated with rheumatoid arthritis in an adult subject, the use comprising once daily administration to the subject, particularly a subject suffering from or susceptible to structural damage associated with rheumatoid arthritis, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In one embodiment, the disclosure is directed to a method of reducing signs and symptoms of rheumatoid arthritis in an adult subject, the method comprising once daily administration to the subject, particularly a human subject suffering from or susceptible to moderately to severely active rheumatoid arthritis, of an extended-release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid-state form of Compound 1 in an amount sufficient to deliver to the subject about 7.5 mg or about 15 mg or about 30 mg or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended-release solid oral dosage form comprising Compound 1 freebase or a pharmaceutically acceptable salt thereof or a solid-state form of Compound 1 for use in reducing signs and symptoms associated with rheumatoid arthritis in an adult subject, the use comprising once daily administration to the subject, particularly a subject suffering from or susceptible to rheumatoid arthritis, of the extended-release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid-state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid-state form of Compound 1, wherein the dosage form sustains release of the Compound 1 freebase or a pharmaceutically acceptable salt thereof or the solid-state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid-state form of Compound 1. In one embodiment, the solid-state form is Freebase Hydrate Form B. In one embodiment, the solid-state form is Freebase Hydrate Form C. In one embodiment, the solid-state form is Freebase Anhydrate Form D. In one embodiment, the solid-state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In the foregoing methods, in one embodiment, the pharmaceutically acceptable polymeric carrier comprises a release control polymer. In one embodiment, the release control polymer is hydroxypropylmethyl cellulose. In one embodiment, the dosage form comprises a pH modifier. In one embodiment, the pH modifier is tartaric acid. In one embodiment, the dosage form comprises from about 10 w/w % to about 35 w/w % tartaric acid. In one embodiment, the dosage form comprises about 10 w/w % tartaric acid. In one embodiment, the dosage form comprises about 20 w/w % tartaric acid. In one embodiment, the dosage form comprises about 30 w/w % tartaric acid.

In another embodiment the methods of the present disclosure further comprise administering Compound 1 or a solid-state form thereof for at least 8 weeks. In another embodiment, the methods of the present disclosure comprise administering Compound 1 or a solid-state form thereof for at least 12 weeks.

In another embodiment, the present disclosure relates to the use of a solid-state form of Compound 1 for treating a condition as described in the various embodiments of the present disclosure.

In another embodiment, the present disclosure relates to a solid-state form of Compound 1 for use in treatment of a condition as described in the various embodiments of the present disclosure.

In another aspect are provide methods of treating pediatric pateints with juvenile idiopathic arthritis (JIA). In some embodiments, the pediatric patient has polyarticular course juvenile idiopathic arthritis (pcJIA), including rheumatoid factor-positive or rheumatoid factor-negative polyarticular JIA, extended oligoarticular JIA, or systemic JIA with active arthritis and without active systemic features.

Non-steroidal anti-inflammatory drugs (NSAIDs) are the mainstay of treatment in JIA, since they are believed to be the least toxic agent in children. They provide symptomatic relief but are not considered to be disease modifying. Disease-modifying anti-rheumatic drugs (DMARDs) such as methotrexate (MTX) and sulfasalazine are effective in JIA whereas hydroxychloroquine, D-penicillamine, and auranofin are not. Most children respond to MTX therapy, which has acceptable toxicity although remission is rare. To a variable extent, systemic use of corticosteroids is frequent in all JIA conditions but particularly for JIA is less desirable due to many deleterious effects. Systemic and intra-articular corticosteroids are being used in JIA in conjunction with NSAIDs and DMARDs. Intra-articular (IA) corticosteroid injections are recommended in JIA patients who have active arthritis regardless of the use of additional concomitant therapy. IA steroids, however, are frequently used and often induce prolonged remission in children with oligoarticular JIA.

Many potent biologic agents are now available for use in the treatment of JIA and are capable of inducing remission in JIA when used as monotherapy or in combination with MTX or other synthetic DMARDs. However, many patients still do not reach a state of remission or low disease activity with these agents or lose response over time. Additionally, given the potential safety concerns associated with the immunomodulatory effects of biologic agents, and given the fact that all biologic agents are administered by injection, novel oral treatment options with an improved benefit/risk profile are warranted to treat JIA. Accordingly, it would be desirable to provide pediatric patients with an alternate therapy for treatment of pcJIA.

JAK inhibition is known to inhibit the IL-6 pathway, and IL-6 in turn is known to be involved in the pathogenesis of both RA and juvenile idiopathic arthritis (JIA). See, e.g., Ou et al. Clin Rheumatol. 2002, 21:52-6; Mangge et al. Arthritis Rheum. 1995, 38(2):211-20; and Mellins et al. Nat Rev Rheumatol. 2011, 7(7):416-26. In particular, inhibition of the JAK1 subtype blocks the signaling of many important pro-inflammatory cytokines, including interleukin (IL)-2, IL-6, IL-7, and IL-15, which are known contributors to inflammatory disorders. Through modulation of these pro-inflammatory cytokine pathways, upadacitinib offers the potential for effective treatment of inflammatory or autoimmune disorders. Without wishing to be bound by any particular theory, it is believed that, based on the differentiated selectivity profile for JAK inhibition, upadacitinib could demonstrate an improved benefit/risk profile compared to other less selective JAK inhibitors or other therapeutic strategies for patients with inflammatory diseases. In particular, it is believed that upadacitinib will provide therapeutic benefit in pcJIA.

In adults, model-estimated area under the plasma upadacitinib concentration curve (AUC) over 0-24 hours (AUC0-24) at steady state were 362 and 720 ng·h/mL after multiple 15 mg and 30 mg once daily (QD) doses, respectively. Accordingly, pediatric doses achieving such exposures are disclosed herein as described above.

As disclosed herein, a prototype oral solution formulation was developed to allow suitable and flexible dosing in younger pediatric patients. Administration of two 6 mg doses of upadacitinib oral solution (1 mg/mL) 12 hours apart resulted in approximately 30% and 20% higher $C_{max}$ and AUC, respectively, relative to a single 15 mg QD upadacitinib (used in Phase 3 RA studies) under fasting conditions;

these results supported the selection of upadacitinib doses in pediatric subjects in the study of Example 1.

Accordingly, in one aspect is provided a method of treating pcJIA in a pediatric patient utilizing pediatric dosing based on body weight as disclosed herein above. The method generally comprises administering upadacitinib to the pediatric patient as a stable oral pharmaceutical formulation or an extended-release tablet. The amount of upadacitinib administered, the oral dose form, and the frequency of dosing (e.g., once or twice daily) will vary based on the weight of the patient.

In some embodiments, the pediatric patient has a body weight in a range from about 10 to less than about 20 kg, the method comprising administering 3 mg of upadacitinib twice daily (3 mg BID) as an oral solution. In some embodiments, the oral solution comprises upadacitinib at a concentration of about 1 mg/mL, and the 3 mg dose is provided BID as about 3 mL of the about 1 mg/mL solution. In some embodiments, the oral solution comprises upadacitinib at a concentration of about 0.5 mg/mL and the 3 mg dose is provided BID as about 6 mL of the about 0.5 mg/mL solution.

In some embodiments, the pediatric patient has a body weight in a range from about 10 to less than about 20 kg, the method comprising administering 6 mg of upadacitinib twice daily (6 mg BID) as an oral solution. In some embodiments, the oral solution comprises upadacitinib at a concentration of about 1 mg/mL, and the 6 mg dose is provided BID as about 6 mL of the about 1 mg/mL solution. In some embodiments, the oral solution comprises upadacitinib at a concentration of about 0.5 mg/mL and the 6 mg dose is provided BID as about 12 mL of the about 0.5 mg/mL solution.

In some embodiments, the pediatric patient has a body weight in a range from about 20 to less than about 30 kg, the method comprising administering 4 mg of upadacitinib twice daily (4 mg BID) as an oral solution. In some embodiments, the oral solution comprises upadacitinib at a concentration of about 1 mg/mL, and the 4 mg dose is provided BID as about 4 mL of the about 1 mg/mL solution. In some embodiments, the oral solution comprises upadacitinib at a concentration of about 0.5 mg/mL and the 4 mg dose is provided BID as about 8 mL of the about 0.5 mg/mL solution.

In some embodiments, the pediatric patient has a body weight in a range from about 20 to less than about 30 kg, the method comprising administering 8 mg of upadacitinib twice daily (8 mg BID) as an oral solution. In some embodiments, the oral solution comprises upadacitinib at a concentration of about 1 mg/mL, and the 8 mg dose is provided BID as about 8 mL of the about 1 mg/mL solution. In some embodiments, the oral solution comprises upadacitinib at a concentration of about 0.5 mg/mL and the 8 mg dose is provided BID as about 16 mL of the about 0.5 mg/mL solution.

In some embodiments, the pediatric patient has a body weight of about 30 kg or greater, the method comprising administering 6 mg of upadacitinib twice daily (6 mg BID) as an oral solution. In some embodiments, the oral solution comprises upadacitinib at a concentration of about 1 mg/mL, and the 6 mg dose is provided BID as about 6 mL of the about 1 mg/mL solution. In some embodiments, the oral solution comprises upadacitinib at a concentration of about 0.5 mg/mL and the 6 mg dose is provided BID as about 12 mL of the about 0.5 mg/mL solution.

In some embodiments, the pediatric patient has a body weight of about 30 kg or greater, the method comprising administering 8 mg of upadacitinib twice daily (8 mg BID) as an oral solution. In some embodiments, the oral solution comprises upadacitinib at a concentration of about 1 mg/mL, and the 8 mg dose is provided BID as about 8 mL of the about 1 mg/mL solution. In some embodiments, the oral solution comprises upadacitinib at a concentration of about 0.5 mg/mL and the 8 mg dose is provided BID as about 16 mL of the about 0.5 mg/mL solution.

In some embodiments, the pediatric patient has a body weight of about 30 kg or greater, the method comprising administering 12 mg of upadacitinib twice daily (12 mg BID) as an oral solution. In some embodiments, the oral solution comprises upadacitinib at a concentration of about 1 mg/mL, and the 12 mg dose is provided BID as about 12 mL of the about 1 mg/mL solution. In some embodiments, the oral solution comprises upadacitinib at a concentration of about 0.5 mg/mL and the 12 mg dose is provided BID as about 24 mL of the about 0.5 mg/mL solution.

In some embodiments, the pediatric patient has a body weight of about 30 kg or greater, the method comprising administering 15 mg of upadacitinib once daily (15 mg QD) as an extended-release tablet. In some embodiments, the pediatric patient has a body weight of about 30 kg or greater, the method comprising administering 30 mg of upadacitinib once daily (30 mg QD) as an extended-release tablet.

In some embodiments, the pediatric patient has a body weight of about 30 kg or greater, the method comprising administering 15 mg of upadacitinib once daily (15 mg QD) as an extended-release tablet. In some embodiments, the pediatric patient has a body weight of about 30 kg or greater, the method comprising administering 30 mg of upadacitinib once daily (30 mg QD) as an extended-release tablet.

In some embodiments, the pediatric patient has a history of arthritis affecting at least 5 joints within the first 6 months of disease (for extended oligoarticular JIA: ≤4 joints during the first 6 months of disease and >4 joints thereafter), as per International League of Associations for Rheumatology (ILAR) criteria.

In some embodiments, the pediatric patient does not have a diagnosis of enthesitis-related arthritis (ERA) or juvenile psoriatic arthritis (JPSA).

In some embodiments, the pediatric patient has 5 or more active joints, defined as the presence of swollen joints (not due to deformity) or, in the absence of swelling, joints with limitation of movement (LOM) plus pain on motion and/or tenderness with palpation, with LOM present in at least three of the active joints.

In some embodiments, the pediatric patient is receiving methotrexate. In such embodiments, the patient should be on a stable dose of ≤20 mg/m2 for at least 8 weeks before the start of administration.

In some embodiments, the pediatric patient is receiving oral glucocorticoids. In such embodiments, the patient should be on a stable dose (no greater than 10 mg/day or 0.2 mg/kg/day, whatever is lower) for at least 1 week before the start of administration.

In some embodiments, the patient achieves one or more of a JIA ACR pediatric 30/50/70/90/100 response, a change from baseline in JADAS10/27/71 responses, low disease activity or remission according to JADAS-based criteria. In some embodiments, the patient achieves one or more of a JIA ACR pediatric 30/50/70/90/100 response at 12 weeks, 24 weeks, or 48 weeks.

In some embodiments, the pediatric patient does not have any of ongoing or active uveitis within 3 months prior to initiating treatment, active TB active infection(s) requiring treatment with parenteral anti-infectives, chronic recurring infection and/or active viral infection, active hepatitis B virus (HBV) or hepatitis C virus (HCV) infection, a positive result of beta-D-glucan.

In some embodiments, the pediatric patient has not been treated with intra-articular or parenteral administration of corticosteroids in the preceding 4 weeks prior to the start of administration.

In some embodiments, the pediatric patient has no history of: any malignancy except for successfully treated non-melanoma skin cancer or localized carcinoma in situ of the cervix, recurrent or disseminated (even a single episode) herpes zoster; disseminated (even a single episode) herpes simplex; human immunodeficiency virus (HIV) infection; previous reception of an organ transplant that requires continued immunosuppression, gastrointestinal perforation (other than appendicitis or penetrating injury), diverticulitis, or significantly increased risk for gastrointestinal perforation; prior exposure to a JAK inhibitor.

In some embodiments, the pediatric patient is not using known moderate or strong inhibitors (e.g., amiodarone, clarithromycin, fluconazole, ciprofloxacin, itraconazole, ketoconazole, quinidine, fluoxetine, and paroxetine) or inducers (e.g., carbamazepine, rifampin, phenobarbital, and phenytoin) of drug metabolizing enzymes.

In some embodiments, the pediatric patient is not using biologic treatment (etanercept, infliximab, adalimumab, abatacept, golimumab, tocilizumab, ustekinumab, certolizumab pegol, canakinumab, anakinra).

In some embodiments, the pediatric patient is not using a JAK inhibitor (e.g., commercially available upadacitinib [Rinvoq®], tofacitinib [Xeljanz®], ruxolitinib [Jakafi®], baricitinib [Olumiant®], peficitinib [Smyraf®], abrocitinib [PF-04965842], or filgotinib).

In some embodiments, the pediatric patient has moderately to severely active pcJIA.

In some embodiments, the pediatric patient has had an inadequate response to one or more DMARDs.

In some embodiments, the pediatric patient has had an inadequate response to one or more TNF blockers.

In some embodiments, the pediatric patient has polyarticular course juvenile idiopathic arthritis (pcJIA), including rheumatoid factor-positive or rheumatoid factor-negative polyarticular JIA, extended oligoarticular JIA, or systemic JIA with active arthritis and without active systemic features.

Non-steroidal anti-inflammatory drugs (NSAIDs) are the mainstay of treatment in JIA, since they are believed to be the least toxic agent in children. They provide symptomatic relief but are not considered to be disease modifying. Disease-modifying anti-rheumatic drugs (DMARDs) such as methotrexate (MTX) and sulfasalazine are effective in JIA whereas hydroxychloroquine, D-penicillamine, and auranofin are not. Most children respond to MTX therapy, which has acceptable toxicity although remission is rare. To a variable extent, systemic use of corticosteroids is frequent in all JIA conditions but particularly for JIA is less desirable due to many deleterious effects. Systemic and intra-articular corticosteroids are being used in JIA in conjunction with NSAIDs and DMARDs. Intra-articular (IA) corticosteroid injections are recommended in JIA patients who have active arthritis regardless of the use of additional concomitant therapy. IA steroids, however, are frequently used and often induce prolonged remission in children with oligoarticular JIA.

Many potent biologic agents are now available for use in the treatment of JIA and are capable of inducing remission in JIA when used as monotherapy or in combination with MTX or other synthetic DMARDs. However, many patients still do not reach a state of remission or low disease activity with these agents or lose response over time. Additionally, given the potential safety concerns associated with the immunomodulatory effects of biologic agents, and given the fact that all biologic agents are administered by injection, novel oral treatment options with an improved benefit/risk profile are warranted to treat JIA. Accordingly, it would be desirable to provide pediatric patients with an alternate therapy for treatment of pcJIA.

JAK inhibition is known to inhibit the IL 6 pathway, and IL-6 in turn is known to be involved in the pathogenesis of both RA and juvenile idiopathic arthritis (JIA). See, e.g., On et al. Clin Rheumatol. 2002, 21:52-6; Mangge et al. Arthritis Rheum. 1995, 38(2):211-20; and Mellins et al. Nat Rev Rheumatol. 2011, 7(7):416-26. In particular, inhibition of the JAK1 subtype blocks the signaling of many important pro-inflammatory cytokines, including interleukin (IL)-2, IL-6, IL-7, and IL-15, which are known contributors to inflammatory disorders. Through modulation of these pro-inflammatory cytokine pathways, upadacitinib offers the potential for effective treatment of inflammatory or autoimmune disorders. Without wishing to be bound by any particular theory, it is believed that, based on the differentiated selectivity profile for JAK inhibition, upadacitinib could demonstrate an improved benefit/risk profile compared to other less selective JAK inhibitors or other therapeutic strategies for patients with inflammatory diseases. In particular, it is believed that upadacitinib will provide therapeutic benefit in pcJIA.

In adults, model-estimated area under the plasma upadacitinib concentration curve (AUC) over 0-24 hours (AUC0-24) at steady state were 362 and 720 ng·h/mL after multiple 15 mg and 30 mg once daily (QD) doses, respectively. Accordingly, pediatric doses achieving such exposures are disclosed herein as described above.

As disclosed herein, a prototype oral solution formulation was developed to allow suitable and flexible dosing in younger pediatric patients. Administration of two 6 mg doses of upadacitinib oral solution (1 mg/mL) 12 hours apart resulted in approximately 30% and 20% higher $C_{max}$ and AUC, respectively, relative to a single 15 mg QD upadacitinib (used in Phase 3 RA studies) under fasting conditions; these results supported the selection of upadacitinib doses in pediatric subjects in the study of Example 1.

Accordingly, in one aspect is provided a method of treating pcJIA in a pediatric patient utilizing pediatric dosing based on body weight as disclosed herein above. The method generally comprises administering upadacitinib to the pediatric patient as a stable oral pharmaceutical formulation or an extended-release tablet. The amount of upadacitinib administered, the oral dose form, and the frequency of dosing (e.g., once or twice daily) will vary based on the weight of the patient.

In some embodiments, the pediatric patient has a body weight in a range from about 10 to less than about 20 kg, the method comprising administering 3 mg of upadacitinib twice daily (3 mg BID) as an oral solution. In some embodiments, the oral solution comprises upadacitinib at a concentration of about 1 mg/mL, and the 3 mg dose is provided BID as about 3 mL of the about 1 mg/mL solution. In some embodiments, the oral solution comprises upadacitinib at a concentration of about 0.5 mg/mL and the 3 mg dose is provided BID as about 6 mL of the about 0.5 mg/mL solution.

In some embodiments, the pediatric patient has a body weight in a range from about 10 to less than about 20 kg, the method comprising administering 6 mg of upadacitinib twice daily (6 mg BID) as an oral solution. In some embodiments, the oral solution comprises upadacitinib at a concentration of about 1 mg/mL, and the 6 mg dose is provided BID as about 6 mL of the about 1 mg/mL solution. In some embodiments, the oral solution comprises upadacitinib at a concentration of about 0.5 mg/mL and the 6 mg dose is provided BID as about 12 mL of the about 0.5 mg/mL solution.

In some embodiments, the pediatric patient has a body weight in a range from about 20 to less than about 30 kg, the method comprising administering 4 mg of upadacitinib twice daily (4 mg BID) as an oral solution. In some embodiments, the oral solution comprises upadacitinib at a concentration of about 1 mg/mL, and the 4 mg dose is provided BID as about 4 mL of the about 1 mg/mL solution. In some embodiments, the oral solution comprises upadacitinib at a concentration of about 0.5 mg/mL and the 4 mg dose is provided BID as about 8 mL of the about 0.5 mg/mL solution.

In some embodiments, the pediatric patient has a body weight in a range from about 20 to less than about 30 kg, the method comprising administering 8 mg of upadacitinib twice daily (8 mg BID) as an oral solution. In some embodiments, the oral solution comprises upadacitinib at a concentration of about 1 mg/mL, and the 8 mg dose is provided BID as about 8 mL of the about 1 mg/mL solution. In some embodiments, the oral solution comprises upadacitinib at a concentration of about 0.5 mg/mL and the 8 mg dose is provided BID as about 16 mL of the about 0.5 mg/mL solution.

In some embodiments, the pediatric patient has a body weight of about 30 kg or greater, the method comprising administering 6 mg of upadacitinib twice daily (6 mg BID) as an oral solution. In some embodiments, the oral solution comprises upadacitinib at a concentration of about 1 mg/mL, and the 6 mg dose is provided BID as about 6 mL of the about 1 mg/mL solution. In some embodiments, the oral solution comprises upadacitinib at a concentration of about 0.5 mg/mL and the 6 mg dose is provided BID as about 12 mL of the about 0.5 mg/mL solution.

In some embodiments, the pediatric patient has a body weight of about 30 kg or greater, the method comprising administering 8 mg of upadacitinib twice daily (8 mg BID) as an oral solution. In some embodiments, the oral solution comprises upadacitinib at a concentration of about 1 mg/mL, and the 8 mg dose is provided BID as about 8 mL of the about 1 mg/mL solution. In some embodiments, the oral solution comprises upadacitinib at a concentration of about 0.5 mg/mL and the 8 mg dose is provided BID as about 16 mL of the about 0.5 mg/mL solution.

In some embodiments, the pediatric patient has a body weight of about 30 kg or greater, the method comprising administering 12 mg of upadacitinib twice daily (12 mg BID) as an oral solution. In some embodiments, the oral solution comprises upadacitinib at a concentration of about 1 mg/mL, and the 12 mg dose is provided BID as about 12 mL of the about 1 mg/mL solution. In some embodiments, the oral solution comprises upadacitinib at a concentration of about 0.5 mg/mL and the 12 mg dose is provided BID as about 24 mL of the about 0.5 mg/mL solution.

In some embodiments, the pediatric patient has a body weight of about 30 kg or greater, the method comprising administering 15 mg of upadacitinib once daily (15 mg QD) as an extended-release tablet. In some embodiments, the pediatric patient has a body weight of about 30 kg or greater, the method comprising administering 30 mg of upadacitinib once daily (30 mg QD) as an extended-release tablet.

In some embodiments, the pediatric patient has a body weight of about 30 kg or greater, the method comprising administering 15 mg of upadacitinib once daily (15 mg QD) as an extended-release tablet. In some embodiments, the pediatric patient has a body weight of about 30 kg or greater, the method comprising administering 30 mg of upadacitinib once daily (30 mg QD) as an extended-release tablet.

In some embodiments, the pediatric patient has a history of arthritis affecting at least 5 joints within the first 6 months of disease (for extended oligoarticular JIA: ≤4 joints during the first 6 months of disease and >4 joints thereafter), as per International League of Associations for Rheumatology (ILAR) criteria.

In some embodiments, the pediatric patient does not have a diagnosis of enthesitis-related arthritis (ERA) or juvenile psoriatic arthritis (JPSA).

In some embodiments, the pediatric patient has 5 or more active joints, defined as the presence of swollen joints (not due to deformity) or, in the absence of swelling, joints with limitation of movement (LOM) plus pain on motion and/or tenderness with palpation, with LOM present in at least three of the active joints.

In some embodiments, the pediatric patient is receiving methotrexate. In such embodiments, the patient should be on a stable dose of ≤20 mg/m2 for at least 8 weeks before the start of administration.

In some embodiments, the pediatric patient is receiving oral glucocorticoids. In such embodiments, the patient should be on a stable dose (no greater than 10 mg/day or 0.2 mg/kg/day, whatever is lower) for at least 1 week before the start of administration.

In some embodiments, the patient achieves one or more of a JIA ACR pediatric 30/50/70/90/100 response, a change from baseline in JADAS10/27/71 responses, low disease activity or remission according to JADAS-based criteria. In some embodiments, the patient achieves one or more of a JIA ACR pediatric 30/50/70/90/100 response at 12 weeks, 24 weeks, or 48 weeks.

In some embodiments, the pediatric patient does not have any of ongoing or active uveitis within 3 months prior to initiating treatment, active TB active infection(s) requiring treatment with parenteral anti-infectives, chronic recurring infection and/or active viral infection, active hepatitis B virus (HBV) or hepatitis C virus (HCV) infection, a positive result of beta-D-glucan.

In some embodiments, the pediatric patient has not been treated with intra-articular or parenteral administration of corticosteroids in the preceding 4 weeks prior to the start of administration.

In some embodiments, the pediatric patient has no history of: any malignancy except for successfully treated non-melanoma skin cancer or localized carcinoma in situ of the cervix, recurrent or disseminated (even a single episode) herpes zoster; disseminated (even a single episode) herpes simplex; human immunodeficiency virus (HIV) infection; previous reception of an organ transplant that requires continued immunosuppression, gastrointestinal perforation (other than appendicitis or penetrating injury), diverticulitis, or significantly increased risk for gastrointestinal perforation; prior exposure to a JAK inhibitor.

In some embodiments, the pediatric patient is not using known moderate or strong inhibitors (e.g., amiodarone, clarithromycin, fluconazole, ciprofloxacin, itraconazole, ketoconazole, quinidine, fluoxetine, and paroxetine) or inducers (e.g., carbamazepine, rifampin, phenobarbital, and phenytoin) of drug metabolizing enzymes.

In some embodiments, the pediatric patient is not using biologic treatment (etanercept, infliximab, adalimumab, abatacept, golimumab, tocilizumab, ustekinumab, certolizumab pegol, canakinumab, anakinra).

In some embodiments, the pediatric patient is not using a JAK inhibitor (e.g., commercially available upadacitinib [Rinvoq®], tofacitinib [Xeljanz®], ruxolitinib [Jakafi®], baricitinib [Olumiant®], peficitinib [Smyraf®], abrocitinib [PF-04965842], or filgotinib).

In some embodiments, the pediatric patient has moderately to severely active pcJIA.

In some embodiments, the pediatric patient has had an inadequate response to one or more DMARDs.

In some embodiments, the pediatric patient has had an inadequate response to one or more TNF blockers.

III. Pharmaceutical Compositions

The present disclosure further relates, in part, to compositions comprising Compound 1 or a pharmaceutically acceptable salt thereof, or one or more solid-state forms of Compound 1. Although the solid-state form may be administered alone or in the form of a pharmaceutical composition, administration generally will be in the form of a pharmaceutical composition. In some embodiments, the composition comprises Compound 1 or a pharmaceutically acceptable salt thereof or a solid-state form of Compound 1 in association with a pharmaceutically acceptable carrier. The preferred composition depends on the method of administration, and typically comprises one or more conventional pharmaceutically acceptable carriers, adjuvants, and/or vehicles (together referred to as "excipients"). Such compositions can be formulated for various routes of systemic or local delivery for example, by oral administration, topical administration, transmucosal administration, rectal administration, intravaginal administration, or administration by subcutaneous, intrathecal, intravenous, intramuscular, intraperitoneal, intranasal, intraocular or intraventricular injection.

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise pH modifiers, such as sodium citrate; magnesium or calcium carbonate or bicarbonate; tartaric acid, fumaric acid, citric acid, succinic acid, malic acid, and phosphoric acid and combinations thereof. Tablets and pills additionally can be prepared with enteric coatings.

In one embodiment, the pharmaceutical composition is a tablet dosage form. In one aspect, the tablet is coated with a pharmaceutically acceptable polymer.

In one embodiment, tablet is a controlled-release formulation, such as an extended-release tablet dosage form (also referred to herein as a modified release or sustained release formulation). Such formulations permit the sustained release of the active ingredient over an extended period of time, as compared to immediate release solid dosage forms, which permit the release of most or all of the active ingredient over a short period of time (e.g., typically around 60 minutes or less). In one aspect, the tablet comprises an active ingredient and at least one additive selected from the group consisting of a release control polymer, a filler, a glidant, a lubricant (e.g., for use in compacting the granules), a pH modifier, a surfactant, and combinations thereof. In one aspect, the tablet comprises an active ingredient, a release control polymer, a filler, a glidant, and a lubricant. In one aspect, the tablet comprises an active ingredient, a release control polymer, a filler, a glidant, a lubricant, and a pH modifier.

In certain embodiments, the release control polymer will be a hydrophilic polymer. Examples of suitable release control polymers include, but are not limited to a cellulose derivative with a viscosity of between 1000 and 150,000 mPA-s, hydroxypropylmethyl cellulose (e.g., Hypromellose 2208 or controlled release grades of hydroxypropylmethyl cellulose, including the E, F, and K series), copolymers of acrylic acid crosslinked with a polyalkenyl polyether (e.g., Carbopol® polymers), hydroxypropyl cellulose, hydroxyethyl cellulose, non-ionic homopolymers of ethylene oxide (e.g., Polyox™), water soluble natural gums of polysaccharides (e.g., xanthan gum, alginate, locust bean gum, etc.), crosslinked starch, polyvinyl acetates, polyvinylpyrrolidone, mixtures of polyvinyl acetates and polyvinyl pyrrolidone, and combinations thereof. In one embodiment, the release control polymer is selected from the group consisting of hydroxypropylmethyl cellulose, copolymers of acrylic acid crosslinked with a polyalkenyl polyether (e.g., Carbopol® polymers), and combinations thereof. Examples of suitable fillers ("bulking agents") include, but are not limited to, microcrystalline cellulose (e.g., Avicel® PH 101; Avicel® PH 102;), mannitol (e.g., Pearlitol® 100 SD or Pearlitol® 200 SD), lactose, sucrose, sorbitol, and the like. In one embodiment, the filler is selected from the group consisting of microcrystalline cellulose, mannitol, and combinations thereof. Examples of suitable glidants include, but are not limited to, silicone dioxide (e.g., colloidal silicon dioxide), calcium silicate, magnesium silicate, talc, and combinations thereof. In one embodiment, the glidant is colloidal silicone dioxide. Examples of suitable lubricants include, but are not limited to, polyethylene glycol (e.g., having a molecular weight of from 1000 to 6000), magnesium stearate, calcium stearate, sodium stearyl fumarate, talc, and the like. In one embodiment, the lubricant is magnesium stearate. Examples of suitable pH modifiers include, but are not limited to, organic acids, such as tartaric acid, citric acid, succinic acid, fumaric acid; sodium citrate; magnesium or calcium carbonate or bicarbonate; and combinations thereof. In one embodiment, the pH modifier is tartaric acid. Examples of suitable surfactants include sodium lauryl sulfate.

In one embodiment, the pharmaceutical composition comprises from about 10 w/w % to about 35 w/w % of a pH modifier, and in particular, tartaric acid, fumaric acid, citric acid, succinic acid, malic acid, or combinations thereof. In other embodiments, the formulation comprises from about 20 w/w % to about 35 w/w %, or from about 20 w/w % to about 30 w/w %, or from about 20 w/w % to about 25 w/w %, or about 10 w/w %, about 15 w/w. %, about 20 w/w %, about 25 w/w % or about 30 w/w % pH modifier. In one embodiment, the pH modifier is tartaric acid.

In one embodiment, the Compound 1 (freebase) or a pharmaceutically acceptable salt thereof or the crystalline hydrate used in the methods of the present disclosure is in a once daily extended-release formulation. In one embodiment, the Compound 1 (freebase) or a pharmaceutically acceptable salt thereof or the crystalline hydrate is in a once daily extended-release formulation, and the formulation delivers about 7.5 mg or about 15 mg or about 30 mg or about 45 mg per unit dosage form (e.g., per tablet or capsule) of Compound 1 (freebase equivalent) orally QD (once daily). In one particular embodiment, the crystalline hydrate is Freebase Hydrate Form C.

In one embodiment, the Compound 1 (freebase) or a pharmaceutically acceptable salt thereof or the crystalline hydrate is in a once daily extended-release formulation, and the formulation delivers 7.5 mg of Compound 1 (freebase equivalent) orally QD (once daily). In some such embodiments, the once daily extended-release formulation will have a relative bioavailability approximately equivalent to that of an immediate release capsule comprising Compound 1 (freebase) or a pharmaceutically acceptable salt thereof or a solid-state form thereof that delivers 3 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended-release formulation, and the formulation delivers 15 mg of Compound 1 (freebase equivalent) orally QD (once daily). In some such embodiments, the once daily extended-release formulation will have a relative bioavailability approximately equivalent to that of an immediate release capsule comprising Compound 1 (freebase) or a pharmaceutically acceptable salt thereof or a solid-state form thereof that delivers 6 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended-release formulation, and the formulation delivers 30 mg of Compound 1 (freebase equivalent) orally QD (once daily). In some such embodiments, the once daily extended-release formulation will have a relative bioavailability approximately equivalent to that of an immediate release capsule comprising Compound 1 (freebase) or a pharmaceutically acceptable salt thereof or a solid-state form thereof that delivers 12 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended-release formulation, and the formulation delivers 45 mg of Compound 1 (freebase equivalent) orally QD (once daily). In some such embodiments, the once daily extended-release formulation will have a relative bioavailability approximately equivalent to that of an immediate release capsule comprising Compound 1 (freebase) or a pharmaceutically acceptable salt thereof or a solid-state form thereof that delivers 18 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In some embodiments, the composition is a stable liquid pharmaceutical composition. In some embodiments, the stable liquid pharmaceutical composition is a stable oral solution. In some embodiments, the stable liquid pharmaceutical composition is a stable oral suspension. Suitable stable liquid pharmaceutical compositions comprise upadacitinib or a pharmaceutically acceptable salt or solid-state form thereof, along with excipients such as buffers, preservatives, sweeteners, flavoring agents, pH adjusting agents, solvents, and the like. In some embodiments, the stable liquid pharmaceutical composition is a stable oral pharmaceutical solution comprising upadacitinib, a buffer and/or pH adjusting agent, a preservative, a sweetener, and water. In some embodiments, the stable liquid pharmaceutical composition is a stable oral pharmaceutical suspension comprising upadacitinib, a buffer and/or pH adjusting agent, a preservative, a sweetener, and water.

The concentration of upadacitinib in the stable liquid pharmaceutical composition may vary. Due to the bitterness of upadacitinib, which is difficult to mask at higher concentrations for palatability (see, e.g., Example 39), it is generally present at about 1 mg/mL or less. In some embodiments, the stable pharmaceutical composition is an oral solution comprising: upadacitinib at a concentration in a range from about 0.3 mg/mL to about 1.2 mg/mL, such as from about 0.3 to about 0.7 mg/mL, or from about 0.8 to about 1.2 mg/mL. In some embodiments, the oral solution comprises upadacitinib at a concentration of about 1 mg/mL, such as from about 0.8, 0.9, or about 1.0, to about 1.1 or about 1.2 mg/mL. In some embodiments, the oral solution comprises upadacitinib at a concentration from about 0.9 mg/mL to about 1.1 mg/mL. In some embodiments, the oral solution comprises upadacitinib at a concentration of 1.0 mg/mL. In some embodiments, the oral solution comprises upadacitinib at a concentration of about 0.5 mg/mL, such as from about 0.3, 0.4, or about 0.5, to about 0.6 or about 0.7 mg/mL. In some embodiments, the oral solution comprises upadacitinib at a concentration from about 0.4 mg/mL to about 0.6 mg/mL. In some embodiments, the oral solution comprises upadacitinib at a concentration of 0.5 mg/mL.

In some embodiments, the oral solution comprises a pH adjusting agent. Suitable pH adjusting agents include acids such as mineral or organic acids. Mineral acids include but are not limited to hydrochloric, sulfuric, and phosphoric acid. As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($-CO_2H$). In some embodiments, the pH adjusting agent is an organic acid. Suitable organic acids include, but are not limited to, benzoic acid, toluic acids, salicylic acid, benzenesulfonic acid, p-toluenesulfonic acid, 2-(4-isobutylphenyl)propanoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid (L), aspartic acid (L), alpha-methylbutyric acid, camphoric acid (+), camphor-10-sulfonic acid (+), cinnamic acid, citric acid, cyclamic acid, dodecylsulfuric acid, ethane-1,2-disulfonic acid, ethanesulfonic acid, fumaric acid, furoic acid, galactaric acid, gentisic acid, glucoheptonic acid, gluconic acid, glucuronic acid, glutamic acid, glutaric acid, glycerophosphoric acid, glycolic acid, hippuric acid, isobutyric acid, isovaleric acid, lactobionic acid, lauric acid, levulinic acid, malic acid, maleic acid, malonic acid, mandelic acid, methanesulfonic acid, naphthalene-1,5-disulfonic acid, naphthalene-2-sulfonic acid, oleic acid, palmitic acid, pamoic acid, phenylacetic acid, pyroglutamic acid, pyruvic acid, sebacic acid, stearic acid, tartaric acid, and undecylenic acid. In some embodiments, the pH adjusting agent is selected from the group consisting of citric acid, phosphoric acid, tartaric acid, succinic acid, formic acid, acetic acid, and combinations thereof. In some embodiments, the pH adjusting agent is citric acid.

In some embodiments, the stable liquid pharmaceutical composition comprises a buffer. Suitable buffers include, but are not limited to, citrate, phosphate, tartrate, succinate, glycinate, glycerophosphate, formate, and acetate. In some embodiments, the buffer is selected from the group consisting of citrate, phosphate, tartrate, succinate, formate, acetate, and combinations thereof. In some embodiments, the buffer is selected from the group consisting of citrate and phosphate. In some embodiments, the buffer is sodium citrate.

The quantity of pH adjusting agent and/or buffer may vary. Generally, the concentration of each is adjusted to provide a desired pH range of the resulting stable liquid pharmaceutical composition. In some embodiments, the stable liquid pharmaceutical composition has a pH in a range from about 2 to about 5, or from about 3 to about 4, or from about 2 to about 3, or from about 4 to about 5, or from about 2.0 to about 2.5, or from about 2.5 to about 3.0, or from about 3.0 to about 3.5, or from about 3.5 to about 4.0, or from about 4.0 to about 4.5, or from about 4.5 to about 5.0, or from about 3.0 to about 3.1, or from about 3.0 to about 3.2, or from about 3.0 to about 3.3, or from about 3.1 to about 3.2, or from about 3.1 to about 3.3, or from about 3.1 to about 3.4, or from about 3.1 to about 3.5, or from about 3.2 to about 3.3, or from about 3.2 to about 3.4, or from about 3.2 to about 3.5, or from about 3.3 to about 3.4, or from about 3.3 to about 3.5. In some embodiments, the stable liquid pharmaceutical composition has a pH of about 3.0, or about 3.1, or about 3.2.

In some embodiments, the stable liquid pharmaceutical composition comprises a preservative. Suitable preservatives include, but are not limited to, benzoic acid, sodium benzoate, benzyl alcohol, ascorbic acid, potassium sorbate, 4-hydroxybenzoic acid, 4-hydroxybenzoate, methyl paraben, propyl paraben, sodium metabisulfite, and combinations thereof. In some embodiments, the preservative is selected from the group consisting of sodium benzoate, benzoic acid, propyl paraben, sodium metabisulfite, potassium sorbate, para-hydroxybenzoic acid, para-hydroxybenzoate, and combinations thereof.

In some embodiments, the stable liquid pharmaceutical composition comprises a sweetener. The sweetener can be any sweetener or combination of sweeteners, in natural or artificial form, or as a combination of natural and artificial sweeteners. Examples of natural sweeteners include fructose, sucrose, glucose, maltose, mannose, galactose, lactose, stevia, honey, and the like. Examples of artificial sweeteners include sucralose, isomaltulose, maltodextrin, saccharin, aspartame, acesulfame K, neotame, and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the sweetener is selected from the group consisting of sucralose, acesulfame potassium, sodium saccharin, neotame, sucrose, maltitol, xylitol, and combinations thereof.

In some embodiments, the stable oral pharmaceutical solution comprises one or more flavoring agents. Any flavorful or aromatic substance capable of altering the taste, fragrance, or both of the solution may be utilized. Flavoring agents may be natural or synthetic. Suitable flavoring agents include, but are not limited to, flavor packages imparting flavors such as cherry, orange, lemon, lime, bubblegum, grape, strawberry, mango, and the like.

In some embodiments, the stable oral pharmaceutical solution comprises a taste modifier. Suitable taste modifiers include, but are not limited to, salts such as sodium chloride, and monoammonium glycyrrhizinate to accentuate sweetness.

In some embodiments, the stable pharmaceutical composition is an oral solution comprising upadacitinib, citric acid, sodium citrate, sodium benzoate, sweetener, and water.

In some embodiments, the stable pharmaceutical composition comprises citric acid in an amount in a range from about 0.1 to about 1 mg/mL.

In some embodiments, the stable pharmaceutical composition comprises sodium citrate in an amount in a range from about 0.01 to about 1 mg/mL.

In some embodiments, the stable pharmaceutical composition comprises sodium benzoate in an amount in a range from about 0.01 to about 0.1 mg/mL.

In some embodiments, the stable pharmaceutical composition comprises a sweetener in an amount in a range from about 1 to about 50 mg/mL.

In particular embodiments, the stable pharmaceutical composition is an oral solution having the formulation provided in Table 1.

TABLE 1

| Formulation of upadacitinib oral solution (1 mg/mL) | |
| --- | --- |
| Component | mg/mL |
| upadacitinib | 0.3-1.2 |
| citric acid, anhydrous | 0.15-0.35 |
| sodium citrate, dihydrate | 0.03-0.06 |
| sodium benzoate | 0.02-0.06 |
| sucralose | 7-11 |
| purified water | q.s to 1 mL |

The pH of the stable oral solution may vary. In some embodiments, the stable oral solution has a pH in a range from about 2 to about 5. In some embodiments, the stable oral solution has a pH in a range from about 3 to about 4. In some embodiments, the stable oral solution has a pH in a range from about 2.5 to about 3.5.

IV. Combination Therapy and Fixed-Dose Combinations

The present disclosure further relates to (i) methods of treatment and uses as previously described that further comprise the administration of one or more additional therapeutic agents (i.e., combination therapies), and (ii) pharmaceutical compositions as previously described that further comprise one or more additional therapeutic agents (i.e., fixed-dose combinations). When administered to a subject in combination with one or more additional therapeutic agents, the solid-state form of Compound 1 and the additional therapeutic agent(s) can be administered as separate dosage forms or as a single dosage form comprising the solid-state form of Compound 1 and the additional therapeutic agent(s). If administered as a separate dosage form, the additional therapeutic agent may be administered either simultaneously with, or sequentially with, the dosage form comprising the solid-state form of Compound 1.

For example, the solid-state forms of the present disclosure may be administered in a pharmaceutically acceptable form either alone or in combination with one or more additional agents that modulate a mammalian immune system or with anti-inflammatory agents. These agents may include but are not limited to cyclosporin A (e.g., SANDIMMUNE® or NEORAL®), rapamycin, FK-506 (tacrolimus), leflunomide, deoxyspergualin, mycophenolate (e.g., CELLCEPT®), azathioprine (e.g., IMURAN®), daclizumab (e.g., ZENAPAX®), OKT3 (e.g., ORTHOCLONE®), AtGam, aspirin, acetaminophen, aminosalicylate, ciprofloxacin, corticosteroid, metronidazole, probiotic, tacrolimus, ibuprofen, naproxen, piroxicam, and anti-inflammatory steroids (e.g., prednisolone or dexamethasone). In certain embodiments, the one or more additional agents are selected from the group consisting of aspirin, acetaminophen, aminosalicylate, ciprofloxacin, corticosteroid, cyclosporine, metronidazole, probiotic, tacrolimus, ibuprofen, naproxen, piroxicam, prednisolone, dexamethasone, anti-inflammatory steroid, methotrexate, chloroquine, azathioprine, hydroxychloroquine, penicillamine, sulfasalazine, leflunomide, tocilizumab, anakinra, abatacept, certolizumab pegol, golimumab, vedolizumab, natalizumab, ustekinumab, rituximab, efalizumab, belimumab, etanercept, infliximab, adalimumab, and immune modulator (e.g., activator) for CD4+CD25+ Treg cells.

Non-limiting examples of therapeutic agents for rheumatoid arthritis with which a compound of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L). Combinations of therapeutic agents may interfere at different points in the autoimmune and subsequent inflammatory cascade. Such examples may include TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept), and also TNFα converting enzyme (TACE) inhibitors; similarly IL-1 inhibitors (Interleukin-1-converting enzyme inhibitors, IL-1RA etc.) may be effective for the same reason. Other combinations include Interleukin 11.

The solid-state form may also be combined with nonbiologic DMARDS or other agents, such as methotrexate, 6-mercaptopurine, azathioprine sulphasalazine, mesalazine, olsalazine chloroquinine/hydroxychloroquine, penicillamine, aurothiomalate (intramuscular and oral), azathioprine, colchicine, corticosteroids (oral, inhaled and local injection), beta-2 adrenoreceptor agonists (salbutamol, terbutaline, salmeterol), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, and 6-mercaptopurines. The solid-state form may also be combined with methotrexate.

Non-limiting examples of therapeutic agents for inflammatory bowel disease (IBD) with which the solid-state form can be combined may include (but are not limited to) the following: budesonide; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g., NIK, IKK, or MAP kinase inhibitors); IL-10 converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and anti-inflammatory cytokines (e.g., IL-4, IL-10, IL-11, IL-13 and TGFβ). The solid-state form may also be combined with methotrexate.

Examples of therapeutic agents for Crohn's disease with which the solid-state form can be combined include the following: TNF antagonists, for example, anti-TNF antibodies, adalimumab (such as HUMIRA™ brand adalimumab), infliximab such as CA2 (REMICADE™ brand infliximab), certolizumab pegol such as CIMZIA™, golimumab such as SIMPONI™ (golimumab), CDP 571, TNFR-Ig constructs, etanercept such as p75TNFRIgG (ENBREL™ brand etanercept) and lenercept such as p55TNFRIgG (Lenercept™) inhibitors and PDE4 inhibitors.

The solid-state form can be combined with corticosteroids, for example, budesonide and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; methylprednisolone sodium succinate; diphenoxylate/atrop sulfate; loperamide hydrochloride; methotrexate;

omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis (MS) with which the solid-state form can be combined include the following: corticosteroids; prednisolone; methylprednisolone; azathioprine; cyclophosphamide; cyclosporine; methotrexate; 4-aminopyridine; tizanidine; interferon-ala (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of the invention can be combined with antibodies to cell surface molecules such as CD2, CD3, CD4, CD8, CD19, CD20, CD25, CD28, CD30, CD40, CD45, CD69, CD80, CD86, CD90 or their ligands. The solid-state form may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1 converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g. IL-4, IL-10, IL-13 and TGFβ). Examples of therapeutic agents for multiple sclerosis in which a compound of the invention can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The solid-state form may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis (AS) with which the solid-state form can be combined include the following: ibuprofen, diclofenac, misoprostol, naproxen, meloxicam, indomethacin, diclofenac, celecoxib, rofecoxib, sulfasalazine, methotrexate, azathioprine, minocycline, prednisone, and anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

Non-limiting examples of therapeutic agents for psoriasis (Ps, such as moderate to severe plaque psoriasis) with which the solid-state form can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874, ustekinumab, and adalimumab (such as HUMIRA™ brand adalimumab).

Non-limiting examples of therapeutic agents for psoriatic arthritis (PsA) with which the solid-state form can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, adalimumab (such as HUMIRA™ brand adalimumab), and efalizumab.

Examples of therapeutic agents for SLE (Lupus) with which the solid-state form can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budesonide, dexamethasone; cytotoxics, for example, azathioprine, cyclophosphamide, mycophenolate mofetil, methotrexate; inhibitors of PDE4 or purine synthesis inhibitor, for example CELLCEPT®. The solid-state form may also be combined with agents such as sulfasalazine, 5-aminosalicylic acid, olsalazine, IMURAN® and agents which interfere with synthesis, production or action of proinflammatory cytokines such as IL-1, for example, caspase inhibitors like IL-10 converting enzyme inhibitors and IL-1ra. The solid-state form may also be used with T cell signaling inhibitors, for example, tyrosine kinase inhibitors; or molecules that target T cell activation molecules, for example, CTLA-4-IgG or anti-B7 family antibodies, anti-PD-1 family antibodies. The solid-state form can be combined with IL-1I or anti-cytokine antibodies, for example, fontolizumab (anti-IFNg antibody), or anti-receptor receptor antibodies, for example, anti-IL-6 receptor antibody and antibodies to B-cell surface molecules. The solid-state form may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

The solid-state form may also be combined with an immune modulator for CD4+CD25+ Treg cells. Treg cells are essential for maintaining normal immune homeostasis. In patients with autoimmune diseases, reduced numbers or functional impairment of Treg cells has been observed, leading to loss of this finely-tuned mechanism. A humanized agonistic monoclonal antibody, BT-061, binds to a unique epitope of human CD4, and induces Treg-specific signaling events that lead to their functional activation. Pre-clinical data using isolated Treg cells and rheumatoid arthritis synovial fluid indicate that BT-061 leads to suppression of CD4+ and CD8+T effector cell proliferation, reduction of the expression of pro-inflammatory cytokines, and increase in the production of the anti-inflammatory cytokine TGFβ. Thus similar immune modulators for CD4+CD25+ Treg cells can also be co-administered with a compound of the invention for treating any of the inflammatory disease/disorder, or an autoimmune disease/disorder described herein, including but not limited to rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, or atopic dermatitis. In certain embodiments, the combination treats rheumatoid arthritis, Crohn's disease, psoriasis, or psoriatic arthritis, including moderately to severely active rheumatoid arthritis, Crohn's disease, psoriasis, or psoriatic arthritis. In certain embodiments, the rheumatoid arthritis, Crohn's disease, psoriasis, or psoriatic arthritis patient being treated has inadequately responded to or has discontinued therapy due to loss of response to or intolerance to a first line therapy (such as a DMARD, including methotrexate) or an anti-TNFα therapy.

In certain embodiments, the immune modulator has one or more (or all) of the following properties: (1) activates a subset of CD4+ T cells comprising CD4+CD25+ regulatory T cells (Treg), or CD4+CD25+ Treg cells; (2) binds only to a special epitope of the human CD4 antigen (such as the IgG-like C2 type 1 domain of CD4), which said epitope of human CD4 may be bound by a mouse IgG1 anti-CD4 monoclonal antibody B-F5 or a humanized version thereof, such as the BT-061 hB-F5 antibody tregalizumab as described in U.S. Pat. No. 7,452,981 (incorporated herein by reference, including all sequences of the VH and VL chains disclosed therein); (3) provides an activation signal to naturally occurring Treg cells but does not activate conventional T cells (e.g., CD4+ T cells that are not activated in (1), CD8+ cytotoxic T cells, etc.); and (4) is not a depleting anti-CD4 antibody that depletes CD4+ T cells, and/or does not appreciably trigger ADCC or CDC.

V. Dosages and Dosing

In certain embodiments, the methods of the present disclosure comprise administering to an adult subject (e.g., a human subject) Compound 1 (freebase), or a pharmaceutically acceptable salt thereof, or a crystalline hydrate of Compound 1 in an amount sufficient to deliver to the subject 15 mg of Compound 1 freebase equivalent. In one embodiment, the freebase or the hydrate is in a once daily extended-release formulation.

In certain embodiments, the methods of the present disclosure comprise administering to an adult subject (e.g., a human subject) 30 mg of Compound 1 (freebase), or a pharmaceutically acceptable salt thereof or a crystalline hydrate of Compound 1 in an amount sufficient to deliver to the subject 30 mg of Compound 1 freebase equivalent. In one embodiment, the freebase or the hydrate is in a once daily extended-release formulation.

In certain embodiments, the methods of the present disclosure comprise administering Compound 1 (upadacitinib) to a pediatric patient.

In some embodiments, the pediatric patient has an age of less than 18 years. In some embodiments, the pediatric patient has an age of less than 12 years. In some embodiments, the pediatric patient has an age of less than 6 years. In some embodiments, the pediatric patient has an age in a range from about 2 to less than about 6 years, in a range from about 6 to less than about 12 years, or in a range from about 12 to less than about 18 years. In some embodiments, the pediatric patient has an age in a range from about 2 to about 18 years, such as about 2, about 3, about 4, about 5, about 6, about 7, about 8, about 9, about 10, about 11, about 12, about 13, about 14, about 15, about 16, about 17, or about 18 years of age. In some embodiments, the pediatric patient is two years of age or older. In some embodiments, the pediatric patient has an age in a range from about 2 to less than 12 years old.

In some embodiments, the pediatric patient has a body weight of at least about 10 kg. In some embodiments, the pediatric patient has a body weight from about 10 kg to less than about 30 kg, such as from about 20 to less than about 20 kg, or from about 20 to less than about 30 kg. In some embodiments, the pediatric patient has a body weight 30 kg or more. In some embodiments, the pediatric patient has an age in a range from about 2 to less than 12 years old and weighs less than 40 kg. In some embodiments, the pediatric patient has an age of 12 years old or greater and weighs less than 40 kg.

In some embodiments, the pediatric patient has a body weight in a range from about 10 to less than about 20 kg, the method comprising administering 3 mg of upadacitinib twice daily (3 mg BID) as an oral solution.

In some embodiments, the oral solution comprises upadacitinib at a concentration of about 1 mg/mL, such as from about 0.8, 0.9, or about 1.0, to about 1.1 or about 1.2 mg/mL. In some embodiments, the oral solution comprises upadacitinib at a concentration from about 0.9 mg/mL to about 1.1 mg/mL. In some embodiments, the oral solution comprises upadacitinib at a concentration of 1.0 mg/mL.

In some embodiments, the oral solution comprises upadacitinib at a concentration of about 1 mg/mL, and the 3 mg dose is provided BID as about 3 mL of the about 1 mg/mL solution.

In some embodiments, the oral solution comprises upadacitinib at a concentration of about 0.5 mg/mL, such as from about 0.3, 0.4, or about 0.5, to about 0.6 or about 0.7 mg/mL. In some embodiments, the oral solution comprises upadacitinib at a concentration from about 0.4 mg/mL to about 0.6 mg/mL. In some embodiments, the oral solution comprises upadacitinib at a concentration of 0.5 mg/mL.

In some embodiments, the oral solution comprises upadacitinib at a concentration of about 0.5 mg/mL and the 3 mg dose is provided BID as about 6 mL of the about 0.5 mg/mL solution.

In some embodiments, the pediatric patient has a body weight in a range from about 10 to less than about 20 kg, the method comprising administering 6 mg of upadacitinib twice daily (6 mg BID) as an oral solution.

In some embodiments, the oral solution comprises upadacitinib at a concentration of about 1 mg/mL, such as from about 0.8, 0.9, or about 1.0, to about 1.1 or about 1.2 mg/mL. In some embodiments, the oral solution comprises upadacitinib at a concentration from about 0.9 mg/mL to about 1.1 mg/mL. In some embodiments, the oral solution comprises upadacitinib at a concentration of 1.0 mg/mL.

In some embodiments, the oral solution comprises upadacitinib at a concentration of about 1 mg/mL, and the 6 mg dose is provided BID as about 6 mL of the about 1 mg/mL solution.

In some embodiments, the oral solution comprises upadacitinib at a concentration of about 0.5 mg/mL, such as from about 0.3, 0.4, or about 0.5, to about 0.6 or about 0.7 mg/mL. In some embodiments, the oral solution comprises upadacitinib at a concentration from about 0.4 mg/mL to about 0.6 mg/mL. In some embodiments, the oral solution comprises upadacitinib at a concentration of 0.5 mg/mL.

In some embodiments, the oral solution comprises upadacitinib at a concentration of about 0.5 mg/mL and the 6 mg dose is provided BID as about 12 mL of the about 0.5 mg/mL solution.

In some embodiments, the pediatric patient has a body weight in a range from about 20 to less than about 30 kg, the method comprising administering 4 mg of upadacitinib twice daily (4 mg BID) as an oral solution. In some embodiments, the pediatric patient has a body weight in a range from about 20 to less than about 30 kg, the method comprising administering 8 mg of upadacitinib twice daily (8 mg BID) as an oral solution.

In some embodiments, the oral solution comprises upadacitinib at a concentration of about 1 mg/mL, such as from about 0.8, 0.9, or about 1.0, to about 1.1 or about 1.2 mg/mL. In some embodiments, the oral solution comprises upadacitinib at a concentration from about 0.9 mg/mL to about 1.1 mg/mL. In some embodiments, the oral solution comprises upadacitinib at a concentration of 1.0 mg/mL.

In some embodiments, the oral solution comprises upadacitinib at a concentration of about 1 mg/mL, and the 8 mg dose is provided BID as about 8 mL of the about 1 mg/mL solution.

In some embodiments, the oral solution comprises upadacitinib at a concentration of about 0.5 mg/mL, such as from about 0.3, 0.4, or about 0.5, to about 0.6 or about 0.7 mg/mL. In some embodiments, the oral solution comprises upadacitinib at a concentration from about 0.4 mg/mL to about 0.6 mg/mL. In some embodiments, the oral solution comprises upadacitinib at a concentration of 0.5 mg/mL.

In some embodiments, the oral solution comprises upadacitinib at a concentration of about 0.5 mg/mL and the 8 mg dose is provided BID as about 16 mL of the about 0.5 mg/mL solution.

In some embodiments, the pediatric patient has a body weight of about 30 kg or greater, the method comprising administering 6 mg of upadacitinib twice daily (6 mg BID) as an oral solution.

In some embodiments, the pediatric patient has a body weight of about 30 kg or greater, the method comprising administering 12 mg of upadacitinib twice daily (12 mg BID) as an oral solution.

In some embodiments, the oral solution comprises upadacitinib at a concentration of about 1 mg/mL, such as from about 0.8, 0.9, or about 1.0, to about 1.1 or about 1.2 mg/mL. In some embodiments, the oral solution comprises upadacitinib at a concentration from about 0.9 mg/mL to about 1.1 mg/mL. In some embodiments, the oral solution comprises upadacitinib at a concentration of 1.0 mg/mL.

In some embodiments, the oral solution comprises upadacitinib at a concentration of about 1 mg/mL, and the 6 mg dose is provided BID as about 6 mL of the about 1 mg/mL solution.

In some embodiments, the oral solution comprises upadacitinib at a concentration of about 1 mg/mL, and the 12 mg dose is provided BID as about 12 mL of the about 1 mg/mL solution.

In some embodiments, the oral solution comprises upadacitinib at a concentration of about 0.5 mg/mL, such as from about 0.3, 0.4, or about 0.5, to about 0.6 or about 0.7 mg/mL. In some embodiments, the oral solution comprises upadacitinib at a concentration from about 0.4 mg/mL to about 0.6 mg/mL. In some embodiments, the oral solution comprises upadacitinib at a concentration of 0.5 mg/mL.

In some embodiments, the oral solution comprises upadacitinib at a concentration of about 0.5 mg/mL and the 6 mg dose is provided BID as about 12 mL of the about 0.5 mg/mL solution.

In some embodiments, the oral solution comprises upadacitinib at a concentration of about 0.5 mg/mL and the 12 mg dose is provided BID as about 24 mL of the about 0.5 mg/mL solution.

In some embodiments, the pediatric patient has a body weight of about 30 kg or greater, the method comprising administering 15 mg of upadacitinib once daily (15 mg QD) as an extended-release tablet.

In some embodiments, the pediatric patient has a body weight of about 30 kg or greater, the method comprising administering 8 mg of upadacitinib twice daily (8 mg BID) as an oral solution.

In some embodiments, the pediatric patient has a body weight of about 30 kg or greater, the method comprising administering 12 mg of upadacitinib twice daily (12 mg BID) as an oral solution.

In some embodiments, the oral solution comprises upadacitinib at a concentration of about 1 mg/mL, such as from about 0.8, 0.9, or about 1.0, to about 1.1 or about 1.2 mg/mL. In some embodiments, the oral solution comprises upadacitinib at a concentration from about 0.9 mg/mL to about 1.1 mg/mL. In some embodiments, the oral solution comprises upadacitinib at a concentration of 1.0 mg/mL.

In some embodiments, the oral solution comprises upadacitinib at a concentration of about 1 mg/mL, and the 8 mg dose is provided BID as about 8 mL of the about 1 mg/mL solution.

In some embodiments, the oral solution comprises upadacitinib at a concentration of about 0.5 mg/mL, such as from about 0.3, 0.4, or about 0.5, to about 0.6 or about 0.7 mg/mL. In some embodiments, the oral solution comprises upadacitinib at a concentration from about 0.4 mg/mL to about 0.6 mg/mL. In some embodiments, the oral solution comprises upadacitinib at a concentration of 0.5 mg/mL.

In some embodiments, the oral solution comprises upadacitinib at a concentration of about 0.5 mg/mL and the 8 mg dose is provided BID as about 16 mL of the about 0.5 mg/mL solution.

In some embodiments, the pediatric patient has a body weight of about 30 kg or greater, the method comprising administering 30 mg of upadacitinib once daily (30 mg QD) as an extended-release tablet.

The maximal concentration achieved (Cmax) with the aforementioned dosing may vary depending on e.g., the dose, the weight of the patient, and the individual patient's metabolism of upadacitinib.

In some embodiments, when an immediate release oral solution as described herein is administered BID to the pediatric subject, a mean Cmax for upadacitinib is achieved in a range from about 20 to about 160 ng/mL.

In some embodiments, when administered twice daily at a dose of 3 or 4 mg each (3 or 4 mg BID) to the pediatric subject, a mean Cmax for upadacitinib is achieved in a range from about 25 to about 50 ng/mL, such as from about 25 to about 35, from about 25 to about 33, from about 25 to about 31, from about 25 to about 29, or from about 25 to about 27 ng/mL.

In some embodiments, when administered twice daily at a dose of 6 or 8 mg each (6 or 8 mg BID) to the pediatric subject, a mean Cmax for upadacitinib is achieved in a range from about 40 to about 100 ng/mL, such as from about 40 to about 95, from about 40 to about 90, from about 40 to about 85, from about 40 to about 80, from about 40 to about 75, from about 40 to about 70, from about 40 to about 65, from about 40 to about 60, from about 40 to about 55, from about 40 to about 50, or from about 40 to about 45 ng/mL.

In some embodiments, when an extended-release 15 mg tablet as described herein is administered once daily (15 mg QD) to the pediatric subject, a mean Cmax for upadacitinib is achieved in a range from about 45 to about 50 ng/mL, such as from about 45 to about 49, from about 45 to about 48, from about 45 to about 46, or from about 45 to about 46 ng/mL.

In some embodiments, when an extended-release 30 mg tablet as described herein is administered once daily (30 mg QD) to the pediatric subject, a mean Cmax for upadacitinib is achieved in a range from about 150 to about 160 ng/mL, such as from about 152 to about 159, from about 153 to about 158, from about 154 to about 156, or from about 154 to about 155 ng/mL.

The mean 24-hour exposure achieved (AUC0-24) with the aforementioned dosing may vary, depending on e.g., the dose, the weight of the patient, the fed vs. fasted condition, and the individual patient's metabolism of upadacitinib.

In some embodiments, when an immediate release oral solution as described herein is administered BID to the pediatric subject, a mean AUC0-24 for upadacitinib is achieved in a range from about 200 to about 700 ng·h/mL.

In some embodiments, when administered twice daily at a dose of 3 or 4 mg each (3 or 4 mg BID) to the pediatric subject, a mean AUC0-24 for upadacitinib is achieved in a range from about, such as from about 220 to about 270 ng·h/mL, such as from about 220 to about 265, from about 220 to about 260, from about 220 to about 255, from about 220 to about 250, from about 220 to about 245, from about 220 to about 240, from about 220 to about 235, from about 220 to about 230, or from about 220 to about 225 ng·h/mL.

In some embodiments, when administered twice daily at a dose of 6 or 8 mg each (6 or 8 mg BID) to the pediatric subject, a mean AUC0-24 for upadacitinib is achieved in a range from about 340 to about 590 ng·h/mL, such as from about 340 to about 580, from about 340 to about 570, from about 340 to about 560, from about 340 to about 550, from about 340 to about 540, from about 340 to about 530, from about 340 to about 520, from about 340 to about 510, from about 340 to about 500, from about 340 to about 490, from about 340 to about 480, from about 340 to about 470, from about 340 to about 460, from about 340 to about 450, from about 340 to about 440, from about 340 to about 430, from about 340 to about 420, from about 340 to about 410, from about 340 to about 400, from about 340 to about 390, from about 340 to about 380, from about 340 to about 370, from about 340 to about 360, from about 340 to about 350, or from about 340 to about 345 ng·h/mL. In some embodiments, when administered twice daily at a dose of 6 or 8 mg each (6 or 8 mg BID) to the pediatric subject, a mean AUC0-24 for upadacitinib is achieved in a range from about 570 to about 590 ng·h/mL, such as from about 570 to about 590, from about 570 to about 588, from about 570 to about 586, from about 570 to about 584, from about 570 to about 582, or from about 570 to about 580 ng·h/mL.

In some embodiments, when an extended-release 15 mg tablet as described herein is administered once daily (15 mg QD) to the pediatric subject, a mean AUC0-24 for upadacitinib is achieved in a range from about 45 to about 50 ng·h/mL, such as from about 45 to about 49, about 46 to about 48, or from about 47 to about 48 ng·h/mL.

In some embodiments, when an extended-release 30 mg tablet as described herein is administered once daily (30 mg QD) to the pediatric subject, a mean AUC0-24 for upadacitinib is achieved in a range from about 650 to about 680 ng/mL, such as from about 660 to about 670, or from about 665 to about 670 ng·h/mL.

The disclosed methods generally comprise orally administering the upadacitinib to the patient daily for a period of time. In some embodiments, the administration is continued at the same dose and dosing frequency over a treatment period. The duration of the treatment period may vary. For example, the treatment period may be at least 14 days, at least one month, 3 months, 4 months, 6 months, 9 months, 1 year, 2 years, 5 years, 10 years, 20 years, 50 years, or more. In some embodiments, the treatment period is 12 weeks. In some embodiments, the treatment period is 156 weeks. In some embodiments, the treatment period is at least 156 weeks.

EXAMPLES

Examples 1-4: Extended-Release Tablets

The Freebase Hydrate Form C and Amorphous Freebase solid-state forms of Compound 1 were formulated into 24 mg extended-release tablets according to the formulations set forth in Table 2.

TABLE 2

| Extended-Release Tablets (no pH modifier) | | | | | |
|---|---|---|---|---|---|
| Component | Function | Ex. 1 (ER1) (mg) | Ex. 2 (ER2) (mg) | Ex. 3 (ER3) (mg) | Ex. 4 (mg) |
| Freebase Hydrate Form C | Active | 24.0 | 24.0 | 24.0 | — |
| Amorphous Freebase | Active | — | — | — | 24.0 |
| Microcrystalline cellulose (Avicel ® PH 102) | Filler | 351.4 | 303.4 | 303.4 | 303.4 |
| HPMC (Methocel ® | Release | 96.0 | 96.0 | — | — |

TABLE 2-continued

Extended-Release Tablets (no pH modifier)

| Component | Function | Ex. 1 (ER1) (mg) | Ex. 2 (ER2) (mg) | Ex .3 (ER3) (mg) | Ex. 4 (mg) |
|---|---|---|---|---|---|
| K100 Premium LVCRLH) | control polymer | | | | |
| HPMC (Methocel ® K4M Premium CR) | Release control polymer | — | 48.0 | 144.0 | 144.0 |
| Colloidal silicon dioxide | Glidant | 3.8 | 3.8 | 3.8 | 3.8 |
| Magnesium stearate impalpable powder | Lubricant | 4.8 | 4.8 | 4.8 | 4.8 |
| Uncoated weight of tablet | | 480.0 | 480.0 | 480.0 | 480.0 |

The formulations were prepared by combining and blending the active, microcrystalline cellulose, hydroxypropyl methyl cellulose (HPMC), and colloidal silicone dioxide. The blend was milled using a Mobil Mill fitted with a 610-micron screen. The magnesium stearate was screened through mesh #30 and was added to the bin and blended.

The lubricated granulation was compressed into 480 mg weight tablets using a rotary tablet press. The tablets may optionally be coated with any suitable film coating.

The effect of solid-state form on the dissolution profile of the tablets was evaluated. In particular, the dissolution profile of the Example 3 (containing Freebase Hydrate Form C as active) and Example 4 (containing Amorphous Freebase as active) tablets was evaluated at pH 6.8 (representative of the pH in the lower intestine). The dissolution test was carried out using the following dissolution parameters and conditions:

Apparatus: USP Dissolution Apparatus 2 and fraction collector
Medium: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: 1, 2, 4, 6, 8, 10, 12, 16, and 20 Hours. Other samples may be taken at other times, as appropriate.
Sample Volume: 1.5 mL obtained automatically, without media replacement.

The medium used for the study was a 0.05 M sodium phosphate buffer solution, pH 6.8±0.05. The medium was prepared using an acid stage medium (0.1 N hydrochloric acid solution) and a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The medium was prepared by mixing 500 mL of the acid stage medium and 400 mL of buffer stage concentrate in an appropriate size container or directly in the dissolution vessel and adjusting the pH with 1 N phosphoric acid or 1 N sodium hydroxide, if the pH was not within 6.8±0.05.

For the dissolution test, one tablet each was added to a dissolution vessel containing 900 mL of the 0.05 M sodium phosphate buffer solution maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % of the labelled amount of active released (% LA Released) was calculated. The formulation containing Freebase Hydrate Form C (Example 3) as the active showed a slower rate of dissolution than the formulation containing Amorphous Freebase (Example 4) as the active at pH 6.8.

The dissolution profile of formulations comprising Freebase Hydrate Form C as an active was further evaluated at pH 6.8 and in a dual pH system. In particular, the dissolution profile of the Example 1 (ER1), Example 2 (ER2), and Example 3 (ER3) tablets at pH 6.8 was carried out as described above. The dissolution profile of the Examples 1-3 tablets was also carried out in a dual pH system using the following dissolution parameters and conditions:

Apparatus: USP Dissolution Apparatus 2 and fraction collector
Medium: Acid Stage: 500 mL of Acid Stage Medium (0.1 N hydrochloric acid solution)
Buffer Stage: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: Acid Stage: 1 Hour
Buffer Stage: 2, 4, 6, 8, 10, 12, 16, and 20 Hours. Other samples may be taken at other times, as appropriate.
Sample Volume: Acid: 1.5 mL obtained automatically, without media replacement.

The acid stage medium is a 0.1 N hydrochloric acid solution. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

For the dissolution test, one tablet each was added to a dissolution vessel containing 500 mL of a 0.1 N hydrochloric acid solution maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, maintained at 37° C. The dissolution test was continued, with the paddles remaining at a speed of 75 RPM. The sample filtrate was the sample preparation.

For the analysis of the sample, conventional liquid chromatography methods were utilized, wherein the % relative standard deviation (RSD) of peak areas was calculated for each set of six standard injections.

After the initial release at the low pH (representative of the pH in the stomach), release of the drug is slowed at the higher pH (representative of the pH in the lower intestine). Therefore, in order to achieve the desired bioavailability, a formulation which allowed pH independent release was required.

Examples 5-12: Extended-Release Tablets

The Freebase Hydrate Form C solid-state form of Compound 1 was formulated into 15 mg, 24 mg, or 30 mg extended-release tablets according to the formulations set forth in Table 3 using direct compression.

TABLE 3

Extended-Release Tablets (tartaric acid pH modifier)

| Component | Function | Ex. 5 (mg) (ER7) | Ex. 6 (mg) | Ex. 7 (mg) | Ex. 8 (mg) (ER8) | Ex. 9 (mg) (ER4) | Ex. 10 (mg) (ER4, no mannitol) | Ex. 11 (mg) (ER5) | Ex. 12 (mg) (ER6) |
|---|---|---|---|---|---|---|---|---|---|
| Freebase Hydrate Form C | Active | 15.4[a] | 15.4[a] | 15.4[a] | 30.7[b] | 24.6[c] | 24.6[c] | 24.6[c] | 24.6[c] |
| Microcrystalline cellulose (Avicel® PH 102) | Filler | 162.4 | 162.4 | 162.4 | 147.1 | 158.0 | 210.6 | 282.6 | 258.6 |
| Mannitol (Pearlitol® 100 SD) | Filler | 52.6 | 52.4 | — | 52.6 | 52.7 | — | — | — |
| Mannitol (Pearlitol® 200 SD) | Filler | — | — | 52.4 | — | — | — | — | — |
| Tartaric acid | pH modifier | 144.0 | 144.0 | 144.0 | 144.0 | 144.0 | 144.0 | 96.0 | 96.0 |
| HPMC (Hypromellose 2208) | Release control polymer | 96.0 | — | — | 96.0 | — | — | — | — |
| HPMC (Methocel® K4M Premium CR) | Release control polymer | — | 96.0 | 96.0 | — | 96.0 | 96.0 | — | — |
| Carbopol® 71G | Release control polymer | — | — | — | — | — | — | 48.0 | 72.1 |
| Carbopol® 971P | Release control polymer | — | — | — | — | — | — | 24.0 | 24.0 |
| Colloidal silicon dioxide | Glidant | 2.4 | 2.4 | 2.4 | 2.4 | — | — | — | — |
| Magnesium stearate impalpable powder | Lubricant | 7.2 | 7.2 | 7.2 | 7.2 | 4.8 | 4.8 | 4.8 | 4.8 |
| Uncoated weight of tablet |  | 480.0 | 479.8 | 479.8 | 480.0 | 480.1 | 480.0 | 480.0 | 480.1 |
| Opadry® II Yellow (PVA based) | Film coat | 14.40 | — | — | 14.40 | — | — | — | — |
| Total weight of tablet |  | 494.39 |  |  | 494.43 | — | — | — | — |

[a]Provides 15 mg of Compound 1 freebase equivalent.
[b]Provides 30 mg of Compound 1 freebase equivalent.
[c]Provides 24 mg of Compound 1 freebase equivalent.

The formulations were prepared by first milling the tartaric acid through a Fitz mill Model M5A, fitted with a 1512-0027 screen. The Freebase Hydrate Form C, microcrystalline cellulose, mannitol (when present), milled tartaric acid, release control polymer, and colloidal silicone dioxide (when present) were combined and blended. The blend was milled using a Mobil Mill fitted with a 610- or 1397-micron screen. The magnesium stearate was screened through mesh #30 and was then added to the bin and blended. The lubricated granulation was compressed into about 480 mg weight tablets using a rotary tablet press.

The Example 5 and 8 tablets were coated using a film coater, which sprayed a solution containing the Opadry® 11 Yellow film coat and purified water until 14.40 mg of coating had been applied to the tablets.

The dissolution profile of the Example 9 (ER4, 24 mg active), Example 10 (ER4, no mannitol, 24 mg active), Example 11 (ER5, 24 mg active), and Example 12 (ER6, 24 mg active) tablets was evaluated at pH 1.2, at pH 6.8, and in a dual pH system. The pH 6.8 study was performed as described above for Examples 3 and 4. For the dual pH study, an acid stage medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH. The mixture was diluted to 6 L with water and mixed. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

The dissolution test was carried out using the following dissolution parameters and conditions:
    Apparatus: USP Dissolution Apparatus 2 and fraction collector
    Medium: Acid Stage: 500 mL of Acid Stage Medium
        Buffer Stage: 900 mL of 50 mM sodium phosphate buffer solution, pH 6.8

Temperature: 37° C.±0.5° C.
RPM: 75 RPM±4%
Filter: 35 μm PE filter, or equivalent, for automatic sampling
Sampling Times: Acid Stage: 1 Hour
  Buffer Stage: 2, 4, 6, 8, 10, 12, 16, and 20 Hours.
  Other samples may be taken at other times, as appropriate.
Sample Volume: Acid and Buffer Stage: 1.5 mL obtained automatically, without media replacement.

For the dissolution test, one tablet each was added to a dissolution vessel containing 500 mL of the acid stage medium, maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, and then the mixture was maintained at 37° C. The dissolution test was continued, with the paddles remaining at a speed of 75 RPM. The sample filtrate was the sample preparation.

For the pH 1.2 study, the dissolution test was carried out using the following dissolution parameters and conditions:
Apparatus: USP Dissolution Apparatus 2 and fraction collector
Medium: 500 mL of Acidic Medium, pH 1.2
Temperature: 37° C.±0.5° C.
RPM: 75 RPM±4%
Filter: 35 μm PE filter, or equivalent, for automatic sampling
Sampling Times: 1, 2, 4, 6, 8, 10, 12, 16, and 20 Hours.
  Other samples may be taken at other times, as appropriate.
Sample Volume: 1.5 mL obtained automatically, without media replacement.

For this study, an acidic medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH of 1.2. The mixture was diluted to 6 L with water and mixed.

For the dissolution test, one tablet each was added to a dissolution vessel containing 500 mL of the acidic medium, maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % relative standard deviation (RSD) of peak areas was calculated for each set of six standard injections. The results shown that pH independence is achieved in the once daily formulations.

The dissolution profile of the Example 5 (ER7), Example 8 (ER8), and Example 9 (ER4) tablets were evaluated in a dual pH system, as described above. The formulations provide an extended-release profile of 80-100% over a period of about 8-10 hours.

The formulations of Examples 5 and 8-12 all exhibited pH independent release of the active ingredient. In contrast, after the initial release at the low pH, release of the active is slowed at the higher pH for the formulations of Examples 1-3. Without wishing to be bound to any particular theory, it is believed that the inclusion of tartaric acid as a pH modifier in the Example 5 and 8-12 formulations contributed to the pH independent release observed for these tablets.

Example 13: Extended Release Tablet

The Freebase Hydrate Form C solid-state form of Compound 1 was formulated into a 7.5 mg extended-release tablet according to the formulation set forth in Table 4.

TABLE 8

Extended Release Tablets (tartaric acid pH modifier)

| Component | Function | Ex. 13 (mg) (ER9) |
|---|---|---|
| Freebase Hydrate Form C* | Active | 7.678[a] |
| Microcrystalline cellulose (Avicel ® PH 102) | Filler | 170.1 |
| Mannitol (Pearlitol ® 100 SD) | Filler | 52.62 |
| Tartaric acid (crystalline) | pH modifier | 144.0 |
| HPMC (Hypromellose 2208) | Release control polymer | 96.0 |
| Colloidal silicon dioxide | Glidant | 2.4 |
| Magnesium stearate | Lubricant | 7.2 |
| Uncoated weight of tablet | | 479.998 |
| Opadry ® II Yellow | Film coat | 14.40 |
| Purified water | Processing aid | n/a |
| Total weight of tablet | | 494.398 |

[a]Provides 7.5 mg of Compound 1 freebase equivalent.

The formulation was prepared by first milling the tartaric acid through a Fitz mill Model M5A, fitted with a 1512-0027 screen. The Freebase Hydrate Form C, microcrystalline cellulose, mannitol, milled tartaric acid, release control polymer, and colloidal silicone dioxide were combined and blended. The blend was milled using a Mobil Mill fitted with a 610-micron screen. The magnesium stearate was screened through mesh #30 and was then added to the bin and blended. The lubricated granulation was compressed into about 480 mg weight tablets using a rotary tablet press.

The tablets were coated using a film coater, which sprayed a solution containing the Opadry® 11 Yellow film coat and purified water until 14.4 mg of coating had been applied to the tablets.

Examples 14-19: Extended-Release Tablets

The Freebase Hydrate Form C solid-state form of Compound 1 was formulated into 15 mg or 30 mg extended-release tablets according to the formulations set forth in Table 5. The tablets were prepared using a wet granulation process, and were compressed into tablets having a core weight of about 480 mg.

TABLE 5

Extended-Release Tablets (tartaric acid pH modifier)

| Component | Function | Ex. 14 (mg) (ER10) | Ex. 15 (mg) (ER11) | Ex. 16 (mg) (ER12) | Ex. 17 (mg) (ER13) | Ex. 18 (mg) (ER14) | Ex. 19 (mg) (ER15) |
|---|---|---|---|---|---|---|---|
| Tablet Core (Intragranular) | | | | | | | |
| Freebase Hydrate Form C | Active | 30.7[a] | 30.7[a] | 30.7[a] | 15.4[b] | 15.4[b] | 15.4[b] |
| Microcrystalline cellulose (Avicel® PH 101) | Filler | 79.9 | 79.9 | 79.9 | 40.0 | 40.0 | 40.0 |
| HPMC (Hypromellose 2208) | Release control polymer | 9.5 | 9.5 | 9.5 | 4.8 | 4.8 | 4.8 |
| Tablet Core (Extragranular) | | | | | | | |
| Microcrystalline cellulose (Avicel® PH 102) | Filler | 67.2 | 67.2 | 67.2 | 122.5 | 122.5 | 122.5 |
| Mannitol | Filler | 52.6 | 100.6 | 148.6 | 52.6 | 100.6 | 148.6 |
| Tartaric acid (crystalline) | pH modifier | 144.0 | 96.0 | 48.0 | 144.0 | 96.0 | 48.0 |
| HPMC (Hypromellose 2208) | Release control polymer | 86.5 | 86.5 | 86.5 | 91.2 | 91.2 | 91.2 |
| Colloidal silicon dioxide/silica | Glidant | 2.4 | 2.4 | 2.4 | 2.4 | 2.4 | 2.4 |
| Magnesium stearate | Lubricant | 7.2 | 7.2 | 7.2 | 7.2 | 7.2 | 7.2 |
| Uncoated weight of tablet | | 480.0 | 480.0 | 480.0 | 480.1 | 480.1 | 480.1 |
| Opadry® II Yellow[c] | Film coat | 14.4 | 14.4 | 14.4 | 14.4 | 14.4 | 14.4 |
| Total weight of tablet | | 494.4 | 494.4 | 494.4 | 494.5 | 494.5 | 494.5 |

[a] Provides 30 mg of Compound 1 freebase equivalent.
[b] Provides 15 mg of Compound 1 freebase equivalent.
[c] Film coat weight is approximate.

The formulation was prepared by first milling the tartaric acid through a Fitz mill Model M5A, fitted with a 1512-0027 screen. The intragranular portion of the hydroxypropylmethyl cellulose release control polymer, the Freebase Hydrate Form C, and intragranular portion of the microcrystalline cellulose filler were added to a granulator, and mixed. Water was sprayed to granulate. The granulated material was then dried and milled using a comill fitted with a 610-micron screen. The milled granulation was then added to the extragranular tablet components other than magnesium stearate and sieved using a comill fitted with a 1397-micron screen, followed by blending. The magnesium stearate was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Example 20: Evaluation of the Effect of Organic Acids on Dissolution Profile of Extended-Release Tablets In this example, the effect of various organic acid pH modifiers (e.g., tartaric acid, citric acid, succinic acid, and fumaric acid) on the release rate of Freebase Hydrate Form C from 24 mg once-daily extended-release (ER) tablets was evaluated. Freebase Hydrate Form C was formulated into 24 mg Extended-Release tablets according to the formulations set forth in Table 6.

TABLE 6

| | | Extended Release Tablets | | | | | | | |
|---|---|---|---|---|---|---|---|---|---|
| | | Tartaric acid | | Citric acid | | Succinic acid | | Fumaric acid | |
| Component | Function | A | B | C | D | F | F | G | H |
| Freebase Hydrate Form C | Active | 24.6 | 24.6 | 24.6 | 24.6 | 24.6 | 24.6 | 24.6 | 24.6 |
| Microcrystalline cellulose (Avicel® PH102) | Filler | 306.6 | 306.6 | 306.6 | 306.6 | 306.6 | 306.6 | 306.6 | 306.6 |
| HPMC (Methocel® K4M) | Release control polymer | 96.0 | — | 96.0 | — | 96.0 | — | 96.0 | — |
| Carbopol® 71G | Release control polymer | — | 96.0 | — | 96.0 | — | 96.0 | — | 96.0 |

TABLE 6-continued

Extended Release Tablets

| Component | Function | Tartaric acid | | Citric acid | | Succinic acid | | Fumaric acid | |
|---|---|---|---|---|---|---|---|---|---|
| | | A | B | C | D | E | F | G | H |
| Organic acid | pH modifier | 48.0 | 48.0 | 48.0 | 48.0 | 48.0 | 48.0 | 48.0 | 48.0 |
| Magnesium stearate | Lubricant | 4.8 | 4.8 | 4.8 | 4.8 | 4.8 | 4.8 | 4.8 | 4.8 |
| Total | | 480.0 | 480.0 | 480.0 | 480.0 | 480.0 | 480.0 | 480.0 | 480.0 |

The formulations were prepared by first milling the organic acid through a Fitz mill Model M5A, fitted with a 1512-0027 screen. The active, microcrystalline cellulose, milled organic acid, and release control polymer, were combined and blended. The blend was milled using a Mobil Mill fitted with a 610-micron screen. The magnesium stearate was screened through mesh #30 and was added to the bin and blended. The lubricated granulation was compressed into 480 mg weight tablets using a rotary tablet press.

The effect of the organic acids on the dissolution profile of the tablets was evaluated at pH 1.2 and pH 6.8. The dissolution tests were carried out using the dissolution parameters and conditions as described above in Examples 3 and 4 and 9-12. For analysis of the sample, conventional liquid chromatography methods were utilized, wherein the % of the labelled amount of active released (% LA Released) was calculated. The results show that organic acids improved dissolution rate at high pH, with tartaric acid showing the best improvement. The formulations comprising the control release polymer Carbopol® with tartaric acid provided near linear release at pH 6.8.

Example 21: Gel pH Measurements for Tablets with Different Amounts of Tartaric Acid To measure the pH of the environment created when Compound 1 reacts with HPMC, the following experiment was performed.

The Freebase Hydrate Form C solid-state form of Compound 1 was formulated into 30 mg extended-release tablets according to the formulations set forth in Table 7A. The tablets were prepared using a wet granulation process, as described in Examples 14-19.

Dissolution media of 0.01 N HCl (pH 2) and 113 mMv sodium phosphate buffer (pH 6.8) was prepared at 37° C. One tablet was added to 500 mL of 0.01 N HCl media and stirred at 75 rpm at 37° C. for one hour in a Vankel VK 7010 dissolution bath. Then 400 mL of sodium phosphate buffer was added. The solution was stirred an additional three hours. The tablet was removed, rinsed with water and dried using laboratory tissues. The gel that formed on the tablet was separated from the dry core for pH measurement. This procedure was repeated three times for each formulation. The pH of the gel formed on the tablets is set forth in Table 7B.

TABLE 7A

Formulations

| Component | Formulation 1 mg/tab | Formulation 2 mg/tab | Formulation 3 mg/tab | Formulation 4 mg/tab | Formulation 5 mg/tab |
|---|---|---|---|---|---|
| Intragranular | | | | | |
| Freebase Hydrate Form C | 30.71 | 30.71 | 30.71 | 30.71 | 30.71 |
| HPMC (Methocel® K4M) | 3.920 | 3.920 | 3.920 | 3.920 | 3.920 |
| Microcrystalline cellulose (Avicel® PH102) | 30.71 | 30.71 | 30.71 | 30.71 | 30.71 |
| extragranular | | | | | |
| Microcrystalline cellulose (Avicel® PH102) | 116.4 | 164.4 | 188.4 | 212.4 | 260.4 |
| Tartaric Acid (milled) | 144.0 | 96.00 | 72.00 | 48.00 | 0.00 |
| Mannitol (Pearlitol® 100SD) | 52.62 | 52.62 | 52.62 | 52.62 | 52.62 |
| HPMC (Methocel® K4M) | 92.08 | 92.08 | 92.08 | 92.08 | 92.08 |
| Colloidal silicon dioxide | 2.400 | 2.400 | 2.400 | 2.400 | 2.400 |

TABLE 7A-continued

| | Formulations | | | | |
|---|---|---|---|---|---|
| Component | Formulation 1 mg/tab | Formulation 2 mg/tab | Formulation 3 mg/tab | Formulation 4 mg/tab | Formulation 5 mg/tab |
| Magnesium Stearate | 7.200 | 7.200 | 7.200 | 7.200 | 7.200 |
| Total | 480.04 | 480.04 | 480.04 | 480.04 | 480.04 |

TABLE 7B pH Results

| Formulation | % Tartaric Acid | $1^{st}$ tablet | $2^{nd}$ tablet | $3^{rd}$ tablet | Average |
|---|---|---|---|---|---|
| 1 | 30 | 2.63 | 2.68 | 2.81 | 2.71 |
| 2 | 20 | 3.17 | 3.09 | 3.23 | 3.16 |
| 3 | 15 | 3.42 | 3.94 | 3.65 | 3.67 |
| 4 | 10 | 3.88 | 3.67 | 3.77 | 3.77 |
| 5 | 0 | 6.26 | 6.21 | 6.55 | 6.34 |

Example 22: Evaluation of the In Vivo Pharmacokinetic Profile of 15 mg Extended-Release Tablets (Fasting)

The pharmacokinetic profile of the 15 mg once-daily extended-release (ER) tablets prepared in Example 5 was evaluated and compared to that of a 12 mg immediate-release (IR) capsule comprising Tartrate Hydrate as the active.

Healthy human subjects (n=11) were administered a single dose of the 12 mg IR capsule (Regimen A) and the 15 mg ER (once-daily) tablet from Example 5 (Regimen B) under fasting conditions in a randomized, two-period, crossover study design. Subjects were administered Regimen A in the first study period and Regimen B in the second study period or administered Regimen B in the first study period and Regimen A in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 8A.

TABLE 8A

Mean (%CV)[c] Pharmacokinetic Parameters for Compound 1 Following Administration of 15 mg ER Tablet and 12 mg IR Capsule Formulations Under Fasting Conditions

| PK Parameter | Units | Regimen A (IR Capsule, 12 mg) | Regimen B (ER Tablet, 15 mg) |
|---|---|---|---|
| $C_{max}$ | ng/mL | 64.6 (16) | 26.0 (37) |
| $T_{max}$[a] | hours | 1.0 (0.5-1.5) | 3.0 (1.0-4.0) |
| $t_{1/2}$[b] | hours | 9.2 (119) | 12.5 (90) |

TABLE 8A-continued

Mean (%CV)[c] Pharmacokinetic Parameters for Compound 1 Following Administration of 15 mg ER Tablet and 12 mg IR Capsule Formulations Under Fasting Conditions

| PK Parameter | Units | Regimen A (IR Capsule, 12 mg) | Regimen B (ER Tablet, 15 mg) |
|---|---|---|---|
| $AUC_t$ | ng · h/mL | 231 (15) | 227 (26) |
| $AUC_{inf}$ | ng · h/mL | 234 (15) | 242 (26) |

[a]Median (minimum, maximum)
[b]Harmonic mean (pseudo-%CV)
[c]Data in parentheses is coefficient of variance of the PK parameter (% CV), unless otherwise indicated.

As can be seen from this data, the 15 mg ER tablet provided a lower $C_{max}$ and comparable AUC to the 12 mg IR capsule under fasting conditions.

The relative bioavailability for a single dose of the once-daily (ER) tablet formulation (Regimen B) relative to the IR capsule formulation (Regimen A) was also determined based on analysis of the natural logarithms of $C_{max}$ and AUC. The results are summarized in Table 8B below.

TABLE 8B

Relative Bioavailability and 90% Confidence Intervals for Bioequivalence Assessment

| | Relative Bioavailability | |
|---|---|---|
| PK Paramenter | Point Estimate | 90% Confidence Interval |
| $C_{max}$ | 0.373 | 0.312-0.446 |
| $AUC_t$ | 0.939 | 0.869-1.013 |
| $AUC_{inf}$ | 0.992 | 0.909-1.082 |

For Regimen B versus Regimen A, the point estimates for the ratios of $AUC_t$ and $AUC_{inf}$ were near unity, and the 90% confidence intervals were within the 0.86-1.09 range.

Example 23: Evaluation of the In Vivo Pharmacokinetic Profile of 30 mg Extended-Release Tablets (Fasting)

The pharmacokinetic profile of the 30 mg once daily extended-release (ER) tablets prepared in Example 8 was evaluated and compared to that of a 24 mg dose of an immediate release (IR) capsule comprising Tartrate Hydrate as the active.

Healthy human subjects (n=12) were administered a single 24 mg dose (two 12 mg IR capsules) (Regimen C) and the 30 mg ER (once daily) tablet from Example 8 (Regimen D) under fasting conditions in a randomized, two-period, cross-over study design. Half the subjects were administered Regimen C in the first study period and Regimen D in the second study period, while the other half were administered Regimen D in the first study period and Regimen C in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 9A.

TABLE 9A

Mean (%CV)[c] Pharmacokinetic Parameters for Compound 1 Following Administration of 30 mg ER Tablet and 24 mg Dose (2 × 12 mg) IR Capsule Formulations Under Fasting Conditions

| PK Parameter | Units | Regimen C (IR Capsules, 24 mg) | Regimen D (ER Tablet, 30 mg) |
|---|---|---|---|
| $C_{max}$ | ng/ml | 176 (37) | 63.7 (33) |
| $T_{max}$[a] | hours | 0.5 (0.5-1.5) | 2.0 (1.5-4.0) |
| $t_{1/2}$[b] | hours | 9.9 (52) | 10.8 (67) |
| $AUC_t$ | ng · h/mL | 520 (25) | 477 (27) |
| $AUC_{inf}$ | ng · h/mL | 524 (25) | 491 (27) |

[a]Median (minimum-maximum)
[b]Harmonic mean (pseudo %CV)
[c]Data in parentheses is the coefficient of variance of the PK parameter (% CV), unless otherwise indicated.

As can be seen from this data, the 30 mg ER tablet provided a lower $C_{max}$ and comparable AUC to the 24 mg dose IR capsule (2×12 mg) under fasting conditions.

The relative bioavailability for a single dose of the once-daily (ER) tablet formulation (Regimen D) relative to the IR capsule formulations (Regimen C) was also determined based on analysis of the natural logarithms of $C_{max}$ and AUC. The results are summarized in Table 9B below.

TABLE 9B

Relative Bioavailability and 90% Confidence Intervals for Bioequivalence Assessment

| | PK Value | | Relative Bioavailability | |
|---|---|---|---|---|
| PK Paramenter | Regimen D | Regimen C (reference) | Point Estimate | 90% Confidence Interval |
| $C_{max}$ | 63.7 | 176 | 0.368 | 0.326-0.415 |
| $AUC_t$ | 477 | 520 | 0.912 | 0.828-1.004 |
| $AUC_{inf}$ | 491 | 524 | 0.933 | 0.845-1.029 |

For Regimen D versus Regimen C, the point estimates for the ratios of $AUC_t$ and $AUC_{inf}$ were near unity, and the 90% confidence intervals were within the 0.82-1.03 range.

Example 24: Comparison of the In Vivo Pharmacokinetic Profile of 30 mg Extended-Release Tablets Under Fasting Versus Fed Conditions The pharmacokinetic profile of the 30 mg extended-release tablets prepared in Example 8 after a high-fat meal was evaluated, and compared to the pharmacokinetic profile of the 30 mg extended-release tablets under fasting conditions (see Example 23).

Following completion of the Example 23 study, the healthy human subjects (n=12) were administered single doses of the 30 mg ER (once daily) tablet from Example 8 after a high-fat meal (Regimen E). Serial blood samples were collected from each subject prior to dosing and for 72 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter, and compared to the pharmacokinetic parameters for the 30 mg tablets administered under fasting conditions (see Example 23, Regimen D). The results are summarized in Table 10A.

TABLE 10A

Mean (%CV)[c] Pharmacokinetic Parameters for Compound 1 Following Administration of 30 mg ER Tablet Under Fasting Conditions or After a High-Fat Meal

| PK Parameter | Units | Regimen D (Fasting) | Regimen E (After High-Fat Meal) |
|---|---|---|---|
| $C_{max}$ | ng/ml | 63.7 (33) | 76.8 (39) |
| $T_{max}$[a] | hours | 2.0 (1.5-4.0) | 4.0 (1.5-8.0) |
| $t_{1/2}$[b] | hours | 10.8 (67) | 11.9 (51) |
| $AUC_t$ | ng · h/mL | 477 (27) | 564 (26) |
| $AUC_{inf}$ | ng · h/mL | 491 (27) | 577 (27) |

[a]Median (minimum-maximum)
[b]Harmonic mean (pseudo-CV%)
[c]Data in parentheses is coefficient of variance of the PK parameter (% CV), unless otherwise indicated.

The relative bioavailability for a single dose of the once-daily (ER) 30 mg tablet formulation after a high-fat meal (Regimen E) relative to the bioavailability of the ER 30 mg tablet under fasting conditions (Regimen D) was also determined based on analysis of the natural logarithms of $C_{max}$ and AUC. The results are summarized in Table 10B below.

TABLE 10B

Relative Bioavailability and 90% Confidence Intervals for Bioequivalence Assessment

| | PK Value | | Relative Bioavailability | |
|---|---|---|---|---|
| PK Paramenter | Regimen E (after high-fat meal) | Regimen D (fasting) | Point Estimate | 90% Confidence Interval |
| $C_{max}$ | 76.8 | 63.7 | 1.197 | 1.027-1.395 |
| $AUC_t$ | 564 | 477 | 1.184 | 1.042-1.344 |
| $AUC_{inf}$ | 577 | 491 | 1.171 | 1.035-1.326 |

As can be seen from Tables 10A and 10B, there was no clinically meaningful food effect for the 30 mg ER tablets. Administration following a high-fat meal increased the Compound 1 mean AUC and $C_{max}$ by 17% and 20%, respectively.

Example 25: Observed Steady State Exposures for 15 mg and 30 mg Extended-Release Tablets Under Non-Fasting Conditions The steady state pharmacokinetic profile of the 15 mg once daily extended-release (ER) tablets (prepared in Example 5) and the 30 mg once daily ER tablets (prepared in Example 8) was evaluated.

Healthy human subjects (n=24) were assigned to one of two regimens. Subjects in Regimen F (n=12) were administered the 15 mg ER tablet from Example 5 once daily for seven days under non-fasting conditions. Subjects in Regimen G (n=12) were administered the 30 mg ER tablet from Example 8 once daily for seven days under non-fasting conditions. On days one and seven, serial blood samples were collected from each subject prior to the daily dosing and up to 24 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 11A.

Example 26: Observed Steady State Exposures for 15 mg Extended-Release Tablets and 6 mg Immediate Release Capsules Under Fasting Conditions The steady state pharmacokinetic profile of the 15 mg once daily extended-release (ER) tablets (prepared in Example 5) under fasting conditions was evaluated and compared to that of a 6 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen K (n=12 at onset; n=11 on Day 7) were administered the 6 mg IR capsule twice daily for seven days under fasting conditions. Subjects in Regimen L (n=12) were administered the 15 mg ER tablet from Example 5 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and

TABLE 11A

Mean (%CV)[e] Pharmacokinetic Parameters for Compound 1 Following Administration of 15mg ER Tablet or 30 mg ER Tablet QD for Seven Days (Non-Fasting)

| PK Parameter | Units | Regimen F (15 mg ER Tablet) | | Regimen G (30 mg ER Tablet) | |
|---|---|---|---|---|---|
| | | Day 1 | Day 7 | Day 1 | Day 7 |
| $C_{max}$ | ng/ml | 36.8 (26) | 36.0 (24) | 74.3 (32) | 79.5 (40) |
| $T_{max}$[a] | hours | 4.0 (3.0-6.0) | 4.0 (2.0-6.0) | 4.0 (2.0-6.0) | 4.0 (1.5-6.0) |
| $AUC_{24}$ | ng · h/mL | 305 (24) | 317 (21) | 517 (30) | 582 (30) |
| $C_{24}$ | ng/mL | 2.42 (45) | 3.22 (46) | 4.27 (48) | 5.25 (44) |
| $C_{trough}$ | ng/mL | — | 2.96 (35) | — | 5.02 (42) |
| $C_{min,ss}$ | ng/mL | — | 2.80 (41) | — | 4.62 (38) |
| Fluctuation Index | % | 291 (14) | 251 (14) | 345 (14) | 306 (17) |
| $t_{1/2}$[b] | hours | — | 9.43 (76) | — | 10.4 (44) |
| $C_{max}$ to $C_{24}$ ratio | | 17 (7.8-44) | 13 (5.6-35) | 17 (9.9-38) | 14 (7.0-30) |
| $C_{max}$/Dose | (ng/ml)/mg | 2.46 (26) | 2.40 (24) | 2.48 (32) | 2.65 (40) |
| $C_{trough}$/Dose | (ng/ml)/mg | 0.16 (45) | 0.21 (46) | 0.14 (48) | 0.18 (44) |
| $AUC_{24}$/Dose | (ng · h/mL)/mg | 20.3 (24) | 21.2 (21) | 17.2 (30) | 19.4 (30) |
| $R_{AUC}$[c] | | — | 1.02 (0.91-1.40) | — | 1.16 (0.92-1.31) |
| $R_{Cmax}$[d] | | — | 1.00 (0.84-1.26) | — | 1.02 (0.82-1.40) |

[a]Median (minimum-maximum)
[b]Harmonic mean (pseudo-%CV)
[c]$R_{AUC}$ = $AUC_{24}$Day7/$AUC_{24}$Day 1; median (range)
[d]$R_{Cmax}$ = $C_{max}$ Day 7/$C_{max}$Day 1; median (range)
[e]Data in parentheses is the coefficient of variance of the PK parameter (% CV), unless otherwiseindicated As can be seen from this data, the observed steady state $C_{max}$ and $AUC_{24}$ following 15 mg QD and 30 mg QD administration are generally consistent with the single dose and food-effect results obtained in Examples 22-24. The bioavailability of the 15 mg and 30 mg ER tablets was 70% to 80% relative to the same dose of IR capsules.

stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 12A.

TABLE 12A

Mean (%CV)[e] Pharmacokinetic Parameters for Compound 1 Following Administration of 6 mg BID (IR) Capsules and 15 mg QD (ER) Tablets for Seven Days (Fasting Conditions)

| PK Parameter | Units | Regimen K (6 mg IR Capsules (BID)) | | Regimen L (15 mg ER Tablet (QD)) | |
| --- | --- | --- | --- | --- | --- |
| | | Day 1 | Day 7 | Day 1 | Day 7 |
| $C_{max}$ | ng/ml | 36.5 (25) | 33.9 (26) | 31.7 (40) | 31.9 (35) |
| $T_{max}$[a] | hours | 1.0 (1.0-13) | 1.0 (0.5-14) | 3.0 (1.5-6.0) | 2.5 (1.5-4.0) |
| $AUC_{24}$ | ng · h/mL | 289 (21) | 288 (22) | 249 (29) | 279 (26) |
| $C_{12}$ | ng/mL | 2.0 (30) | 2.8 (24) | — | — |
| $C_{24}$ | ng/ml | 3.2 (36) | 3.6 (23) | 1.9 (42) | 3.1 (37) |
| $C_{min}$ | ng/ml | — | 2.7 | — | 3.1 (37) |
| Fluctuation Index | % | 303 (13) | 259 (13) | 299 (22) | 246 (21) |
| $t_{1/2}$[b] | hours | — | 14.7 (77) | — | 10.3 (76) |
| $C_{max}$ to $C_{24}$ ratio[a] | — | 12 (7.7-19) | 8.8 (7.4-13) | 22 (5.8-43) | 12 (4.2-20) |
| $C_{max}$ to $C_{min}$ ratio[a] | — | — | 13 (8.3-18) | — | 12 (4.2-20) |
| $AUC_{24}$/Dose | (ng · h/mL)/mg | 24.8 (23) | 24.0 (22) | 16.6 (29) | 18.6 (26) |
| $R_{AUC}$[c] | — | — | 1.02 (0.88-1.09) | — | 1.11 (0.87-1.99) |
| $R_{Cmax}$[d] | — | — | 0.97 (0.68-1.17) | — | 1.01 (0.65-3.01) |

[a]Median (minimum-maximum)
[b]Harmonic mean (pseudo-%CV)
[c]$R_{AUC}$ = $AUC_{24}$Day7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for the once-daily (ER) tablet formulation (Regimen L) relative to the twice daily (IR) capsule formulation (Regimen K) at steady state was also determined based on analysis of the natural logarithms of $C_{max}$, $AUC_{24}$, $C_{min}$, and $C_{24}$. The results are summarized in Table 12B below.

TABLE 12B

Relative Bioavailability Estimates and 90% Confidence Intervals for 15 mg QD Tablets Relative to 6 mg BID Capsules at Steady State under Fasting Conditions

| PK Parameter | Relative Bioavailability | |
| --- | --- | --- |
| | Point Estimate | 90% Confidence Interval |
| $C_{max}$ | 0.909 | 0.736-1.122 |
| $AUC_{24}$ | 0.939 | 0.837-1.053 |
| $C_{min}$ | 1.090 | 0.852-1.395 |

The ratio of steady-state AUC for the 15 mg QD tablets relative to the 6 mg BID capsules was approximately 1, with the 90% confidence intervals within the equivalence boundaries. The ratio of the steady-state $C_{min}$ was approximately 1 for the 15 mg QD tablet relative to the 6 mg BID capsules.

At steady state under fasting conditions, the 15 mg QD tablets provided equivalent $AUC_{24}$ and comparable $C_{max}$ and $C_{min}$ relative to the 6 mg BID capsules. The steady state $C_{max}$ was 10% lower for the 15 mg QD tablet compared to the 6 mg BID capsule.

Example 27: Observed Steady State Exposures for 30 mg Extended-Release Tablets and 12 mg Immediate Release Capsules Under Fasting Conditions The steady state pharmacokinetic profile of the 30 mg once daily extended-release (ER) tablets (prepared in Example 8) under fasting conditions was evaluated and compared to that of a 12 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen M (n=11) were administered the 12 mg IR capsule twice daily for seven days under fasting conditions. Subjects in Regimen N (n=12 at onset; n=11 at Day 7) were administered the 30 mg ER tablet from Example 8 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 13A. The mean plasma concentration of Compound 1 at each time point measured for each of the two regimens is set forth in FIG. 22.

TABLE 13A

Mean (%CV)[e] Pharmacokinetic Parameters for Compound 1 Following Administration of 12 mg BID (IR) Capsules and 30 mg QD (ER) Tablets for Seven Days (Fasting Conditions)

| PK Parameter | Units | Regimen M (12 mg IR Capsules (BID)) | | Regimen N (30 mg ER Tablet (QD)) | |
|---|---|---|---|---|---|
| | | Day 1 | Day 7 | Day 1 | Day 7 |
| $C_{max}$ | ng/ml | 80.8 (23) | 73.9 (19) | 65.7 (22) | 68.2 (30) |
| $T_{max}$[a] | hours | 1.0 (0.5-13) | 1.0 (0.5-1.5) | 2.5 (1.5-4.0) | 3.0 (2.0-4.0) |
| $AUC_{24}$ | ng · h/mL | 497 (15) | 534 (18) | 454 (23) | 525 (23) |
| $C_{12}$ | ng/ml | 3.0 (46) | 4.1 (55) | — | — |
| $C_{24}$ | ng/mL | 6.5 (54) | 6.9 (37) | 2.8 (37) | 4.4 (39) |
| $C_{min}$ | ng/ml | — | 3.8 (58) | — | 3.8 (43) |
| Fluctuation Index | % | 388 (15) | 317 (14) | 349 (12) | 291 (17) |
| $t_{1/2}$[b] | hours | — | 7.3 (60) | — | 14.4 (64) |
| $C_{max}$ to $C_{24}$ ratio[a] | | 15 (5.4-20) | 12 (5.9-16) | 29 (13-38) | 17 (4.1-33) |
| $C_{max}$ to $C_{min}$ ratio[a] | — | — | 19 (8.4-31) | — | 17 (11-37) |
| $AUC_{24}$/Dose | (ng · h/mL)/mg | 21.1 (15) | 22.3 (18) | 15.1 (22) | 17.5 (23) |
| $R_{AUC}$[c] | — | — | 1.08 (0.97-1.18) | — | 1.11 (0.79-1.67) |
| $R_{Cmax}$[d] | — | — | 0.98 (0.65-1.18) | — | 1.03 (0.40-1.82) |

[a]Median (minimum-maximum)
[b]Harmonic mean (pseudo-%CV)
[c]$R_{AUC}$ = $AUC_{24}$Day7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for a single dose of the once-daily (ER) tablet formulation (Regimen N) relative to the twice daily (IR) capsule formulation (Regimen M) was also determined based on analysis of the natural logarithms of $C_{max}$, $AUC_{24}$, $C_{min}$, and $C_{24}$. The results are summarized in Table 13B below.

TABLE 13B

Relative Bioavailability Estimates and 90% Confidence Intervals for 30 mg QD Tablets Relative to 12 mg BID Capsules at Steady State under Fasting Conditions

| PK Parameter | Relative Bioavailability | |
|---|---|---|
| | Point Estimate | 90% Confidence Interval |
| $C_{max}$ | 0.900 | 0.732-1.107 |
| $AUC_{24}$ | 0.974 | 0.869-1.092 |
| $C_{min}$ | 0.874 | 0.747-1.022 |

The ratio of steady-state AUC for the 30 mg QD tablets relative to the 12 mg BID capsules was approximately 1, with the 90% confidence intervals within the equivalence boundaries. The steady-state $C_{min}$ for the 30 mg QD tablet was approximately 13% lower than for the 12 mg BID capsules. Outliers with high $C_{min}$ in the 12 mg BID dose may have contributed to this difference.

The pre-morning dose trough concentration ($C_{trough}$) for the 12 mg BID capsules and 30 mg QD tablets was determined prior to the morning dose on Days 2-8. The results show that, at steady state under fasting conditions, the 30 mg QD tablets provided equivalent $AUC_{24}$ and comparable $C_{max}$ and $C_{min}$ relative to the 12 mg BID capsules. The steady state $C_{max}$ was 10% lower for the 30 mg QD tablet compared to the 12 mg BID capsules.

Example 28: Comparison of AM vs. PM Pharmacokinetic Profile Following Administration of 6 mg or 12 mg Immediate Release Capsules Under Fasting Conditions The pharmacokinetic profile of the 6 mg immediate release (IR) twice daily (BID) capsules and the 12 mg IR twice daily capsules was determined on Day 7 of Regimen K (Example 26) and Regimen M (Example 27), respectively, after administration of the morning (AM dose) and evening (PM dose). The results are summarized in Table 14.

TABLE 14

Mean (%CV)[b] Pharmacokinetic Parameters for Compound 1 Following Administration of AM and PM Doses of 6 mg and 12 mg Immediate Release Capsules on Day 7 (Fasting Conditions)

| PK Parameter | Units | Regimen K (6 mg IR Capsules) | | Regimen M (12 mg IR Capsules) | |
|---|---|---|---|---|---|
| | | AM Dose | PM Dose[c] | AM Dose | PM Dose[c] |
| $C_{max}$ | ng/ml | 33.6 (28) | 24.4 (22) | 73.9 (19) | 46.0 (26) |
| $T_{max}$[a] | hours | 1 (0.5-1.5) | 2 (1.0-3.0) | 1 (0.5-1.5) | 3 (1.0-4.0) |
| $AUC_{12}$ | ng · h/mL | 152 (26) | 153 (19) | 290 (19) | 244 (19) |
| $C_{12}$ | ng/mL | 2.76 (24) | 3.63 (23) | 4.1 (55) | 6.94 (37) |
| $C_{max}/C_{12}$ | — | 12.3 (23) | 6.9 (22) | 18.0 (30) | 7.4 (39) |

[a]Median (Minimum-Maximum)
[b]Data in parentheses is the coefficient of variance of the PK parameter (% CV), unless otherwise indicated
[c]The PM dose was administered 3 hours after starting dinner and 4 hours before a snack.

Example 29: Evaluation of the In Vivo Pharmacokinetic Profile of 30 mg Extended-Release Tablets The pharmacokinetic profiles of the 30 mg once-daily extended-release (ER) tablets that were prepared in Examples 14 (ER10, 30% tartaric acid), 15 (ER11, 20% tartaric acid), and 16 (ER12, 10% tartaric acid) using wet granulation were evaluated, and compared to that of the 30 mg ER tablet that was prepared in Example 8 (ER8, 30% tartaric acid) using direct compression (no wet granulation).

The effect of a high-fat meal on the Example 14, 15, and 16 formulations was also evaluated.

Healthy human subjects (n=36) were administered a single dose of the 30 mg ER (once daily) tablet from Example 8 (ER8), Example 14 (ER10), Example 15 (ER11), and Example 16 (ER12) under fasting conditions or after a high-fat meal (non-fasting), in an open-label, randomized, four-period, incomplete crossover study. Doses in the four periods were separated by at least four days. Dosing regimens were as set forth below in Table 15A.

TABLE 15A

Dosing Regimens

| Regimen | Dose | Formulation | Fasting/Non-Fasting |
|---|---|---|---|
| A | Single 30 mg | Example 8 (ER8) | Fasting |
| B | Single 30 mg | Example 14 (ER10) | Fasting |
| C | Single 30 mg | Example 14 (ER10) | Non-Fasting |
| D | Single 30 mg | Example 15 (ER11) | Fasting |
| E | Single 30 mg | Example 15 (ER11) | Non-Fasting |
| F | Single 30 mg | Example 16 (ER12) | Fasting |
| G | Single 30 mg | Example 16 (ER12) | Non-Fasting |

Serial blood samples were collected from each subject prior to dosing and for 72 hours after dosing in each study period. Upon collection, the samples were promptly placed in an ice bath, and within 1 hour after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Bioavailability Under Fasting Conditions

The results for administration under fasting conditions are summarized in Table 15B.

TABLE 15B

Mean (% CV)[c] Pharmacokinetic Parameters for Compound 1 Following Administration of a Single 30 mg Dose of Various Compound 1 Once-Daily Formulations Prepared Using Wet Granulation Compared to Administration of a Single 30 mg Dose of a Compound 1 Once-Daily Formulation Prepared Via Direct Compression Under Fasting Conditions

| PK Parameter | Units | Regimen A (ER8) (n = 36) | Regimen B (ER10) (n = 24) | Regimen D (ER11) (n = 24) | Regimen F (ER12) (n = 24) |
|---|---|---|---|---|---|
| $C_{max}$ | ng/mL | 57.0 (33) | 55.8 (27) | 61.0 (25) | 58.6 (34) |
| $T_{max}$[a] | hours | 2.5 (1.0-4.0) | 3.0 (1.0-4.0) | 2.0 (1.0-4.0) | 2.0 (1.0-4.0) |
| $AUC_t$ | ng · h/mL | 495 (24) | 473 (24) | 487 (22) | 481 (23) |
| $AUC_{inf}$ | ng · h/mL | 513 (26) | 484 (24) | 499 (22) | 495 (23) |
| $t_{1/2}$[b] | hours | 9.2 (61) | 10.1 (50) | 9.0 (61) | 9.3 (63) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the three once-daily (ER) tablet formulations prepared using wet granulation (Regimens B, D, and F) relative to the ER tablet prepared via direct compression (no wet granulation) (Regimen A) was also determined based on analysis of the natural logarithms of $C_{max}$, $AUC_t$, and $AUC_{inf}$. The results are summarized in Table 15C below.

TABLE 15C

Bioavailability for Three Compound 1 Once-Daily Formulations Prepared Using Wet Granulation (30 mg; ER10, ER11, ER12) Relative to a Formulation Prepared Via Direct Compression (30 mg, ER8) under Fasting Conditions

| | | Relative Bioavailability | |
|---|---|---|---|
| Regimens | PK Parameter | Point Estimate | 90% Confidence Interval |
| Regimen B (ER10) vs. Regimen A (ER8) | $C_{max}$ | 1.024 | 0.917-1.143 |
| | $AUC_t$ | 0.990 | 0.933-1.049 |
| | $AUC_{inf}$ | 0.976 | 0.918-1.037 |
| Regimen D (ER11) vs. Regimen A (ER8) | $C_{max}$ | 1.063 | 0.952-1.187 |
| | $AUC_t$ | 0.985 | 0.929-1.044 |
| | $AUC_{inf}$ | 0.977 | 0.919-1.038 |
| Regimen F (ER12) vs. Regimen A (ER8) | $C_{max}$ | 1.034 | 0.926-1.154 |
| | $AUC_t$ | 0.958 | 0.904-1.016 |
| | $AUC_{inf}$ | 0.958 | 0.901-1.018 |

As can be seen from this data, all three of the 30 mg tablets prepared using wet granulation (ER10, ER11, and ER12) were bioequivalent under fasting conditions to the tablet prepared via direct compression (no wet granulation).

Effect of a High-Fat Meal on Example 37 Formulation (ER10)

The effect of a high-fat meal on the pharmacokinetic parameters of the Example 14 (ER10, 30 mg active, 30% tartaric acid) formulation is summarized in Table 15D.

TABLE 15D

Mean (% CV)$^c$ Pharmacokinetic Parameters for Compound 1 Following Administration of Single 30 mg Dose of the Once-Daily Tablet Formulation ER10 under Fasting Conditions and After High-Fat Meal

| PK Parameter | Units | Regimen B (ER10, fasting) (n = 24) | Regimen C (ER10, high fat meal) (n = 12) |
|---|---|---|---|
| $C_{max}$ | ng/mL | 55.8 (27) | 76.3 (30) |
| $T_{max}{}^a$ | hours | 3.0 (1.0-4.0) | 4.0 (1.5-8.0) |
| $AUC_t$ | ng · h/mL | 473 (24) | 605 (23) |
| $AUC_{inf}$ | ng · h/mL | 484 (24) | 609 (23) |
| $t_{1/2}{}^b$ | hours | 10.1 (50) | 9.1 (35) |

$^a$Median (minimum-maximum)
$^b$Harmonic mean (pseudo-% CV)
$^c$Data in parentheses is coefficient of variance of the PK parameter (% CV), unless otherwise indicated.

The relative bioavailability for a single dose of the Example 14 formulation (ER10) administered after a high-fat meal relative to administration under fasting conditions was also determined based on analysis of the natural logarithms of $C_{max}$, $AUC_t$, and $AUC_{inf}$. The results are summarized in Table 15E below.

TABLE 15E

Bioavailability of Single Dose of the 30 mg Once-Daily Tablet ER10 Administered after High-Fat Meal Relative to under Fasting Conditions

| | | Relative Bioavailability | |
|---|---|---|---|
| | PK Parameter | Point Estimate | 90% Confidence Interval |
| Regimen C (ER10, high-fat meal) vs. Regimen B (ER10, fasting) | $C_{max}$ | 1.322 | 1.134-1.541 |
| | $AUC_t$ | 1.296 | 1.194-1.405 |
| | $AUC_{inf}$ | 1.278 | 1.174-1.392 |

As can be seen from this data, a high-fat meal increased the $C_{max}$ and $AUC_{inf}$ for the ER10 formulation (30 mg active, 30% tartaric acid) by about 32% and 28%, respectively.

Effect of a High-Fat Meal on Example 15 Formulation (ER11)

The effect of a high-fat meal on the pharmacokinetic parameters of the Example 15 (ER11, 30 mg, 20% tartaric acid) formulation is summarized in Table 15F.

TABLE 15F

Mean (% CV)$^c$ Pharmacokinetic Parameters for Compound 1 Following Administration of Single 30 mg Dose of the Once-Daily Tablet Formulation ER11 under Fasting Conditions and After High-Fat Meal

| PK Parameter | Units | Regimen D (ER11, fasting) (n = 24) | Regimen E (ER11, high fat meal) (n = 12) |
|---|---|---|---|
| $C_{max}$ | ng/mL | 61.0 (25) | 82.2 (33) |
| $T_{max}{}^a$ | hours | 2.0 (1.0-4.0) | 4.0 (3.0-8.0) |
| $AUC_t$ | ng · h/mL | 487 (22) | 648 (24) |
| $AUC_{inf}$ | ng · h/mL | 499 (22) | 657 (24) |
| $t_{1/2}{}^b$ | hours | 9.0 (61) | 9.7 (53) |

$^a$Median (minimum-maximum)
$^b$Harmonic mean (pseudo-% CV)
$^c$Data in parentheses is coefficient of variance of the PK parameter (% CV), unless otherwise indicated.

The relative bioavailability for a single dose of the Example 15 formulation (ER11) administered after a high-fat meal relative to administration under fasting conditions was also determined based on analysis of the natural logarithms of $C_{max}$, $AUC_t$, and $AUC_{inf}$. The results are summarized in Table 15G below.

TABLE 15G

Bioavailability of Single Dose of the 30 mg Once-Daily Tablet ER11 Administered after High-Fat Meal Relative to under Fasting Conditions

| | | Relative Bioavailability | |
|---|---|---|---|
| | PK Parameter | Point Estimate | 90% Confidence Interval |
| Regimen E (ER11, high-fat meal) vs. Regimen D (ER11, fasting) | $C_{max}$ | 1.343 | 1.153-1.563 |
| | $AUC_t$ | 1.305 | 1.204-1.415 |
| | $AUC_{inf}$ | 1.285 | 1.181-1.398 |

As can be seen from this data, a high-fat meal increased the $C_{max}$ and $AUC_{inf}$ for the ER11 formulation (30 mg active, 20% tartaric acid) by about 34% and 29%, respectively, which was a similar food effect as that observed for the Example 14 (ER10) tablet.

Effect of a High-Fat Meal on Example 16 Formulation (ER12)

The effect of a high-fat meal on the pharmacokinetic parameters of the Example 16 (ER12, 30 mg active, 10% tartaric acid) formulation is summarized in Table 15H.

TABLE 15H

Mean (% CV)[c] Pharmacokinetic Parameters for Compound 1 Following Administration of Single 30 mg Dose of the Once-Daily Tablet Formulation ER12 under Fasting Conditions and After High-Fat Meal

| PK Parameter | Units | Regimen E (ER12, fasting) (n = 24) | Regimen G (ER12, high fat meal) (n = 12) |
|---|---|---|---|
| $C_{max}$ | ng/mL | 58.6 (34) | 84.2 (33) |
| $T_{max}$[a] | hours | 2.0 (1.0-4.0) | 4.0 (4.0-6.0) |
| $AUC_t$ | ng · h/mL | 481 (23) | 615 (24) |
| $AUC_{inf}$ | ng · h/mL | 495 (23) | 622 (23) |
| $t_{1/2}$[b] | hours | 9.3 (63) | 11.7 (91) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 16 formulation (ER12) administered after a high-fat meal relative to administration under fasting conditions was also determined based on analysis of the natural logarithms of $C_{max}$, $AUC_t$, and $AUC_{inf}$. The results are summarized in Table 15I below.

TABLE 15I

Bioavailability of Single Dose of the 30 mg Once-Daily Tablet ER12 Administered after High-Fat Meal Relative to under Fasting Conditions

| | PK Parameter | Relative Bioavailability Point Estimate | 90% Confidence Interval |
|---|---|---|---|
| Regimen G (ER12, high-fat meal) vs. Regimen F (ER12, fasting) | $C_{max}$ | 1.527 | 1.314-1.774 |
| | $AUC_t$ | 1.295 | 1.196-1.402 |
| | $AUC_{inf}$ | 1.272 | 1.171-1.381 |

As can be seen from this data, a high-fat meal increased the $C_{max}$ and $AUC_{inf}$ for the ER12 formulation (30 mg active, 10% tartaric acid) by about 53% and 27%, respectively.

Example 30: Predicted Pharmacokinetic Parameters for 15 mg Extended-Release Tablets The mean pharmacokinetic parameters under fasting conditions for the once daily (QD) 15 mg extended-release tablets prepared in Examples 17 (ER13), 18 (ER14), and 19 (ER15) using wet granulation were extrapolated from the single dose data obtained in Example 29 for the Examples 14 (ER10), 15 (ER11), and 16 (ER12) formulations, respectively, under fasting conditions. The results are set forth in Table 16A.

TABLE 16A

Predicted Mean Pharmacokinetic Parameters under Fasting Conditions for Compound 1 Following Administration of Single 15 mg Once-Daily Formulations (Extrapolated from Single-Dose Profiles in Example 52 for 30 mg Doses)

| PK Parameters | Units | Single 15 mg Dose (ER 13) | Single 15 mg dose (ER14) | Single 15 mg dose (ER15) |
|---|---|---|---|---|
| $C_{max}$ | ng/mL | 27.9 | 30.5 | 29.3 |
| $T_{max}$[a] | h | 3.0 | 2.0 | 2.0 |
| $AUC_{inf}$ | ng · h/mL | 242 | 250 | 248 |

[a]Median (minimum-maximum)

Example 31: Preliminary Data from Phase 1 Study in Healthy Volunteers and Patients with Rheumatoid Arthritis Compound 1 has been studied in 2 Phase 1 studies, first in human single ascending dose study (Study MI3-401, described in WO 2015/061665, and referred to herein as Study 1), and then in a multiple ascending dose study (Study MI3-845, also generally referred to in WO 2015/061665, and referred to herein as Study 2).

In Study 1, a total of 42 healthy volunteers received a single dose of Compound 1. In Study 2, a total of 32 healthy volunteers received multiple doses of Compound 1 for 14 days (Study 2, Part 1). In addition, 14 patients with RA were enrolled and completed the double-blind Part 2 of Study 2. The study was designed as a multiple dose, randomized, multicenter trial, with the primary objective as assessing the safety, tolerability, and PK of multiple ascending doses of Compound 1 in healthy adult volunteers and to assess the safety, tolerability, and PK of multiple doses of Compound 1 in patients with RA who are on a stable methotrexate regimen.

Details of Study 1 and Study 2 and results obtained therefrom are provided below.

Study 1—Single-Dose Escalation in Healthy Subjects

Study 1 was a single-dose escalation evaluation of Compound 1. Study 1 was designed as a single-site, randomized, double-blind, placebo-controlled study. Fifty-six subjects in general good health were randomized to receive single doses of Compound 1 immediate release capsules comprising Tartrate Hydrate (1, 3, 6, 12, 24, 36, and 48 mg) or placebo in a 3:1 ratio with 8 subjects in each dose level. Study drug was administered following at least 10 hours of fasting. The study was conducted at PPD Development (Austin, TX). Subjects were confined to the study site and supervised for approximately 8 consecutive days. Study protocol and informed consent were approved by RCRC institutional review board (IRB) (Austin, TX).

Study 2—Multiple-Dose Escalation

In Study 2, multiple twice-daily (BID) doses of immediate release capsules comprising Tartrate Hydrate were administered to healthy subjects (Part 1) or to subjects with rheumatoid arthritis (RA) receiving stable doses of methotrexate (Part 2). Both evaluations followed randomized, double-blind, placebo-controlled designs. Part 1 was conducted at PPD Development (Austin, TX) and Part 2 was conducted at two sites: Aspen Clinical Research (Orem, UT) and Altoona Center for Clinical Research (Duncansville, PA). Study protocol and informed consents were approved by RCRC IRB (Austin, TX) and Quorum Review IRB (Seattle, WA).

Study 2-Part 1—Multiple-Dose Escalation in Healthy Subjects

The objective of Part 1 of the multiple-dose study was to characterize the pharmacokinetics, safety, and tolerability of multiple oral doses of Compound 1 immediate release capsules comprising Tartrate Hydrate in healthy subjects. Four escalating dosing regimens (3, 6, 12, and 24 mg Compound 1 or matching placebo twice daily for 13 consecutive days and once in the morning on Day 14) were evaluated. Study drug was administered approximately 30 minutes after a standard breakfast (in the morning) or a snack (in the evening). Forty-four healthy subjects participated in this part of the study with 11 subjects per dose group (8:3 Compound 1: placebo ratio). Subjects were confined to the study site and supervised for approximately 18 days.

Study 2-Part 2—Multiple-Dose Evaluation in Subjects with RA

The objective of Part 2 of the multiple dose study was to assess the pharmacokinetics, safety, and tolerability of multiple oral doses of Compound 1 immediate release capsules comprising Tartrate Hydrate in subjects with mild to moderate RA who were on stable methotrexate treatment. This evaluation was designed to enroll approximately 32 subjects randomized in a 1:1:1:1 ratio to one of four parallel twice-daily regimens (6, 12, and 24 mg Compound 1 and placebo). Subjects received study drug for 26 consecutive days (Study Days 3 through 28) and a single morning dose of study drug on Study Day 29.

Compound 1 was administered following breakfast for the morning dose and dinner or snack for the evening dose. Subjects were on methotrexate therapy for at least 3 months and on a stable dose of 10 to 25 mg/week of methotrexate for at least 4 weeks prior to the first dose of study drug administered on Study Day 3 and continued their weekly stable dose of methotrexate on Study Days 1, 8, 15, 22 and 29. Subjects were confined to the study site for a total of 10 days—from Day 1 to Day 4 and from Day 27 to Day 31.

Study Participants

Subjects underwent screening procedures within 30 days prior to the initial administration of study drug. Subjects signed a written informed consent prior to the initiation of any screening or study-specific procedures. Subjects were eligible for study participation if they were men or women between 18 and 55 years of age (Study 1 and Study 2—Part 1) or 18 to 75 years of age (Study 2—Part 2); judged to be in good general health based upon the results of medical history, laboratory profile, physical examination, chest x-ray, and 12-lead electrocardiogram (ECG); and their body mass index (BMI) was within 19 to 29 kg/m² (Study 1 and Study 2—Part 1) or within 19 to 39 kg/m² (Study 2—Part 2) at screening. Subjects were considered eligible to participate in Study 2—Part 2 if they had diagnosis of RA based on the 2010 American College of Rheumatology/European League against Rheumatism criteria ≥6 months, have been on methotrexate therapy ≥3 months (and folate or equivalent for at least 2 weeks prior to Study Day 1), on a stable methotrexate dose of 10 to 25 mg/week for at least 4 weeks prior to the first dose of study drug administered on Study Day 3.

In both studies, subjects were excluded if they had any clinically significant abnormalities, infection, major febrile illness, hospitalization, or had any clinically relevant surgical procedure within 30 days prior to the first dose of study drug; had positive test result for hepatitis A virus immunoglobulin M, hepatitis B surface antigen, or hepatitis C virus antibody, or HIV antibodies at Screening; had history or evidence of active or latent tuberculosis; had history of diabetes or lymphoproliferative disease or evidence of immunosuppression (except for use of methotrexate in Study 2—Part 2); or had clinically significant findings at Screening as determined by the principal investigator. Additionally, subjects in Study 2—Part 2 were excluded if they had a history of acute inflammatory joint disease of different origin other than RA or had current or expected need for oral intake of >10 mg prednisone/day or equivalent corticosteroid therapy.

Pharmacokinetic Sampling

In healthy subjects, serial blood samples were collected over 72 hours after single dosing (Study 1) or over 12 hours after the first dose (Study Day 1) and over 72 hours after the last dose (Study Day 14) of study drug (Study 2-Part 1). In subjects with RA, serial blood samples were collected over 48 hours on Study Day 1 for methotrexate assay, over 12 hours following the first Study drug dose on Study Day 3 for Compound 1 assay, over 12 hours following the morning Study drug dose on Study Day 28 for Compound 1 assay, and over 48 hours following the last Study drug dose on Study Day 29 for Compound 1 and methotrexate assays. Pre-dose trough samples were collected prior to the morning dose on Study Days 5, 6, 7, 13, and 14 in Study 2—Part 1 to assess attainment of steady state.

Urine for Compound 1 assay was collected over a 12-hour interval after the last dose was administered on Study Day 14 in Study 2—Part 1 and on Study Days 28 and 29 in Study 2—Part 2. Urine for methotrexate assay was collected for 48 hours on Study Day 1 and Study Day 29.

Plasma and urine concentrations of Compound 1 and methotrexate were determined using validated liquid chromatography method with mass spectrometric detection methods. The lower limits of quantitation (LLOQ) for Compound 1 and methotrexate in plasma were established at 0.0503 ng/mL and 1.00 ng/mL, respectively. The LLOQ for Compound 1 and methotrexate in urine were established at 1.01 ng/mL and 0.0500 g/mL, respectively. Samples quantified below the LLOQ were reported as zero. For Compound 1 assays, inter-run variability (measured as % coefficient of variation [% CV]) was ≤9.5% for plasma ≤8.4% for urine and the mean absolute bias was ≤6.7% for plasma and ≤5.9% for urine. For methotrexate assay, inter-run variability (% CV) was ≤3.9% for plasma and ≤5.2% for urine and the mean absolute bias was ≤5.4% in plasma and ≤13.1% in urine.

Pharmacokinetic Analyses

Compound 1 and methotrexate pharmacokinetic parameters were determined using non-compartmental analyses with Phoenix software (Version 6.3, Certara, Princeton, NJ, USA). Calculated pharmacokinetic parameters included the maximum observed plasma concentration ($C_{max}$), time to $C_{max}$ ($T_{max}$), trough plasma concentration ($C_{trough}$), the apparent terminal phase elimination rate constant ($\beta$), the terminal phase elimination half-life ($t_{1/2}$), the area under the plasma concentration-time curve (AUC) [from time 0 to time of the last measurable concentration (AUC), from time 0 to infinity ($AUC_\infty$) for single dosing, and over a 12-hour dosing interval ($AUC_{0-12}$, or $AUC_{12,ss}$) for multiple dosing and the apparent oral clearance (CL/F). Compound 1 functional half-life ($t_{1/2}F$) following multiple dosing was calculated as $\ln(2)/(\ln[C_{max}/C_{trough}]/\tau)$ at steady state, where $\tau$ is the 12-hour dosing interval (Dutta et al., *Clin. Drug Investig.*, 2006, Vol. 26(12), pp. 681-690). The accumulation ratio (Rac) was calculated as the ratio of Compound 1 $AUC_{0-12}$ on Day 14 to Day 1 (Study 2—Part 1) or Day 28 to Day 3 (Study 2—Part 2). The percentage of Compound 1 dose recovered unchanged in urine ($f_e$%) at steady state was calculated as the amount of Compound 1 recovered in urine over the 0 to 12-hour interval (Au, $_{0-12}$), divided by the administered dose and multiplied by 100. Renal clearance (CLr) was calculated as Au, $_{0-12}/AUC_{0-12}$ at steady state. Methotrexate $f_e$% was calculated as the amount of methotrexate recovered in urine over the 0 to 48-hour interval (Au, $_{0-48}$), divided by the administered dose and multiplied by 100. CLr of methotrexate was calculated as Au, $_{0-48}/AUC_{0-48}$. The effect of co-administration of methotrexate on Compound 1 exposure was assessed from the ratios of Compound 1 $AUC_{0-12}$ and $C_{max}$ on Study Day 29 to Study Day 28. The effect of Compound 1 on methotrexate exposure was assessed from the ratios of methotrexate $AUC_\infty$ and $C_{max}$ on Study Day 29 to Study Day 1.

Safety and Tolerability Assessment

Safety was evaluated based on assessments of adverse events, vital signs, physical examination, laboratory metrics, and 12-lead electrocardiogram (ECG). All subjects who received at least one dose of study drug were included in the safety analyses. Subjects who were administered placebo multiple-dose evaluation in subjects with RA (Study 2—Part 2) was discontinued early due to slow recruitment rate and 14 subjects with RA were actually enrolled and completed this evaluation. No early withdrawals occurred in any of the three evaluations. A summary of demographic data is presented in Table 17A.

TABLE 17A

Baseline Demographics of Study Participants

|  | Study 1 | | Study 2-Part 1 | | Study 2-Part 2 | |
| --- | --- | --- | --- | --- | --- | --- |
|  | Compound 1 N = 42 | Placebo N = 14 | Compound 1 N = 32 | Placebo N = 12 | Compound 1 N = 11 | Placebo N = 3 |
| Mean Age, years ± SD | 31.0 ± 9.8 | 32.4 ± 8.6 | 33.3 ± 9.9 | 30.7 ± 5.0 | 59.3 ± 8.3 | 58.7 ± 14.3 |
| Mean Weight, kg ± SD | 74.7 ± 10.1 | 74.3 ± 8.8 | 74.1 ± 9.9 | 78.4 ± 13.6 | 78.5 ± 14.9 | 62.5 ± 6.9 |
| Mean Height, cm ± SD | 171 ± 8.9 | 171 ± 10.2 | 172 ± 7.9 | 177 ± 6.2 | 171 ± 7.3 | 165 ± 9.9 |
| Sex, number (%) | 35 males (83.3%), 7 females (16.7%) | 11 males (79%), 3 females (21%) | 29 males (91%), 3 females (9%) | 12 males (100%) | 6 males (54.5%), 5 females (45.5%) | 3 females (100%) |
| Race, number (%) | 30 White (71%), 10 Black (24%), 1 Asian (2%), 1 Other (2%) | 11 White (79%), 3 Black (21%) | 23 White (72%), 9 Black (28%) | 9 White (75%), 2 Black (17%), 1 Asian (8%) | 10 White (91%), 1 Black (9%) | 2 White (67%), 1 Asian (33%) | were pooled into a single group within each study or study part. Laboratory test values and vital signs measurements that were above or below the reference range were identified. Subjects were followed-up for a total of 7 days in Study 1, 35 days in Study 2—Part 1, and 57 days in Study 2—Part 2. In healthy subjects, clinical adverse events were graded as described in the Guidance for Industry Toxicity Grading Scale for Healthy Adult and Adolescent Volunteers Enrolled in Preventive Vaccine Clinical Trials (September 2007). In subjects with RA, the severity of adverse events was rated by the investigator as mild (transient and easily tolerated by the subject), moderate (causes subject discomfort and interrupts the subject's usual activities), or severe (causes considerable interference with the subject's usual activities and may be incapacitating or life-threatening). One subject in Study 2—Part 2 was randomized to the placebo arm but received Compound 1 in error on Study Days 10 to 16. Therefore, this subject was included with the Compound 1 cohort for safety assessments.

Statistical Analyses

Dose proportionality for Compound 1 in healthy subjects was tested using the natural logarithms of dose-normalized $C_{max}$ and AUC following single dosing (Study 1) or for steady-state dose-normalized $C_{max}$, $C_{trough}$, and AUC following multiple dosing (Study 2—Part 1) assessments. Attainment of steady-state following multiple doses in healthy volunteers was assessed by testing the logarithmic transformation of Compound 1 morning pre-dose concentrations for Study Days 5, 6, 7, 13, and 14 by repeated measures analysis. Statistical analyses were performed using SAS software (Version 9.3; SAS institute Inc., Cary, NC, USA).

Results

Demographics and Subject Disposition

A total of 56 healthy subjects were enrolled in and completed the single-dose evaluation (Study 1) and 44 healthy subjects were enrolled in and completed the multiple-dose evaluation (Study 2—Part 1). Enrollment in the Compound 1 Single- and Multiple-Dose Pharmacokinetics in Healthy Volunteers Compound 1 plasma concentrations reached peak levels at approximately 1 to 2 hours after oral dosing of the immediate release capsule formulation. Compound 1 plasma concentrations declined bi-exponentially afterwards with a terminal elimination $t_{1/2}$ of approximately 6 to 15 hours after single dosing (Table 17B) and of 8 to 16 hours after multiple twice-daily dosing (Table 17C). Compound 1 functional half-life, estimated from $C_{max}$ to $C_{trough}$ ratio at steady-state, was approximately 3 hours. After multiple dosing, there was a small but statistically significant (p<0.05) difference between Compound 1 pre-dose concentrations on Study Day 13 (13% lower) compared with Study Day 5. There was no statistically significant difference in Compound 1 pre-dose concentration on Study Day 13 and Study Day 14, indicating that steady-state was achieved by Study Day 13. At steady-state, the median accumulation ratios for Compound 1 $AUC_{0-12}$ were approximately 1.0 over the evaluated dose range (Table 17C).

In the single dose evaluation, 1 mg dose group was excluded from the statistical analyses for $AUC_\infty$ as the majority of samples collected at the terminal phase were below the limit of quantitation for all subjects. There was no statistically significant difference in dose-normalized $C_{max}$ between the highest (48 mg) and the lowest (1 mg) dose of Compound 1, and there was no statistically significant trend for change in the dose-normalized $C_{max}$ values with dose. There was no trend for change in Compound 1 dose-normalized $AUC_\infty$ with doses over the 3 to 36 mg dose range (P>0.05); however, the dose-normalized $AUC_\infty$ following single 48 mg dose was 40% lower than that following 3 mg dose (p<0.05).

Following multiple dosing in healthy subjects, there was no statistically significant difference (p>0.05) in Compound 1 dose-normalized steady-state $C_{max}$, $C_{trough}$, or AUC for the 24 mg twice-daily regimen compared to the 3, 6, or 12 mg twice-daily regimens.

Overall, Compound 1 exposures appeared to be dose proportional particularly over the single dose range of 3 to 36 mg and the multiple dose range of 3 mg to 24 mg BID.

TABLE 17B

Pharmacokinetic parameters (mean ± standard deviation) of Compound 1 after administration of single doses of the immediate release formulation to healthy subjects

| Pharmacokinetic Parameters (Units) | 1 mg Cpd. 1 (N = 6) | 3 mg Cpd. 1 (N = 6) | 6 mg Cpd. 1 (N = 6) | 12 mg Cpd. 1 (N = 6) | 24 mg Cpd. 1 (N = 6) | 36 mg Cpd. 1 (N = 6) | 48 mg Cpd. 1 (N = 6) |
|---|---|---|---|---|---|---|---|
| $C_{max}$ (ng/mL) | 7.72 ± 2.36 | 25.0 ± 6.88 | 38.9 ± 9.96 | 82.9 ± 12.1 | 158 ± 18.4 | 277 ± 44.5 | 314 ± 81.9 |
| $T_{max}$ (h) [a] | 1.3 (1.0-2.0) | 1.0 (1.0-1.5) | 1.0 (1.0-1.5) | 1.3 (0.5-1.5) | 1.3 (1.0-1.5) | 0.8 (0.5-1.0) | 1.0 (0.5-1.0) |
| $t_{1/2}$ (h) [b] | — | 5.9 ± 2.4 | 11.0 ± 3.4 | 12.1 ± 7.4 | 14.5 ± 9.0 | 6.4 ± 4.0 | 12.2 ± 3.5 |
| $AUC_t$ (ng · h/mL) | 29.8 ± 5.78 | 102 ± 27.5 | 159 ± 37.5 | 329 ± 48.9 | 612 ± 78.6 | 909 ± 201 | 1030 ± 174 |
| $AUC_\infty$ (ng · h/mL) | — | 103 ± 27.6 | 160 ± 37.6 | 331 ± 49.8 | 615 ± 78.1 | 911 ± 202 | 1040 ± 174 |
| CL/F (L/h) | — | 31.3 ± 10.4 | 39.1 ± 9.06 | 37.0 ± 6.32 | 39.5 ± 4.92 | 41.1 ± 8.35 | 47.6 ± 8.97 |

[a] Median (range)
[b] Terminal elimination half-life, presented as harmonic mean ± pseudo-standard deviation

TABLE 17C

Steady-State (Day 14) Pharmacokinetic parameters (mean ± standard deviation) of Compound 1 following administration of multiple twice-daily oral doses of the immediate release formulation to healthy subjects

| PK Parameters (Units) | 3 mg BID (N = 8) | 6 mg BID (N = 8) | 12 mg BID (N = 8) | 24 mg BID (N = 8) |
|---|---|---|---|---|
| $C_{max}$ (ng/mL) | 18.5 ± 5.41 | 28.8 ± 3.67 | 57.6 ± 11.0 | 119 ± 16.9 |
| $T_{max}$ (h) | 1.5 (0.5-3.0) | 2.0 (1.5-3.0) | 2.3 (1.5-3.0) | 1.8 (1.5-2.0) |
| $AUC_{0-12}$ (ng · h/mL) | 78.3 ± 20.3 | 138 ± 16.7 | 271 ± 52.7 | 529 ± 62.6 |
| $C_{trough}$ (ng/mL) | 1.46 ± 0.50 | 2.29 ± 0.41 | 4.54 ± 1.55 | 9.50 ± 2.57 |
| $t_{1/2}$ (h) [a] | 15.7 ± 10.6 | 13.6 ± 8.5 | 7.6 ± 4.8 | 8.0 ± 4.2 |
| $t_{1/2}F$ (h) [b] | 3.2 ± 0.4 | 3.3 ± 0.3 | 3.2 ± 0.5 | 3.3 ± 0.4 |
| CL/F (L/h) | 40.7 ± 10.6 | 43.9 ± 5.4 | 45.5 ± 8.04 | 46.1 ± 6.44 |
| $CL_r$ (L/h) | 7.5 ± 2.34 | 8.1 ± 1.8 | 9.7 ± 2.3 | 8.6 ± 2.8 |
| $f_e$ (%) | 19 ± 5 | 19 ± 6 | 21 ± 4 | 19 ± 6 |
| $R_{ac}$ $AUC_{0-12}$ [c] | 1.1 (0.9-1.2) | 1.0 (0.9-1.2) | 1.0 (0.9-1.1) | 1.0 (0.8-1.3) |

[a] Terminal elimination half-life.
[b] Functional half-life calculated from $C_{max}$ to $C_{trough}$ ratio at steady state.
[c] Accumulation ratio for $AUC_{0-12}$.
Harmonic mean ± pseudo-standard deviation are presented for $t_{1/2}$ and $t_{1/2}F$. Median and range (minimum to maximum) are presented for $T_{max}$ and $R_{ac}$ $AUC_{0-12}$. BID: twice-daily.

Compound 1 Multiple-Dose Pharmacokinetics in Subjects with RA

In subjects with RA who were on stable doses of methotrexate, Compound 1 plasma concentrations reached peak levels at 1 to 2 hours after dosing (Table 17D). The mean terminal elimination half-life of Compound 1 ranged from approximately 10 to 14 hours, and the functional half-life was approximately 4 hours. The median accumulation ratio of Compound 1 after 26 days of twice-daily dosing ranged from 0.8 to 1.4. The median ratio of Compound 1 $C_{max}$ and $AUC_{0-12}$ when administered with methotrexate (on Study Day 29) to those when administered without methotrexate (Study Day 28) ranged from 0.9 to 1.2, indicating a lack of significant effect of methotrexate co-administration on Compound 1 pharmacokinetics. The ratio of Compound 1 exposure in subjects with rheumatoid arthritis to Compound 1 exposure in healthy subjects ranged from 1.1 (24 mg twice-daily dose) to 1.6 (6 mg twice-daily dose) for $AUC_{0-12}$ and from 1.2 (24 mg twice-daily dose) to 1.7 (6 mg twice-daily dose) for $C_{max}$.

TABLE 17D

Pharmacokinetic parameters (mean ± standard deviation) of Compound 1 following administration of multiple twice-daily oral doses to subjects with mild to moderate rheumatoid arthritis on stable doses of methotrexate

| PK Parameters (Units) | Compound 1 6 mg BID (N = 4) Day 28 | Compound 1 6 mg BID (N = 4) Day 29 | Compound 1 12 mg BID (N = 3) Day 28 | Compound 1 12 mg BID (N = 3) Day 29 | Compound 1 24 mg BID (N = 3) Day 28 | Compound 1 24 mg BID (N = 3) Day 29 |
|---|---|---|---|---|---|---|
| $C_{max}$ (ng/mL) | 47.1 ± 7.47 | 42.4 ± 8.85 | 71.1 ± 14.8 | 60.8 ± 4.01 | 129 ± 39.0 | 154 ± 39.5 |
| $T_{max}$ (h) | 1.5 (1.0-2.0) | 2.0 (1.5-3.0) | 2.0 (1.5-2.0) | 2.0 (1.5-3.0) | 1.5 (1.5-4.0) | 1.0 (0.5-1.5) |
| $AUC_{0-12}$ (ng · h/mL) | 231 ± 48.5 | 215 ± 49.2 | 334 ± 49.4 | 338 ± 14.5 | 637 ± 143 | 665 ± 89.8 |
| $C_{trough}$ (ng/mL) | 5.81 ± 3.06 | 4.63 ± 3.48 | 5.41 ± 0.98 | 6.44 ± 1.09 | 15.3 ± 1.86 | 14.9 ± 4.37 |
| $t_{1/2}$ (h) [a] | — | 9.5 ± 3.6 | — | 14.4 ± 5.3 | — | 11.5 ± 7.6 |
| $t_{1/2}F$ (h) [b] | — | 3.5 ± 0.9 | — | 3.7 ± 0.2 | — | 3.6 ± 0.1 |
| CL/F (L/h) | 26.7 ± 4.96 | 29.0 ± 5.92 | 36.4 ± 5.44 | 35.6 ± 1.56 | 39.1 ± 9.79 | 36.5 ± 4.70 |
| $CL_r$ (L/h) | 6.94 ± 4.04 | 4.93 ± 2.41 | 6.27 ± 2.79 | 4.96 ± 3.34 | 6.31 ± 0.96 | 8.60 ± 1.30 |
| $f_e$ (%) | 25 ± 14 | 16 ± 5 | 17 ± 8 | 14 ± 10 | 17 ± 5 | 24 ± 2 |
| $R_{ac}$ $AUC_{0-12}$ [d] | 1.4 (1.0-1.8) | — | 1.2 (0.9-1.4) | — | 1.3 (1.2-1.4) | — |

TABLE 17D-continued

Pharmacokinetic parameters (mean ± standard deviation) of Compound 1 following administration of multiple twice-daily oral doses to subjects with mild to moderate rheumatoid arthritis on stable doses of methotrexate

| PK Parameters | Compound 1 6 mg BID (N = 4) | | Compound 1 12 mg BID (N = 3) Study Day | | Compound 1 24 mg BID (N = 3) | |
|---|---|---|---|---|---|---|
| (Units) | Day 28 | Day 29 | Day 28 | Day 29 | Day 28 | Day 29 |
| Day 29/Day 28 $AUC_{0-12}$ Ratio[e] | 0.9 (0.9- 1.0) | | 1.0 (0.9-11) | | 1.0 (0.9-1.2) | |

[a]Terminal elimination half-life.
[b]Functional half-life calculated from Cmax to Ctrough ratio at steady state.
[c]Accumulation ratio for $AUC_{0-12}$.
Harmonic mean ± pseudo-standard deviation are presented for $t_{1/2}$ and $t_{1/2}F$. Median and range (minimum to maximum) are presented for $T_{max}$, accumulation ratios, and Day 29/Day 28 ratios.
BID: twice-daily Effect of Compound 1 Co-Administration on Methotrexate Exposure Pharmacokinetic parameters of methotrexate when administered before (Study Day 1) and after administration of multiple doses of Compound 1 (Day 29) are summarized in Table 17E. Since methotrexate was administered weekly and has a short plasma half-life, no plasma accumulation was expected with repeated dosing and $AUC_\infty$ was calculated for both Days 1 and 29. The median ratio for methotrexate $AUC_\infty$ and $C_{max}$ when administered after multiple doses of Compound 1 (on Study Day 29) to that when administered without Compound 1 (on Study Day 1) ranged from 0.9 to 1.1 and from 0.8 to 1.2, respectively. There was no observed change in methotrexate dose-normalized $AUC_\infty$ when administered with or without Compound 1.

Safety and Tolerability

Across all three evaluations, a total of 74 healthy subjects and 11 subjects with RA received Compound 1 and a total of 26 healthy subjects and 3 subjects with RA received placebo. There were no dose-limiting toxicities or safety concerns with Compound 1 from the single doses up to 48 mg or multiple doses up to 24 mg twice daily. Notably, the safety and tolerability profile of Compound 1 was comparable between subjects who received Compound 1 or placebo, and between healthy subjects and subjects with RA on background treatment of methotrexate, though the number of subjects with RA was limited. There was no evidence of a dose or time dependency for the incidence of adverse events in either healthy subjects or subjects with RA. There were no study discontinuations due to adverse events, no serious adverse events and no clinically significant changes in ECG parameters, or laboratory metrics in any of the subjects or treatment groups. The maximum tolerated dose

TABLE 17E

Pharmacokinetic parameters (mean ± standard deviation) of methotrexate following administration to subjects with RA alone (Day 1) or concomitant with Compound 1 (Day 29)

| PK Parameters | Compound 1 6 mg BID Group (N = 4) | | Compound 1 12 mg BID Group (N = 3) | | Compound 1 24 mg BID Group (N = 3) | | Placebo (N = 4) | |
|---|---|---|---|---|---|---|---|---|
| | Methotrexate Dose (mg) | | | | | | | |
| | 16.3 ± 6.6 | | 14.2 ± 5.2 | | 14.2 ± 1.4 | | 17.5 ± 5.0 | |
| (Units) | Day 1 | Day 29 | Day 1 | Day 29 | Day 1 | Day 29 | Day 1 | Day 29 |
| $C_{max}$ (ng/mL) | 245 ± 63.6 | 228 ± 23.0 | 278 ± 44.0 | 255 ± 99.9 | 196 ± 58.6 | 256 ± 29.3 | 318 ± 138 | 354 ± 182 |
| $T_{max}$ (h) | 2.5 (1.5-6.0) | 1.8 (1.0-2.0) | 3.0 (2.0-3.0) | 2.5 (2.5-3.0) | 3.0 (0-3.0) | 2.5 (2.0-3.0) | 1.8 (1.5-3.0) | 1.8 (1.0-4.0) |
| $AUC_\infty$ (ng · h/mL) | 1470 ± 494 | 1490 ± 424 | 1670 ± 393 | 1780 ± 791 | 966 ± 365 | 1370 ± 324 | 1640 ± 470 | 1590 ± 458 |
| $t_{1/2}$ (h)[a] | 4.0 ± 2.6 | 4.7 ± 1.3 | 4.0 ± 0.3 | 4.2 ± 0.6 | 3.0 ± 1.1 | 3.1 ± 1.3 | 3.9 ± 0.5 | 3.8 ± 0.3 |
| CL/F (L/h) | 11.8 ± 6.43 | 10.9 ± 3.43 | 8.36 ± 1.28 | 8.14 ± 1.03 | 16.9 ± 8.89 | 10.6 ± 1.61 | 11.2 ± 3.81 | 11.3 ± 2.66 |
| $CL_r$ (L/h) | 6.63 ± 3.79 | 5.43 ± 2.02 | 6.13 ± 1.93 | 4.78 ± 2.28 | 7.46 ± 0.70 | 6.43 ± 0.75 | 4.32 ± 1.12 | 5.80 ± 1.08 |
| $f_e$ (%) | 58 ± 29 | 51 ± 20 | 74 ± 19 | 59 ± 26 | 54 ± 25 | 63 ± 4 | 45 ± 25 | 57 ± 26 |
| $AUC_\infty$ Ratio[b] | — | 1.0 (0.8-1.4) | — | 0.9 (0.9-1.3) | — | 1.1 (1.0-3.1) | — | 0.9 (0.8-1.2) |

[a]Terminal elimination half-life presented as harmonic mean ± pseudo-standard deviation.
[b]Ratio of methotrexate exposure ($AUC_\infty$) on Study Day 29 to that on Study Day 1; median and range (minimum to maximum) are presented.

of Compound 1 was not reached in the single or multiple dose studies. Adverse events that were reported by at least two subjects in Compound 1 or placebo groups in Study 1 or Study 2—Part 1 are presented in Table 17F.

placebo (a total of 3 subjects). Five subjects in the Compound 1 dose groups and two subjects in the placebo group experienced at least one TEAE. In the Compound 1 dose groups, 7 TEAEs were reported: nausea, vomiting, viral

TABLE 17F

Treatment-emergent adverse events reported by two or more healthy subjects administered Compound 1 or placebo in the single and multiple ascending dose evaluations

| | Single doses (Study 1) | | | | | | | | |
|---|---|---|---|---|---|---|---|---|---|
| System Organ Class MedDRA Preferred Term | Placebo (N = 14) | 1 mg Compound 1 (N = 6) | 3 mg Compound 1 (N = 6) | 6 mg Compound 1 (N = 6) | 12 mg Compound 1 (N = 6) | 24 mg Compound 1 (N = 6) | 36 mg Compound 1 (N = 6) | 48 ng Compound 1 (N = 6) | Total Compound 1 (N = 42) |
| Any Adverse Event | 3 (21.4%) | 0 | 0 | 1 (16.7%) | 0 | 1 (16.7%) | 2 (33.3%) | 2 (33.3%) | 6 (14.3%) |
| Headache | 0 | 0 | 0 | 0 | 0 | 0 | 0 | 2 (33.3%) | 2 (4.8%) |
| Presyncope* | 0 | 0 | 0 | 1 (16.7%) | 0 | 1 (16.7%) | 0 | 0 | 2 (4.8%) |

| | Multiple twice-daily doses (Study 2-Part 1) | | | | | |
|---|---|---|---|---|---|---|
| System Organ Class MedDRA Preferred Term | Placebo (N = 12) | 3 mg Compound 1 (N = 8) | 6 mg Compound 1 (N = 8) | 12 mg Compound 1 (N = 8) | 24 mg Compound 1 (N = 8) | Total Compound 1 (n = 32) |
| Any Adverse Event | 7 (58.3%) | 2 (25.0%) | 2 (25.0%) | 3 (37.5%) | 4 (50.0%) | 11 (34.4%) |
| Abdominal Discomfort | 3 (25.0%) | 0 | 0 | 0 | 0 | 0 |
| Abdominal Pain | 0 | 0 | 1 (12.5%) | 0 | 1 (12.5%) | 2 (6.3%) |
| Diarrhoea | 1 (8.3%) | 0 | 1 (12.5%) | 1 (12.5%) | 0 | 2 (6.3%) |
| Nasopharyngitis | 2 (16.7%) | 1 (12.5%) | 1 (12.5%) | 0 | 0 | 2 (6.3%) |
| Headache | 2 (16.7%) | 0 | 2 (25.0%) | 2 (25.0%) | 1 (12.5%) | 5 (15.6%) |

*The two cases of presyncope were associated with venipuncture. In healthy subjects who were administered single doses of either Compound 1 (1, 3, 6, 12, 24, 36, and 48 mg) or placebo in Study 1, 14.3% (6/42) and 21.4% (3/14) of subjects, respectively, reported to have one or more treatment-emergent adverse events (TEAEs). All TEAEs were accessed as mild in severity. The adverse events reported by more than one subject who received Compound 1 were headache and presyncope (1 subject in 6 mg and 1 subject in 24 mg dose group) in association with venipuncture (see Table 17F).

In healthy subjects who were administered multiple doses of Compound 1 (3, 6, 12, and 24 mg BID) or placebo for 14 consecutive days in Study 2—Part 1, 34% (11/32) and 58% (7/12) of subjects, respectively, reported one or more TEAEs. The overall incidences of TEAEs were numerically higher at higher doses of Compound 1; 2 (25.0%), 2 (25.0%), 3(37.5%) and 4 (50%) subjects in the 3 mg, 6 mg, 12 mg and 24 mg dose groups, respectively; however, these rates were lower than that was observed in the placebo group (58%). All TEAEs were reported as mild in severity. Four events occurred in at least two subjects who received Compound 1: headache, abdominal pain, diarrhea, and nasopharyngitis; three of these events also occurred in subjects who received placebo: headache, diarrhea and nasopharyngitis (Table 17F).

There were no clinically significant changes in any hematologic parameters after multiple-dose administration in healthy subjects for 14 days. With increasing doses of Compound 1, there were statistically significant downward trends in mean levels of hemoglobin, RBCs, WBCs and neutrophils; however, even at the 24 mg dose, the mean levels were within the normal reference range. The mean changes in reticulocyte counts with increasing dose of Compound 1 compared to placebo were not statistically significant, suggesting no evidence of a dose related effect on reticulocyte counts after 14 days of Compound 1 treatment. Total cholesterol, HDL-cholesterol, and LDL-cholesterol showed a statistically significant upward trend with increasing Compound 1 dose compared with placebo; however, the final mean values for these lipid parameters in the Compound 1 dose groups remained within the normal reference range.

Subjects with mild to moderate RA on stable background doses of methotrexate, in Study 2-Part 2, were administered multiple doses of Compound 1 (a total of 11 subjects) or gastroenteritis, upper respiratory tract infection, post-traumatic neck syndrome, back pain, and insomnia. All TEAEs were reported by the investigators as mild or moderate in severity, and no adverse event was reported in more than one subject in any treatment group. There was no evidence of a dose relationship with any of these events. Notably, as these subjects with RA received a stable background dose of methotrexate, there were no changes in hepatobiliary metrics for those receiving Compound 1. There was also no evidence of a Compound 1 dose-related effect on renal function in these subjects with RA, as evaluated by serum creatinine and blood urea nitrogen values.

Discussion

Compound 1 was well-tolerated after single doses up to 48 mg and multiple twice daily doses up to 24 mg of Compound 1 immediate-release formulation. All adverse events occurred after single- or multiple-dose administrations were mild to moderate in nature with comparable frequency between subjects who received Compound 1 or placebo. No anemia, serious infections, or clinically significant changes in hematology, hepatobiliary or renal laboratory metrics was observed with 14 days of repeated Compound 1 dosing in healthy volunteers or 27 days of dosing in RA patients.

Compound 1 displayed multi-exponential plasma disposition with a functional half-life of 3 to 4 hours across the dose range of 3 to 24 mg twice daily of the immediate-release formulation in healthy volunteers and subjects with RA. The terminal elimination half-life of Compound 1 ranged from 6 to 16 hours across the different dose levels. However, given the multi-exponential disposition of Compound 1, the longer terminal half-life is less relevant clinically than the functional half-life (Dutta et al., Clin. Drug Investig., 2006, Vol. 26(12), pp. 681-690; Sahin, Pharm. Res., 2008, Vol. 25(12), pp. 2869-77). Consistent with a shorter functional half-life, there was no accumulation across the evaluated 3 to 24 mg twice-daily dose range. While there are no solid clinical data to suggest that extended exposure is needed for efficacy of JAK inhibitor (i.e., to determine whether efficacy is concentration driven or AUC driven), the pharmacokinetic profile of the immediate-release formulation of Compound 1 appears to be generally more suited for twice-daily dosing than for once-daily dosing.

Compound 1 displayed dose-proportional pharmacokinetics particularly over the 3 to 36 mg dose range, which encompasses the dose ranges evaluated in Phase 2b clinical trials in RA (3 to 18 mg BID and 24 mg QD), or that is currently being evaluated in Crohn's disease (3 to 24 mg BID).

It has been reported previously that the JAK inhibitors tofacitinib and filgotinib have higher exposures in subjects with RA than those in healthy volunteers (see FDA, "Clinical Pharmacology and Biopharmaceutics Review(s)—Tofacitinib", Application Number 203214Orig1s000, Center for Drug Evaluation and Research, 2011; Namour et al., Clin. Pharmacokinet., 2015, Vol. 54, pp. 859-874). Compound 1's apparent oral clearance was 23% lower in subjects with RA (leading to approximately 30% higher exposure), on average across all dose groups, compared to healthy subjects. In general, older subjects are expected to have lower renal and metabolic capacity compared to younger subjects (Mangoni, Br. J Clin. Pharmacol., 2004, Vol. 57(1), pp. 6-14). RA subjects who received multiple doses of Compound 1 were 26 years older, on average, than the healthy subjects evaluated in Study 2 (Table 21A); therefore, age cannot be excluded as potential contributor to the apparently 30% higher exposure of Compound 1 in RA subjects than in healthy subjects.

Methotrexate remains the first line therapy for treatment of RA and is often used with biologic DMARDs or in combination with other csDMARDs (see Ma, et al., Rheumatology (Oxford), 2010, Vol. 49(1), pp. 91-8; Singh, et al., Arthritis Care Res. (Hoboken), 2012, Vol. 64(5), pp. 625-39; Smolen, et al., Ann. Rheum. Dis., 2014, Vol. 73(3), pp. 492-509). Therefore, at least in a subset of the RA patients, it is expected that Compound 1 will be added to the first line therapy, methotrexate; thus, it was important to confirm a lack of any potential interaction between Compound 1 and methotrexate. The ratios of Compound 1 AUC and Cmax values when administered with methotrexate to those when administered alone indicate lack of significant effect of methotrexate on Compound 1 (Table 21D). Similarly, Compound 1 did not have any significant effect on methotrexate exposures (Table 21E). This was consistent with the observed safety and tolerability profiles in these two populations.

In summary, Compound 1 displayed favorable safety and tolerability profiles over single doses up to 48 mg and multiple doses up to 24 mg twice daily for 14 days in healthy subjects and for 27 days in subjects with RA. Compound 1 demonstrated a pharmacokinetic profile suitable for twice-daily dosing with the immediate release formulation. There was no pharmacokinetic interaction between methotrexate and Compound 1 and there was no accumulation of Compound 1 with repeated administration.

Example 32: Treatment of Moderately to Severely Active Rheumatoid Arthritis in Patients Who have Inadequately Responded to or are Intolerant to Anti-TNF Therapy The following example briefly describes the results of a Phase 2b, 12-week, randomized, double-blind, parallel-group, placebo-controlled study in which adult subjects with moderately to severely active rheumatoid arthritis (RA) who have inadequately responded to or who are intolerant to an anti-tumor necrosis factor (TNF) therapy were treated with Compound 1.

The study was conducted in accordance with the International Conference on Harmonisation guidelines, applicable regulations, and the principles of the Declaration of Helsinki. The study protocol was approved by an independent ethics committee or institutional review board. All patients provided written informed consent before participating in any study-related procedures.

Participants

Adult men and women aged 18 years or older, who had been diagnosed with RA and fulfilled either the 1987 revised American College of Rheumatology (ACR) classification criteria (Arnett et al, Arthritis Rheum., 1988, Vol. 31(3), pp. 315-324) or the 2010 ACR/European League Against Rheumatism (EULAR) criteria (Smolen et al, Ann. Rheum. Dis., 2010, Vol. 69(6), pp. 964-975) were enrolled in the study. Active RA was defined as subjects having ≥6 swollen joints (based on a 66-joint count); ≥6 tender joints (based on a 68-joint count); and high-sensitivity C-reactive protein (hsCRP)>upper limit of normal (ULN=5 mg/L) or seropositivity for both rheumatoid factor (RF) and anti-cyclic citrullinated peptide (CCP). Eligible subjects must have been treated with >1 anti-TNF biologic agent for ≥3 months but continued to experience active RA or discontinued anti-TNF biologic therapy because of intolerance or toxicity. In addition, subjects with prior exposure to non-anti-TNF biologic therapy were allowed to enroll, as long as they had failed ≥1 anti-TNF biologic. All biologic therapies had to be washed out prior to randomization: ≥4 weeks for etanercept, ≥8 weeks for adalimumab, infliximab, certolizumab, and golimumab, >8 weeks for abatacept, >12 weeks for tocilizumab, and >1 year for rituximab. A stable dose of methotrexate (7.5-25 mg/week) was required throughout the study. Key exclusion criteria were prior exposure to a JAK inhibitor, or a need for any immunosuppressant other than methotrexate. Subjects with serum aspartate transaminase (AST) or alanine transaminase (ALT)>1.5×ULN or absolute neutrophil count (ANC)<1,200/μL or absolute lymphocytes count <750/μL at screening were excluded.

Study Design and Treatment

The study was a phase 2b, 12-week, randomized, double-blind, parallel-group, placebo-controlled study conducted at 123 sites, enrolling patients in the United States (176 patients, 64%) and Puerto Rico (11 patients, 4%); Australia and New Zealand (6 patients, 2%); Western Europe including Belgium, Spain and Great Britain (29 patients, 11%); Eastern Europe including Czech Republic, Hungary, Poland (54 patients, 20%).

Subjects were equally randomized to receive oral immediate-release doses of Compound 1 (immediate release capsules comprising Tartrate Hydrate) at 3 mg BID, 6 mg BID, 12 mg BID or 18 mg BID, or matching placebo BID, for 12 weeks. Randomization was performed centrally, according to a blocked randomization schedule, by investigators enrolling via an interactive voice response system. Subjects, caregivers, investigators, joint assessors, and the study team were blinded to the treatment administered. Placebo and Compound 1 capsules were identical in appearance. Subjects should have been taking an oral supplement of folic acid (or equivalent) from four weeks prior to baseline and throughout the study. Subjects were allowed to continue stable doses of methotrexate and non-steroidal anti-inflammatory drugs (NSAIDS), acetaminophen, or oral corticosteroids (equivalent to prednisone ≤10 mg).

Assessments

The primary efficacy endpoint was the proportion of subjects achieving an ACR20 response at Week 12. Secondary endpoints included the proportions of subjects achieving an ACR50/ACR70 response and the proportion of subjects achieving 28-joint count disease activity score based on C-reactive protein (DAS28(CRP))≤3.2, or <2.6, at Week 12. Among the other endpoints were the proportion of subjects achieving low disease activity (LDA) or clinical remission (CR) based on Clinical Disease Activity Index (CDAI) criteria (LDA, CDAI≤10; CR, ≤2.8); change in DAS28 (CRP), and change in the Health Assessment Questionnaire-Disability Index (HAQ-DI) (Anderson et al, *Arthritis Care Res.* (Hoboken), 2012, Vol. 64(5), pp. 640-647), including the proportion of subjects achieving minimal clinically important difference (MCID) of −0.22 (Strand et al, *Rheumatology* (Oxford), 2006, Vol. 45(12), pp. 1505-1513). A post hoc analysis was performed to determine the proportion of subjects who had a sustained ACR20 response, defined as achievement of the ACR20 criteria at every visit (at Weeks 2, 4, 6, 8 and 12).

Safety was evaluated at each scheduled visit during treatment and for 30 days after the last dose of study drug on the basis of AEs, serious AEs, vital signs, and laboratory tests (hematology, blood chemistry, and urinalysis). Adverse events were coded according to the Medical Dictionary for Regulatory Activities (MedDRA, version 17.1). Descriptions of AE severity and post-baseline laboratory changes were based on the Rheumatology Common Toxicity Criteria v. 2.0, developed by the OMERACT Drug Safety Working Group (Woodworth et al., 2007, *J. Rheumatol., Vol.* 34(6), ppl. 1401-14).

Statistical Methods

All efficacy analyses were conducted in modified intent-to-treat population, which consisted of all randomized patients who received ≥1 dose of study drug. For ACR response rates, the last observation carried forward (LOCF) was the primary missing data imputation method and non-responder imputation (NRI) was also used to assess the robustness of the results. For continuous endpoints including DAS28 (CRP), LOCF missing data imputation was implemented; NRI is reported for binary endpoints. Binary endpoints including ACR response rates were analyzed using chi-square test with normal approximation when comparing each Compound 1 treatment group to placebo group. Continuous endpoints were analyzed using an Analysis of Covariance (ANCOVA) model with treatment group as a factor and baseline measurement as the covariate. The Multiple Comparison Procedure and Modeling (MCPMod) method was implemented to detect any non-flat dose-response relationship by evaluating several non-linear dose-response models at the same time. P-values were not corrected for multiple comparisons.

Assuming ACR20 response rates of 25% in the placebo group and 55% in any Compound 1 group, a sample size of 50 subjects per group (250 patients total) was estimated to provide at least 80% power to detect a 30% difference in response rates between the placebo group and a Compound 1 group when using a 1-sided test with an alpha level of 0.05.

Results

Subject Disposition and Baseline Characteristics

Figure 4:
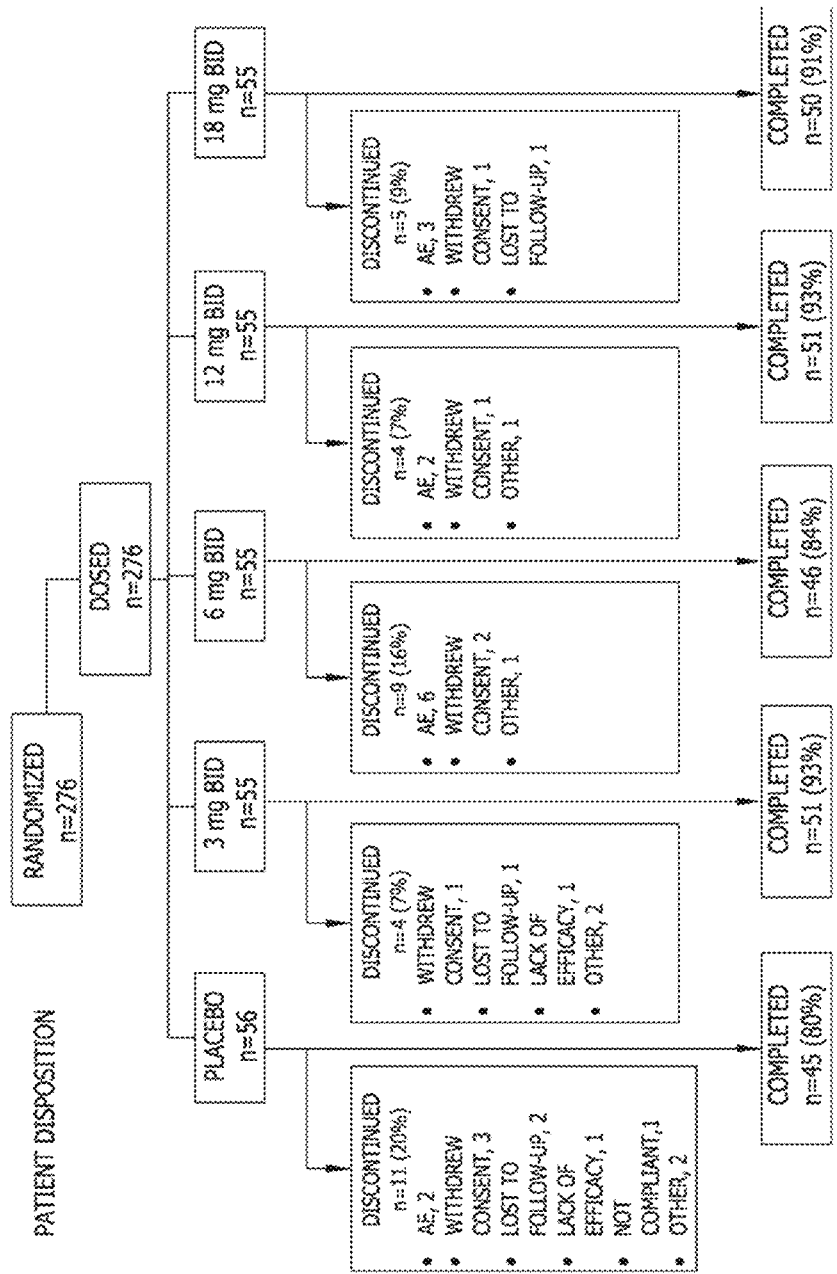
FIG. 4 shows the subject disposition for the study described in Example 32.

In total, 276 subjects were randomized; all received their intended treatment. The overall study completion rate was 88% (FIG. 4). Baseline subject characteristics and disease activity were generally similar among treatment groups (see Table 18A). The mean duration since RA diagnosis was 12 years. Seventy-two percent of subjects had prior exposure to only one anti-TNF, 28% to ≥2 anti-TNFs, and 20% of subjects were also exposed to non-anti-TNF biologics. At baseline, subjects had mean swollen and tender joint counts of 18 (out of 66 joints) and 28 (out of 68 joints), respectively; 60% subjects had an elevated hsCRP and mean DAS28(CRP) was 5.8.

TABLE 18A

Baseline Patient Characteristics and Disease Activity

| | Placebo (n = 56) | Compound 1 | | | |
| | | 3 mg BID (n = 55) | 6 mg BID (n = 55) | 12 mg BID (n = 55) | 18 mg BID (n = 55) |
| --- | --- | --- | --- | --- | --- |
| Characteristic | | | | | |
| Female, number (%) | 48 (86) | 43 (78) | 43 (78) | 44 (80) | 42 (76) |
| Age, years, mean (SD) | 58 (12) | 57 (13) | 56 (12) | 59 (11) | 57 (12) |
| Duration since RA diagnosis, years, mean (SD) | 12.1 (9.0) | 11.8 (9.4) | 12.3 (10.6) | 12.2 (10.2) | 10.9 (7.7) |
| RF positive, number (%) | 49 (88) | 43 (78) | 45 (82) | 45 (82) | 48 (87) |
| Anti-CCP positive, number (%) | 48 (86) | 45 (82) | 45 (82) | 45 (82) | 47 (86) |
| Used ≥1 prior anti-TNF agent, number (%) | 42 (76) | 39 (71) | 38 (70) | 38 (72) | 38 (69) |
| Used ≥2 prior anti-TNF agents, number (%) | 13 (24) | 16 (29) | 16 (30) | 15 (28) | 17 (31) |
| Used prior non-anti-TNF agents, number (%)* | 9 (16) | 10 (18) | 14 (26) | 14 (26) | 7 (13) |
| Disease activity | | | | | |
| TJC68, mean (SD) | 28 (15) | 28 (15) | 30 (16) | 26 (16) | 26 (15) |
| SJC66, mean (SD) | 19 (12) | 17 (10) | 17 (10) | 17 (10) | 18 (10) |
| HAQ-DI, mean (SD) | 1.6 (0.7) | 1.5 (0.7) | 1.6 (0.7) | 1.6 (0.6) | 1.5 (0.6) |
| DAS28(CRP), mean (SD) | 5.8 (0.9) | 5.7 (0.9) | 5.9 (0.9) | 5.7 (0.9) | 5.8 (1.0) |
| CDAI, mean (SD) | 41 (12) | 40 (13) | 42 (12) | 40 (12) | 41 (14) |

TABLE 18A-continued

Baseline Patient Characteristics and Disease Activity

|  | Placebo (n = 56) | Compound 1 | | | |
|---|---|---|---|---|---|
|  |  | 3 mg BID (n = 55) | 6 mg BID (n = 55) | 12 mg BID (n = 55) | 18 mg BID (n = 55) |
| hsCRP, mg/L, mean (SD)‡ | 10.1 (13.2) | 11.4 (11.8) | 18.6 (27.4) | 14.4 (23.0) | 14.0 (15.1) |
| hsCRP > ULN,† n (%)‡ | 28 (50) | 35 (64) | 34 (62) | 33 (60) | 35 (64) |

Abbreviations: BID—twice daily; CDAI—Clinical Disease Activity Index; DAS28(CRP)—Disease Activity Score-28 joints using C-reactive protein; HAQ-DI—Health Assessment Questionnaire-Disability Index; hsCRP—high-sensitivity C-reactive protein; RA—rheumatoid arthritis; SJC66—swollen joint count using 66 joints; TJC68—tender joint count using 68 joints; TNF—tumor necrosis factor; ULN—upper limit of normal.
*Non-TNF biologic agents.
†ULN = 5 mg/L.
‡Subjects with normal hsCRP could be enrolled as long as they were positive for rheumatoid factor and anti-cyclic citrullinated peptide.
Modified intent-to-treat population.
Percentages were calculated using non-missing values Efficacy The primary analysis based on LOCF revealed that an ACR20 response was achieved by 55.6% (P=0.033), 63.5% (P=0.004), 72.7% (P<0.001), and 70.9% (P<0.001) in subjects treated with Compound 1 at 3, 6, 12, and 18 mg BID, respectively, compared with 35.2% in subjects who received placebo. Analysis based on NRI also demonstrated a statistically significant improvement in ACR20 response rate in subjects who received any dose of Compound 1 compared with those who received placebo (FIG. 1A). A significant dose-response relationship was observed for all doses of Compound 1 (P<0.01). The ACR20 response rates (NRI) at Week 12 were similar among patients who had received 1 versus ≥2 prior anti-TNFs (FIG. 1B). ACR50 and ACR70 response rates were significantly higher at Compound 1 doses of ≥6 mg BID versus placebo (FIG. 1A).

Figure 2A:
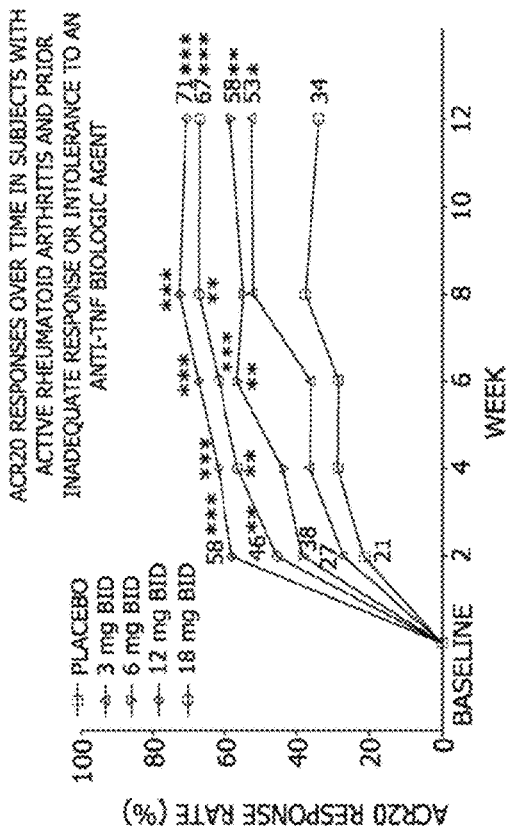
Figure 2C:
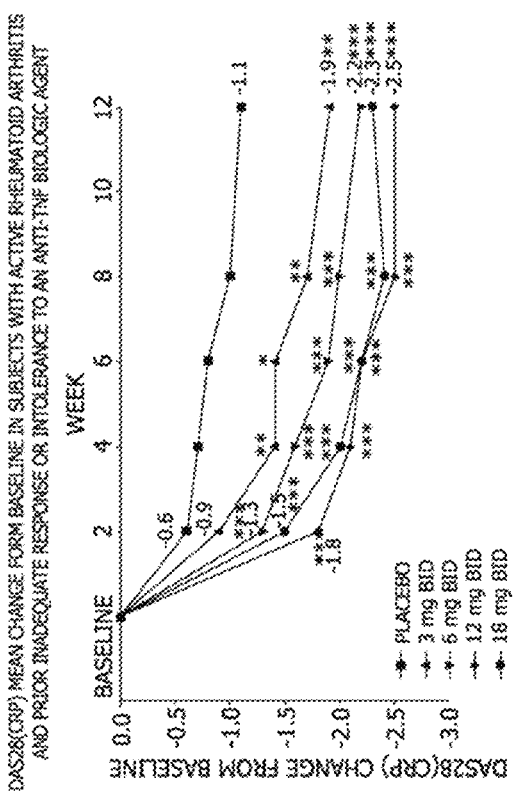
Figure 2D:
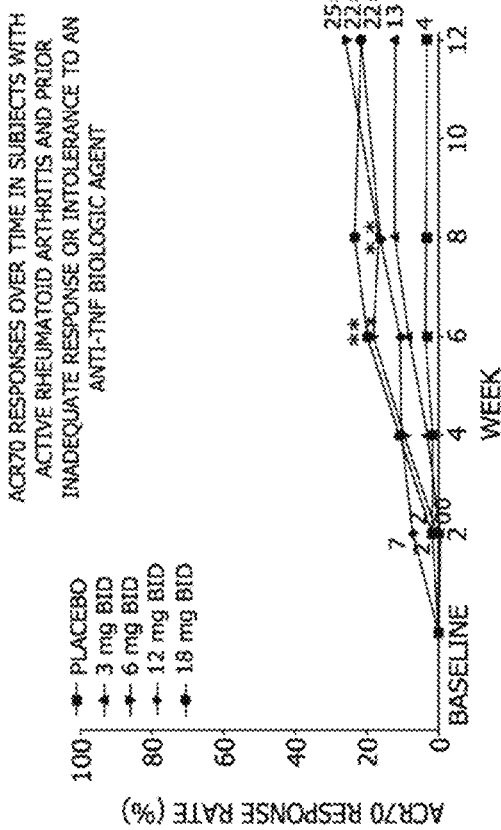

Significant differences in ACR20 response rates (NRI) were observed at the first post-baseline assessment (Week 2) in subjects treated with Compound 1 12 mg BID and 18 mg BID versus placebo (P≤0.007; FIG. 2A); the maximum response rate (71%) was observed with the 12 mg BID dose by Week 8 and plateaued thereafter. Starting at Week 4, there were significantly greater ACR50 response rates with Compound 1 doses ≥6 mg BID versus placebo; the maximum response rate (42%) was observed with the 18 mg BID dose by week 8 and plateaued thereafter (FIG. 2B). Improvements in ACR70 response rates better than placebo were observed starting at Week 6, with peak response of up to 25% at Week 12 (FIG. 2C). A sustained ACR20 response (at every visit between Week 2 through 12, NRI) was achieved by 13%, 22%, 40% and 27% of subjects in the Compound 1 3 mg, 6 mg, 12 mg and 18 mg BID groups respectively, versus 4% in the placebo group. Significant improvements in DAS28(CRP) (LOCF) occurred at the Week 2 assessment with Compound 1 at ≥6 mg BID versus placebo (P<0.001; FIG. 2D).

Figure 2E:
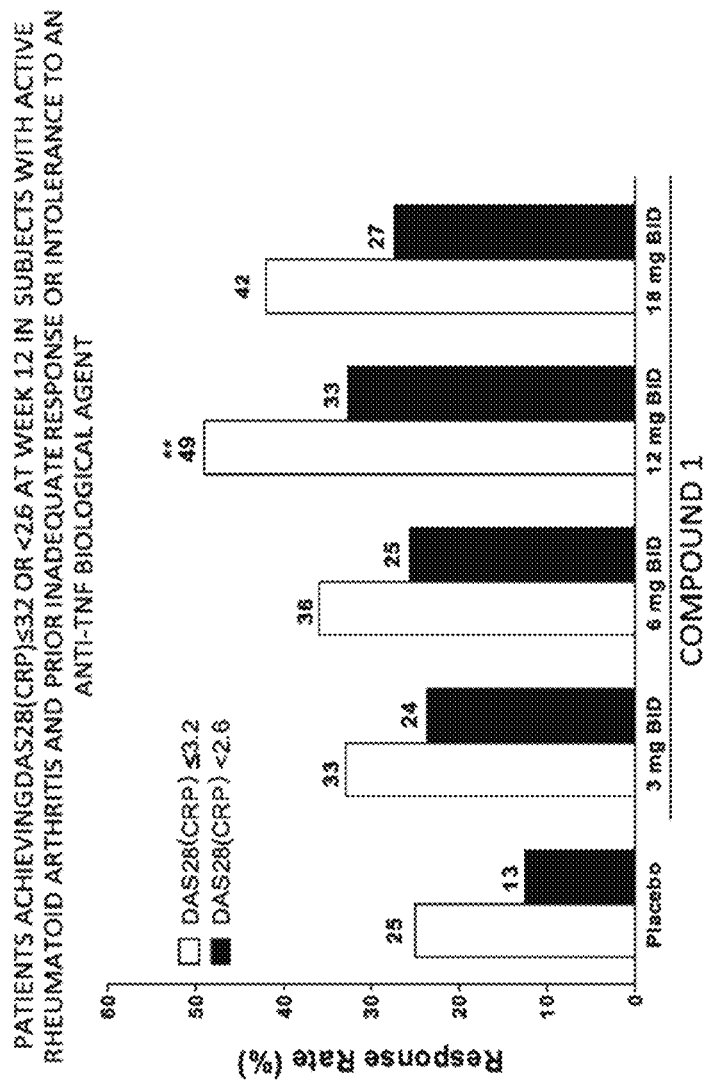
FIG. 2E shows the subjects achieving a DAS28(CRP) score of ≤3.2 or <2.6 at week 12 in the same population.

A higher percentage of subjects receiving Compound 1 (any dose) achieved DAS28(CRP)≤3.2 or <2.6, versus placebo at Week 12 (NRI, FIGS. 2E and 2F) with the difference being statistically significantly for the Compound 1 12 mg BID group (DAS28(CRP)≤3.2, 49%; DAS28(CRP)<2.6, 33%, P<0.01) compared with placebo (25% and 13%, respectively). Similarly, a higher percentage of patients treated with any dose of Compound 1 achieved CDAI LDA or CR criteria versus placebo at Week 12 (NRI, FIG. 2F). At Week 12, treatment with Compound 1 at 12 mg BID also resulted in statistically significant mean changes from baseline in individual components of the ACR score compared with placebo (Table 18B). In addition, a significantly greater proportion of patients achieved the MCID for HAQ-DI with Compound 1 ≥6 mg BID (58%-64%) as compared with placebo (44%).

TABLE 18B

Mean Changes From Baseline in ACR Components at Week 12

| ACR Component | Placebo (n = 55) | Compound 1 | | | |
|---|---|---|---|---|---|
|  |  | 3 mg BID (n = 54) | 6 mg BID (n = 53) | 12 mg BID (n = 55) | 18 mg BID (n = 55) |
| TJC68 | −9.3 | −13.4 | −15.7** | −16.8** | −15.1* |
|  | (−12.5, −6.1) | (−16.6, −10.1) | (−19.0, −12.5) | (−20.1, −13.6) | (−18.3, −11.9) |
| SJC66 | −6.4 | −9.5 | −9.2 | −10.0* | −9.2 |
|  | (−8.7, −4.2) | (−11.8, −7.2) | (−11.4, −6.9) | (−12.3, −7.8) | (−11.5, −7.0) |
| Patient's assessment of pain | −16.5 | −24.7 | −31.4**,† | −36.3*** | −35.0*** |
|  | (−23.5, −9.5) | (−31.8, −17.6) | (−38.6, −24.2) | (−43.3, −29.3) | (−42.0, −27.9) |
| PhGA | −29.6‡ | −33.8 | −37.5 | −43.5*** | −42.4** |
|  | (−35.3, −23.8) | (−39.4, −28.1) | (−43.2, −31.7) | (−49.1, −37.9) | (−48.0, −36.8) |
| PtGA | −20.0 | −24.2 | −29.9† | −37.4*** | −33.5**,† |
|  | (−27.0, −13.0) | (−31.3, −17.1) | (−37.1, −22.6) | (−44.4, −30.4) | (−40.6, −26.5) |
| HAQ-DI | −0.2 | −0.3 | −0.5**,† | −0.5* | −0.5**,† |
|  | (−0.4, −0.1) | (−0.4, −0.1) | (−0.6, −0.3) | (−0.6, −0.3) | (−0.7, −0.4) |
| HAQ-DI ≤ MCID, § n (%), 95% CI | 24 (44), 31-57 | 27 (50), 37-63 | 30 (58), 44-71† | 35 (64), 51-76 | 34 (63), 50-76† |

TABLE 18B-continued

Mean Changes From Baseline in ACR Components at Week 12

| | | Compound 1 | | | |
|---|---|---|---|---|---|
| ACR Component | Placebo (n = 55) | 3 mg BID (n = 54) | 6 mg BID (n = 53) | 12 mg BID (n = 55) | 18 mg BID (n = 55) |
| hsCRP, mg/L | −0.4 (−4.6, 3.9) | −7.9* (−12.2, −3.6) | −9.7** (−14.1, −5.4) | −6.8* (−11.1, −2.6) | −6.9* (−11.1, −2.6) |

Data are mean (95% CI), unless otherwise noted.
Abbreviations: ACR—American College of Rheumatology; BID—twice daily; HAQ-DI—Health Assessment Questionnaire-Disability Index; hsCRP—high-sensitivity C-reactive protein; LOCF—last observation carried forward; MCID—minimal clinically important difference; PhGA—physician's global assessment of disease activity; PtGA—patient global assessment of disease activity; RA—rheumatoid arthritis; SJC66—swollen joint count using 66 joints; TJC68—tender joint count using 68 joints.
*$P < 0.05$;
**$P < 0.01$;
***$P < 0.001$ relative to placebo.
†1 patient with missing data.
‡2 patients with missing data.
§ MCID = −0.22.
Modified intent-to-treat population (LOCF).

Safety

The percentage of subjects with any treatment-emergent AEs was numerically higher in a dose-dependent manner for the Compound 1 6, 12 and 18 mg BID treatment groups compared with placebo (Table 18C). Most reported AEs were considered mild to moderate in severity. The most commonly observed AEs were headache, nausea, upper respiratory tract infection, and urinary tract infection. The incidences of serious AEs and severe AEs were low, without an apparent dose-response relationship (Table 18C). Five subjects in the Compound 1 dose groups reported seven serious AEs (3 mg BID; one subject each with pancreatitis and pulmonary embolism, 6 mg BID; one subject with pulmonary embolism and deep vein thrombosis, one patient with TIA and benign prostate hyperplasia, 18 mg BID dose; one subject acute respiratory failure). One subject on placebo experienced a serious AE of bronchiectasis. The overall infection rates were similar for the Compound 1 3- and 6 mg BID dose groups and placebo (20%, 22%, and 23%, respectively), but were higher in the Compound 1 12- and 18 mg BID dose groups (40% and 38%). No serious infections were reported in any of the Compound 1 treatment groups. Herpes zoster occurred in two subjects in the placebo group (4%) and three subjects who received Compound 1 (1%, one case each in the 3-, 12- and 18 mg BID groups; all were isolated to a single dermatome). The two reported events of hepatic disorders in the 18 mg BID dose group and one event in the placebo group were attributed to increased transaminases; none were serious. There was an adjudicated case of transient ischemic attack (left ventricular hypertrophy, classified as mild) in one subject in the Compound 1 6 mg BID group. One patient in the 6 mg BID group had one event each of basal cell carcinoma and squamous cell carcinoma. There were no opportunistic infections or deaths during the study period.

Dose-dependent increases in low-density lipoprotein cholesterol (LDL-C) and high-density lipoprotein cholesterol (HDL-C) were observed; however, the ratios of LDL-C/HDL-C remained the same through Week 12. Of the subjects with normal AST or ALT at baseline, 6-18% of patients on Compound 1 had elevated AST at least twice, and 4-11% had elevated ALT at least twice, versus 2% and 6% on placebo, respectively. The number of these subjects was higher in the higher dose groups. Most of the elevations were Grade 1 (for AST and ALT, ≥1.2-<1.6×ULN) and Grade 2 (1.6-3.0×ULN). One subject each (2%) in the Compound 1 3 mg BID and placebo group (2%) had a Grade 3 ALT elevation (3.0-8.0×ULN). Of the subjects with normal creatinine at baseline, 4-14% subjects on Compound 1 had elevated creatinine at least twice versus none in the placebo group. One subject in the 18 mg BID group had a Grade 3 elevation (≥1.9-≤3.0×ULN). The elevations did not result in discontinuation of any subject from the study.

Figure 3A:
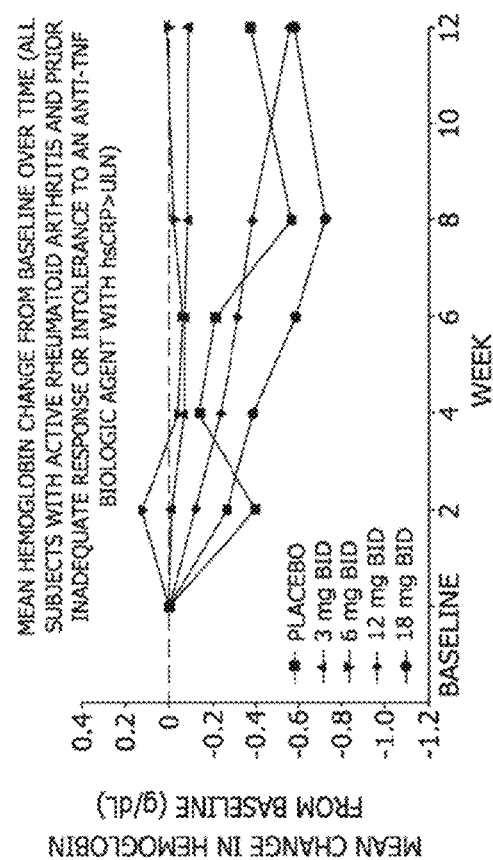
FIG. 3A shows the mean hemoglobin levels over time for all subjects following administration of placebo or various doses of Compound 1 to subjects with active rheumatoid arthritis and prior inadequate response or intolerance to an anti-TNF biologic agent (safety population with observed data (no imputation of missing values)).
Figure 3B:
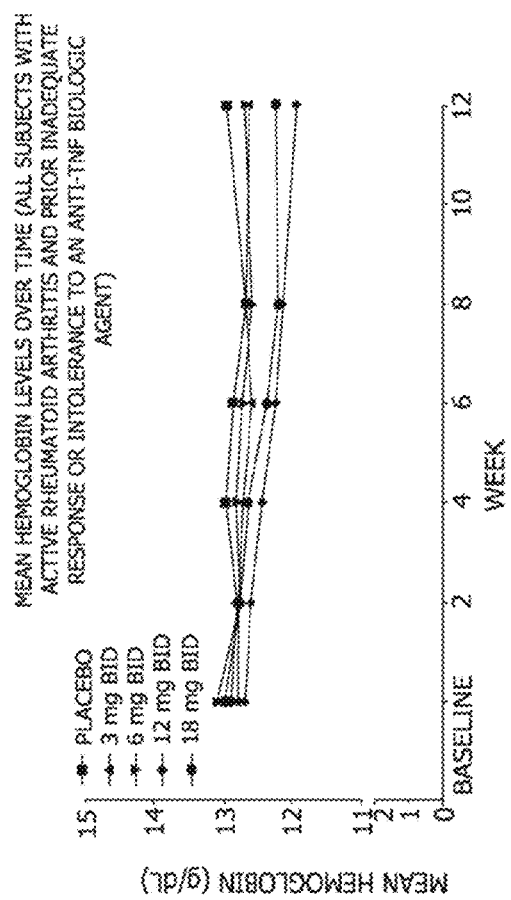
FIG. 3B shows the mean hemoglobin change from baseline over time in subjects with high-sensitivity C-reactive protein (hsCRP) greater than the upper limit of normal (ULN) (normal ranges for hemoglobin: 11.5-15.5 g/dL in females and 13.2-17.0 g/dL in males; ULN for hsCRP=5 mg/L).

Decreases from baseline in mean hemoglobin levels were observed in a dose-dependent manner with Compound 1, although mean hemoglobin levels remained within the normal range across all dose groups during the study (FIG. 3A). Twenty-six out of 219 subjects (11.9%) in the Compound 1 groups had a Grade 2 decrease in hemoglobin (from 15-20 g/L); 14/219 subjects (6.4%) had a Grade 3 decrease (from 21-29 g/L); 8/219 subjects (3.7%) had a Grade 4 decrease (>30 g/L). The majority (79%) of these decreases were transient (only one occurrence) and one subject discontinued the study due to reported AE of low hemoglobin. However, in subjects with underlying systemic inflammation, as measured by elevated baseline hsCRP, treatment with Compound 1 at 3- or 6 mg BID resulted in mean increases from baseline in hemoglobin levels compared with placebo (FIG. 3B).

Decreases in mean circulating leukocytes, neutrophils (Table 18D) and natural killer (NK) cells were also observed, and one subject discontinued study drug due to leukopenia. Only NK cell reductions appeared to be dose related. The mean percentage change in NK cells was +16.5±46.6 in the placebo group; a dose-dependent decrease was seen in subjects treated with Compound 1 (−15.8±25.3 in the 3 mg BID group, −18.3±47.4 in the 6 mg BID group, −28.0±37.3 in the 12 mg BID group, and −42.6±31.7 in the 18 mg BID group). At all doses of Compound 1, there was a transient mean increase in total lymphocytes, which returned to baseline level by Week 12, except in the 18 mg dose group. There were two subjects in the 18 mg dose group with Grade 4 lymphocyte reduction; one subject was reported to have vaginal and urinary tract infection, and the other herpes zoster. One subject had a Grade 4 neutrophil reduction, which was not associated with a serious infection.

TABLE 18C

Adverse Events Summary

| | | Compound 1 | | | |
|---|---|---|---|---|---|
| | Placebo (n = 56) | 3 mg BID (n = 55) | 6 mg BID (n = 55) | 12 mg BID (n = 55) | 18 mg BID (n = 55) |
| AE, n (%) | | | | | |
| Any AE | 25 (45) | 26 (47) | 31 (56) | 37 (67) | 39 (71) |
| Any serious AE | 1 (2) | 2 (4) | 2 (4) | 0 | 1 (2) |
| Any severe AE | 2 (4) | 1 (2) | 2 (4) | 2 (4) | 1 (2) |
| Any AE leading to discontinuation | 2 (4) | 0 | 6 (11) | 2 (4) | 3 (5) |
| Any death | 0 | 0 | 0 | 0 | 0 |
| AEs of special interest | | | | | |
| Infection | 13 (23) | 11 (20) | 12 (22) | 22 (40) | 21 (38) |
| Serious infection | 1 (2) | 0 | 0 | 0 | 0 |
| Cardiovascular event | 0 | 0 | 1 (2)† | 0 | 0 |
| Herpes zoster | 2 (4) | 1 (2) | 0 | 1 (2) | 1 (2) |
| Hepatic disorder* | 1 (2) | 0 | 0 | 0 | 2 (4) |
| Malignancy | 0 | 0 | 1 (2)‡ | 0 | 0 |

Abbreviations: AE—adverse event; BID—twice daily.
*AEs as reported by the investigator.
†The cardiovascular event was adjudicated as a transient ischemic attack.
‡One patient with basal cell and squamous cell carcinoma.
Safety population

TABLE 18D

Mean Change Over Time in Select Hematology Parameters and Incidence of Patients With Abnormalities

| | | Compound 1 | | | |
|---|---|---|---|---|---|
| Abnormality, number (%) | Placebo (n = 56)* | 3 mg BID (n = 55)* | 6 mg BID (n = 55)* | 12 mg BID (n = 55) | 18 mg BID (n = 55) |
| Neutrophils × $10^9$/L | | | | | |
| Grade 2 (1.0-1.4) | 1 (2) | 0 | 3 (6) | 4 (7) | 7 (13) |
| Grade 3 (0.5-0.9) | 0 | 0 | 0 | 2 (4) | 1 (2) |
| Grade 4 (<0.5) | 0 | 0 | 0 | 1 (2) | 0 |
| Lymphocytes × $10^9$/L | | | | | |
| Grade 2 (1.0-1.4) | 18 (33) | 14 (26) | 19 (35) | 14 (25) | 26 (47) |
| Grade 3 (0.5-0.9) | 9 (16) | 8 (15) | 8 (15) | 11 (20) | 9 (16) |
| Grade 4 (<0.5) | 0 | 1 (2) | 1 (2) | 0 | 2 (4) |

BID—twice daily.
*1 subject with missing data.
Safety population.
Grading based on OMERACT Rheumatology Common Toxicity Criteria v.2.0

Discussion

In this study, a broad dose range of Compound 1 (dosed up to 18 mg BID) was tested to assess efficacy and safety in subjects with an inadequate response or intolerance to anti-TNF biologic therapies. At all doses, Compound 1 demonstrated rapid and robust efficacy as shown by significantly greater improvements in clinical and functional outcomes compared to placebo. The onset of improvement with Compound 1 treatment was rapid with up to 58% of subjects achieving an ACR20 response as early as 2 weeks after treatment. The proportion of ACR20 responders reached a maximum at 8 weeks and plateaued at 71% through Week 12. Improvements in ACR50 (up to 42%) and ACR70 (up to 25%) response rates in the Compound 1 groups also reached a maximum before Week 12. The speed of the response is in contrast to the 3-6 months observed for many biologic therapies (Bathon, et al., *The New England Journal of Medicine,* 2000, Vol. 343(22), pp. 1586-93; Keystone, et al., *Arthritis and Rheumatism,* 2008, Vol. 58(11), pp. 3319-29; Keystone, et al., *Arthritis and Rheumatism,* 2004, Vol. 50(5), pp. 1400-11) and comparable with that observed for other JAK inhibitors, baricitinib and tofacitinib in TNF-IR patients. (Burmester, et al., *Lancet* (London, England), 2013, Vol. 381(9865), pp. 451-60; Genovese, et al., *European League Against Rheumatism,* 2015; 2015). In addition, the ACR20 response rate was comparable between subjects with two or more prior anti TNF therapies and those with only one prior anti-TNF. In general, the maximum efficacy was observed at the 12 mg BID dose.

Despite producing significant clinical improvement in different spectra of RA patients, there are safety concerns with JAK inhibitors, predominantly around impairing the body's ability to fight infections, viral reactivation, as well as altering hematopoietic homeostasis that could link to anemia. The most commonly reported adverse events with JAK inhibitors are infections, herpes zoster, pulmonary tuberculosis, cryptococcal pneumonia and pneumocystis pneumonitis (Fleischmann, et al., Arthritis Rheumatol., 2015, Vol. 67(2), pp. 334-43; Genovese, et al., Arthritis Rheumatol., 2016, Vol. 68(1), pp. 46-55). In addition, increases in total cholesterol, elevation of transaminase and serum creatinine, decreases in neutrophil counts and anemia are also observed. (Burmester, et al., Lancet (London, England), 2013, Vol. 381(9865), pp. 451-60; Genovese, et al., Arthritis Rheumatol., 2016, Vol. 68(1), pp. 46-55; Keystone, et al., Annals of the Rheumatic Diseases, 2015, Vol. 174(2), pp. 333-40).

In the current study, a broad range of doses of Compound 1 were tested to assess the selectivity of Compound 1 in vivo. Overall, Compound 1 demonstrated an acceptable safety and tolerability profile at all doses in this refractory RA population. There was no serious infection, although the proportion of overall infection rates was higher at the two highest doses of Compound 1 (12 mg and 18 mg BID). The most commonly observed infections with Compound 1 were bronchitis, upper respiratory, and urinary tract infections. The incidence of herpes zoster was similar in the placebo group (two subjects, 4%) and the Compound 1 treatment groups (three subjects, 1%), and all were non-disseminated.

At the 12 mg BID and 18 mg BID doses, there was a modest decrease in mean hemoglobin levels by Week 12, although the mean hemoglobin levels remained within the normal range. Notably, in subjects with elevated hsCRP at baseline, who were receiving 3 or 6 mg BID Compound 1, mean hemoglobin levels increased compared to placebo treatment, possibly due to a reduction of systemic inflammation while minimizing inhibitory effects on JAK2.

Circulating NK cells, which function as the critical mediator of host immunity against malignancy and infections, were measured as a pharmacodynamic readout of IL-15 inhibition. With increasing doses of Compound 1 there was a greater decrease in mean circulating NK cell counts. At the maximally efficacious dose, 12 mg BID, NK cells decreased by 28% from baseline, with proportionally smaller decreases in NK cells observed at lower doses. Given the fact that IL-15 signaling involves a heterodimer of JAK1 and JAK3, this was to be expected at higher doses of Compound 1. It is unclear how much each of the heterodimeric components (JAK1 and JAK3) contributes to the overall IL-15 signaling. However, it is possible that at higher exposure of Compound 1, the threshold for in-vivo selectivity for JAK1 compared to JAK3 is lowered in the context of the JAK1/JAK3 heterodimer. Of note, for tofacitinib at 5 mg BID, the reported median decrease in NK cells at week 24 was ~35%, with greater reduction at 10 mg BID or higher doses of tofacitinib (van Vollenhoven et al., Annals of the Rheumatic Diseases, 2015, pp. 258-9; Addendum to Primary Clinical Review, NDA 203,214, Center for Drug Evaluation and Research). However, it is important to note that the significance of NK cell reduction, especially what is considered clinically meaningful reduction in NK cells in terms of predicting clinical events (i.e. onset of viral reactivation) is lacking. A significant association with the changes in nadir NK cells and treated infection rates with tofacitinib treatment was observed (van Vollenhoven et al., Annals of the Rheumatic Diseases, 2015, pp. 258-9). No association of the reduced NK cells with clinical events was observed in the current study.

As reported with other JAK inhibitors, a dose-dependent elevation of low-density lipoprotein cholesterol and high density lipoprotein cholesterol levels was observed with Compound 1, however, the ratio of LDL-C/HDL-C remained unchanged. For the other laboratory parameters of interest, i.e, serum transaminases, WBC, neutrophil, or lymphocytes, the mean changes were unremarkable and lacked apparent dose relationship, with only one subject discontinuing the study early due to leukopenia.

In summary, the results of the current study demonstrated safety and efficacy of a selective JAK1 inhibitor, Compound 1, in a difficult-to-treat population of RA patients who had an inadequate response or intolerance to anti-TNF biologic therapies.

Example 33: Treatment of Moderately to Severely Active Rheumatoid Arthritis in Patients Who have Inadequately Responded to Methotrexate The following example briefly describes the results of a Phase 2b, 12-week, randomized, double-blind, parallel-group, placebo-controlled study in which adult subjects with moderately to severely active rheumatoid arthritis (RA) who have inadequately responded to stable methotrexate therapy were treated with Compound 1.

Patients

Men and women aged ≥18 years with active RA and inadequate response to methotrexate were included in the study. Diagnosis of RA was based on the 1987 revised American College of Rheumatology (ACR) classification criteria (Arnett et al, Arthritis Rheum., 1988, Vol. 31(3), pp. 315-324) or the 2010 ACR/European League Against Rheumatism (EULAR) criteria (Smolen et al, Ann. Rheum. Dis., 2010, Vol. 69(6), pp. 964-975). Active RA was defined by minimum disease activity criteria of ≥6 swollen joints (based on 66 joint counts) at screening and baseline; ≥6 tender joints (based on 68 joint counts) at screening and baseline; and high-sensitivity C-reactive protein (hsCRP) greater than the upper limit of normal (ULN) or positive test results for both rheumatoid factor and anti-cyclic citrullinated peptide (CCP) at screening. Eligible patients had been receiving methotrexate for ≥3 months, with a stable prescription (7.5-25 mg/week) for ≥4 weeks before baseline. Stable doses of methotrexate were continued throughout the study. In addition, all patients were requested to take a dietary supplement of oral folic acid (or equivalent) from 4 weeks prior to baseline and throughout study participation. All other oral disease-modifying antirheumatic drugs (DMARDs) were discontinued before baseline for ≥5 times the mean terminal elimination half-life of the specific DMARD to ensure washout. High-potency opiates (e.g., oxycodone, methadone, morphine) were discontinued ≥4 weeks before baseline. All patients had a negative tuberculosis screening assessment or, if there was evidence of a latent tuberculosis infection, completed ≥2 weeks of tuberculosis prophylaxis or had documented completion of a full course of tuberculosis prophylaxis before baseline. Patients were allowed to receive nonsteroidal anti-inflammatory drugs, acetaminophen, oral/inhaled corticosteroids, and low-potency opiates. Patients were excluded if they had received JAK inhibitor therapy or any other investigational or approved biologic RA therapy.

Treatment

Patients were randomized in a 1:1:1:1:1:1 ratio in a double-blind manner to oral doses of Compound 1 (immediate release capsules comprising Tartrate Hydrate) 3 mg BID, 6 mg BID, 12 mg BID, 18 mg BID, or 24 mg QD (two 12 mg tablets administered at the same time), or placebo BID for 12 weeks. Patients were randomized using an interactive voice/web response system according to a blocked randomization schedule. Investigators, patients, and other study personnel were blinded to the treatment assignments throughout the study. To maintain blinding, the placebo and active treatments had an identical appearance. Patients were instructed to take their doses (6 capsules total, split into 2 batches of 3) at approximately the same times each day.

Assessments

The primary efficacy endpoint was a ≥20% improvement in ACR criteria (ACR20) at week 12. Other endpoints included ACR50 and ACR70 response rates; change in 28-joint Disease Activity Score using C-reactive protein (DAS28(CRP)); change in Clinical Disease Activity Index (CDAI); the proportion of patients achieving low disease activity (LDA) or clinical remission based on DAS28(CRP) and CDAI criteria; and change in the Health Assessment Questionnaire Disability Index (HAQ-DI). The minimal clinically important difference (MCID) on the HAQ-DI, which is a decrease of ≥0.22, (Strand et al, 2006) was also evaluated.

Safety was evaluated during treatment and for 30 days after the last dose of study drug on the basis of adverse events (AEs), vital signs, physical examinations, and laboratory tests. AEs were coded using the Medical Dictionary for Regulatory Activities (MeDRA), version 17.1.

(45 per randomized treatment group) was targeted give 80% power to establish a real difference of 30% in the primary efficacy endpoint (ACR20 response rate at week 12), assuming the response rate would be 30% in the placebo group and 60% in at least 1 of the Compound 1 dose groups.

Results

Patients

Figure 5A:
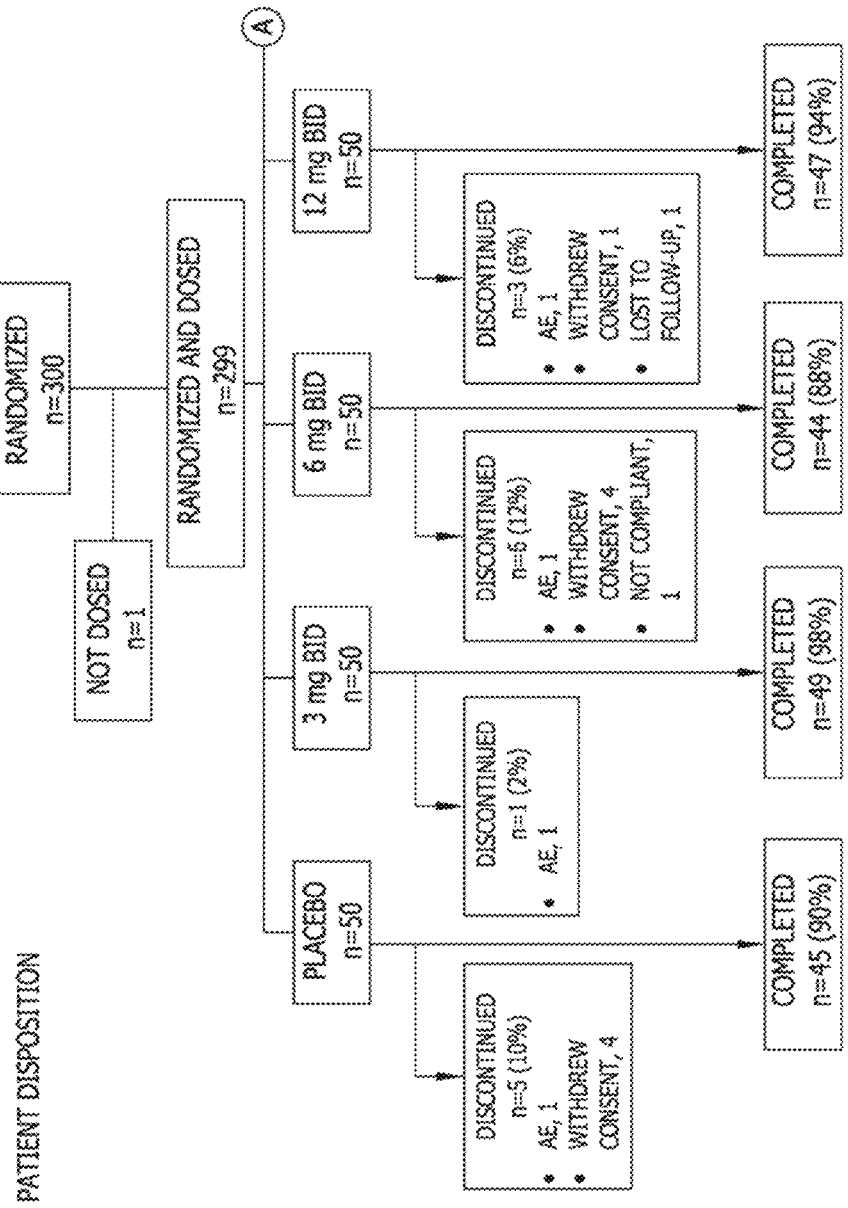
FIGS. 5A and 5B show the subject disposition for the study described in Example 33.
Figure 5B:
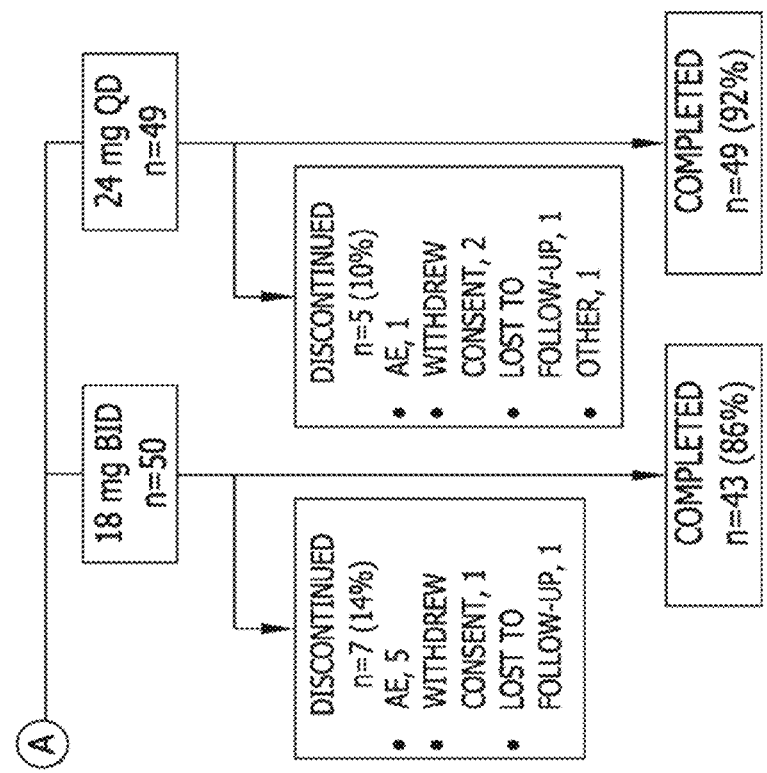

A total of 300 patients were randomized, and 299 received placebo (n=50) or Compound 1 3 mg BID (n=50), 6 mg BID (n=50), 12 mg BID (n=50), 18 mg BID (n=50), or 24 mg QD (n=49). Overall, 91% of patients completed the study, with similar discontinuation rates across treatment groups and no apparent relationship between Compound 1 dose and discontinuation (FIGS. 5A and 5B). Demographic and clinical characteristics at baseline were balanced among treatment groups (Table 19A). Patients were from Eastern Europe (61%), CentralSouth America (18%), the United States (10%), Western Europe (8%), or other regions (4%). Patients had a mean disease duration of 6.9 years and (7.7 had used 1 prior non-methotrexate DMARD. Of note, patients with normal hsCRP could be enrolled if they were positive for rheumatoid factor and anti-CCP antibody. Approximately 43% of patients had hsCRP values ≤ULN at baseline.

TABLE 19A

Baseline Characteristics and Disease Activity in Patients With Inadequate Response to Methotrexate

| Characteristic | Placebo (n = 50) | Compound 1 | | | | |
| --- | --- | --- | --- | --- | --- | --- |
| | | 3 mg BID (n = 50) | 6 mg BID (n = 50) | 12 mg BID (n = 50) | 18 mg BID (n = 50) | 24 mg QD (n = 49) |
| Female, number (%) | 38 (76) | 40 (80) | 34 (68) | 41 (82) | 42 (84) | 42 (86) |
| Age, years, mean (SD) | 55 (12) | 53 (12) | 55 (12) | 56 (12) | 55 (14) | 56 (12) |
| Years since RA diagnosis, mean (SD) | 5.9 (5.3) | 3.9 (3.8) | 7.0 (5.5) | 9.3 (8.6) | 7.3 (7.9) | 8.3 (7.1) |
| RF positive, number (%) | 41 (82) | 45 (90) | 46 (92) | 44 (88) | 41 (82) | 44 (90) |
| Anti-CCP positive, number (%) | 39 (78) | 40 (80) | 45 (90) | 43 (86) | 40 (80) | 45 (92) |
| Methotrexate dose, mg, mean (SD) | 16 (4) | 16 (4) | 16 (4) | 14 (4) | 15 (5) | 15 (4) |
| Prednisolone dose, mg, mean (SD) | 0 | | | 0 | 0 | 0 |
| ≥1 prior non-MTX DMARD, number (%) | 7 (14) | 6 (12) | 12 (24) | 11 (22) | 5 (10) | 12 (24) |
| 1 | 6 (12) | 4 (8) | 10 (20) | 9 (18) | 2 (4) | 8 (16) |
| 2 | 1 (2) | 2 (4) | 1 (2) | 1 (2) | 1 (2) | 3 (6) |
| ≥3 | 0 | 0 | 1 (2) | 1 (2) | 2 (4) | 1 (2) |
| Disease Activity | | | | | | |
| TJC68, mean (SD) | 29 (16) | 27 (15) | 28 (16) | 28 (13) | 27 (15) | 28 (16) |
| SJC66, mean (SD) | 19 (12) | 15 (8) | 19 (12) | 17 (11) | 17 (12) | 18 (13) |
| HAQ-DI, mean (SD) | 1.4 (0.7) | 1.3 (0.7) | 1.6 (0.7) | 1.5 (0.6) | 1.6 (0.6) | 1.5 (0.7) |
| DAS28 (CRP), mean (SD) | 5.6 (1.1) | 5.5 (1.1) | 5.8 (1.0) | 5.6 (0.9) | 5.7 (0.8) | 5.7 (1.0) |
| CDAI, mean (SD) | 40 (14) | 38 (13) | 43 (14) | 39 (12) | 40 (13) | 41 (13) |
| hsCRP, mg/L, mean (SD) | 15 (26) | 11 (15) | 17 (20) | 11 (15) | 13 (15) | 14 (16) |
| hsCRP > ULN,* number (%) | 27 (54) | 25 (50) | 31 (62) | 26 (52) | 28 (56) | 33 (67) |

Statistical Analyses

The per-protocol primary efficacy analysis was conducted in a modified intent-to-treat population, including all randomized patients who take at least 1 dose of study drug, with last observation carried forward (LOCF) imputation; data were also analyzed with nonresponder imputation (NRI).

Figure 6:
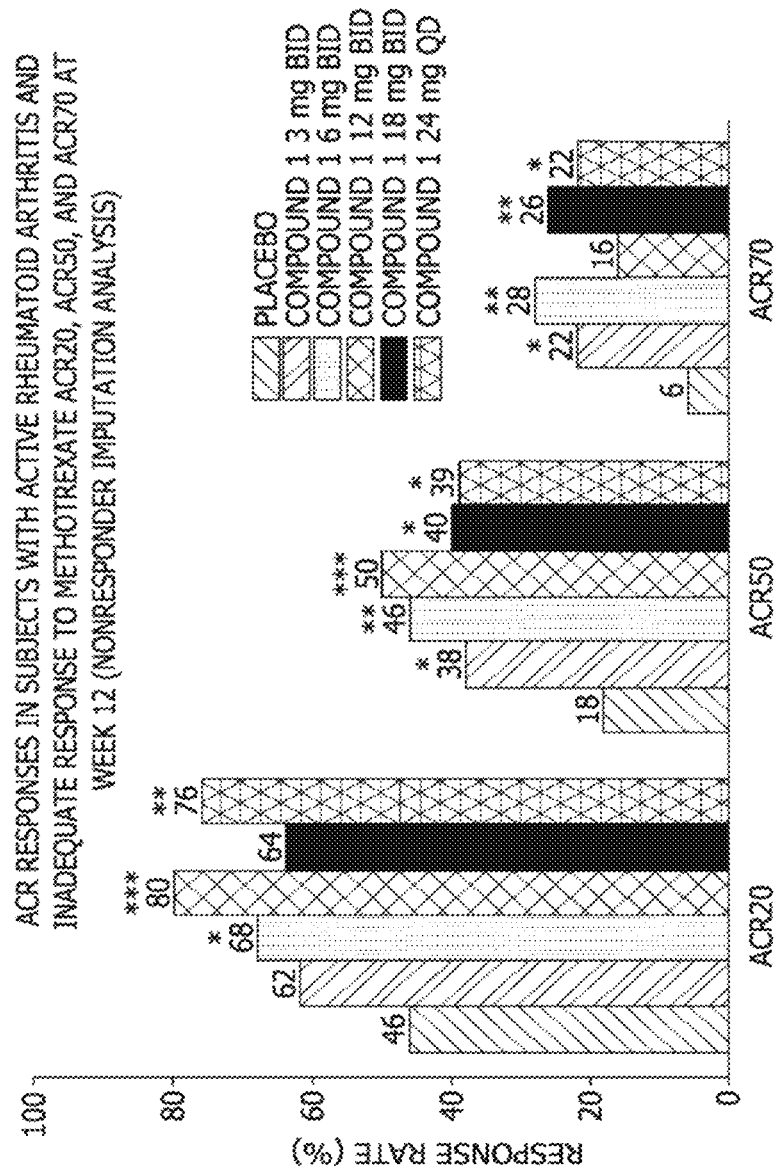
FIG. 6 shows the ACR20, ACR50, and ACR70 responses at week 12 following administration of placebo or various doses of Compound 1 to subjects with active rheumatoid arthritis and inadequate response to methotrexate (*P<0.05; P<0.01; *P<0.001 relative to placebo; modified intent-to-treat population with NRI of missing values).
Figure 7A:
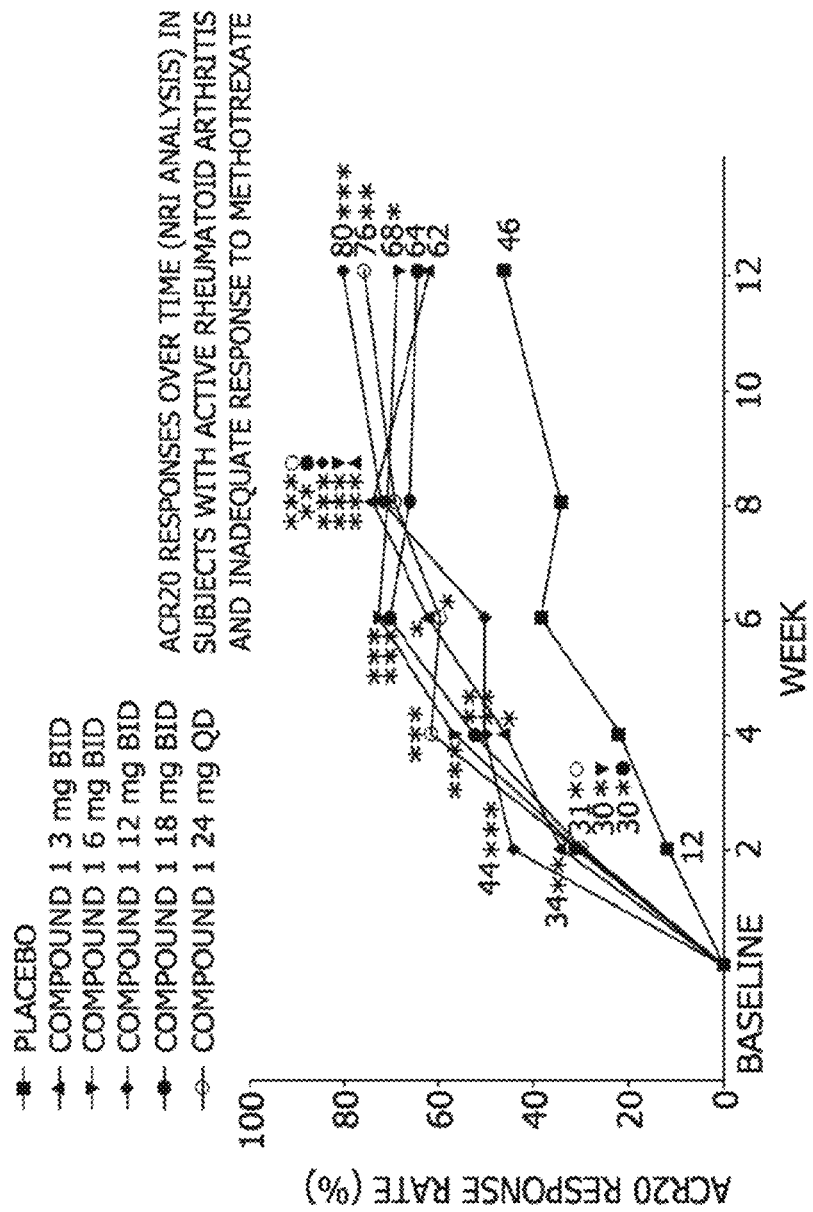
Figure 7C:
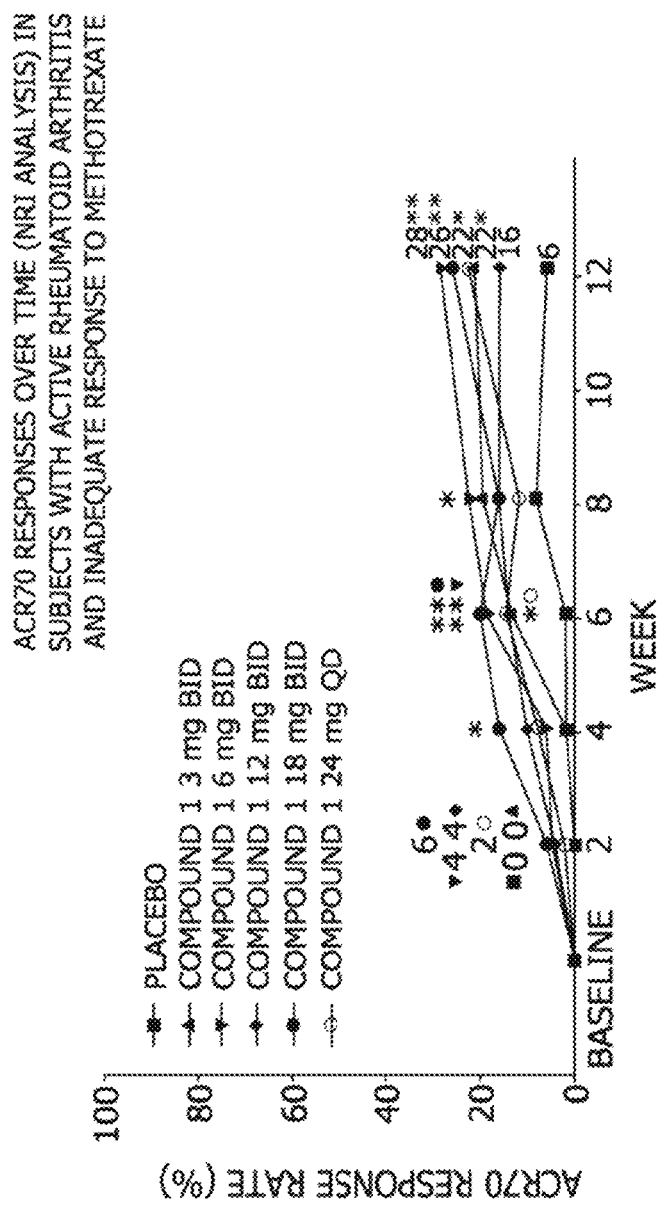

Statistical tests were 1-sided with a significance level of 0.05 for efficacy analyses and 2-sided with a significance level of 0.05 for all other analyses. A sample of 270 patients Efficacy The primary per-protocol endpoint, ACR20 at week 12 (LOCF imputation), was met at every dose of Compound 1 except the lowest dose of 3 mg BID. The proportions of patients with ACR20 were 65% (P=0.153), 73% (P=0.18), 82% (P=0.001), 77% (P=0.008), and 82% (P=0.001) at 3 mg BID, 6 mg BID, 12 mg BID, 18 mg BID, and 24 mg QD, respectively, versus the placebo response rate (50%). ACR20 responses (NRI) were significantly higher with Compound 1 at 6 mg BID (68%), 12 mg BID (80%), and 24 mg QD (76%) versus placebo (46%; FIG. 6). Responses with more stringent criteria, i.e., ACR50 and ACR70, were achieved at week 12 by significantly higher percentages of patients who received Compound 1 versus placebo at all doses except 12 mg BID for ACR70 response (NRI; FIG. 6). ACR20 response rates increased over time with Compound 1 to reach mean maximum values at weeks 6 to 12 (FIG. 7A). ACR50 responses were significant from week 4 onward and plateaued at week 8 (FIG. 7B); ACR70 responses also appeared to plateau by week 8, with some further improvements up to week 12 (FIG. 7C). At the first assessment (week 2), ACR20 responses with Compound 1 ranged from 30% to 44% and were significantly higher at all doses in patients who received Compound 1 versus placebo (12%). Mean decreases in DAS28(CRP) improved over time from baseline, ranging from −2.2 to −2.6 with Compound 1 at week 12, and were significantly lower compared with placebo (−1.3) at all Compound 1 doses and every time point (FIG. 7D).

Figure 8A:
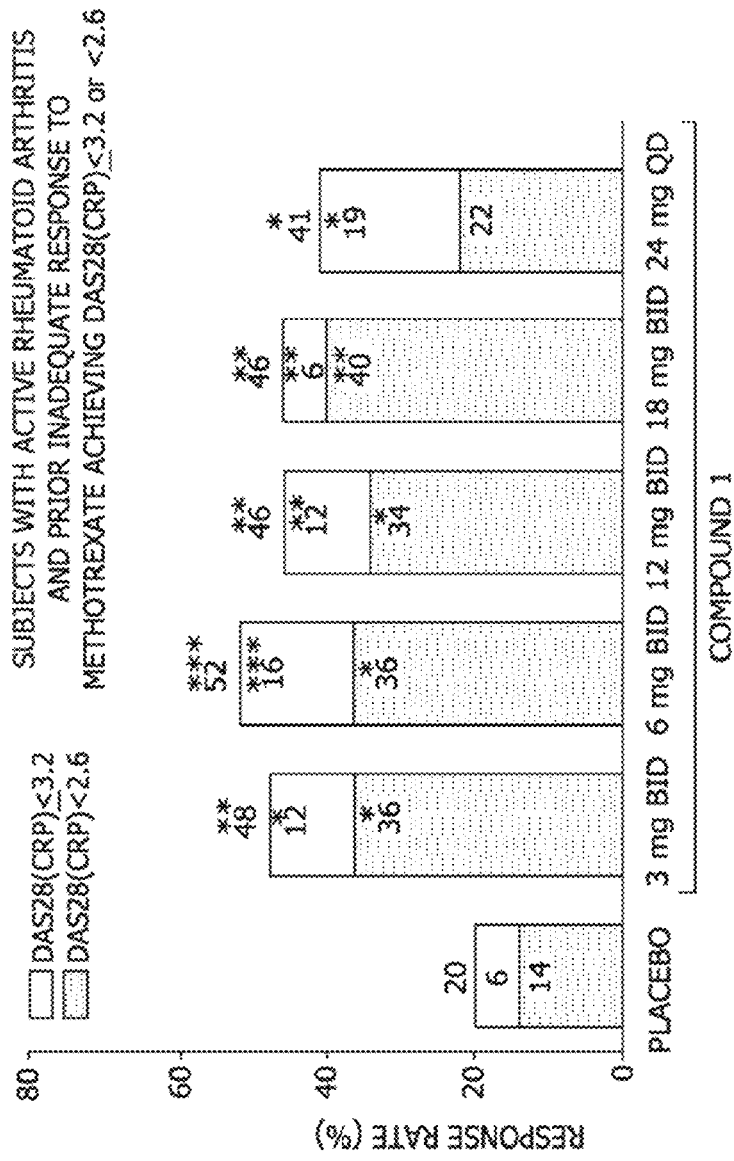
FIGS. 8A and 8B show subjects achieving a DAS28 (CRP) score of ≤3.2 or <2.6 (FIG. 8A) or CDAI of ≤10 or ≤2.8) at week 12 following administration of placebo or various doses of Compound 1 to subjects with active rheumatoid arthritis and inadequate response to methotrexate (*P<0.05; P<0.01; *P<0.001 relative to placebo; modified intent-to-treat population (NRI)). For FIGS. 8A and 8B, the bottom number indicates the percentage of subjects who achieved both cutoff values, the middle number indicates the percentage of subjects who achieved the less stringent cutoff but not the more stringent cutoff value, and the top number indicates the percentage of patients who achieved either cutoff value.
Figure 8B:
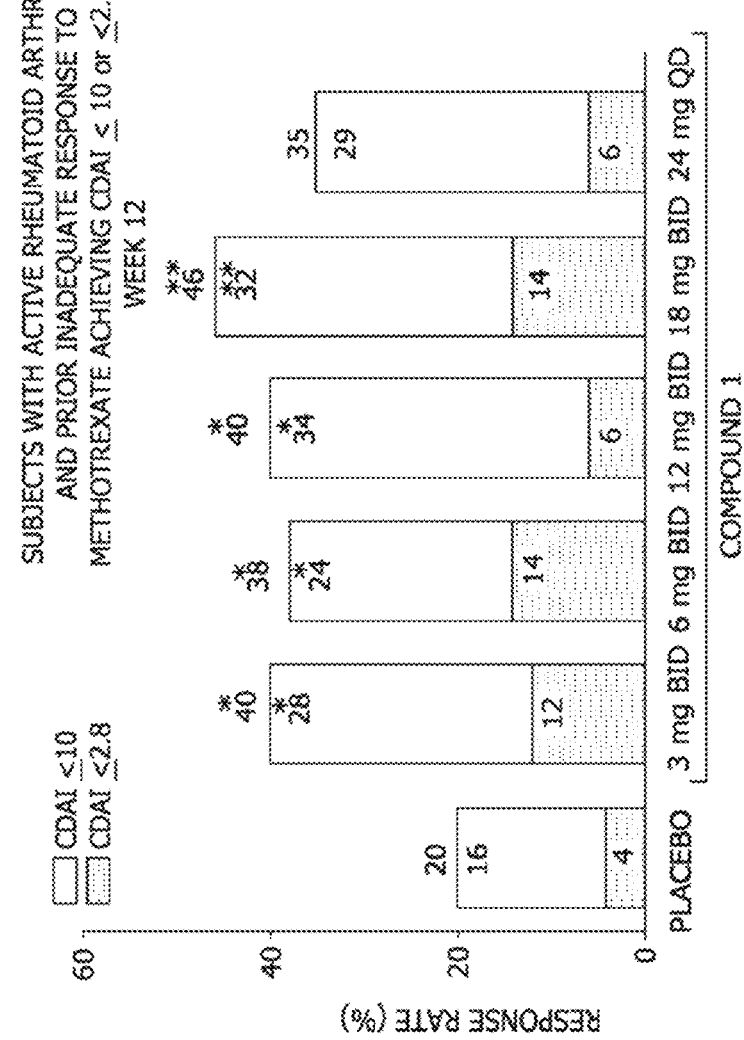

Higher percentages of patients who received Compound 1 achieved DAS28(CRP)≤3.2 or <2.6 compared with placebo. The DAS28(CRP)≤3.2 cutoff was achieved by a significantly higher percentage of patients (41%-52%) at all doses of Compound 1 compared with placebo (20%); the <2.6 cutoff was achieved by significantly higher proportions (34%-40%) with Compound 1 compared with placebo (14%) at all doses except 24 mg QD (22%; FIG. 8A). Similarly, CDAI≤10 was achieved by a significantly higher percentage of patients (40%-46%) compared with placebo (20%) with Compound 1 at all doses except 24 mg QD (35%; FIG. 8B).

Improvements from baseline in ACR component scores were larger with Compound 1 compared with placebo, reaching statistical significance for most comparisons at doses of 6 mg BID and greater (Table 19B). Changes from baseline on the HAQ-DI at week 12 with Compound 1 ranged from −0.6 to −0.8 and were significantly greater than that seen with placebo (−0.4) for all but the Compound 1 24 mg QD dose (−0.6). Numerically, more patients in the Compound 1 dose groups ≥6 mg BID (69%-88%) met the MCID at week 12 compared with placebo (67%); the study was not powered for this analysis, and the comparisons versus placebo mostly were not statistically significant.

TABLE 19B

Mean Changes From Baseline in ACR Components at Week 12

| ACR Component | Placebo (n = 50) | Compound 1 | | | | |
| --- | --- | --- | --- | --- | --- | --- |
| | | 3 mg BID (n = 50) | 6 mg BID (n = 50) | 12 mg BID (n = 50) | 18 mg BID (n = 50) | 24 mg QD (n = 49) |
| TJC68 | −14.4 | −15.9 | −19.2* | −19.2* | −17.4 | −18.9* |
| SJC66 | −9.9 | −12.1 | −11.9 | −12.7* | −13.2* | −13.1* |
| Patient's assessment of pain | −19.9 | −25.3 | −33.8** | −33.4** | −34.9** | −29.8* |
| Physician's global assessment of disease activity | −28.0 | −34.7 | −43.0*** | −45.6*** | −36.6* | −37.6* |
| Patient's global assessment of disease activity | −17.5 | −26.9 | −31.4** | −23.8 | −29.1* | −24.1 |
| HAQ-DI | −0.4 | −0.6* | −0.7** | −0.8*** | −0.6* | −0.6 |
| HAQ-DI ≤ MCID,§ number (%), 95% CI | 30 (67), 53-80 | 33 (67), 54-81 | 34 (69), 57-82 | 44 (88), 79-97 | 35 (74), 62-87 | 38 (78), 66-89 |
| hsCRP | −0.4 | −10.5*** | −8.8*** | −8.9*** | −7.5** | −8.4*** |

Abbreviations: ACR-American College of Rheumatology;
BID-twice daily;
HAQ-DI-Health Assessment Questionnaire Disability Index;
hsCRP-high-sensitivity C-reactive protein;
LOCF-last observation carried forward;
MCID-minimal clinically important difference;
QD-once daily;
RA-rheumatoid arthritis;
SJC66-swollen joint count using 66 joints;
TJC68-tender joint count using 68 joints.
*$P < 0.05$;
**$P < 0.01$;
***$P < 0.001$ relative to placebo.
§MCID = −0.22.
Modified intent-to-treat population with LOCF imputation of missing values. 95% CIs were calculated based on a normal approximation to the binomial distribution.

As can be seen from these results, Compound 1 had an early onset of action in subjects who have demonstrated a prior inadequate response to methotrexate. In particular, ACR20 response rates improved starting at week 2, with a maximum effect achieved as early as week 6, with continued improvement in some dose groups through week 12. ACR50 (maximum efficacy up to 50%) and ACR70 (maximum efficacy up to 28%) response rates also quickly plateaued by about week 8. Compound 1 showed a dose-dependent efficacy that seemed to reach a maximum at 12 mg BID.

Safety

The safety and tolerability profile of Compound 1 across doses was acceptable (Table 19C). Incidence of any AE was statistically significantly higher with Compound 1 overall versus placebo (45% vs 26%; P=0.012), with a trend of dose dependence. Among common AEs, those that occurred in >3% patients in any group were abdominal pain, abdominal pain upper, back pain, blood creatine phosphokinase increased, cough, diarrhea, dyslipidemia, dyspepsia, gastroenteritis, headache, herpes zoster, influenza, leukopenia, nasopharyngitis, upper respiratory tract infection, urinary tract infection, white blood cell count decreased, and wound. Most AEs in the Compound 1 treatment groups were mild or moderate in severity. Severe AEs occurred in 1 patient each with Compound 1 at 6 mg BID (lung cancer at posttreatment day 10 in a 79-year-old male patient with family and smoking histories; the patient died 3 months later), 12 mg BID (pyrexia), 18 mg BID (hyperbilirubinemia), and 24 mg QD (head injury). There were 2 serious AEs with Compound 1 that were considered possibly related to study drug: community-acquired pneumonia at 12 mg BID and syncope at 24 mg QD. Infections overall occurred in 20% of patients who received Compound 1 and 14% who received placebo, with no tendency towards higher rates at higher doses. Three herpes zoster infections, 1 with Compound 1 at 3 mg BID and 2 at 24 mg QD, involved 1 dermatome per patient. A patient in the Compound 1 6 mg BID group, aged 79 years and with a history of smoking, was diagnosed with lung cancer 10 days after stopping study treatment and died 3 months later.

At week 12, mean values for alanine aminotransferase (ALT) were significantly higher with Compound 1 18 mg BID than with placebo; mean values for aspartate aminotransferase (AST) were significantly higher than placebo with all Compound 1 doses >3 mg BID (Table 19D). However, grade 3/4 ALT or AST abnormalities during the study were sporadic, with no clear dose dependence (Table 23E). Creatinine and creatine phosphokinase levels were significantly higher in all Compound 1 dose groups compared with placebo. Compound 1 was associated with elevations in high-density and low-density lipoprotein cholesterol (HDL-C; LDL-C); HDL-C elevation was statistically significant at 6 mg BID, whereas LDL-C values were significantly higher than placebo for all Compound 1 doses; however, the ratios of LDL-C/HDL-C remained the same through week 12. There were no significant decreases in lymphocyte or neutrophil levels between placebo and Compound 1 dose groups by week 12. Grade 3 lymphocyte values occurred with placebo and all doses of Compound 1; grade 4 values occurred in 1 patient each with Compound 1 at 3 mg BID and 18 mg BID (Table 19E). Grade 3 neutrophil values occurred with Compound 1 at 12 mg BID (1 patient), 18 mg BID (3 patients), and 24 mg QD (1 patient). Natural killer (NK) cell percentages were significantly lower than placebo with Compound 1 doses ≥6 mg BID (Table 23D).

Figure 9B:
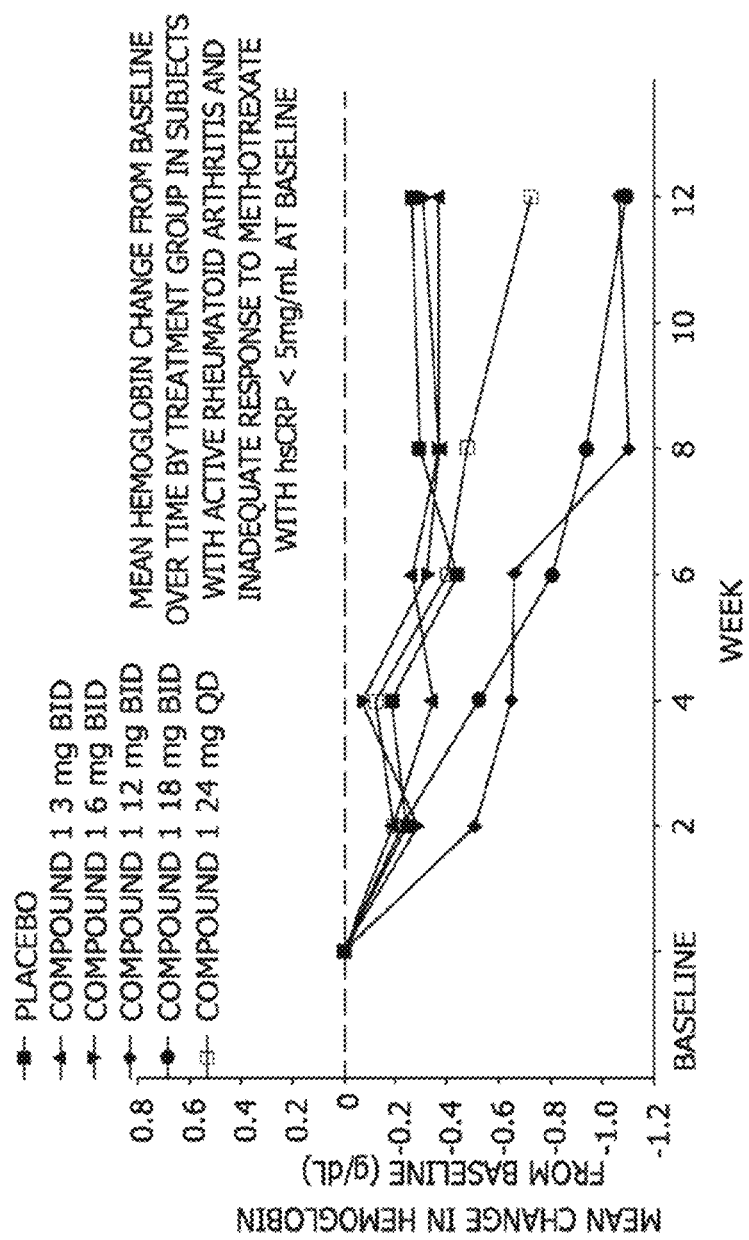
Figure 9C:
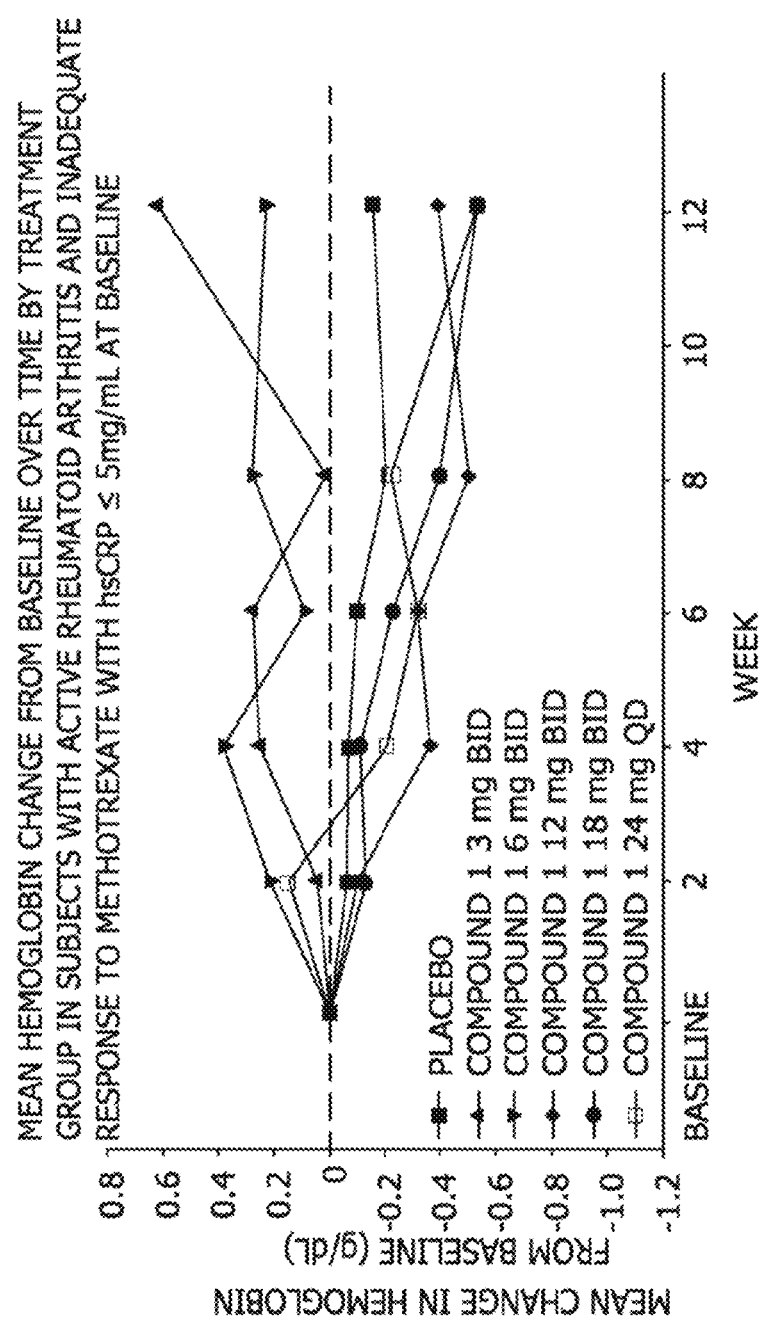

Mean changes in hemoglobin over time in all patients, patients with hsCRP values ≤5 mg/mL, and patients with hsCRP values >5 mg/mL are shown in FIGS. 9A-9C. Mean hemoglobin values remained stable or increased at lower doses, most notably in patients with elevated CRP at baseline. Dose-dependent decreases in hemoglobin were seen at higher doses without clinical impact.

TABLE 19C

Adverse Events Summary

| AE, number (%) | Placebo (n = 50) | Compound 1 | | | | |
|---|---|---|---|---|---|---|
| | | 3 mg BID (n = 50) | 6 mg BID (n = 50) | 12 mg BID (n = 50) | 18 mg BID (n = 50) | 24 mg QD (n = 49) |
| Overall AEs | | | | | | |
| Any AE | 13 (26) | 19 (38) | 23 (46) | 29 (58) | 25 (50) | 17 (35) |
| Any AE possibly drug related* | 6 (12) | 5 (10) | 6 (12) | 17 (34) | 11 (22) | 5 (10) |
| Any serious AE | 0 | 0 | 2 (4) | 1 (2) | 3 (6) | 2 (4) |
| Any serious AE possibly drug related* | 0 | 0 | 0 | 1 (2) | 0 | 1 (2) |
| Any severe AE | 0 | 0 | 1 (2) | 1 (2) | 1 (2) | 1 (2) |
| Any AE leading to discontinuation | 1 (2) | 1 (2) | 1 (2) | 1 (2) | 5 (10) | 1 (2) |
| Any AE leading to death | 0 | 0 | 0 | 0 | 0 | 0 |
| AEs ≥3% in any group | | | | | | |
| Abdominal pain | 0 | 1 (2) | 1 (2) | 2 (4) | 0 | 1 (2) |
| Abdominal pain upper | 0 | 0 | 0 | 2 (4) | 1 (2) | 1 (2) |
| Back pain | 0 | 1 (2) | 3 (6) | 1 (2) | 0 | 1 (2) |
| Blood creatine phosphokinase increased | 0 | 0 | 0 | 3 (6) | 2 (4) | 1 (2) |
| Cough | 0 | 1 (2) | 1 (2) | 3 (6) | 1 (2) | 0 |
| Diarrhea | 0 | 0 | 1 (2) | 3 (6) | 1 (2) | 1 (2) |
| Dyslipidemia | 0 | 1 (2) | 0 | 3 (6) | 0 | 0 |
| Dyspepsia | 1 (2) | 0 | 0 | 0 | 2 (4) | 0 |
| Gastroenteritis | 0 | 2 (4) | 0 | 0 | 0 | 1 (2) |
| Headache | 1 (2) | 2 (4) | 1 (2) | 3 (6) | 0 | 1 (2) |
| Herpes zoster | 0 | 1 (2) | 0 | 0 | 0 | 2 (4) |
| Influenza | 0 | 0 | 0 | 4 (8) | 1 (2) | 0 |
| Leukopenia | 0 | 0 | 0 | 3 (6) | 1 (2) | 0 |
| Nasopharyngitis | 1 (2) | 1 (2) | 2 (4) | 4 (8) | 2 (4) | 3 (6) |
| Upper respiratory tract infection | 0 | 0 | 1 (2) | 1 (2) | 2 (4) | 0 |
| Urinary tract infection | 2 (4) | 2 (4) | 2 (4) | 2 (4) | 0 | 2 (4) |
| White blood cell count decreased | 0 | 0 | 1 (2) | 0 | 2 (4) | 0 |
| Wound | 0 | 0 | 2 (4) | 0 | 0 | 0 |

TABLE 19C-continued

Adverse Events Summary

| | | Compound 1 | | | | |
|---|---|---|---|---|---|---|
| AE, number (%) | Placebo (n = 50) | 3 mg BID (n = 50) | 6 mg BID (n = 50) | 12 mg BID (n = 50) | 18 mg BID (n = 50) | 24 mg QD (n = 49) |
| AEs of special interest | | | | | | |
| Infection | 7 (14) | 10 (20) | 7 (14) | 12 (24) | 11 (22) | 9 (18) |
| Serious infection | 0 | 0 | 0 | 1 (2) | 0 | 0 |
| Cardiovascular event | 0 | 0 | 0 | 0 | 0 | 1 (2)* |
| Herpes zoster† | 0 | 1 (2) | 0 | 0 | 0 | 2 (4) |
| Hepatic disorder | 0 | 0 | 0 | 0 | 2 (4) | 0 |
| Malignancy | 0 | 0 | 1 (2)‡ | 0 | 0 | 0 |

Abbreviations: AE-adverse event;
BID-twice daily;
QD-once daily.
*The cardiovascular event was a cerebrovascular accident and was adjudicated as an ischemic stroke.
†The events of herpes zoster involved 1 dermatome per patient.
‡Lung cancer at posttreatment day 10 in a 79-year-old male patient with family and smoking histories. The patient died 3 months later. Safety analysis population.

TABLE 19D

Mean Changes in Laboratory Values of Interest at Week 12

| | | Compound 1 | | | | |
|---|---|---|---|---|---|---|
| Mean (SD) Value | Placebo (n = 50) | 3 mg BID (n = 50) | 6 mg BID (n = 50) | 12 mg BID (n = 50) | 18 mg BID (n = 50) | 24 mg QD (n = 49) |
| ALT, U/L | −1.3 (15.4) | −1.1 (20.7) | 6.5 (10.0) | 7.0 (31.8) | 8.5 (18.5)* | 5.3 (20.7) |
| AST, U/L | −0.1 (8.4) | 1.9 (11.9) | 6.6 (5.5)** | 7.6 (14.3)** | 7.7 (11.3)** | 4.8 (10.9)* |
| HDL-C, mmol/L | 0.01 (0.21) | 0.12 (0.32) | 0.17 (0.26)* | 0.13 (0.30) | 0.13 (0.43) | 0.13 (0.33) |
| LDL-C, mmol/L | −0.05 (0.43) | 0.28 (0.82)* | 0.34 (0.71)* | 0.49 (0.93)** | 0.27 (0.83)* | 0.32 (0.62)** |
| Creatinine, μmol/L | −0.9 (7.9) | 2.0 (8.2)** | 4.9 (9.1)** | 4.3 (7.1)** | 4.6 (10.2)** | 5.4 (8.5)** |
| Creatine phosphokinase, U/L | −7.7 (90.1) | 40.2 (46.5)* | 82.5 (80.6)** | 100.4 (126.5)** | 108.7 (140.2)** | 59.4 (94.0)** |
| Lymphocytes, ×10$^9$/L | −0.09 (0.50) | 0.12 (0.58) | 0.01 (0.79) | −0.08 (0.67) | −0.12 (0.53) | −0.13 (0.49) |
| Neutrophils, ×10$^9$/L | −0.5 (2.20) | −1.1 (2.13) | −0.9 (1.60) | −0.9 (1.90) | −0.9 (2.16) | −0.4 (1.99) |
| NK cells, CD3−/16−/56+, %† | −0.1 (4.46) | −1.3 (4.54) | −3.1 (4.09)** | −3.3 (4.67)** | −5.3 (4.24)** | −4.9 (5.12)** |

Abbreviations: ALT-alanine aminotransferase;
AST-aspartate aminotransferase;
BID-twice daily;
HDL-C-high-density lipoprotein cholesterol;
LDL-C-low-density lipoprotein cholesterol;
NK-natural killer;
QD-once daily.
*P < 0.05;
**P < 0.01 relative to placebo;
P value for difference between treatment groups in baseline and mean change from baseline using a contrast within the one-way analysis of variance.
†Mean percentage change from baseline at week 12. Safety analysis population.

TABLE 19E

Incidence of Patients With Laboratory Abnormalities at Week 12

| | | Compound 1 | | | | |
|---|---|---|---|---|---|---|
| | Placebo (n = 50) | 3 mg BID (n = 50) | 6 mg BID (n = 50) | 12 mg BID (n = 50) | 18 mg BID (n = 50) | 24 mg QD (n = 49) |
| ALT, U/L | | | | | | |
| Grade 3 (3.0-8.0 × ULN) | 0 | 0 | 1 | 2 | 1 | 0 |

TABLE 19E-continued

Incidence of Patients With Laboratory Abnormalities at Week 12

| | | | Compound 1 | | | |
|---|---|---|---|---|---|---|
| | Placebo (n = 50) | 3 mg BID (n = 50) | 6 mg BID (n = 50) | 12 mg BID (n = 50) | 18 mg BID (n = 50) | 24 mg QD (n = 49) |
| Grade 4 (>8.0 × ULN) | 0 | 0 | 0 | 0 | 1 | 0 |
| AST, U/L | | | | | | |
| Grade 3 (3.0-8.0 × ULN) | 0 | 1 | 1 | 0 | 1 | 0 |
| Grade 4 (>8.0 × ULN) | 0 | 0 | 0 | 0 | 0 | 0 |
| Neutrophils, ×10$^9$/L | | | | | | |
| Grade 3 (0.5-0.9) | 0 | 0 | 0 | 1 | 3 | 1 |
| Grade 4 (<0.5) | 0 | 0 | 0 | 0 | 0 | 0 |
| Lymphocytes, ×10$^9$/L | | | | | | |
| Grade 3 (0.5-0.9) | 7 | 8 | 13 | 16 | 17 | 15 |
| Grade 4 (0.5) | 0 | 1 | 0 | 0 | 1 | 0 |

Abbreviations: ALT-alanine aminotransferase;
AST-aspartate aminotransferase;
BID-twice daily;
QD-once daily;
ULN-upper limit of normal.

As can be seen from these results, the safety and tolerability profile of Compound 1 was acceptable across doses.

Figure 10:
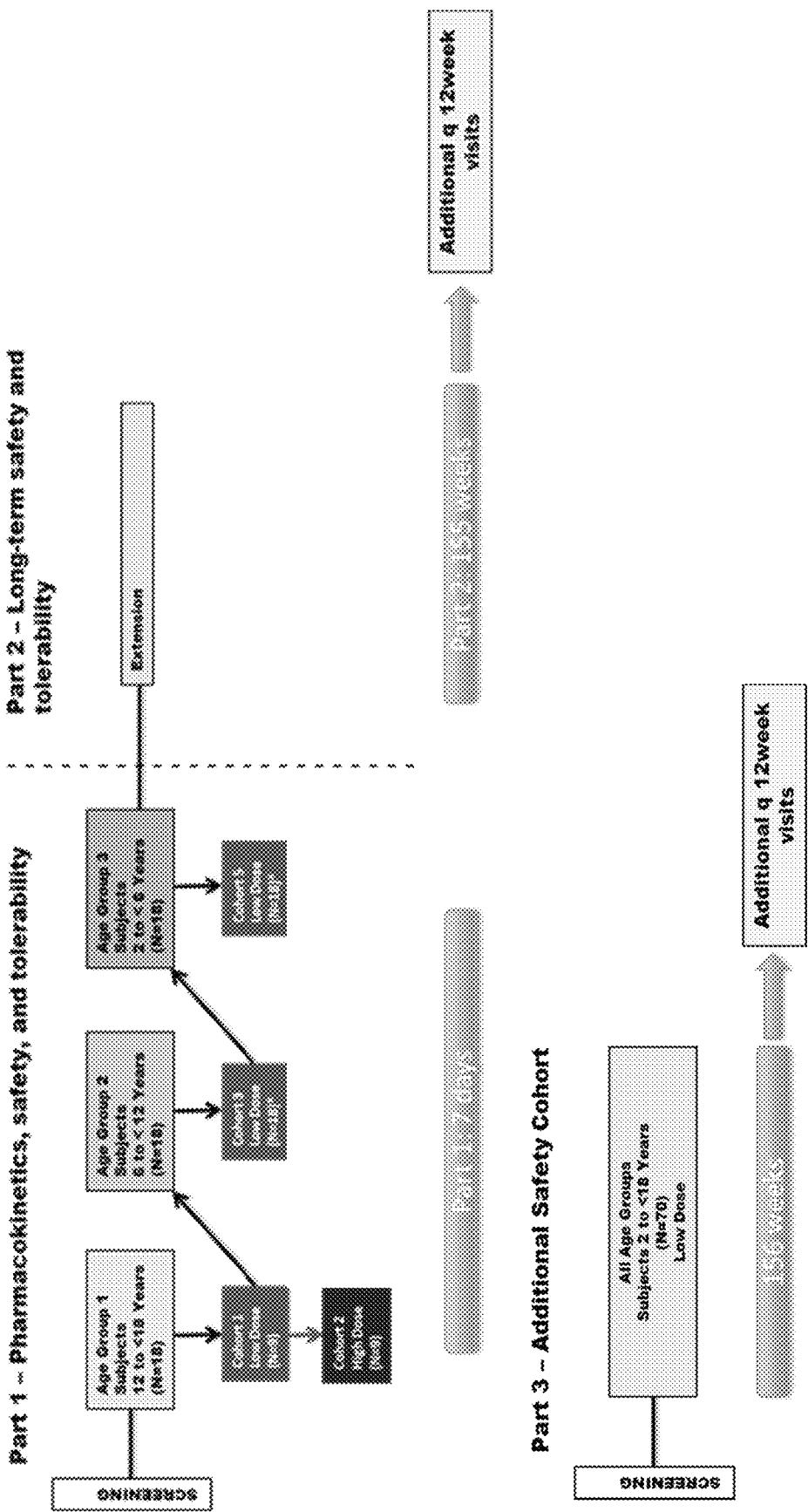
FIG. 10 is a schematic illustration of a clinical study in pediatric polyarticular course juvenile idiopathic arthritis patients according to a non-limiting embodiment of the disclosure.

Example 34: Evaluation of the Pharmacokinetics and Safety of Upadacitinib in Pediatric Subjects with Polyarticular Course Juvenile Idiopathic Arthritis Investigational Plan This was a Phase 1, multiple-dose, open-label study consisting of three parts in approximately 124 pediatric subjects ages 2 to less than 18 years with pcJIA. A schematic of the study is shown in FIG. 10. Part 1 was a multiple-dose, open-label, multiple-cohort study. Two sequential multiple-ascending dose levels (Low Dose and High Dose levels) were evaluated in the 12 to <18 years age group (Group 1), and one dose level (Low Dose) was evaluated in the two younger age groups (Group 2: 6 to <12 years, and Group 3: 2 to <6 years). Low Dose and High Dose cohorts in age group 1 enrolled 9 subjects each. Low Dose cohorts in age groups 2 and 3 enrolled approximately 18 subjects each.

Upadacitinib dose was administered based on subject's body weight according to three defined body weight categories per dose level. The study enrolled at least 10 subjects below 30 kg. Recruitment of subjects was conducted through a staggered approach based on age. Subjects who completed Part 1 and were benefiting from study drug with no ongoing adverse events of special interest or serious adverse events, based on investigator's clinical judgment and with subject/family's agreement, had the option to enroll in Part 2 to receive open-label upadacitinib. Part 2 was an open-label, long-term extension to evaluate long-term safety and tolerability of upadacitinib. Subjects in Part 2 received open-label upadacitinib at the equivalent of the Low Dose level per body weight category. At Week 156, if the investigator believed the subject was still benefiting from treatment, they had an option to continue treatment until the end of the study. Part 3 was an additional safety cohort. This additional safety cohort enrolling approximately 70 subjects from all age groups (2 to <18 years) was added to evaluate long-term safety and tolerability of upadacitinib without intensive pharmacokinetic sample collection. Part 3 was open to age groups in which Part 1 enrollment was completed. Subjects in Part 3 received open-label upadacitinib at the equivalent of the Low Dose level per body weight category, and, after the baseline and screening visits, followed an identical visit schedule as subjects in Part 2, without intensive pharmacokinetic sampling. Doses were adjusted during the study for any of the body weight categories after review of results from the subjects who completed Study Part 1.

Eligibility Criteria

Male or female subjects, ages 2 to less than 18 years, and total body weight of 10 kg or higher at the time of Screening.

Diagnosed with pcJIA (rheumatoid factor-positive or rheumatoid factor-negative polyarticular JIA, extended oligoarticular JIA, or systemic JIA with active arthritis and without active systemic features) with a history of arthritis affecting at least 5 joints within the first 6 months of disease (for extended oligoarticular JIA: ≤4 joints during the first 6 months of disease and >4 joints thereafter), as per International League of Associations for Rheumatology (ILAR) criteria.

Subject must not have a diagnosis of enthesitis-related arthritis (ERA) or juvenile psoriatic arthritis (JPSA).

Have 5 or more active joints at the time of Screening, defined as the presence of swollen joints (not due to deformity) or, in the absence of swelling, joints with limitation of movement (LOM) plus pain on motion and/or tenderness with palpation, with LOM present in at least three of the active joints.

If receiving methotrexate (MTX), have been taking MTX for at least 12 weeks immediately before and including Study Day 1 on a stable dose of ≤20 mg/m$^2$ for at least 8 weeks before and including Study Day 1; in addition, subjects should take either folic acid or folinic acid according to local standard of care.

If on oral glucocorticoids, must have been taking oral glucocorticoids at a stable dose (no greater than 10 mg/day or 0.2 mg/kg/day, whatever is lower) for at least 1 week before and including Study Day 1.

No prior exposure to JAK inhibitor.

No ongoing or active uveitis within 3 months prior to Study Day 1.

Subject has not been treated with intra-articular or parenteral administration of corticosteroids in the preceding 4 weeks prior to Study Day 1.

No history of any malignancy except for successfully treated non-melanoma skin cancer or localized carcinoma in situ of the cervix.

No history of clinically significant (per investigator's judgment) drug or alcohol abuse within the last 6 months.

No history of an allergic reaction or significant sensitivity to constituents of the study drug (and its excipients) and/or other products in the same class.

No current or past history of infection including:

No history of recurrent or disseminated (even a single episode) herpes zoster;

No history of disseminated (even a single episode) herpes simplex;

No human immunodeficiency virus (HIV) infection;

Subject does not have active TB or meet TB exclusionary parameters (specific requirements for TB testing are provided in the Operations Manual);

No active infection(s) requiring treatment with parenteral anti-infectives within 30 days, or oral anti-infectives within 14 days prior to Study Day 1;

No chronic recurring infection and/or active viral infection that, based on the investigator's clinical assessment, makes the subject an unsuitable candidate for the study;

No active hepatitis B virus (HBV) or hepatitis C virus (HCV) infection defined as:

HBV: hepatitis B surface antigen (HBs Ag) positive (+) or detected sensitivity on the HBV deoxyribonucleic acid (DNA) PCR qualitative test for subjects who are hepatitis B core antibody (HBc Ab) positive (+);

HCV: HCV ribonucleic acid (RNA) detectable in any subject with anti-HCV antibody (HCV Ab).

Subject has not been a previous recipient of an organ transplant that requires continued immunosuppression.

No history of gastrointestinal perforation (other than appendicitis or penetrating injury), diverticulitis, or significantly increased risk for gastrointestinal perforation per investigator judgment.

No conditions that could interfere with drug absorption including, but not limited to, short bowel syndrome.

No current use of known moderate or strong inhibitors (e.g., amiodarone, clarithromycin, fluconazole, ciprofloxacin, itraconazole, ketoconazole, quinidine, fluoxetine, and paroxetine) or inducers (e.g., carbamazepine, rifampin, phenobarbital, and phenytoin) of drug metabolizing enzymes within 30 days prior to the first dose of study drug through the end of the Part 1 of the study. No systemic use of known strong cytochrome P450 3A isoform subfamily (CYP3A) inhibitors or inducers from the start of Part 2 or Part 3 of the study through study completion.

Prohibited Medications and Therapy

In addition to the medications listed in the eligibility criteria, the following was NOT allowed:

Prior use of biologic treatment must have been discontinued prior to Study Day 1 (etanercept, 4 weeks; infliximab, adalimumab or abatacept, 8 weeks; golimumab, 10 weeks; tocilizumab, ustekinumab, and certolizumab pegol, 12 weeks; canakinumab, 10 weeks; anakinra, 1 week) and is also prohibited during the study. Note: If there is proper documentation of undetectable drug level measured by a commercially available assay for any of the approved biologics above, there is no minimum washout prior to Baseline.

Immunosuppressant medications must have been discontinued at least 30 days or 5-half-lives prior to study drug administration through the end of the study.

Known current use of moderate or strong inhibitors (e.g., amiodarone, clarithromycin, fluconazole, ciprofloxacin, itraconazole, ketoconazole, quinidine, fluoxetine, and paroxetine) or inducers (e.g., carbamazepine, rifampin, phenobarbital, and phenytoin) of drug metabolizing enzymes within 30 days prior to the first dose of study drug and through the end of Part 1 of the study. Systemic use of known strong CYP3A inhibitors or inducers from the start of Part 2 or Part 3 through the end of the study.

Live vaccines were not permitted during Part 1 of study participation. If the subject and investigator choose to administer live vaccines, these vaccinations were completed, when possible (per local label) at least 4 weeks (8 weeks in Japan) before first dose of study drug with appropriate precautions. Although not mandated by the protocol, vaccines recommended by local guidelines should be considered. If a live vaccine must be administered during Part 2 or Part 3 of study participation, hold study drug for at least 4 weeks (8 weeks in Japan) prior to the vaccination and at least 4 weeks (8 weeks in Japan) after the vaccination. Thereafter, study drug may be resumed at the investigator's discretion with appropriate precautions.

Investigational drugs must have been discontinued within 30 days or 5 half-lives of the drug (whichever is longer) prior to the first dose of study drug. Investigational drugs are also prohibited during the study.

JAK inhibitors (e.g., commercially available upadacitinib [Rinvoq®], tofacitinib [Xeljanz®], ruxolitinib [Jakafi®], baricitinib [Olumiant®], peficitinib [Smyraf®], abrocitinib [PF-04965842], and filgotinib) were prohibited medications during the study.

The following were allowed concomitant medications/therapy:

Stable doses of non-steroidal anti-inflammatory drugs (NSAIDs)

Stable doses of low-dose glucocorticoids (≤0.2 mg/kg/day prednisone; daily maximum, 10 mg)

Stable doses of methotrexate ([MTX]; ≤20 mg/m² body surface area/week)

Study Drug and Duration of Treatment

The study drug was upadacitinib in the following formats and doses: 7.5 mg tablet, oral; 15 mg tablet, oral; 30 mg tablet, oral; 1 mg/mL solution, oral; 0.5 mg/mL solution, oral. In Part 1, the dose was administered according to three body weight categories. Subjects were categorized based on age group, and the dose administered for seven consecutive days will be based on three different body weight categories per dose level shown in Table 20. The doses evaluated in this study were predicted to provide comparable upadacitinib plasma exposures in each body weight category to those provided by 15 mg QD and 30 mg QD using the extended-release formulation in adult RA subjects. Doses were selected based on population pharmacokinetic analysis of upadacitinib in healthy adults and in adult subjects with RA, and pharmacokinetic simulations across the different body weight categories assuming allometric (weight-based) scaling of upadacitinib pharmacokinetic parameters (volume of distribution and clearance parameters).

The doses selected for this study account for the difference in oral bioavailability between the extended-release tablet formulation and the oral solution. Based on the population pharmacokinetic analyses across Phase 1 through 3 studies, the median (90% prediction interval) upadacitinib average plasma exposures over a dosing interval are 15.1 ng/mL (8.96 ng/mL to 32.7 ng/mL) for 15 mg QD and 30.0 ng/mL (18.1 ng/mL to 63.8 ng/mL) for 30 mg QD using the extended-release formulation in adult RA patients; similar exposures were predicted to be achieved in pediatric patients by the low and high doses, respectively, within each body weight category based on pharmacokinetic simulations (Table 20). Doses were adjusted during the study for any of the body weight categories after review of results from the subjects who completed Part 1.

TABLE 20

Upadacitinib Dosing by Body Weight Category and Dose Level

| | Body Weight Category* | | |
|---|---|---|---|
| Dose Level | 10 to <20 kg | 20 to <30 kg | ≥30 kg |
| Low Dose | 3 mg BID Oral Solution | 4 mg BID Oral Solution | 15 mg QD Tablet (or 6 mg BID Oral Solution if unable to swallow tablet) |
| High Dose | 6 mg BID Oral Solution | 8 mg BID Oral Solution | 30 mg QD Tablet (or 12 mg BID Oral Solution if unable to swallow tablet) |

BID = twice daily;
QD = once daily

Subjects in Part 2 received open-label upadacitinib at the Low Dose level described in Table 20. At Week 156, if the investigator believed the subject was still benefiting from treatment, they had the option to continue treatment at the equivalent of the Low Dose level per body weight category until the end of the study.

Dose Adjustment Criteria

For each subject, upadacitinib dose in Part 1 was based on the subject's body weight at Screening and the assigned study cohort. When preliminary pharmacokinetic and clinical data (following Part 1 Day 7 intensive pharmacokinetic sampling) from at least 4 subjects was available in a cohort, these data were used to adjust doses, if needed, for subjects who were enrolled (including subjects in Parts 2 and 3) and for subjects who were subsequently enrolled. Additional criteria were considered for making dose adjustment decisions for Part 1 to ensure safe and efficacious exposures.

Subjects who were receiving upadacitinib in Part 2 continued to receive the same dose until their next scheduled visit (unless earlier dose adjustment was deemed necessary by the investigator). On the next scheduled visit, subjects in Part 2 received upadacitinib according to the dosing regimen (Table 20) for the remaining duration of the study. Subjects weighing >30 kg had the option to receive upadacitinib oral solution if unable to swallow the tablet (see Table 20). For subjects in Part 2 who underwent dose adjustments, blood samples for upadacitinib pharmacokinetics were collected prior to dosing and at 1 hour and 2 hours after dosing from subjects at an unscheduled visit that was 4-6 weeks after the subject's dose adjustment visit. The timing of the last two doses administered prior to the pre-dose trough pharmacokinetic sample and the timing of the blood sample collections were recorded to the nearest minute. At the same unscheduled visit, blood samples for clinical laboratory testing were also collected.

Subjects in Parts 2 and 3 were dosed according to the Low Dose level per body weight category (Table 20) or as determined based on data available from Part 1. A change in the subject's body weight category was determined by the investigator at any of the study visits in Parts 2 and 3. A pharmacokinetic blood sample was collected in subjects in Parts 2 and 3 when dose was modified due to change in the subjects' body weight.

Study Objectives and Endpoints

Part 1:

To evaluate the pharmacokinetics, safety, and tolerability of multiple doses of upadacitinib in pediatric subjects with pcJIA. To evaluate the palatability of upadacitinib oral solution in pediatric subjects. To evaluate descriptive efficacy of upadacitinib in pcJIA.

Part 2:

To evaluate the long-term safety and tolerability of upadacitinib in pediatric subjects with pcJIA who completed Part 1. To evaluate descriptive efficacy of upadacitinib in pcJIA.

Part 3:

To evaluate the long-term safety and tolerability of upadacitinib in pediatric subjects with pcJIA. To evaluate descriptive efficacy of upadacitinib in pcJIA.

During Part 2 and Part 3, subjects who did not achieve at least 20% improvement in total number of active joints (joints with swelling not due to deformity or joints with LOM and with pain, tenderness, or both) compared to baseline at 2 consecutive visits on or after Week 8 discontinued study drug and received treatment at the investigator's discretion in accordance with local standard-of-care.

Safety Endpoints

Safety evaluations included incidence of Treatment Emergent Adverse Events (TEAEs), physical examination results, change in vital sign measurements, and clinical laboratory testing (hematology and chemistry) as measures of safety and tolerability for the entire study duration.

Pharmacokinetic Endpoints

For Part 1, the values for the pharmacokinetic parameters of upadacitinib including $C_{max}$, time to maximum observed plasma concentration ($T_{max}$), area under the plasma concentration versus time curve during a dosing interval ($AUC_{tau}$) on Day 7, apparent oral clearance at steady state (CL/F), and half-life were determined using non-compartmental methods.

Efficacy Endpoints

The following efficacy parameters were used to determine JIA American College of Rheumatology (ACR) response and Juvenile Arthritis Disease Activity Score (JADAS) were collected:

Total number of active joints defined as:
  joints with swelling not due to deformity, OR
  joints with limitation of movement [LOM] with pain, tenderness or both
Number of joints with LOM
Childhood Health Assessment Questionnaire (C-HAQ)
Physician's Global Assessment of Disease Activity (visual analog scale [VAS])
Patient's/Caregiver's Global Assessment of Overall Well Being (VAS)
Erythrocyte sedimentation rate (ESR)
C-reactive protein (CRP)

Based on these parameters, the following composite efficacy endpoints were evaluated:

JIA ACR pediatric 30/50/70/90/100 responses
Change from Baseline in JADAS10/27/71 responses, as well as JADAS-based criteria for low disease activity and remission (if deemed useful and appropriate).

Example 35: Pharmacokinetics of Upadacitinib in Pediatric Patients with Polyarticular Course Juvenile Idiopathic Arthritis (pcJIA); Analysis of Interim Results of Example 34

Objective

The primary objective of this analysis was to characterize the pharmacokinetics from a Phase 1 study of upadacitinib in children with pcJIA (PK analysis of Example 34).

Method

Patients (N=51) diagnosed with pcJIA were enrolled into one of four groups in an open-label, multiple-dose study (Group 1, 12 to <18 years, low dose; Group 2, 12 to <18 years, high dose; Group 3, 6 to <12 years, low dose; Group 4, 2 to <6 years, low dose). The low and high doses were selected to provide comparable plasma exposures in pediatrics to 15 mg and 30 mg QD doses of ER tablet formulation in adults, respectively. Patients received bodyweight-based upadacitinib doses either as twice-daily (BID) immediate-release (IR) oral solution or QD extended-release (ER) tablet formulation. Pharmacokinetic assessment was performed at steady state on Study Day 7, after which all patients might continue the study with low dose.

Results

A summary of the demographics of the enrolled subjects is provided in Table 21. Pharmacokinetic results from 49 patients with evaluable drug concentrations on Study Day 7 were reported.

In Group 1, the geometric mean upadacitinib maximum plasma concentration ($C_{max}$) and $AUC_{0-24}$ at steady state were 35.1 ng/mL and 269 ng·h/mL, respectively.

In Group 2, the geometric mean upadacitinib $C_{max}$ and $AUC_{0-24}$ were 69.8 ng/mL and 553 ng·h/mL, respectively.

In Group 3, the geometric mean upadacitinib $C_{max}$ and $AUC_{0-24}$ were 51.0 ng/mL and 346 ng·h/mL, respectively.

In Group 4, the geometric mean upadacitinib $C_{max}$ and $AUC_{0-24}$ were 46.6 ng/mL and 369 ng·h/mL, respectively.

Figure 11:
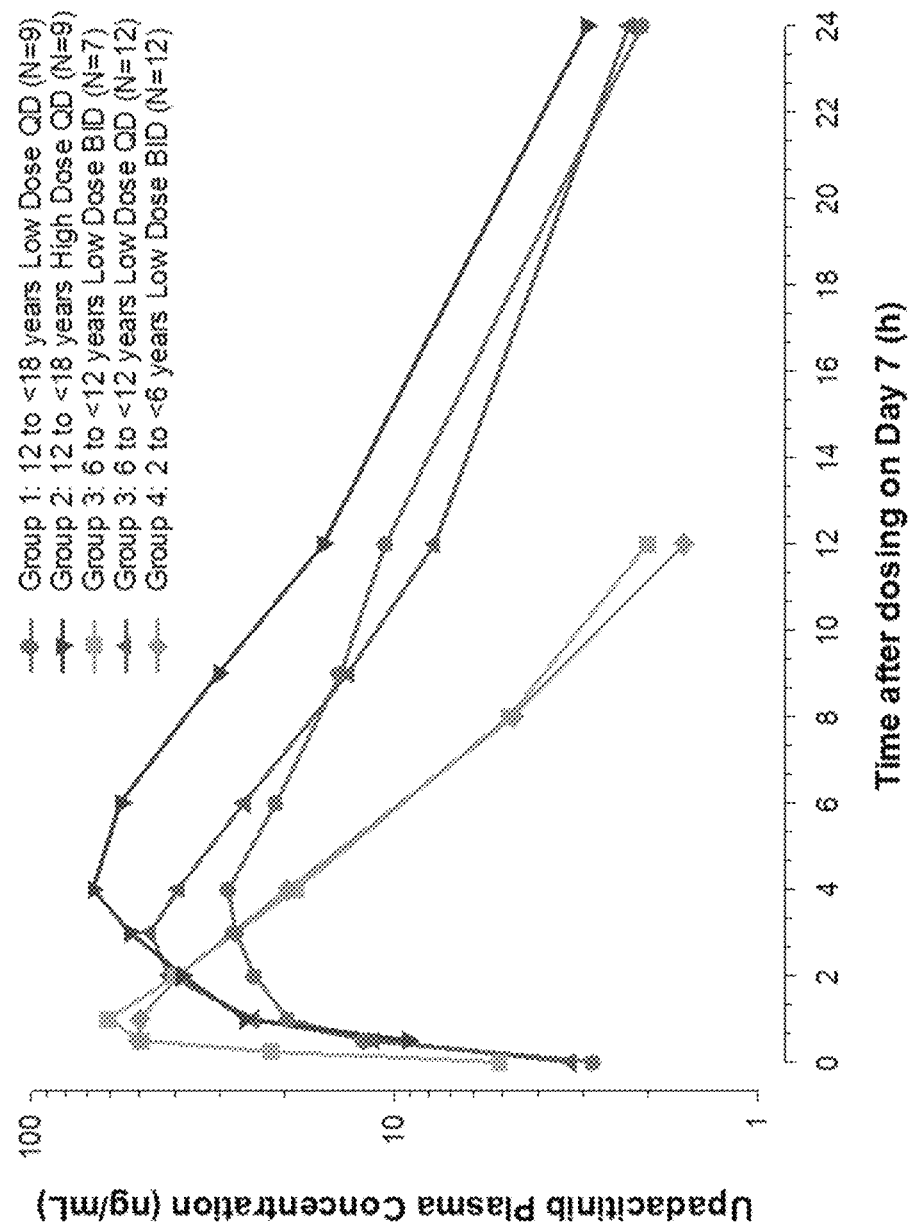
FIG. 11 is a graphical depiction of mean upadacitinib plasma concentration-time profiles in pediatric polyarticular course juvenile idiopathic arthritis patients according to non-limiting embodiments of the disclosure.

The median time to maximum upadacitinib concentration was approximately 3 hours and 1 hour; and the harmonic mean functional half-life was approximately 5 hours and 2 hours for the QD ER tablet and the BID IR solution regimens, respectively. Upadacitinib apparent oral clearance increased in pcJIA patients with increasing bodyweight. The mean upadacitinib plasma concentration-time profiles of each group are presented by dosing regimen in FIG. 11. Overall, the data indicate that upadacitinib plasma exposures in pediatric patients with pcJIA were comparable to target adult RA patients at the evaluated dosing regimens with the ER tablet or IR solution and at both low and high dose levels. These results support the use of a bodyweight-based dosing regimen in upadacitinib pediatric studies.

TABLE 21

Demographics Summary of Enrolled Pediatric pcJIA Patients

|  |  | Group 1 (N = 9) | Group 2 (N = 9) | Group 3 (N = 19) | Group 4 (N = 14[a]) |
|---|---|---|---|---|---|
| Age (years) | Mean ± SD | 14.9 ± 1.5 | 13.9 ± 1.2 | 9.5 ± 1.6 | 3.6 ± 1.5 |
|  | (Range) | (13 - 17) | (12-16) | (6-12) | (2-6) |
| Weight (kg) | Mean ± SD | 61.3 ± 14.6 | 51.7 ±1 | 37.8 ± 14.4 (19.7 – 72.1) | 15.1 ± 3.2 (11.0 – 22.5) |
|  | (Range) | (42.0-92.9) | 13.0 (32.5-71.5) |  |  |
| Sex | Male, N (%) | 2 (22.2) | 1 (11.1) | 4 (21.1) | 3 (21.4) |
|  | Female, N (%) | 7 (77.8) | 8 (88.9) | 15 (78.9) | 11 (78.6) |
| Dose Form N (%) | Oral Solution, | 0 (0.0) | 0 (0.0) | 7 (36.8) | 14 (100.0) |
|  | Tablet, N (%) | 9 (100.0) | 9 (100.0) | 12 (63.2) | 0 (0.0) |

[a]Two subjects were excluded from pharmacokinetic analysis. One subject mistakenly received half dose and the other subject had incomplete PK sample collection.

Example 36: Safety and Efficacy of Upadacitinib for Pediatric Patients with Polyarticular Course Juvenile Idiopathic Arthritis: An Interim Analysis of an Open-label, Phase 1 Trial (Analysis of Interim Results of Example 1 through Week 12)

Objective

The objective of this study was to evaluate the safety and efficacy of upadacitinib in pediatric patients with pcJIA by age groups.

Method

This open-label, 3-part, Phase 1 trial (NCT03725007) enrolled pediatric patients aged 2 to <18 years with pcJIA and ≥5 active joints at 31 sites across North America, Europe, and Asia In part 1, two sequential multiple ascending UPA dose groups (low: 3 mg or 4 mg twice-daily oral solution, or 15 mg once-daily tablet; high: 6 mg or 8 mg oral solution, or 30 mg tablet) were administered based on body weight groups (10 to <20, 20 to <30, and ≥30 kg) and age groups (2 to <6, 6 to <12, and 12 to <18 years of age) for 7 days. In part 2 (long-term extension of part 1) and part 3 (additional safety cohort), low-dose UPA (3 mg or 4 mg oral solution, or 15 mg tablet) was administered based on body weight groups for up to 156 weeks. Efficacy endpoints included the American College of Rheumatology (ACR) response 30, 50, and 70; the Childhood Health Assessment Questionnaire (C-HAQ); and the 27-point Juvenile Arthritis Disease Activity Score (JADAS-27) at week 12 among patients treated in part 1 and part 2. This was an interim analysis.

Results

Figure 12D:
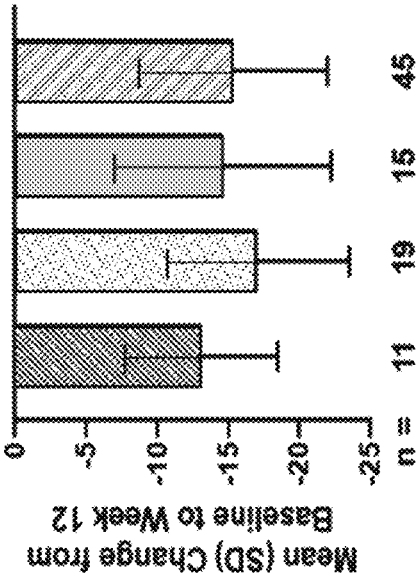
Figure 12E:
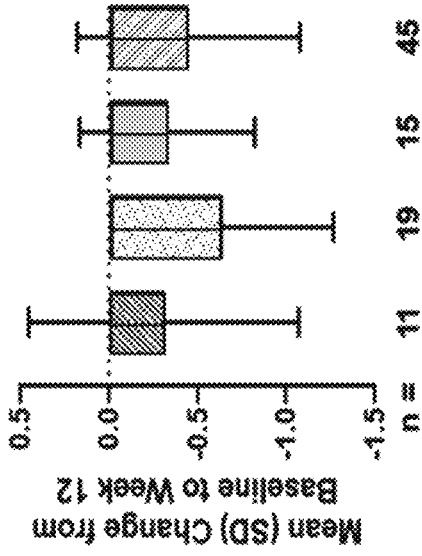

A total of 57 pediatric patients with mean (SD) age of 9.5 (4.4) years, 78.9% female, and mean (SD) weight of 38.1 (20.4) kg received UPA. In part 1, 8 (15.7%) out of 51 patients reported adverse events (AEs) through 7 days; no patients reported serious AEs or AEs leading to treatment discontinuation. In part 2 and part 3, 52 (91.2%) out of 57 patients reported AEs that were predominately mild to moderate in severity (Table 22). Rates of AEs were generally highest among patients 12 to <18 years of age. The most common AEs of special interest included elevated creatine phosphokinase (n=6/57, 10.5%), hepatic disorder (n=3/57, 5.3%), and neutropenia (n=2/57, 3.5%). Six (31.6%) out of 19 patients in the 12 to <18 years of age group reported serious AEs and 2 (10.5%) reported AEs leading to treatment discontinuation. No deaths occurred. A high proportion of patients across all age groups achieved ACR30, ACR50, and ACR70 response at week 12 (FIGS. 12A, 12B, and 12C, respectively). Referring to FIGS. 12A-12C, numbers above the bars are the proportion of patients with response and (n/N). Improvement from baseline to week 12 in C-HAQ and JADAS-27 scores was observed across all age groups (FIGS. 12D and 12E, respectively). Overall, in pediatric patients with pcJIA, upadacitinib was safe and well tolerated and associated with improvements in disease activity in a high proportion of patients at week 12 of this interim analysis.

TABLE 22

Interim Analysis of Safety of Upadacitinib up to 156 Weeks

| AE, n (%) | Age 2 to <6 years n = 14 | Age 6 to <12 years n = 24 | Age 12 to <18 years n = 19 | Total N = 57 |
|---|---|---|---|---|
| Any AE | 11 (78.6) | 22 (91.7) | 19 (100) | 52 (91.2) |
| Any serious AE | 0 | 0 | 6 (31.6) | 6 (10.5) |
| AE leading to discontinuation of study drug | 0 | 0 | 2 (10.5) | 2 (3.5) |
| Deaths | 0 | 0 | 0 | 0 |
| AEs of special interest | | | | |
| Serious infections | 0 | 0 | 1 (5.3) | 1 (1.8) |
| Opportunistic infection | 0 | 0 | 1 (5.3) | 1 (1.8) |
| Hepatic disorder | 0 | 2 (8.3) | 1 (5.3) | 3 (5.3) |
| Anemia | 1 (7.1) | 0 | 0 | 1 (1.8) |
| Neutropenia | 0 | 2 (8.3) | 0 | 2 (3.5) |
| Lymphopenia | 0 | 0 | 1 (5.3) | 1 (1.8) |
| Elevated creatine phosphokinase (CPK) | 0 | 3 (12.5) | 3 (15.8) | 6 (10.5) |

Example 37: Pharmacokinetics Safety, and Tolerability of Upadacitinib in Children with Atopic Dermatitis The objective of this study was to characterize the pharmacokinetics (PK), safety, and tolerability of upadacitinib in children with severe atopic dermatitis (AD).
Method
This was an open-label, multiple-dose study. AD patients (N=35) were enrolled into four cohorts (Cohort 1, 6 to <12 years with low dose; Cohort 2, 6 to <12 years with high dose; Cohort 3, 2 to <6 years with low dose; Cohort 4, 2 to <6 years with high dose). Upadacitinib was administered based on body weight with either BID oral solution or QD extended-release tablet. The low and high doses were selected to provide comparable plasma exposure in pediatric patients to 15 mg and 30 mg QD doses in adults, respectively. PK was evaluated on Day 7 post first dose. Safety was evaluated throughout the study. Exploratory efficacy parameters were collected at specified timepoints.
Results
Geometric mean $C_{max}$ and AUC over 0-24 hours at steady-state were 33.1 and 35.2 ng/mL and 249 and 264 ng·h/mL in Cohorts 1 and 3; 95.5 and 101 ng/mL and 523 and 625 ng·h/mL in Cohorts 2 and 4, respectively.
Upadacitinib was generally safe and well tolerated. The most common AEs were COVID infection, headache, and abdominal discomfort. No new safety risks were identified compared to the known safety profile for upadacitinib.
In the 29 subjects with available interim efficacy results at week 12, 34.5% achieved validated Investigator's Global Assessment scale for AD score of 0 or 1 and 69.0% achieved Eczema Area and Severity Index by at least 75% at Week 12 with treatment of upadacitinib. Overall, the findings support the use of a bodyweight-based dosing regimen for further investigation of upadacitinib in upcoming Phase 3 clinical trials in pediatric AD patients.

Figure 13:
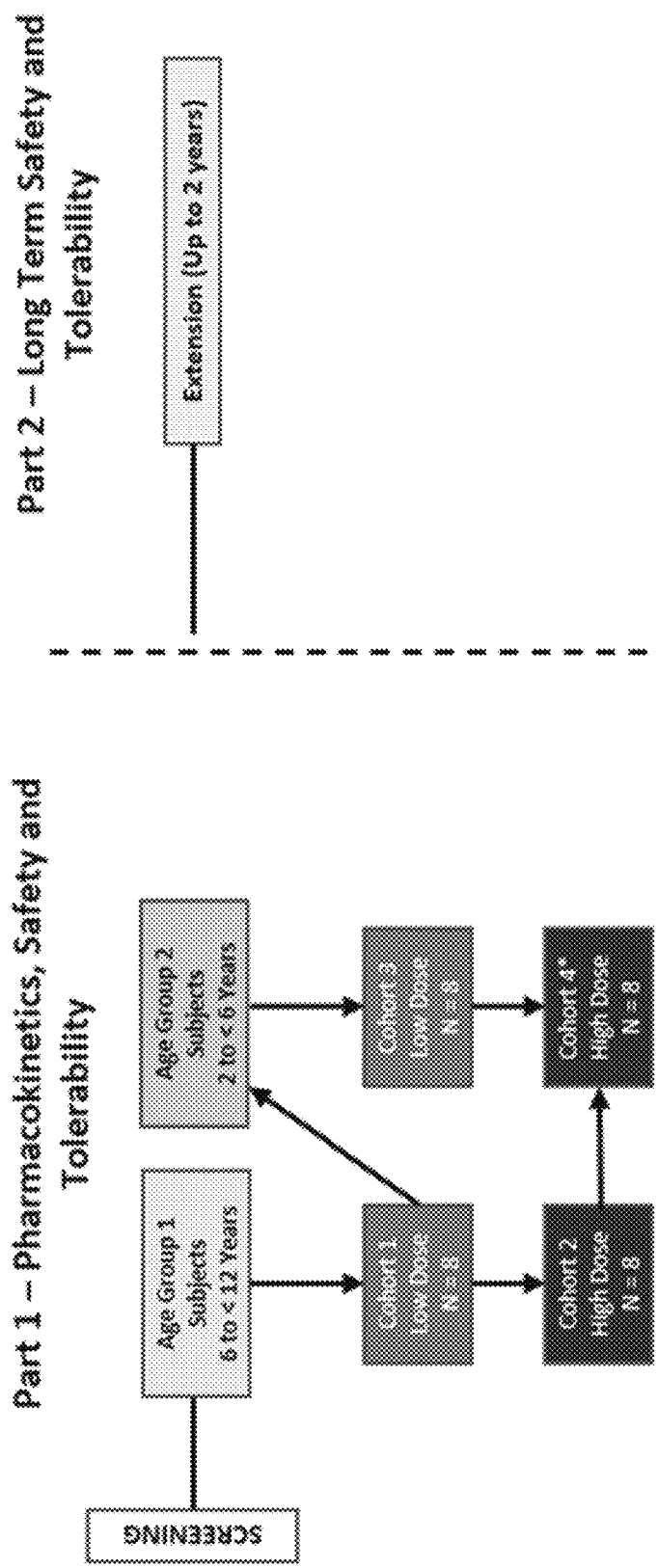
FIG. 13 is a schematic illustration of a clinical study in pediatric atopic dermatitis patients according to a non-limiting embodiment of the disclosure.
Figure 14B:
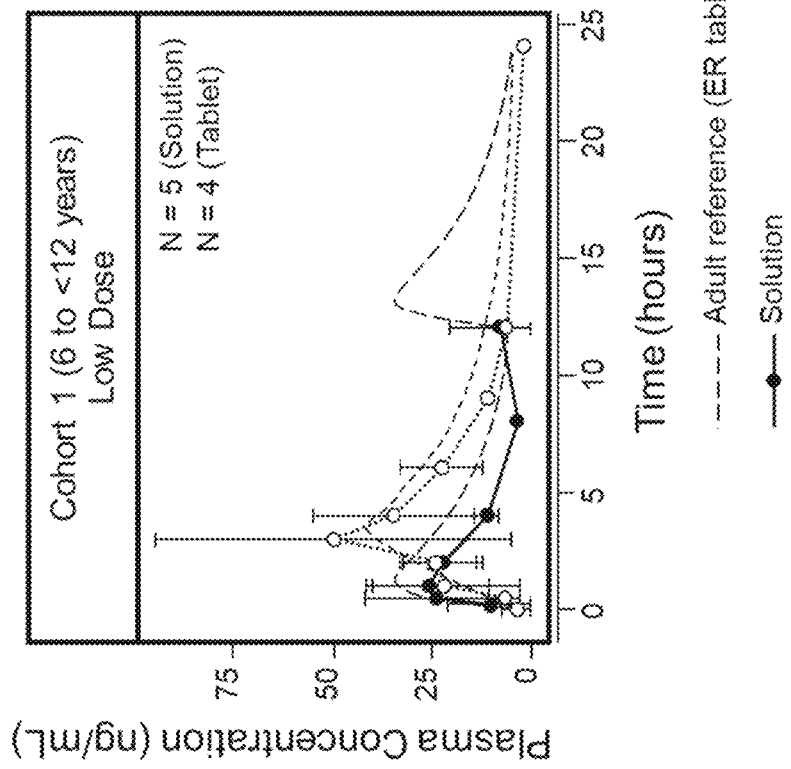
Figure 14A:
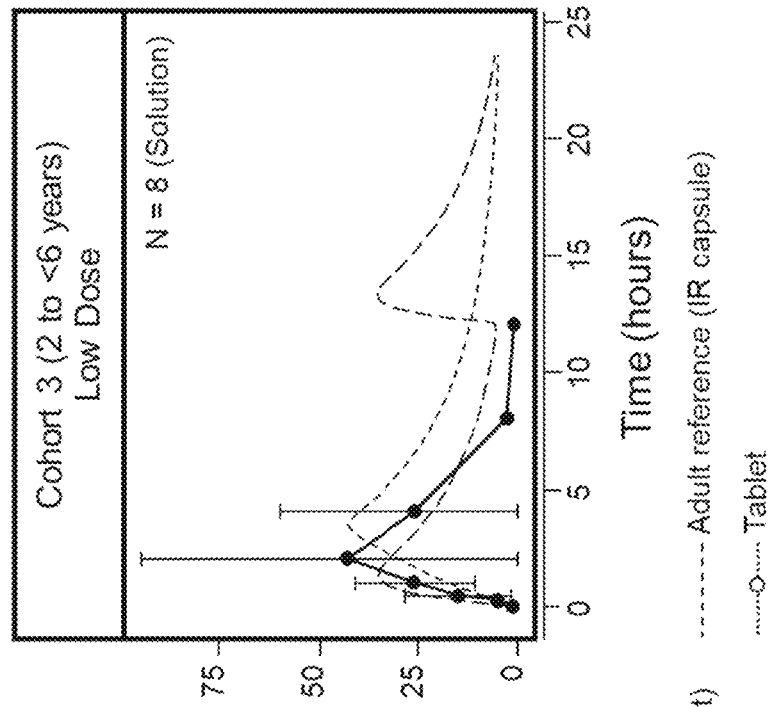

Example 38: Upadacitinib for the Treatment of Severe Atopic Dermatitis in Pediatric Subjects This study was an open-label, multiple-dose phase 1 study to evaluate the pharmacokinetic (PK), safety, and tolerability of upadacitinib in pediatric subjects with severe atopic dermatitis (AD), which remains ongoing.
Study Design
A schematic of the study design is provided in FIG. 13. With reference to FIG. 13, the study consisted of two parts.
Part 1 was a multiple-dose, open-label, multiple-cohort study that consisted of two sequential multiple-ascending dose groups (Low Dose and High Dose levels) in the two age groups. (Group 1: 6 to <12 years and Group 2: 2 to <6 years). Upadacitinib dose was administered based on subject's body weight according to pre-defined body weight categories per dose level with at least 4 subjects in each body weight category (Table 23). The objectives of Part 1 were to evaluate the pharmacokinetics, activity, safety, and tolerability of multiple doses of upadacitinib in pediatric subjects with severe atopic dermatitis and to evaluate the palatability of upadacitinib oral solution in pediatric subjects.
Part 2 was a multiple-dose, open-label, long-term extension to evaluate long term safety and tolerability of upadacitinib. Subjects in Part 2 received open-label upadacitinib at the equivalent of the Low Dose level per the body weight category.

TABLE 23

Upadacitinib Dosing by Body Weight Category and Dose Level for Subjects 2 to <12 years

| | Body Weight Category* Current Dosing Scheme Starting with Protocol Version 4.0 | | |
|---|---|---|---|
| Dose Level | 10 to <20 kg | 20 to <30 kg | ≥30 kg |
| Low Dose | 3 mg BID Oral Solution | 4 mg BID Oral Solution | 15 mg QD Tablet (Or 6 mg BID Oral Solution if unable to swallow tablet) |
| High Dose | 6 mg BID Oral Solution | 8 mg BID Oral Solution | 30 mg QD Tablet (Or 12 mg BID Oral Solution if unable to swallow tablet) |

| | Previous Dosing Scheme Before Protocol Version 4.0 | | | |
|---|---|---|---|---|
| Dose Level | 10 to <15 kg | 15 to <25 kg | 25 to <40 kg | ≥40 kg |
| Low Dose | 1.6 mg BID IR Oral Solution | 2 mg BID IR Oral Solution | 7.5 mg QD ER Tablet or 3 mg BID IR Oral Solution | 15 mg QD ER Tablet or 6 mg BID IR Oral Solution |
| High Dose | 3.2 mg BID IR Oral Solution | 4 mg BID IR Oral Solution | 15 mg QD ER Tablet or 6 mg BID IR Oral Solution | 30 mg QD ER Tablet or 12 mg BID IR Oral Solution |

BID = twice daily;
QD = once daily
*At least 4 children will be enrolled in each weight category.

Subjects who completed Part 1 had the option to enroll in Part 2 and receive open-label low dose upadacitinib. During Part 2 of the study, concomitant topical medications for AD were allowed during the study per investigator discretion. Subjects with an Eczema Area Severity Index (EASI) score worsening of 25% or more compared with their Baseline EASI score at any 2 consecutive scheduled study visits after Week 4 or subjects who did not achieve at least a 50% improvement in their EASI score compared to baseline at 2 consecutive visits on or after Week 8 discontinued study drug and received treatment at investigator's discretion and in accordance with local standard-of-care.

Key Eligibility Criteria

Male or female subjects, ages 2 years to less than 12 years at Screening, and total body weight 10 kg or higher at the time of baseline were eligible to enroll. Criteria for AD included:

Subject diagnosed with AD with onset of symptoms at least 6 months prior to baseline Subject meets Hanifin and Rajka criteria for AD.

Active disease as defined by the following disease activity criteria at the Screening and Baseline Visits (all must be met):

Eczema Area and Severity Index score ≥21;

Validated Investigator Global Assessment for AD (vIGA-AD) score equal to 4;

≥15% body surface area of AD involvement

Have documented history (within 12 months prior to the Baseline Visit) of inadequate response or intolerance to topical corticosteroids (TCS) and topical calcineurin inhibitor (TCI) OR for whom use of TCS and TCIs is otherwise medically inadvisable.

Study Population

Between 31 Jan. 2019 and 18 Mar. 2022, a total of 32 subjects enrolled in the study and received at least one dose of upadacitinib. Enrollment into Cohort 4 is ongoing. An additional 20 subjects were screen failures. The most common reason for pre-screen failure was the inability of subjects to meet the Hanifin and Rayka criteria for AD. One subject (3.1%) and 10 subjects (32.3%) in Part 1 and Part 2, respectively, discontinued upadacitinib. In Part 2, the most common reason for discontinuation was lack of efficacy (n=4, 12.9%) and adverse event (n=3, 9.7%).

The median duration of upadacitinib exposure across all study subjects in Part 1 was 7.0 days (range: 1 to 9 days) and 170 days (range: 1 to 770 days) in Part 2 (Table 24).

tinib at the revised dosing regimen. There was one additional subject who was enrolled in Cohort 3 but withdrew informed consent before PK assessment. This subject was therefore not included in PK analyses. For the analyses of plasma concentration versus time profiles and pharmacokinetic parameters, data from all these subjects were summarized based on cohort and dosage form (FIGS. 14A-14D and Table 28).

Preliminary Clinical Efficacy

Clinical efficacy parameters were collected as exploratory measures and to facilitate the assessment of benefit-risk to justify a continuation of Low Dose upadacitinib during Part 2, the long-term safety and tolerability portion of the study. No formal statistical comparisons were planned. Since all cohorts received Low Dose upadacitinib in Part 2, the overall population was summarized for efficacy.

The pharmacodynamic activity of upadacitinib was demonstrated by efficacy outcome measures that evaluated improvements from baseline across multiple study timepoints. A validated Investigator's Global Assessment scale for Atopic Dermatitis (vIGA-AD) score of 0 or 1 (with at least two grades of reduction from baseline) at Week 12 was achieved by 9/27 subjects (33.3%) in the overall population across cohorts as of the data cutoff (Table 29), signifying achievement of clear or almost clear skin. Notably, activity was observed in the overall population despite 10 subjects in Cohorts 1, 2, and 3 requiring a dose increase to adequately reach the target upadacitinib plasma exposure.

Change from baseline of the Eczema Area and Severity Index by at least 75% (EASI 75) at Week 12 was achieved by 19/27 subjects (70.4%) for the overall population across cohorts as of the data cutoff (Table 30). The mean and median percent change from baseline of the EASI score at Week 12 for the overall population across cohorts was −79.8% and −82.9%, respectively as of the data cutoff (Table 31). For Table 29 to Table 31, results are listed for the overall population, the cohort of 2 to <6 years of age, the cohort of 6 to <12 years of age, subjects enrolled under the original

TABLE 24

Duration of Exposure

| | Part 1 | | | | |
|---|---|---|---|---|---|
| | Cohort 1 (N = 9) | Cohort 2 (N = 8) | Cohort 3 (N = 9) | Cohort 4 (N = 6) | Total (N = 32) |
| Median duration of exposure, days (range) | 7.0 (7-7) | 7.0 (7-7) | 7.0 (1-9) | 7.0 (7-7) | 7.0 (1-9) |
| | Part 2 | | | | |
| | Aged 6 to <12 years (N = 17) | | Aged 2 to <6 years (N = 14) | | Total (N = 31) |
| | 425 (1-770) | | 23.0 (1-623) | | 170 (1-770) |

Demographics (Table 25) and baseline disease characteristics (Table 26) for all subjects enrolled are summarized. The majority of subjects who received upadacitinib were female (n=18, 56.3%), White (n=19, 59.4%), and the median age was 6.0 years (range: 2 to 11 years).

Preliminary Clinical Pharmacokinetics

A summary of upadacitinib PK parameters on Day 7 are provided in FIGS. 14A, 14B, 14C, and 14D and Table 27. For Cohorts 1, 2, 3 and 4, there were 9, 8, 6, and 0 subjects who received upadacitinib at the original protocol defined dosing regimen and 0, 0, 2 and 6 subjects received upadacidosing scheme, and subjects enrolled after the dosing scheme was readjusted to reach the target upadacitinib plasma exposure.

Efficacy outcomes are also summarized for the subgroup of 8 subjects from Cohorts 3 and 4, who were treated with a revised upadacitinib dosing scheme from study entry. Although efficacy outcomes from only 7 of these subjects are available at Week 12, all subjects achieved an EASI 75 response at Week 12. The outcomes of EASI 75, vIGA-AD 0/1 and percent change from baseline of the EASI score in these subjects were consistent with those in the overall population at respective timepoints. For those 10 subjects enrolled under protocol version 3.0 or earlier whose dose was increased at different points in time due to the dose modification implemented with protocol v4.0, response rates as measured by EASI75 and vIGA-AD score of 0 or 1 (with at least two grades of reduction from baseline) numerically improved 12 weeks after the dose increase.

TABLE 25

Demographics

|  | Cohort 1 (N = 9) | Cohort 2 (N = 8) | Cohort 3 (N = 9) | Cohort 4 (N = 6) | Total (N = 32) |
|---|---|---|---|---|---|
| Sex, n (%) | | | | | |
| Male | 3 (33.3) | 2 (25.0) | 4 (44.4) | 5.1 (83.3) | 14 (43.8) |
| Female | 6 (66.7) | 6 (75.0) | 5 (55.6) | 1 (16.7) | 18 (56.3) |
| Age, years, median (range) | 8.0 (6-11) | 7.5 (6-10) | 4.0 (2-5) | 3.0 (2-4) | 6.0 (2-11) |
| Race, n (%) | | | | | |
| White | 4 (44.4) | 6 (75.0) | 6 (66.7) | 3 (50.0) | 19 (59.4) |
| Black or African American | 3 (33.3) | 1 (12.5) | 2 (22.2) | 2 (33.3) | 8 (25.0) |
| Asian | 1 (11.1) | 1 (12.5) | 1 (11.1) | 0 | 3 (9.4) |
| American Indian/Alaska Native | 0 | 0 | 0 | 0 | 0 |
| Native Hawaiian or Other Pacific Islander | 0 | 0 | 0 | 0 | 0 |
| Other Multiple Ethnicity, n (%) | 1 (11.1) | 0 | 0 | 1 (16.7) | 2 (6.3) |
| Hispanic or Latino | 4 (44.4) | 2 (25.0) | 2 (22.2) | 0 | 8 (25.0) |

TABLE 25-continued

Demographics

|  | Cohort 1 (N = 9) | Cohort 2 (N = 8) | Cohort 3 (N = 9) | Cohort 4 (N = 6) | Total (N = 32) |
|---|---|---|---|---|---|
| Not Hispanic or Latino | 5 (55.6) | 6 (75.0) | 7 (77.8) | 6 (100) | 24 (75.0) |
| Weight, kg, median (range) | 26.8 (20.7-45.0) | 33.7 (20.4-56.6) | 18.8 (13.1-26.2) | 15.2 (13.7-18.4) | 22.0 (13.1-56.6) |
| BMI, kg/m2, median (range) | 15.9 (14.5-23.6) | 21.1 (14.4-32.7) | 16.0 (14.6-24.9) | 16.2 (14.2-20.6) | 16.2 (14.2-32.7) |

TABLE 26

Baseline Disease Characteristics

|  | Cohort 1 (N = 9) | Cohort 2 (N = 8) | Cohort 3 (N = 9) | Cohort 4 (N = 6) | Total (N = 32) |
|---|---|---|---|---|---|
| Baseline VIGA-AD, n (%) <4 | 0 9 (100) | 0 8 (100) | 0 9 (100) | 0 6 (100) | 0 32 (100) |
| EASI, median (range) | 27.4 (22.0-59.7) | 31.6 (23.4-53.0) | 28.8 (21.6-47.0) | 28.5 (24.3-32.7) | 28.8 (21.6-59.7) |
| BSA (%) | 50.0 (20-98) | 40.5 (28-100) | 44.0 (25-76) | 56.0 (45-80) | 50.0 (20-100) |
| Disease history, n (%) Yes No | 5 (55.6) 4 (44.4) | 1(12.5) 7 (87.5) | 3 (33.3) 6 (66.7) | 1 (16.7) 5 (83.3) | 10 (31.3) 22 (68.8) |

BSA = body surface area
EASI = Eczema Area and Severity Index

TABLE 27

Summary of Pharmacokinetic Parameters of Upadacitinib in Pediatric Subjects with AD

| Pharmacokinetic Parameter Low Dose | 6 to <12 years (N=17) Cohort 1 | | 2 to <6 years (N = 13) Cohort 3 |
|---|---|---|---|
| | IR Solution (N = 5) | ER Tablet (N = 4) | IR Solution (N = 7) |
| $C_{max}$ (ng/ml) | 24.7 (27.9, 53) | 47.7 (57.2, 72) | 35.2 (47.4, 103) |
| $T_{max}{}^a$ (h) | 1.0 (0.5, 2.0) | 2.5 (1.0, 4.0) | 2.0 (1.0, 4.0) |
| $t_{1/2}{}^b$ (h) | 2.35 (0.59) | 5.79 (1.20) | 1.67 (0.66) |
| $AUC_{0-24}{}^c$ (ng · h/mL) | 224 (248, 55) | 283 (289, 23) | 264 (349, 107) |
| $CL_{ss}/F$ (L/h) | 19.3 (20.2, 31) | 31.5 (34.2, 48) | 15.6 (18.6, 52) |

| High Dose | Cohort 2 | | Cohort 4 |
|---|---|---|---|
| | IR Solution (N = 3) | ER Tablet (N = 5) | IR Solution (N = 6) |
| $C_{max}$ (ng/ml) | 43.2 (46.8, 43) | 154 (166, 50) | 96.9 (111, 51) |
| $T_{max}{}^a$ (h) | 2.0 (0.25, 4.0) | 2.0 (0.5, 3.0) | 0.75 (0.25, 1.0) |
| $t_{1/2}{}^b$ (h) | 1.68 (0.34) | 4.93 (1.06) | 2.25 (0.514) |

TABLE 27-continued

Summary of Pharmacokinetic Parameters of Upadacitinib in Pediatric Subjects with AD

| AUC$_{0-24}$<sup>c</sup> (ng · h/mL) | 347 (355, 25) | 668 (679, 20) | 579 (633, 38) |
| CL$_{ss}$/F (L/h) | 23.0 (23.6, 27) | 39.1 (42.3, 37) | 20.7 (23.6, 66) |

AUC$_{0-24}$ = area under the plasma concentration-time curve over the last 24 hr dosing interval;
BID = twice daily;
C$_{max}$ = maximal concentration;
CL$_{ss}$/F = apparent total body clearance after oral administration (at steady state);
ER = extended-release;
IR = immediate release;
QD = once daily;
t$_{1/2}$ = half-life;
T$_{max}$ = time to maximal concentration
a. Median (min-max).
b. Harmonic mean (pseudo standard deviation); half-life within a dosing interval.
c. AUC$_{0-24}$ for solution formulated was calculated as AUC$_{0-12}$ × 2.
Note:
Parameters are expressed as geometric mean (mean, % coefficient of variation) unless otherwise noted.

TABLE 28

Proportion of Subjects Achieving vIGA-AD of 0 or 1 with at Least Two Grades of Reduction from Baseline at Week 12 (As Observed)

|  | N | Responder, n (%) | 95% CI |
|---|---|---|---|
| Week 12 Overall | 27 | 9 (33.3) | 16.5-54.0 |
| Age 2 to <6 years | 12 | 3 (25.0) | 5.5-57.2 |
| Age 6 to <12 years | 15 | 6 (40.0) | 16.3-67.7 |
| Enrollment up to protocol v3.0 | 20 | 6 (30.0) | 11.9-54.3 |
| Enrollment on or after protocol v4.0 | 7 | 3 (42.9) | 9.9-81.6 |

Exact confidence intervals based on Clopper-Pearson method.

TABLE 29

Proportion of Subjects Achieving EASI 75 at Week 12 (As Observed) (Intention-to-Treat Population)

|  | N | Responder, n (%) | 95% CI |
|---|---|---|---|
| Week 12 Overall | 27 | 19 (70.4) | 49.8-86.2 |
| Age 2 to <6 years | 12 | 9 (75.0) | 42.8-94.5 |
| Age 6 to <12 years | 15 | 10 (66.7) | 38.4-88.2 |
| Enrollment up to protocol v3.0 | 20 | 12 (60.0) | 36.1-80.9 |
| Enrollment on or after protocol v4.0 | 7 | 7 (100) | 59.0-100.0 |

Exact confidence intervals based on Clopper-Pearson method.

TABLE 30

Change and Percent Change in EASI at Week 12 (As Observed) (Intention-to-Treat Population)

|  |  | Change in EASI | | Percent Change in EASI | |
|---|---|---|---|---|---|
|  | N | Mean | Median | Mean | Median |
| Week 12 Overall | 27 | −24.9 (9.61) | −23.8 (−29.0, −18.2) | −79.8 (19.0) | −82.9 (−93.0, −69.4) |
| Age 2 to <6 years | 12 | −24.8 (6.27) | −25.2 (−26.8, −20.4) | −82.0 (14.6) | −82.8 (−92.5, −73.3) |
| Age 6 to <12 years | 15 | −25.0 (11.86) | −23.7 (−30.1, −16.3) | −78.0 (22.3) | −85.7 (−94.6, −60.0) |
| Enrollment up to protocol v3.0 | 20 | −24.3 (10.55) | −23.8 (−28.1, −17.1) | −76.6 (20.8) | −82.8 (−90.8, −64.6) |
| Enrollment on or after protocol v4.0 | 7 | −26.5 (6.58) | −25.2 (−31.9, −22.6) | −88.8 (8.8) | −88.8 (−98.5, −81.3) |

IQR = interquartile range
SD = standard deviation

Example 39: Upadacitinib Immediate Release Liquid Formulation

For pediatric use, an oral solution was developed to improve acceptability (palatability and swallowability), stability, and manufacturability. Specifically, a stable oral pharmaceutical solution of upadacitinib at 1 mg/mL and 0.5 mg/mL were prepared. Upadacitinib has good solubility at low pH (shown in Table 31). Thus, low pH buffers such as citrate, phosphate, tartrate, and formate are suitable to prepare the oral solution. Buffers with higher pH ranges such as succinate and acetate are also suitable (refer to Example 40) but will result in an oral suspension. Citrate buffer was selected because it has favorable pKa (~3.1), which is close to the final pH of the oral solution. Accordingly, a formulation was developed based on the solubility of upadacitinib in liquid with citric acid and sodium citrate added to completely dissolve upadacitinib.

Upadacitinib has strong bitterness above concentrations of 0.1 mg/mL. An acceptable and palatable formulation has a bitter intensity below 1.0. Hence, a sweetener, taste masking or modifier agent, and flavoring agent can mitigate the bitter taste of upadacitinib. Sweeteners or combinations of sweeteners such as acesulfame potassium, sodium saccharin, sucralose, neotame, sucrose, maltitol, and xylitol are suitable for this oral solution. Taste modifiers such as sodium chloride, citric acid and monoammonium glycyrrhinizate are also suitable for this oral solution. Flavoring agents such as cherry, orange, bubblegum, strawberry, and mango can enhance the acceptability of the formulation.

Upadacitinib oral solution contains water and sweetener that are potential causes of microbial growth. Upadacitinib oral solution is also a multi-dose formulation. Hence preservative is added into the formulation to prevent microbial proliferation. Preservatives such as sodium benzoate and propyl paraben are suitable based on the final pH of the oral solution. Other preservatives such as sodium metabisulfite, benzoic acid, para-hydroxybenzoate, potassium sorbate and para-hydroxybenzoic acid can also be used based on the final pH of the oral solution or suspension.

The upadacitinib 1 mg/mL oral solution C contained citric acid, sodium citrate, sucralose, sodium benzoate, and water. The 1 mg/mL oral solution C was clear and colorless to light yellow. The composition of certain 1 mg/mL and 0.5 mg/mL oral solutions is shown in Table 32.

TABLE 31

Solubility of upadacitinib in different aqueous media at 37° C.

| Medium | pH (Nominal) | pH (Final) | Solubility (mg/mL) |
| --- | --- | --- | --- |
| 0.1 N HCl | 1.0 | 2.57 | 38.4 ± 1.5 |
| 50 mM phosphate | 2.01 | 3.08 | 10.5 ± 0.1 |
| 50 mM citrate | 3.00 | 3.39 | 4.48 ± 0.08 |
| 50 mM citrate | 4.01 | 4.16 | 1.00 ± 0.01 |
| 50 mM citrate | 5.03 | 5.01 | 0.289 ± 0.006 |
| 50 mM citrate | 6.01 | 5.96 | 0.196 ± 0.001 |
| 50 mM phosphate | 7.02 | 7.14 | 0.194 ± 0.001 |
| 50 mM phosphate | 8.02 | 7.99 | 0.200 ± 0.013 |
| 50 mM carbonate | 9.02 | 9.11 | 0.199 ± 0.006 |
| Water | 6.02 | 6.92 | 0.240 ± 0.004 |
| Fed State Simulated Intestinal Fluid (FeSSIF) | 5.01 | 5.10 | 0.455 ± 0.006 |
| FeSSIF | 6.50 | 6.58 | 0.262 ± 0.003 |

TABLE 32

Compositions of proposed upadacitinib oral solutions

| | | Quantity (g) | | |
| --- | --- | --- | --- | --- |
| Formulation Component | Function | A 1 mg/mL | B 0.5 mg/mL | C 1 mg/mL |
| upadacitinib freebase | Active | 0.100 | 0.050 | 0.100 |
| sodium benzoate | Preservative | 0.050 | 0.030 | 0.030 |
| citric acid, anhydrous | pH modifier | 0.288 | 0.213 | 0.213 |
| sodium citrate, dihydrate | Buffer | — | 0.116 | 0.045 |
| sucralose | Sweetener | 0.900 | 0.900 | 0.900 |
| purified water | Solvent | q.s. to 100 | q.s. to 100 | q.s. to 100 |

Example 40. Upadacitinib Immediate Release or Extended-Release Liquid Formulation (Suspension)

An immediate release oral suspension is prepared to accommodate higher dosage strength or higher pH. The buffers, preservatives, and sweeteners listed in Example 39 can be applied in this formulation. Generally, an extended-release liquid formulation is prepared to provide extended-release of upadacitinib for once-daily administration using a release rate modifier, such as an ion exchange resin. The liquid dosage forms comprise an upadacitinib-ion exchange resin complex. The upadacitinib-ion exchange resin complex comprises upadacitinib or a pharmaceutically acceptable salt thereof bound to an ion exchange resin. Suitable ion exchange resins include, but are not limited to, a sulfonated copolymer comprising styrene and divinylbenzene. In some such embodiments, the mobile, or exchangeable, cation is sodium. An exemplary cation ion exchange resin is Amber-Lite™ IRP 69 (DuPont).

Example 41: Safety and Efficacy of Upadacitinib for Pediatric Patients with Polyarticular Course Juvenile Idiopathic Arthritis: An Interim Analysis of an Open-Label, Phase 1 Trial (Analysis of Interim Results of Example 1 Through Week 48)

Figure 15:
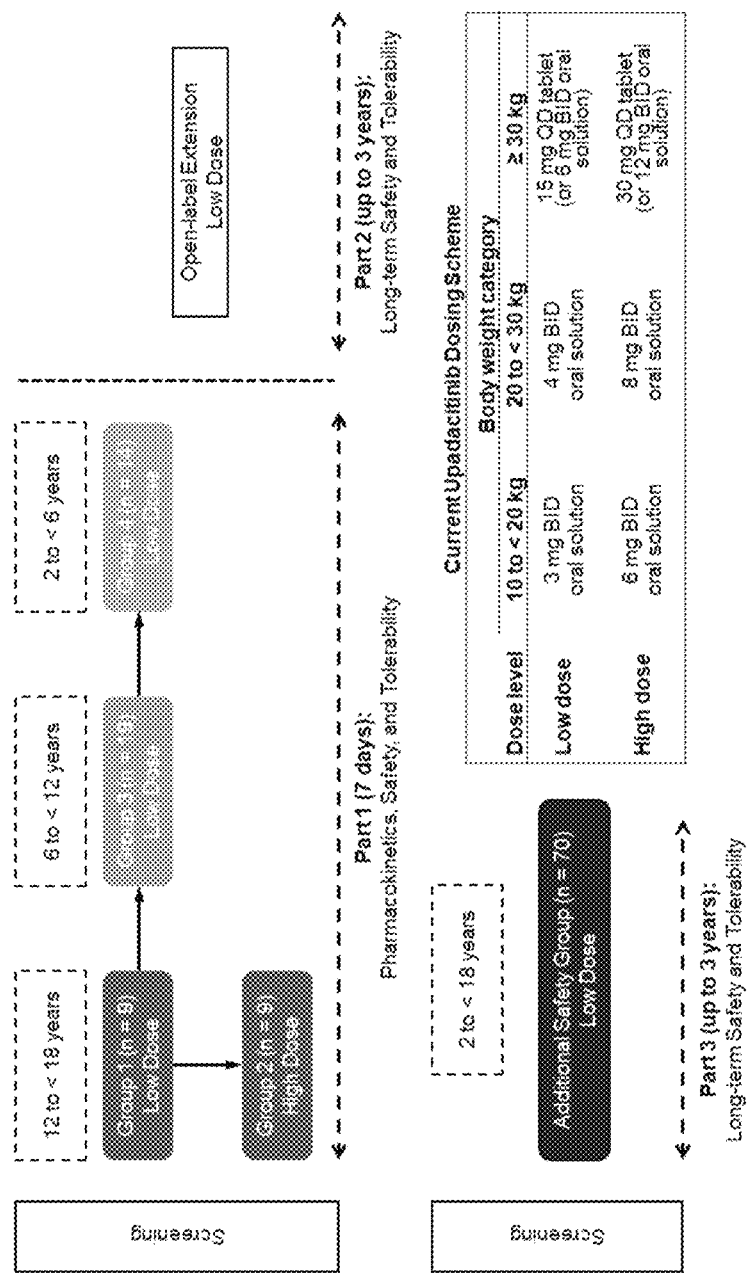
FIG. 15 is a schematic illustration of a clinical study in pediatric polyarticular course juvenile idiopathic arthritis patients according to a non-limiting embodiment of the disclosure.

This Example provides additional data through week 48 for the study described in Example 34.
Objective
The objective of this study was to evaluate the pharmacokinetics, efficacy, and safety of upadacitinib in pediatric patients with polyarticular-course juvenile idiopathic arthritis (pcJIA).
Method
As described above in Example 34, this was an open-label, phase 1 study, enrolling patients aged 2 to <18 years with pcJIA. Patients received bodyweight-based upadacitinib doses using a twice-daily (BID) oral solution or once-daily (QD) extended-release tablet (See Table 33). The study included a 7-day pharmacokinetic assessment, followed by a long-term efficacy and safety evaluation for up to 156 weeks, including an additional long-term safety cohort. This interim analysis includes all available pharmacokinetic and safety data and efficacy data collected through Week 48, excluding patients enrolled in the long-term safety cohort. A schematic depiction of the study design including body weight categories is provided as FIG. 15.

TABLE 33

Upadacitinib Dosing by Body Weight Category and Dose Level for Subjects 2 to <12 years

| Body Weight Category* | | |
| --- | --- | --- |
| Current Dosing Scheme Starting with Protocol Version 4.0 | | |
| Dose Level 10 to <20 kg | 20 to <30 kg | ≥30 kg |

TABLE 33-continued

Upadacitinib Dosing by Body Weight Category and Dose Level for Subjects 2 to <12 years

| | | | |
|---|---|---|---|
| Low Dose | 3 mg BID Oral Solution | 4 mg BID Oral Solution | 15 mg QD Tablet (Or 6 mg BID Oral Solution if unable to swallow tablet) |
| High Dose | 6 mg BID Oral Solution | 8 mg BID Oral Solution | 30 mg QD Tablet (Or 12 mg BID Oral Solution if unable to swallow tablet) |

Previous Dosing Scheme Before Protocol Version 4.0

| Dose Level | 10 to <15 kg | 15 to <25 kg | 25 to <40 kg | ≥40 kg |
|---|---|---|---|---|
| Low Dose | 1.6 mg BID IR Oral Solution | 2 mg BID IR Oral Solution | 7.5 mg QD ER Tablet or 3 mg BID IR Oral Solution | 15 mg QD ER Tablet or 6 mg BID IR Oral Solution |
| High Dose | 3.2 mg BID IR Oral Solution | 4 mg BID IR Oral Solution | 15 mg QD ER Tablet or 6 mg BID IR Oral Solution | 30 mg QD ER Tablet or 12 mg BID IR Oral Solution |

BID = twice daily;
QD = once daily
*At least 4 children will be enrolled in each weight category.

Results

Patients and Disposition

Figure 16:
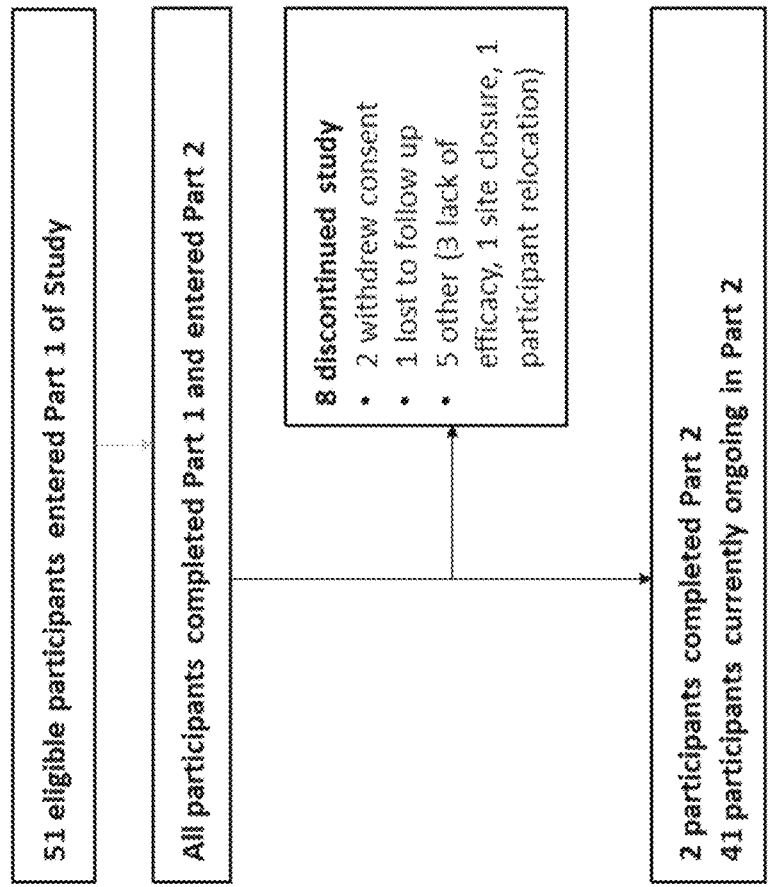
FIG. 16 is a schematic illustration of patient disposition in the clinical study of Example 34.
Figure 18A:
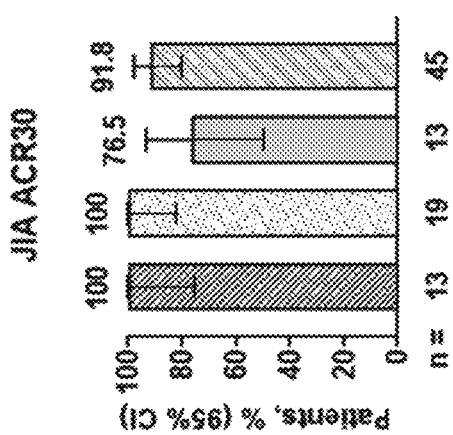
FIGS. 18A to 18E are a series of graphical depictions of efficacy of upadacitinib at week 12 according to various measures and stratified by age group in pediatric polyarticular course juvenile idiopathic arthritis patients according to non-limiting embodiments of the disclosure.
Figure 18B:
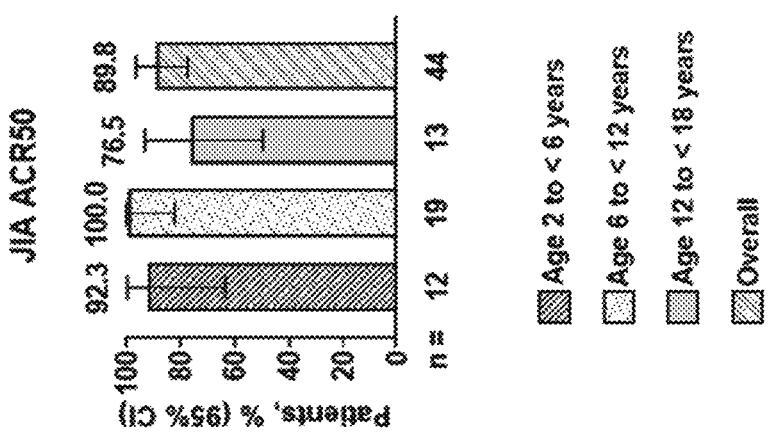
Figure 18C:
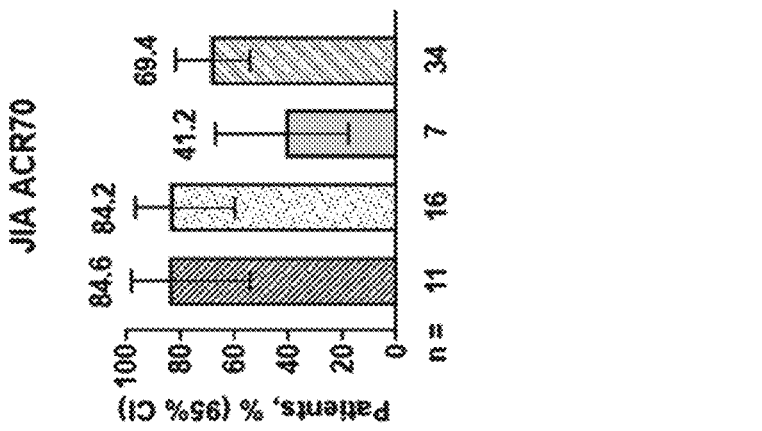
Figure 18E:
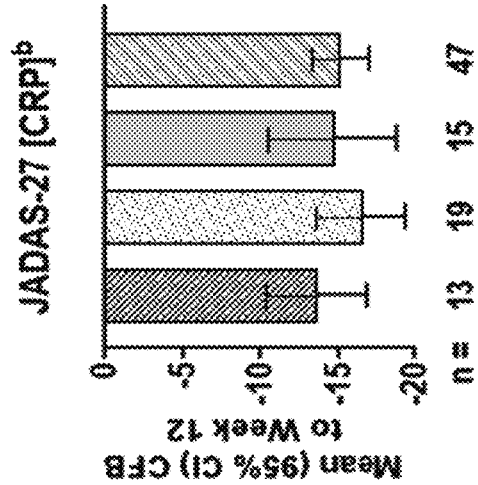
Figure 18D:
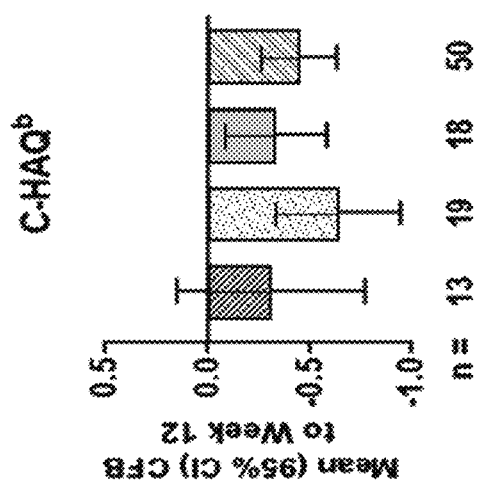

A summary of the patient disposition is provided as FIG. 16. A summary of the patient demographics and disease characteristics is provided in Table 34. With reference to Table 34, the majority of enrolled patients were female (45/57, 78.9%) and had RF-negative polyarticular JRA (42/57, 73.7%). The enrolled patients were between 2 to 17 years old, with a mean disease duration of 3 years. At baseline, 23 (40.4%) patients received methotrexate, 11 (19.3%) patients received oral corticosteroids, and 14 (24.6%) patients reported prior use of bDMARDs.

TABLE 34

Baseline Demographics and Disease Characteristics

| Mean +/− SD (Range) or n (%) | All patients (n = 57) |
|---|---|
| Female, n (%) | 45 (78.9) |
| Age, years, mean ± SD (range) | 9.5 ± 4.41 (2-17) |
| White, n (%) | 55 (96.5) |
| Weight, kg, mean ± SD (range) | 38.05 ± 20.380 (11.0-92.9) |
| pcJIA Type | |
| Extended oligoarticular JIA, n (%) | 7 (12.3) |
| RF-negative polyarticular JIA, n (%) | 42 (73.7) |
| RF-positive polyarticular JIA, n (%) | 7 (12.3) |
| Systemic JIA w active arthritis and w/o active systemic features, n (%) | 1 (1.8) |
| Duration of pcJIA diagnosis, years, mean ± SD (range) | 2.959 ± 3.3387 (0.05-13.23) |
| Active joints, mean ± SD (range) | 11.1 ± 7.74 (5-48) |
| C-HAQ | 1.047 ± 0.7746 (0.00-2.88) |
| CRP (mg/L) | 9.11 ± 18.958 (0.2-92.3) |
| ESR (n = 53) | 19.5 ± 19.02 (2-94) |
| Oral corticosteroids, n (%) | 11 (19.3) |
| Methotrexate, n (%) | 23 (40.4) |
| Prior exposure to bDMARDs | 14 (24.6) | bDMARDs, biological disease-modifying antirheumatic drugs;
CRP, c-reactive protein (normal range ≤2.87 mg/L);
JIA, juvenile idiopathic arthritis;
ESR, erythrocyte sedimentation rate (normal range 3-15 mm/hr);
pcJIA, polyarticular-course juvenile idiopathic arthritis;
n, number of patients;

TABLE 34-continued

Baseline Demographics and Disease Characteristics

| Mean +/− SD (Range) or n (%) | All patients (n = 57) |
|---|---|

RF, rheumatoid factor;
SD, standard deviation

Pharmacokinetics

The mean plasma concentration-time profiles by dose level and formulations compared to adult reference profiles simulated based on pharmacokinetic analyses of upadacitinib data in phase 3 RA studies are presented in FIGS. 17A-17C. Adult RA reference represents median (dashed line) and ($5^{th}$, $95^{th}$) percentiles (shaded area) of upadacitinib model-predicted plasma concentrations in adult patients with RA following administration of QD tablets. These reference pharmacokinetic profiles were simulated using a previously developed model for RA patients. The symbols with decreased opacity (over 12-24 hour) for the IR BID regimens are replicated from the observed data (over 0-12 hour) to account for difference in dosing frequency between the BID oral solution and QD tablet formulations.

A summary of the pharmacokinetic parameters of upadacitinib at steady state (i.e., on Day 7) after administration of upadacitinib in patients enrolled in Part 1 is provided in Table 35. During the pharmacokinetic assessment, 13 patients in Group 3 and 12 patients in Group 4 received revised doses, and all other patients received the original doses. Upadacitinib Cmax was reached within approximately 3 hours and 1 hour following the administration of the ER tablet and the IR oral solution formulations, respectively. Upadacitinib functional $t_{1/2}$ was approximately 5 hours within a QD dosing interval for the ER tablet and 2 hours within a BID dosing interval for the IR solution.

TABLE 35

Geometric Mean (Mean, % CV) Pharmacokinetic Parameters of Upadacitinib by Study Group and Dosing Regimen (Part 1)

| Pharmacokinetic parameters (units) | Age 12 to <18 years | | Age 6 to <12 years | | | Age 2 to <6 years Group 4: |
|---|---|---|---|---|---|---|
| | Group 1: | Group 2: | Group 3: low dose | | | low dose |
| | low dose QD tablet (n = 9) | high dose QD tablet (n = 9) | QD tablet (n = 12) | BID solution (n = 7) | Combined$^g$ (n = 19) | BID solution (n = 12)$^i$ |
| $C_{max}$ (ng/ml) | 35.1 | 69.8 | 46.9 | 58.9 | 51.0 | 46.6 |
| | (37.2, 35) | (71.2, 19) | (52.3, 46) | (62.5, 35) | (56.1, 41) | (55.8, 56) |
| $T_{max}^a$ (h) | 3.0 | 4.0 | 3.0 | 1.0 | — | 1.0 |
| | (1.0-6.0) | (2.0-6.0) | (1.0-6.0)$^f$ | (0.5-1.0) | | (0.5-2.0) |
| Functional | 5.53 | 4.79 | 5.20 | 2.39 | — | 2.33 |
| $t_{1/2}^b$ (h) | (1.77) | (1.12) | (0.949)$^f$ | (0.277) | | (0.351)$^j$ |
| $AUC_{tau}$ | 269 | 553 | 318 | 198 | — | 184 |
| (ng·h/mL) | (282, 32)$^e$ | (572, 26) | (351, 41) | (209, 36) | | (217, 61)$^j$ |
| $AUC_{0-24}^c$ | 269 | 553 | 318 | 397 | 346 | 369 |
| (ng·h/mL) | (282, 32)$^e$ | (572, 26) | (351, 41)$^f$ | (417, 36) | (377, 38)$^h$ | (433, 61)$^j$ |
| $CL_{ss}/F$ (L/h) | 55.7 | 46.5 | 41.6 | 19.7 | — | 15.0 |
| | (58.2, 32)$^e$ | (49, 38) | (46.7, 67)$^f$ | (20.2, 25) | | (16.8, 49)$^j$ |
| $CL_{ss}/F\_adjusted^d$ | 38.1 | 31.8 | 28.5 | 19.7 | 24.7 | 15.0 |
| (L/h) | (39.8, 32)$^e$ | (33.5, 38) | (32.0, 67)$^f$ | (20.2, 25) | (27.4, 65)$^h$ | (16.8, 49)$^j$ |

AUC, area under the plasma concentration-time curve from time 0 to 24 hr ($AUC_{0-24}$) or over a dose interval ($AUC_{tau}$);
BID, twice daily;
Cmax, maximal plasma concentration;
$CL_{ss}/F$, apparent oral clearance at steady state;
$CL_{ss}/F\_adjusted$, $CL_{ss}/F$ adjusted for bioavailability;
n, number of patients;
QD, once daily;
$T_{max}$, time to maximal plasma concentration;
functional $t_{1/2}$, functional half-life.
$^a$Median (minimum through maximum).
$^b$Harmonic mean (pseudo-standard deviation).
$^c$For QD tablet, $AUC_{0-24} = AUC_{tau}$; for BID oral solution, $AUC_{0-24} = AUC_{tau} \times 2$.
$^d$$CL_{ss}/F$ adjusted for the difference in bioavailability between formulations. For QD tablet, $CL_{ss}/F\_adjusted = 0.684 \times CL_{ss}/F$; For BID oral solution, $CL_{ss}/F\_adjusted = CL_{ss}/F$.
$^e$n = 8.
$^f$n = 11.
$^g$$C_{max}$, $AUC_{0-24}$, and $CL_{ss}/F\_adjusted$ of the ER tablet and IR oral solution formulations are combined and summarized together for Group 3.
$^h$n = 18.
$^i$One patient was excluded for receiving an incorrect dose during the entire Part 1 period, and another patient that did not receive a dose on Day 7 due to an AE of vomiting was also excluded.
$^j$n = 10.

Efficacy

Figure 19A:
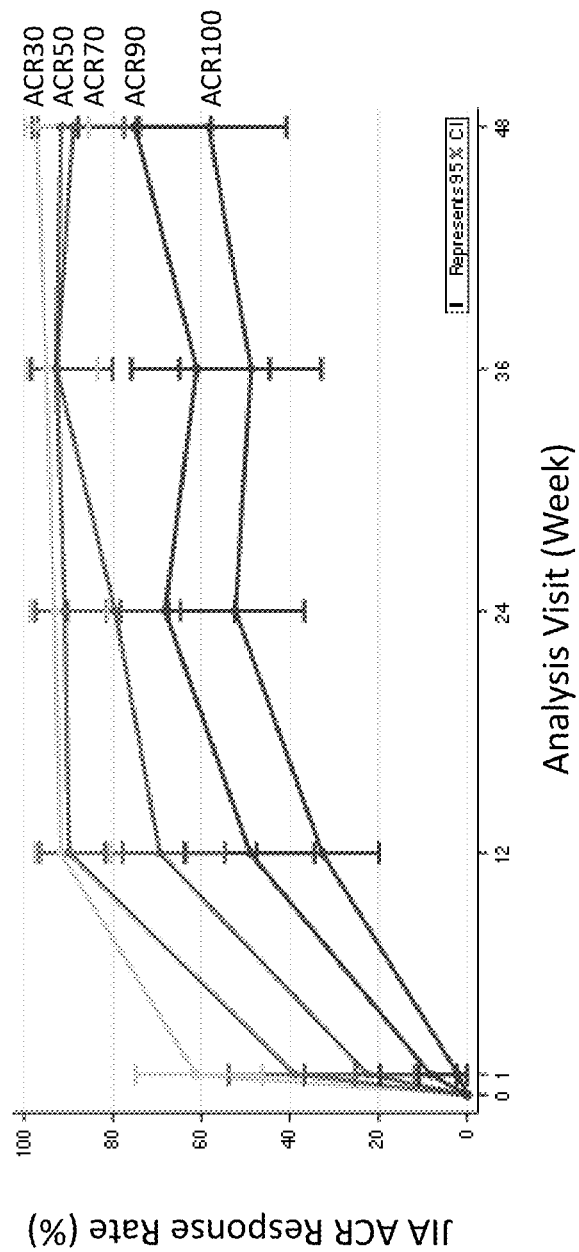
FIG. 19A is a graphical depiction of efficacy of upadacitinib over time through week 48 according to JIA ACR response rate in pediatric polyarticular course juvenile idiopathic arthritis patients according to non-limiting embodiments of the disclosure.
Figure 19B:
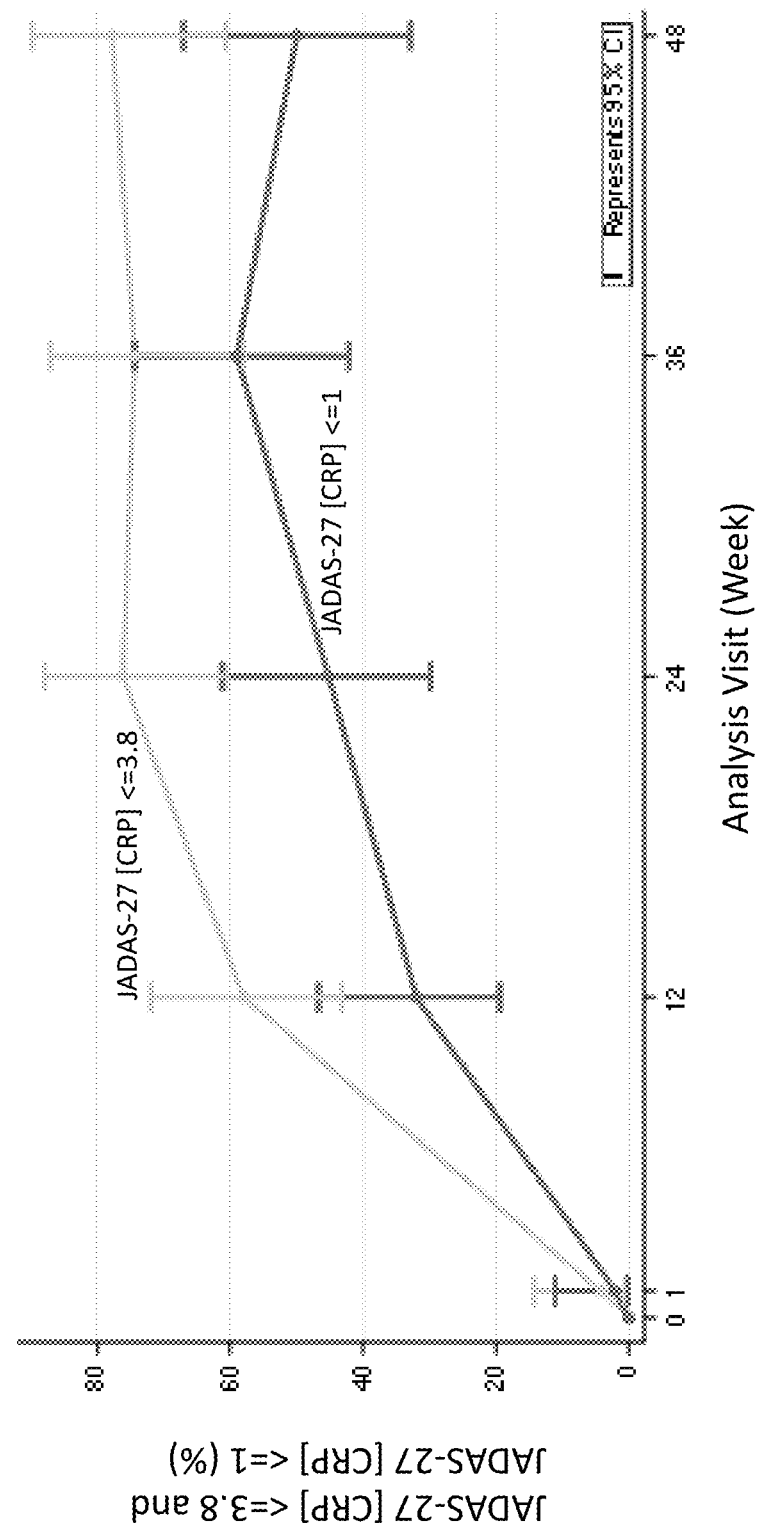
FIG. 19B is a graphical depiction of efficacy of upadacitinib over time through week 48 according to JADAS-27 [CRP] response rate in pediatric polyarticular course juvenile idiopathic arthritis patients according to non-limiting embodiments of the disclosure.
Figure 19C:
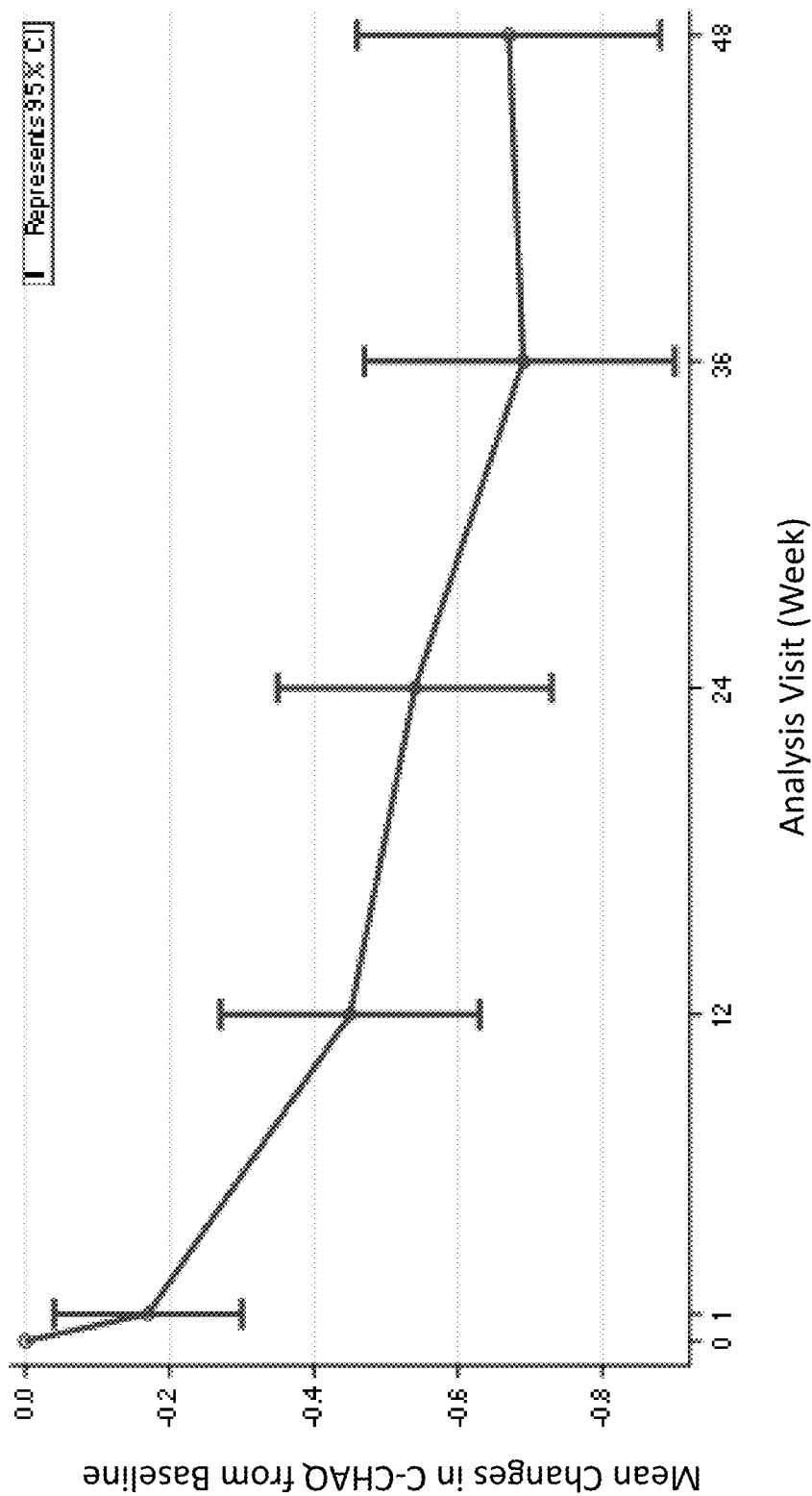
FIG. 19C is a graphical depiction of efficacy of upadacitinib over time through week 48 according to mean change in C-CHAQ from baseline in pediatric polyarticular course juvenile idiopathic arthritis patients according to non-limiting embodiments of the disclosure.
Figure 19D:
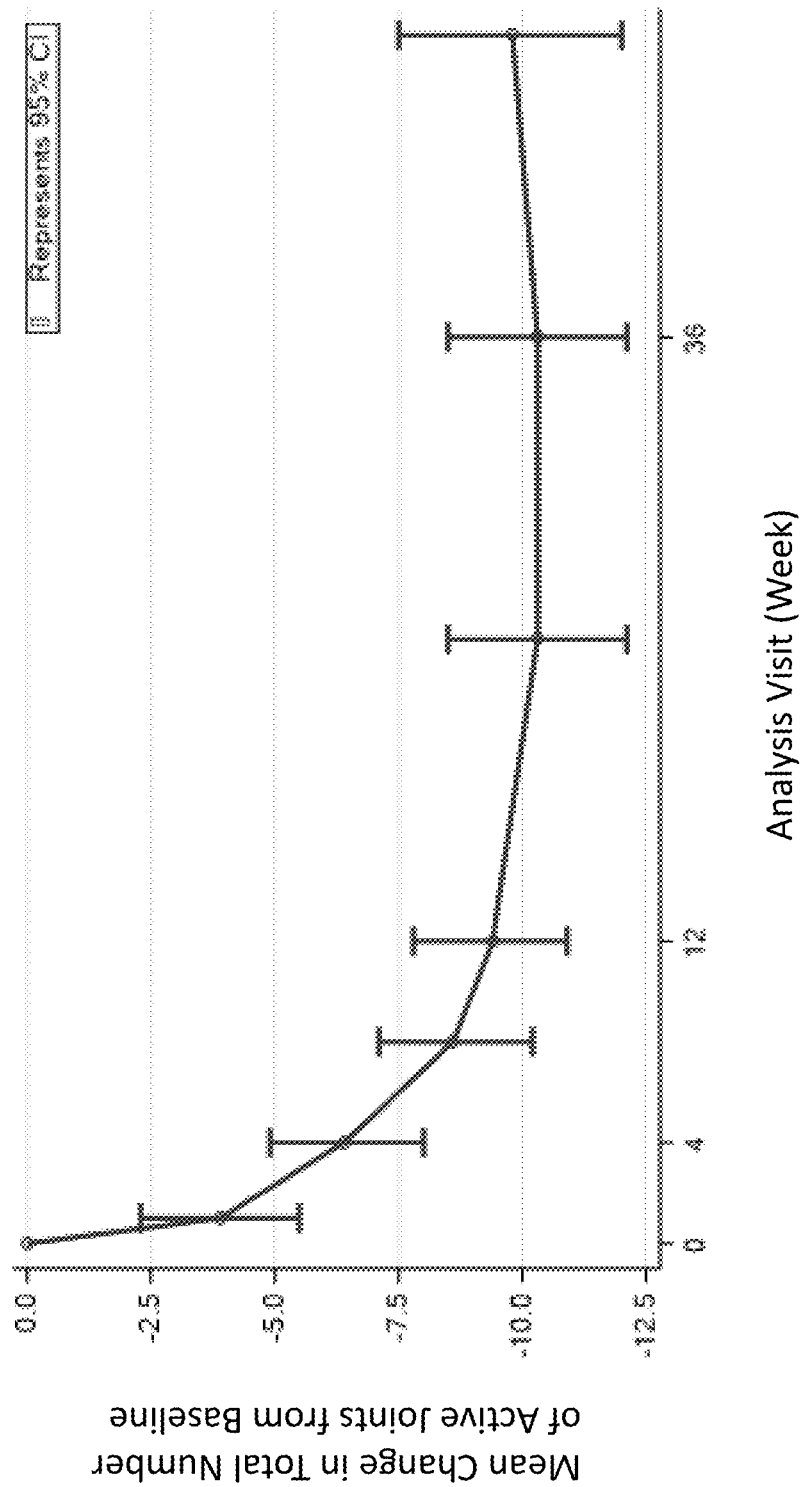
FIG. 19D is a graphical depiction of efficacy of upadacitinib over time through week 48 according to mean change in total number of active joints from baseline in pediatric polyarticular course juvenile idiopathic arthritis patients according to non-limiting embodiments of the disclosure.

Up to the data cutoff date, 50 of 51 patients from Parts 1 and 2 had efficacy results available at Week 12, and 37 patients had efficacy results available through Week 48, by which point 35 of the 37 patients were being treated with the revised upadacitinib dosing scheme. A summary of the JIA ACR 30/50/70 responses, C-HAQ, and JADAS-27 CRP at Week 12 is presented in FIGS. 18A to 18E, respectively. Overall, the percentage of patients in Parts 1 and 2 who achieved JIA ACR 30/50/70/90/100 response at Week 12 were 91.8/89.8/69.4/49.0/32.7%. The two younger age groups (2 to <6 years and 6 to <12 years) had similar improvements in JIA ACR responses, and the oldest age group (12 to <18 years) had numerically lower rates of JIA ACR responses compared to the younger age groups without statistical significance. Response to upadacitinib was rapid, with 61.2% of patients achieving JIA ACR 30 as early as Week 1. JIA ACR responses continued to improve at Week 24 and were generally maintained through Week 48 (FIG. 19A). Additional key efficacy measurements, including C-HAQ, total number of active joints, Physician's Global Assessment of Disease Activity (VAS), Patient/Parent Global Assessment of Overall Well Being (VAS), and JADAS-27 CRP, JADAS-27 ESR, ESR, and CRP are summarized in Table 36. Across these efficacy measures at Week 12, improvement from baseline was observed in all age groups and changes from baseline were consistent between the age groups. Changes in JADAS-27 ESR were similar to those for JADAS-27 CRP. Twenty-nine (29) of 50 patients (58%) achieved JADAS-27 CRP≤3.8 and 16 of 50 patients (32%) achieved JADAS-27 CRP≤1 at Week 12. The proportions of patients achieving these responses further increased at Week 24 and were generally maintained through Week 48 (FIGS. 19B, 19C, and 19D).

TABLE 36

Summary of Select Efficacy Endpoints at Week 12 (Parts 1 and 2)

| Efficacy Endpoint Age Group | n | Baseline Mean | Visit Mean | Within Group Change from Baseline Mean (95% CI) | Median (Min, Max) |
|---|---|---|---|---|---|
| C-HAQ | | | | | |
| 2 to <6 years | 13 | 0.85 | 0.54 | −0.31 (−0.77, 0.15) | −0.38 (−1.3, 1.1) |
| 6 to <12 years | 19 | 1.07 | 0.43 | −0.64 (−0.95, −0.34) | −0.38 (−1.9, 1.1) |
| 12 to <18 years | 18 | 1.04 | 0.71 | −0.33 (−0.58, −0.09) | −0.31 (−1.1, 0.5) |
| Overall | 50 | 1.00 | 0.56 | −0.45 (−0.63, −0.27) | −0.38 (−1.9, 1.1) |
| Total Number of Active Joints | | | | | |
| 2 to <6 years | 13 | 8.1 | 1.1 | −7.0 (−8.8, −5.2) | −6.0 (−12, −3) |
| 6 to <12 years | 19 | 11.6 | 1.4 | −10.2 (−13.0, −7.5) | −8.0 (−24, −4) |
| 12 to <18 years | 18 | 11.7 | 1.5 | −10.2 (−13.3, −7.2) | −9.0 (−25, 0) |
| Overall | 50 | 10.7 | 1.3 | −9.4 (−10.9, −7.8) | −8.0 (−25, 0) |
| Physician's Global Assessment of Disease Activity (VAS) | | | | | |
| 2 to <6 years | 13 | 51.6 | 6.1 | −45.5 (−53.6, −37.5) | −49.0 (−72, −25) |
| 6 to <12 years | 19 | 59.3 | 4.1 | −55.3 (−65.2, −45.3) | −55.0 (−100, −28) |
| 12 to <18 years | 15 | 62.4 | 16.1 | −46.3 (−63.2, −29.4) | −41.0 (−94, 9) |
| Overall | 47 | 58.2 | 8.4 | −49.7 (−56.4, −43.0) | −49.0 (−100, 9) |
| Patient/Parent Global Assessment of Overall Well Being (VAS) | | | | | |
| 2 to <6 years | 13 | 48.4 | 15.6 | −32.8 (−52.2, −13.4) | −38.0 (−81, 37) |
| 6 to <12 years | 19 | 42.3 | 13.5 | −28.8 (−39.2, −18.4) | −29.0 (−61, 9) |
| 12 to <18 years | 18 | 45.8 | 26.2 | −19.6 (−28.3, −10.8) | −23.0 (−45, 8) |
| Overall | 50 | 45.1 | 18.6 | −26.5 (−33.2, −19.8) | −26.0 (−81, 37) |
| JADAS27-CRP | | | | | |
| 2 to <6 years | 13 | 16.81 | 3.17 | −13.65 (−16.88, −10.42) | −12.86 (−22.4, −5.1) |
| 6 to <12 years | 19 | 19.40 | 2.85 | −16.55 (−19.42, −13.68) | −16.90 (−28.9, −7.2) |
| 12 to <18 years | 15 | 20.30 | 5.58 | −14.72 (−18.88, −10.55) | −14.40 (−31.1, −0.3) |
| Overall | 47 | 18.97 | 3.81 | −15.16 (−17.02, −13.30) | −14.59 (−31.1, −0.3) |
| JADAS27-ESR | | | | | |
| 2 to <6 years | 11 | 16.23 | 3.14 | −13.09 (−16.73, −9.46) | −13.70 (−22.4, −5.8) |
| 6 to <12 years | 19 | 19.91 | 2.83 | −17.08 (−20.19, −13.98) | −16.90 (−30.6, −7.2) |
| 12 to <18 years | 15 | 20.41 | 5.78 | −14.63 (−18.86, −10.41) | −13.70 (−31.7, −0.2) |
| Overall | 45 | 19.18 | 3.89 | −15.29 (−17.30, −13.28) | −14.40 (−31.7, −0.2) |
| ESR | | | | | |
| 2 to <6 years | 9 | 25.6 | 11.2 | −14.3 (−25.9, −2.8) | −7.0 (−39, 2) |
| 6 to <12 years | 19 | 18.8 | 8.9 | −9.9 (−17.3, −2.5) | −4.0 (−41, 7) |
| 12 to <18 years | 16 | 13.6 | 13.3 | −0.3 (−5.8, 5.3) | −2.5 (−17, 26) |
| Overall | 44 | 18.3 | 11.0 | −7.3 (−11.7, −2.9) | −4.0 (−41, 26) |
| CRP | | | | | |
| 2 to <6 years | 11 | 19.362 | 0.933 | −18.429 (−36.310, −0.548) | −4.450 (−77.05, 0.06) |
| 6 to <12 years | 18 | 4.573 | 1.312 | −3.261 (−6.110, −0.412) | −0.820 (−16.70, 5.50) |
| 12 to <18 years | 18 | 2.777 | 2.981 | 0.204 (−2.836, 3.245) | −0.150 (−16.49, 17.20) |
| Overall | 47 | 7.346 | 1.862 | −5.484 (−9.981, −0.987) | −0.390 (−77.05, 17.20) |

| Efficacy Endpoint Age Group | n | Responder n (%), [95% CI] |
|---|---|---|
| JADAS27-CRP ≤3.8 (minimal disease activity) | | |
| 2 to <6 years | 13 | 9 (69.2), [38.6, 90.9] |
| 6 to <12 years | 19 | 13 (68.4), [43.4, 87.4] |
| 12 to <18 years | 18 | 7 (38.9), [17.3, 64.3] |
| Overall | 50 | 29 (58.0), [43.2, 71.8] |
| JADAS27-CRP ≤1 (inactive disease) | | |
| 2 to <6 years | 13 | 5 (38.5), [13.9, 68.4] |
| 6 to <12 years | 19 | 9 (47.4), [24.4, 71.1] |
| 12 to <18 years | 18 | 2 (11.1), [1.4, 34.7] |
| Overall | 50 | 16 (32.0), [19.5, 46.7] |

Discussion

In this open-label Phase 1 study, upadacitinib administered as a fixed dose per body weight category was efficacious and well tolerated in pediatric patients with pcJIA. The observed upadacitinib pharmacokinetics in pediatric patients with pcJIA for the QD regimen using the ER formulation and the BID regimen using the IR formulation were consistent with the characterized upadacitinib pharmacokinetics in adults for the respective formulations.

The original dosing regimen of upadacitinib was selected by leveraging pharmacokinetic data of upadacitinib in adult patients with RA and allometric scaling of clearance and volume of distribution based on body weight, with a goal of achieving upadacitinib exposures in patients with pcJIA similar to the exposures which were shown to be optimal in adult RA patients. In this study, a preliminary population pharmacokinetic analysis indicated that the apparent oral clearance of upadacitinib in pediatric patients was underestimated when an estimate of upadacitinib clearance from adult RA patients with a typical exponent of 0.75 was used to describe the relationship between body weight and clearance. Accordingly, a revised dosing regimen was developed and utilized in the younger pediatric patients (the majority of 6 to <12 years and 2 to <6 years) to enable the attainment of upadacitinib exposures comparable to the target exposures in adults with RA. Based on previous analyses, the median ($5^{th}$, $95^{th}$ percentile) upadacitinib area under the plasma concentration-time curve (AUC) at steady state in adult patients with RA in phase 3 trials was 358 (234, 701) and 708 (466, 1332) ng·h/mL after daily administration of 15 mg and 30 mg ER tablets, respectively. Compared to the target median adult exposure ($AUC_{0-24}$), the relative median upadacitinib $AUC_{0-24}$ within each group in this study ranged from approximately 0.77 to 1.07 (Table 37). In the younger pediatric patients, where the majority received revised doses, the observed upadacitinib exposures were nearly identical to the target exposures in adult patients with a ratio of 1.01.

In this study, an IR BID oral solution formulation was used for patients with lower body weight (i.e., <30 kg) or unable to swallow tablets. Despite distinct pharmacokinetic profiles due to different dosing frequency, the BID oral solution is expected to provide similar efficacy in pcJIA relative to the QD tablet if similar upadacitinib $AUC_{0-24}$ can be achieved. This is supported by previously conducted exposure-response analyses of key efficacy endpoints in adult RA patients, where a model developed based on data from a BID capsule formulation in phase 2 studies successfully predicted the observed efficacy of the QD tablet formulation in phase 3 studies. The analyses showed that the upadacitinib BID IR and QD ER regimens providing similar $AUC_{0-24}$ were predicted to achieve similar efficacy responses.

Based on the descriptive analyses of efficacy endpoints, improvements in measures of pcJIA disease activity, pain, function, and overall well-being were observed after administration of upadacitinib at Week 12 in this study and were generally maintained through Week 48. Improvements with upadacitinib were observed across the evaluated age groups, which included patients with pcJIA ages 2 to <18 years old, with numerically higher response rates in patients ages 2 to <12 years than those 12 to <18 years. Notably, most patients in the oldest age group had longer disease duration and prior bDMARDs exposure. In comparison, most patients in the younger age groups had shorter disease duration and no prior bDMARD exposure (Table 34). There were no patients with a history of uveitis and no uveitis events occurred during the study. The safety profile of upadacitinib in pediatric patients with pcJIA was generally consistent with the currently known safety profile of upadacitinib in adults and adolescents with inflammatory conditions.

Overall, upadacitinib was well tolerated and efficacious in patients with pcJIA across all age groups (age 2 to <18 years) with plasma exposures comparable to adult RA patients at the evaluated dosing regimens. No new safety risks were observed in pcJIA patients, and the benefit-risk profile of upadacitinib was assessed as favorable based on the safety and efficacy outcomes of the study to date.

TABLE 37

Comparison of Upadacitinib Plasma Exposures between Pediatric Patients with pcJIA and Adult Patients with RA

| | Median $AUC_{0-24}$ (ng · h/mL) | Ratio to Adults |
|---|---|---|
| Low-dose level (corresponding totff the 15 mg ER tablet in adults) | | |
| Adult Patients with RA | 358 | |
| Group 1 (12 to <18 years) | 278 | 0.78 |
| Group 3 (6 to <12 years) | 383 | 1.07 |
| Group 4 (2 to <6 years) | 360 | 1.01 |
| High-dose level (corresponding to the 30 mg ER tablet in adults) | | |
| Adult Patients with RA | 708 | |
| Group 2 (12 to <18 years) | 547 | 0.77 |

ER, extended-release; pcJIA, polyarticular-course juvenile idiopathic arthritis; RA, rheumatoid arthritis All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed:

1. A method for treating juvenile idiopathic arthritis in a human patient in need thereof, comprising orally administering once daily to the patient a tablet comprising a therapeutically effective amount of (3S,4R)-3-ethyl-4-(3H-imidazo [1,2-a]pyrrolo [2,3-e]pyrazin-8-yl)-N-(2,2,2-trifluoroethyl) pyrrolidine-1-carboxamide (Compound 1), wherein the therapeutically effective amount is 15 mg.

2. The method of claim 1, wherein the patient achieves an ACR50 score at week 12 of treatment.

3. The method of claim 1, wherein the patient achieves an ACR70 score at week 12 of treatment.

4. A method for treating polyarticular course juvenile idiopathic arthritis (pcJIA) in a pediatric patient in need thereof, the method comprising administering a therapeutically effective amount of upadacitinib to the pediatric patient, wherein:
   if the pediatric patient has a body weight in a range from about 10 kg to less than about 20 kg, administering upadacitinib twice daily as an oral pharmaceutical solution at a dose of 3 mg each (3 mg BID);
   if the pediatric patient has a body weight in a range from about 20 kg to less than about 30 kg, administering upadacitinib twice daily as an oral pharmaceutical solution at a dose of 4 mg each (4 mg BID); and
   if the pediatric patient has a body weight of about 30 kg or greater, administering upadacitinib twice daily as an oral pharmaceutical solution at a dose of 6 mg each (6 mg BID), or administering upadacitinib once daily as a tablet at a dose of 15 mg (15 mg QD).

5. The method of claim 4, wherein the pediatric patient has a body weight in a range from about 10 kg to less than about 20 kg, and the method comprises administering upadacitinib twice daily as an oral pharmaceutical solution at a dose of 3 mg each (3 mg BID).

6. The method of claim 4, wherein the pediatric patient has a body weight in a range from about 20 kg to less than about 30 kg, and the method comprises administering upadacitinib twice daily as an oral pharmaceutical solution at a dose of 4 mg each (4 mg BID).

7. The method of claim 4, wherein the pediatric patient has a body weight of about 30 kg or greater, and the method comprises administering upadacitinib twice daily as an oral pharmaceutical solution at a dose of 6 mg each (6 mg BID).

8. The method of claim 4, wherein the pediatric patient has a body weight of about 30 kg or greater, and the method comprises administering upadacitinib once daily as a tablet at a dose of 15 mg (15 mg QD).

9. The method of claim 4, wherein the pcJIA is rheumatoid factor-positive JIA.

10. The method of claim 4, wherein the pcJIA is rheumatoid factor-negative polyarticular JIA.

11. The method of claim 4, wherein the pcJIA is extended oligoarticular JIA.

12. The method of claim 4, wherein the pcJIA is systemic JIA with active arthritis and without active systemic features.

13. The method of claim 4, wherein the pediatric patient achieves a JIA ACR pediatric 30 response at 12 weeks after the first daily administration.

14. The method of claim 4, wherein the pediatric patient achieves a JIA ACR pediatric 50 response at 12 weeks after the first daily administration.

15. The method of claim 4, wherein the pediatric patient achieves a JIA ACR pediatric 70 response at 12 weeks after the first daily administration.

16. The method of claim 4, wherein the pediatric patient achieves a JIA ACR pediatric 90 response at 12 weeks after the first daily administration.

17. The method of claim 4, wherein the pediatric patient achieves a JIA ACR pediatric 30 response at 48 weeks after the first daily administration.

18. The method of claim 4, wherein the pediatric patient achieves a JIA ACR pediatric 50 response at 48 weeks after the first daily administration.

19. The method of claim 4, wherein the pediatric patient achieves a JIA ACR pediatric 70 response at 48 weeks after the first daily administration.

20. The method of claim 4, wherein the pediatric patient achieves a JIA ACR pediatric 90 response at 48 weeks after the first daily administration.

21. The method of claim 1, wherein the subject has had an inadequate response or intolerance to one or more disease-modifying antirheumatic drugs (DMARDs).

22. The method of claim 21, wherein the DMARD is methotrexate.

23. The method of claim 21, wherein the DMARD is an anti-TNF biologic agent.

24. The method of claim 4, wherein the subject has had an inadequate response or intolerance to one or more disease-modifying antirheumatic drugs (DMARDs).

25. The method of claim 24, wherein the DMARD is methotrexate.

26. The method of claim 24, wherein the DMARD is an anti-TNF biologic agent.

27. The method of claim 4, wherein the pediatric patient has an age in a range from about 2 to less than about 18 years.

28. The method of claim 27, wherein the subject has had an inadequate response or intolerance to one or more disease-modifying antirheumatic drugs (DMARDs).

29. The method of claim 28, wherein the DMARD is methotrexate.

30. The method of claim 28, wherein the DMARD is an anti-TNF biologic agent.

\* \* \* \* \*